US010944061B2

(12) United States Patent
Watanabe et al.

(10) Patent No.: US 10,944,061 B2
(45) Date of Patent: Mar. 9, 2021

(54) ORGANIC ELECTROLUMINESCENT ELEMENT AND COMPOUND

(75) Inventors: Kousuke Watanabe, Kanagawa (JP); Wataru Sotoyama, Kanagawa (JP)

(73) Assignee: UDC IRELAND LIMITED, Dublin (IE)

( * ) Notice: Subject to any disclaimer, the term of this patent is extended or adjusted under 35 U.S.C. 154(b) by 935 days.

(21) Appl. No.: 13/820,385

(22) PCT Filed: Sep. 5, 2011

(86) PCT No.: PCT/JP2011/070191

§ 371 (c)(1), (2), (4) Date: Jul. 1, 2013

(87) PCT Pub. No.: WO2012/033063

PCT Pub. Date: Mar. 15, 2012

(65) Prior Publication Data

US 2013/0270530 A1 Oct. 17, 2013

(30) Foreign Application Priority Data

Sep. 8, 2010 (JP) ............................ JP2010-201490
Mar. 31, 2011 (JP) ............................ JP2011-080874

(51) Int. Cl.

| | |
|---|---|
| ***H01L 51/54*** | (2006.01) |
| ***H01L 51/00*** | (2006.01) |
| ***C07D 333/76*** | (2006.01) |
| ***C07D 307/91*** | (2006.01) |
| *H01L 51/50* | (2006.01) |
| *H01L 51/52* | (2006.01) |

(52) U.S. Cl.

CPC ........ *H01L 51/0074* (2013.01); *C07D 307/91* (2013.01); *C07D 333/76* (2013.01); *H01L 51/0073* (2013.01); *H01L 51/0072* (2013.01); *H01L 51/0085* (2013.01); *H01L 51/0087* (2013.01); *H01L 51/0089* (2013.01); *H01L 51/5016* (2013.01); *H01L 51/5048* (2013.01); *H01L 51/5246* (2013.01); *H01L 51/5268* (2013.01)

(58) Field of Classification Search

CPC .. C07D 333/76; C07D 307/91; C07D 405/02; C07D 405/04; C07D 405/14; C07D 327/04; C07D 407/02; C07D 407/04; C07D 407/14; C07D 409/02; C07D 409/04; C07D 409/14; H01L 51/0073; H01L 51/0074; H01L 51/5016; H01L 51/5048; H01L 51/5072; H01L 51/0085; H01L 51/0087; H01L 51/0089; H01L 51/5246; H01L 51/5268

USPC ................. 428/690, 917, 691; 313/504, 505, 313/500–512; 257/E51.05, 40, 88–104, 257/E51.001–E51.052; 549/43, 460; 427/58, 66; 252/301.16–301.35

See application file for complete search history.

(56) References Cited

U.S. PATENT DOCUMENTS

| | | | | |
|---|---|---|---|---|
| 2006/0134538 A1* | 6/2006 | Radu | C07D 311/82 | 430/58.15 |
| 2009/0121627 A1* | 5/2009 | Radu | C07D 311/82 | 313/504 |
| 2009/0167162 A1* | 7/2009 | Lin | C07D 409/14 | 313/504 |
| 2009/0224658 A1* | 9/2009 | Iwakuma | C07F 7/0812 | 313/504 |
| 2010/0038634 A1* | 2/2010 | Nagao | C07D 307/91 | 257/40 |
| 2011/0278551 A1* | 11/2011 | Yabunouchi | C07D 405/12 | 257/40 |
| 2013/0320312 A1* | 12/2013 | Watanabe | C07D 215/04 | 257/40 |
| 2015/0069332 A1* | 3/2015 | Kitamura | C07D 307/91 | 257/40 |

FOREIGN PATENT DOCUMENTS

| | | |
|---|---|---|
| JP | 5109485 | 4/1993 |
| JP | 2000260565 | 9/2000 |
| JP | 2004214050 | 7/2004 |
| JP | 2004214050 A * | 7/2004 |
| JP | 2005314239 | 11/2005 |
| JP | 200763501 | 3/2007 |
| JP | 2007126403 | 5/2007 |
| JP | 2007126403 A * | 5/2007 |

(Continued)

OTHER PUBLICATIONS

Kinoshita et al., Machine Translation of JP-2004214050-A (2004) pp. 1-41. (Year: 2004).*
Nagao et al., Machine Translation of WO-2009069537-A1, (2009), pp. 1-24. (Year: 2009).*
Iwakuma et al., Machine Translation of JP-2009155300-A, (2009), pp. 1-32. (Year: 2009).*
Katakura Rie, machine translation of WO-2010004877-A1 (2010) pp. 1-41. (Year: 2010).*
Nishizeki, Masahito, machine translation of JP-2010215759-A (2010) pp. 1-42. (Year: 2010).*
Tamaru et al., Machine Translation of WO 2010/004877 A1, (2010), pp. 1-50. (Year: 2010).*

(Continued)

*Primary Examiner* — Dylan C Kershner
(74) *Attorney, Agent, or Firm* — Riverside Law LLP

(57) ABSTRACT

An organic electroluminescence device having high efficiency, low in driving voltage and excellent in durability and a compound useful for the organic electroluminescence device are provided.

An organic electroluminescence device comprising, a substrate having thereon: a pair of electrodes of an anode and a cathode; and at least one organic layer comprising a light-emitting layer between the pair of electrodes, and the light-emitting layer contains at least one kind of a phosphorescent material, and at least either one layer of the at least one organic layer contains a specific compound having a dibenzothiophene or dibenzofuran structure, and the compound.

20 Claims, 2 Drawing Sheets

(56) References Cited

FOREIGN PATENT DOCUMENTS

| | | | | | |
|---|---|---|---|---|---|
| JP | 2008545729 | | | 12/2008 | |
| JP | 2009155300 | A | * | 7/2009 | |
| JP | 2009263579 | | | 11/2009 | |
| JP | 2009267257 | | | 11/2009 | |
| JP | WO 2010044342 | A1 | * | 4/2010 | ............. C09K 11/06 |
| JP | 4474493 | | | 6/2010 | |
| JP | WO 2010061824 | A1 | * | 6/2010 | ........... C07D 405/12 |
| JP | 2010215759 | A | * | 9/2010 | |
| WO | 2005090365 | | | 9/2005 | |
| WO | 2007043484 | | | 4/2007 | |
| WO | 2007069569 | | | 6/2007 | |
| WO | 2009072596 | | | 6/2008 | |
| WO | 2009008099 | | | 1/2009 | |
| WO | 2009021126 | | | 2/2009 | |
| WO | 2009069537 | | | 6/2009 | |
| WO | 2009073245 | | | 6/2009 | |
| WO | WO-2009069537 | A1 | * | 6/2009 | ........... C07D 307/91 |
| WO | WO 2009021126 | A9 | * | 9/2009 | ............. C07C 15/38 |
| WO | WO-2010004877 | A1 | * | 1/2010 | ............. C09K 11/06 |
| WO | 2010044342 | | | 4/2010 | |
| WO | WO-2010126270 | A1 | * | 11/2010 | ........... C07D 401/14 |

OTHER PUBLICATIONS

Chen, Run-Feng et al. "Structural, Electronic, and Optical Properties of 9-Heterofluorenes: A Quantum Chemical Study". Journal of Computational Chemistry, vol. 28, pp. 2091-2101.
Sako, et al. "The Formation of Cyclic Compounds From Derivatives of Diphenyl. Part II. The Formation of 4,5,9,10-Dibenzopyrene and 4, 5-Diphenyl-Diphenylene Oxide From 6, 6'-Diphenyl-Diphenyl-2, 2'-Terazonium Sulphate." Bull. Chem. Soc. Japan, 9 (1934) 55.

* cited by examiner

ORGANIC ELECTROLUMINESCENT ELEMENT AND COMPOUND

CROSS-REFERENCE TO RELATED APPLICATIONS

The present application is a U.S. National Stage Entry of International Application No. PCT/JP2011/070191, filed 5 Sep. 2011, which claims priority benefit from Japanese Patent Application No. 2010-201490, filed 8 Sep. 2010, and Japanese Patent Application No. 2011-080874, filed 31 Mar. 2011, all of which are incorporated by reference herein in their entirety.

TECHNICAL FIELD

The present invention relates to an organic electroluminescence device, and a compound for use in the device.

BACKGROUND ART

Since organic electroluminescence devices (hereinafter also referred to as “devices” or “organic EL devices”) are capable of obtaining light emission of high luminance by a low voltage driving, they are actively researched and developed. An organic electroluminescence device has an organic layer between a pair of electrodes, and electrons injected from the cathode and holes injected from the anode are recombined in the organic layer, and generated energy of exciton is used for emission of light.

Patent Document 1 discloses that a specific compound having a benzothiophene structure or a benzofuran structure is effective for providing an organic EL device excellent in light emitting efficiency, pixel defect and heat resistance, and having a long duration of life. Patent Documents 3 to 11 and Non-Patent Document 1 also disclose a specific compound having a benzothiophene structure or a benzofuran structure as useful for an organic EL device.

Patent Document 2 discloses an iridium compound having a specific structure for providing an organic electroluminescence device excellent in various performances.

PRIOR ART DOCUMENT

Patent Document

Patent Document 1: WO 07/069,569
Patent Document 2: WO 09/073,245
Patent Document 3: WO 08/085,344
Patent Document 4: US 2006/0134538
Patent Document 5: WO 09/008,099
Patent Document 6: JP-A-2004-214050
Patent Document 7: JP-A-2005-314239
Patent Document 8: JP-A-2007-63501
Patent Document 9: JP-A-2009-263579
Patent Document 10: JP-A-2009-267257
Patent Document 11: WO 08/72596

Non-Patent Document

Non-Patent Document 1: Bull. Chem. Soc. Japan, 9 (1934) 55

SUMMARY OF THE INVENTION

Problems that the Invention is to Solve

With regard to conventional organic electroluminescence devices as in Patent Documents 1 to 11, it is further required to be excellent in efficiency and durability and capable of driving at a low voltage.

That is to say, an object of the present invention is to provide an organic electroluminescence device having high efficiency, capable of driving at a low voltage and excellent in durability.

Another object of the invention is to provide a compound useful for an organic electroluminescence device as a host material and an electron transporting material, and a composition and a film containing the same compound. A further object of the invention is to provide a light emission apparatus, a display apparatus and an illumination apparatus including the organic electroluminescence device of the invention.

Means for Solving the Problems

From the examinations of the present inventors, it has been found that an organic electroluminescence device having high efficiency, capable of driving at a low voltage and excellent in durability can be provided by using a specific compound of the invention having a dibenzothiophene structure or a dibenzofuran structure bonding to an aromatic ring at the 3-position. It is presumed that lowering of the driving voltage is due to the increase in affinity of electron.

That is, the invention can be achieved by the following means.

[1]

An organic electroluminescence device comprising, a substrate having thereon: a pair of electrodes of an anode and a cathode; and at least one organic layer comprising a light-emitting layer between the pair of electrodes, wherein at least one layer of the at least one organic layer comprises at least one compound represented by formula (1):

(1)

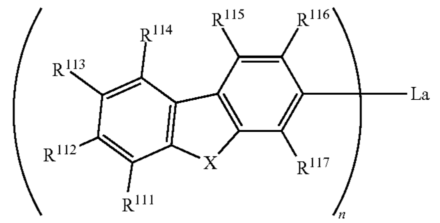

In formula (1), each of X independently represents an oxygen atom or a sulfur atom; each of $R^{111}$ to $R^{114}$ independently represents a hydrogen atom, an alkyl group, a fluorine atom, or a cyano group; each of $R^{115}$ to $R^{117}$ independently represents a hydrogen atom or a substituent; n represents an integer of 1 or more; contiguous two of $R^{111}$ to $R^{116}$ are not bonded to each other to form an aromatic 6-membered ring; and La represents an n-valent aromatic group, but does not represent a condensed polycyclic aromatic hydrocarbon group, and the n-valent aromatic group represented by La may further have a substituent, and when n represents 2 or more and the compound represented by formula (1) has a benzene ring as La or a part of La, and has a structure in which a plurality of dibenzofuran (when X represents an oxygen atom) or dibenzothiophene (when X represents a sulfur atom) in formula (1) are bonded to the benzene ring, the benzene ring has at least one hydrogen atom.

The organic electroluminescence device as claimed in claim 1, wherein La is an n-valent aromatic group comprising an aromatic group represented by formula (AR) or a group in which a plurality of aromatic groups each represented by formula (AR) are linked by a single bond:

(AR)

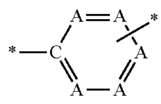

wherein A represents =C(R)— or =N— for forming an aromatic ring, R represents a substituent, the number of nitrogen atoms as A is 0 to 3, and when the number of nitrogen atoms as A is 1 to 3, a plurality of R may be bonded to form a cyclic structure, and * means a bonding hand.

[3]

The organic electroluminescence device as claimed in claim 2, wherein La is an aromatic group in which 2 to 10 aromatic groups each represented by formula (AR) are linked.

[4]

The organic electroluminescence device as claimed in any of claims 1 to 3, wherein the light-emitting layer comprises an iridium complex.

[5]

The organic electroluminescence device as claimed in any of claims 1 to 4, wherein the iridium complex is represented by formula (T-1):

(T-1)

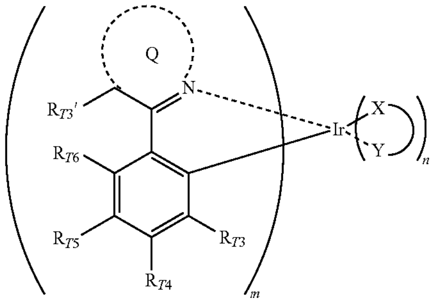

In formula (T-1), each of $R_{T3}'$, $R_{T3}$, $R_{T4}$, $R_{T5}$ and $R_{T6}$ independently represents a hydrogen atom or a substituent, contiguous arbitrary two of $R_{T3}$, $R_{T4}$, $R_{T5}$ and $R_{T6}$ may be bonded to each other to form a condensed 4- to 7-membered ring, and the condensed 4- to 7-membered ring is cycloalkyl, aryl or heteroaryl, and the condensed 4- to 7-membered ring may further have a substituent, $R_{T3}'$ and $R_{T6}$ may be linked to form a ring by a linking group selected from $—C(R_T)_2—C(R_T)_2—$, $—CR_T═CR_T—$, $—C(R_T)_2—$, —O—, $—NR_T—$, $—O—C(R_T)_2—$, $—NR_T—C(R_T)_2—$ and $—N═CR_T—$, and each of $R_T$ independently represents a hydrogen atom, an alkyl group, an alkenyl group, an alkynyl group, an aryl group, or a heteroaryl group, and these groups may further have a substituent, ring Q represents a 5- or 6-membered aromatic heterocyclic ring comprising a nitrogen atom or a condensed aromatic heterocyclic ring comprising a nitrogen atom, and (X—Y) represents an auxiliary ligand, m represents an integer of 1 to 3, n represents an integer of 0 to 2, and m+n=3.

[6]

A compound represented by formula (1):

(1)

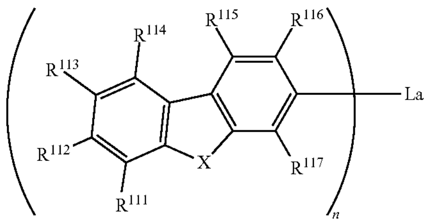

In formula (1), each of X independently represents an oxygen atom or a sulfur atom; each of $R^{111}$ to $R^{8114}$ independently represents a hydrogen atom, an alkyl group, a fluorine atom, or a cyano group; each of $R^{115}$ to $R^{117}$ independently represents a hydrogen atom or a substituent; n represents an integer of 1 or more; contiguous two of $R^{111}$ to $R^{116}$ are not bonded to each other to form an aromatic 6-membered ring; and La represents an n-valent aromatic group, but does not represent a condensed polycyclic aromatic hydrocarbon group, and the n-valent aromatic group represented by La may further have a substituent, and when n represents 2 or more and the compound represented by formula (1) has a benzene ring as La or a part of La, and has a structure in which a plurality of dibenzofuran (when X represents an oxygen atom) or dibenzothiophene (when X represents a sulfur atom) in formula (1) are bonded to the benzene ring, the benzene ring has at least one hydrogen atom.

[7]

A film comprising the compound represented by formula (1) described in any of claims 1 to 3.

[8]

A light emission apparatus comprising the organic electroluminescence device as claimed in any of claims 1 to 5.

[9]

A display apparatus comprising the organic electroluminescence device as claimed in any of claims 1 to 5.

[10]

An illumination apparatus comprising the organic electroluminescence device as claimed in any of claims 1 to 5.

Advantage of the Invention

According to the invention an organic luminescence device having high efficiency, capable of driving at a low voltage and excellent in durability can be provided.

MODE FOR CARRYING OUT THE INVENTION

Figure 1:
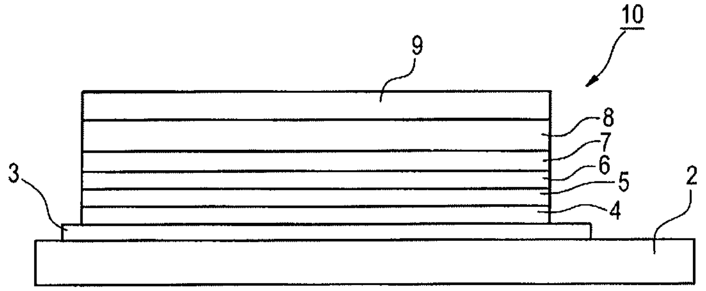
FIG. 1 is a schematic drawing showing an example of the constitution of an organic electroluminescence device according to the invention.

The hydrogen atom in the description of the following formula (1) also includes isotopes (deuterium atoms and the like), and the atoms further constituting substituents mean to also include the isotopes thereof.

In the invention, "a substituent" may be substituted. For example, "an alkyl group" in the invention also includes an alkyl group substituted with a fluorine atom, (e.g., a trifluoromethyl group) and an alkyl group substituted with an aryl group (e.g., a triphenylmethyl group). "An alkyl group having 1 to 6 carbon atoms" means that the number of carbon atoms as all the groups including the group which is substituted is 1 to 6.

Substituent group A is defined as follows in the invention.

(Substituent Group A)

Substituent group A include an alkyl group (preferably having 1 to 30 carbon atoms, more preferably 1 to 20 carbon atoms, and especially preferably 1 to 10 carbon atoms, e.g., methyl, ethyl, isopropyl, tert-butyl, n-octyl, n-decyl, n-hexadecyl, cyclopropyl, cyclopentyl, cyclohexyl and the like are exemplified), an alkenyl group (preferably having 2 to 30 carbon atoms, more preferably 2 to 20 carbon atoms, and especially preferably 2 to 10 carbon atoms, e.g., vinyl, allyl, 2-butenyl, 3-pentenyl and the like are exemplified), an alkynyl group (preferably having 2 to 30 carbon atoms, more preferably 2 to 20 carbon atoms, and especially preferably 2 to 10 carbon atoms, e.g., propargyl, 3-pentynyl and the like are exemplified), an aryl group (preferably having 6 to 30 carbon atoms, more preferably 6 to 20 carbon atoms, and especially preferably 6 to 12 carbon atoms, e.g., phenyl, p-methylphenyl, naphthyl, anthracenyl and the like are exemplified), an amino group (preferably having 0 to 30 carbon atoms, more preferably 0 to 20 carbon atoms, and especially preferably 0 to 10 carbon atoms, e.g., dimethylamino, diethylamino, dibenzylamino, diphenylamino, ditolylamino and the like are exemplified), an alkoxy group (preferably having 1 to 30 carbon atoms, more preferably 1 to 20 carbon atoms, and especially preferably 1 to 10 carbon atoms, e.g., methoxy, ethoxy, butoxy, 2-ethylhexyloxy and the like are exemplified), an aryloxy group (preferably having 6 to 30 carbon atoms, more preferably 6 to 20 carbon atoms, and especially preferably 6 to 12 carbon atoms, e.g., phenyloxy, 1-naphthyloxy, 2-naphthyloxy and the like are exemplified), a heterocyclic oxy group (preferably having 1 to 30 carbon atoms, more preferably 1 to 20 carbon atoms, and especially preferably 1 to 12 carbon atoms, e.g., pyridyloxy, pyrazyloxy, pyrimidyloxy, quinolyloxy and the like are exemplified), an acyl group (preferably having 2 to 30 carbon atoms, more preferably 2 to 20 carbon atoms, and especially preferably 2 to 12 carbon atoms, e.g., acetyl, benzoyl, formyl, pivaloyl and the like are exemplified), an alkoxycarbonyl group (preferably having 2 to 30 carbon atoms, more preferably 2 to 20 carbon atoms, and especially preferably 2 to 12 carbon atoms, e.g., methoxycarbonyl, ethoxycarbonyl and the like are exemplified), an aryloxycarbonyl group (preferably having 7 to 30 carbon atoms, more preferably 7 to 20 carbon atoms, and especially preferably 7 to 12 carbon atoms, e.g., phenyloxycarbonyl and the like are exemplified), an acyloxy group (preferably having 2 to 30 carbon atoms, more preferably 2 to 20 carbon atoms, and especially preferably 2 to 10 carbon atoms, e.g., acetoxy, benzoyloxy and the like are exemplified), an alkylthio group (preferably having 1 to 30 carbon atoms, more preferably 1 to 20 carbon atoms, and especially preferably 1 to 12 carbon atoms, e.g., methylthio, ethylthio and the like are exemplified), an arylthio group (preferably having 6 to 30 carbon atoms, more preferably 6 to 20 carbon atoms, and especially preferably 6 to 12 carbon atoms, e.g., phenylthio and the like are exemplified), a heterocyclic thio group (preferably having 1 to 30 carbon atoms, more preferably 1 to 20 carbon atoms, and especially preferably 1 to 12 carbon atoms, e.g., pyridylthio, 2-benzimidazolylthio, 2-benzoxazolylthio, 2-benzothiazolylthio and the like are exemplified), a sulfonyl group (preferably having 1 to 30 carbon atoms, more preferably 1 to 20 carbon atoms, and especially preferably 1 to 12 carbon atoms, e.g., mesyl, tosyl and the like are exemplified), a sulfonyl group (preferably having 1 to 30 carbon atoms, more preferably 1 to 20 carbon atoms, and especially preferably 1 to 12 carbon atoms, e.g., methanesulfinyl, benzenesulfinyl and the like are exemplified), a halogen atom (e.g., a fluorine atom, a chlorine atom, a bromine atom, and an iodine atom), a cyano group, a sulfo group, a carboxyl group, a nitro group, a sulfino group, an imino group, a heterocyclic group (also including an aromatic heterocyclic group, and preferably having 1 to 30 carbon atoms, and more preferably 1 to 12 carbon atoms, the examples of the heteroatoms include e.g., a nitrogen atom, an oxygen atom, a sulfur atom, a phosphorus atom, a silicon atom, a selenium atom, and a tellurium atom, and specifically pyridyl, pyrazinyl, pyrimidyl, pyridazinyl, pyrrolyl, pyrazolyl, triazolyl, imidazolyl, oxazolyl, thiazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzimidazolyl, benzothiazolyl, a carbazolyl group, an azepinyl group, a silolyl group and the like are exemplified), a silyl group (preferably having 3 to 40 carbon atoms, more preferably 3 to 30 carbon atoms, and especially preferably 3 to 24 carbon atoms, e.g., trimethylsilyl, triphenylsilyl and the like are exemplified), a silyloxy group (preferably having 3 to 40 carbon atoms, more preferably 3 to 30 carbon atoms, and especially preferably 3 to 24 carbon atoms, e.g., trimethylsilyloxy, triphenylsilyloxy and the like are exemplified), and a phosphoryl group (e.g., a diphenylphosphoryl group, a dimethylphosphoryl group and the like are exemplified). These substituents may further be substituted, and as further substituents, the groups selected from the above substituent group A can be exemplified.

The organic electroluminescence device in the invention is an organic electroluminescence device comprising a substrate having thereon a pair of electrodes, the anode and the cathode, and at least one organic layer including a light-emitting layer between the pair of electrodes, and at least either one layer of the above at least one organic layer contains a compound represented by formula (1).

The invention also relates to a compound represented by formula (1). The compound represented by formula (1) is useful as a charge transporting material or a material for an organic electroluminescence device.

[Compound represented by formula (1)]

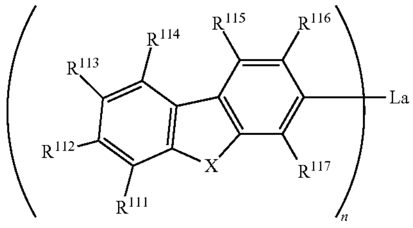

(1)

In formula (1), each of X independently represents an oxygen atom or a sulfur atom; each of $R^{111}$ to $R^{114}$ independently represents a hydrogen atom, an alkyl group, a fluorine atom, or a cyano group; each of $R^{115}$ to $R^{117}$ independently represents a hydrogen atom or a substituent; n represents an integer of 1 or more; contiguous two of $R^{111}$ to $R^{116}$ are not bonded to each other to form an aromatic 6-membered ring; and La represents an n-valent aromatic group, but does not represent a condensed polycyclic aromatic hydrocarbon group, and the n-valent aromatic group represented by La may further have a substituent, when n represents 2 or more and the compound represented by formula (1) has a benzene ring as La or a part of La, and has a structure in which a plurality of dibenzofuran (when X represents an oxygen atom) or dibenzothiophene (when X represents a sulfur atom) in formula (1) are bonded to the benzene ring, the benzene ring has at least one hydrogen atom. As the substituent on the benzene ring, the groups belonging to substituent group A are exemplified, but the substituent is preferably a group not an alkoxy group.

n is preferably 1 to 6, more preferably 2 to 4, and still more preferably 2 or 3.

X preferably represents a sulfur atom in the point of durability. X preferably represents an oxygen atom in the point of efficiency.

Each of $R^{111}$ to $R^{114}$ independently represents a hydrogen atom, an alkyl group, a fluorine atom, or a cyano group, by which LUMO level becomes a preferred range, as a result a driving voltage lowers and durability is improved. It is more preferred for each of $R^{111}$ to $R^{114}$ to represents a hydrogen atom, a fluorine atom, or a cyano group from the viewpoint of LUMO level, it is still more preferred to represent a hydrogen atom or a cyano group, and to represent a hydrogen atom is most preferred.

The alkyl group represented by $R^{111}$ to $R^{114}$ is a straight chain, branched chain or cyclic alkyl group, preferably an alkyl group having 1 to 18 carbon atoms, more preferably an alkyl group having 1 to 12 carbon atoms, and still more preferably an alkyl group having 1 to 6 carbon atoms.

The substituents represented by $R^{115}$ to $R^{117}$ are not especially restricted and, for example, the exemplified substituents as substituent group A can be exemplified.

Each of $R^{115}$ to $R^{117}$ independently preferably represents a hydrogen atom, an alkyl group, an aryl group or a cyano group, more preferably a hydrogen atom, an alkyl group or an aryl group, still more preferably a hydrogen atom or an aryl group, and especially preferably a hydrogen atom.

The alkyl group represented by $R^{115}$ to $R^{117}$ is a straight chain, branched chain or cyclic alkyl group, preferably an alkyl group having 1 to 18 carbon atoms, more preferably an alkyl group having 1 to 12 carbon atoms, and still more preferably an alkyl group having 1 to 6 carbon atoms.

The alkyl group represented by $R^{115}$ to $R^{117}$ is especially preferably any of a methyl group, an ethyl group, an n-propyl group, an i-propyl group, an n-butyl group, a t-butyl group, an i-butyl group, an n-pentyl group, a neopentyl group, a t-amyl group, an s-isoamyl group, a cyclopentyl group, an n-hexyl group, and a cyclohexyl group, and most preferably any of a methyl group, an i-propyl group, an n-butyl group, and a t-butyl group.

The aryl group represented by $R^{115}$ to $R^{117}$ is an aryl group preferably having 6 to 30 carbon atoms, more preferably 6 to 20 carbon atoms, and especially preferably 6 to 12 carbon atoms, and, for example, a phenyl group, a biphenyl group, a p-methylphenyl group, a naphthyl group, an anthranyl group are exemplified, preferably a phenyl group, a biphenyl group, and a terphenyl group, and more preferably a phenyl group.

The substituent represented by $R^{115}$ to $R^{117}$ may further have a substituent, and as the examples of the further substituents, an alkyl group and an aryl group can be exemplified. The alkyl group as the further substituent has the same meaning with the alkyl group represented by $R^{115}$ to $R^{117}$ and preferred groups are also the same. The aryl group as the further substituent is preferably an aryl group having 6 to 30 carbon atoms, more preferably 6 to 20 carbon atoms, and especially preferably 6 to 14 carbon atoms, and a phenyl group is preferred.

La represents an n-valent aromatic group, but does not represent a condensed polycyclic aromatic hydrocarbon group. The n-valent aromatic group represented by La is preferably a group including an arylene group, a heteroarylene group, or a linking group of linking an arylene group and a heteroarylene group in a chain-state. From the point of a charge transporting property, a group including an arylene group is preferred.

In view of heat resistance, durability and a sublimation property, the total number of aromatic rings in the group including the linking group is preferably 2 to 15 including the carbon atoms of the further substituent, more preferably 2 to 10, and especially preferably 3 to 8.

As the arylene groups, e.g., a phenylene group, a biphenylene group, a terphenylene group, a quaterphenylene group and a quinquephenylene group are exemplified.

As the heteroarylene groups, e.g., a pyridine ring group, a pyrimidine ring group, a triazine ring group, a dibenzothiophenyl group, and a dibenzofuranyl group are exemplified, and a pyridine ring group, a pyrimidine ring group, and a triazine ring group are preferred.

These groups may further have a substituent. In the heteroarylene group, contiguous substituents may be linked to form a ring. As such cyclic structures, 5- or 6-membered aromatic rings, e.g., a benzene ring, a pyridine ring, a thiophene ring, and a furan ring can be exemplified.

As the further substituents, an alkyl group, an aryl group and a heteroaryl group can be exemplified. The alkyl group as the further substituent has the same meaning with the alkyl group represented by $R^{111}$ to $R^{117}$ and preferred groups are also the same. The aryl group as the further substituent is preferably an aryl group having 6 to 30 carbon atoms, more preferably 6 to 20 carbon atoms, and especially preferably 6 to 14 carbon atoms, and preferably a phenyl group, a biphenyl group and a terphenyl group, and more preferably a phenyl group. The heteroaryl group as the further substituent preferably has 4 to 30 carbon atoms, and more preferably 4 to 20 carbon atoms. The examples thereof include a pyridyl group, a pyrazinyl group, a pyrimidinyl group, a pyridazinyl group, a triazinyl group, a thiophenyl group, a furanyl group, an oxazolyl group, a thiazolyl group, an imidazolyl group, a pyrazolyl group, a triazolyl group, an oxadiazolyl group, a thiadiazolyl group, a dibenzothiophenyl group, and a dibenzofuranyl group, and preferably a pyridyl group, a pyrimidinyl group, a pyridazinyl group, and a triazinyl group.

The n-valent aromatic group represented by La is preferably an n-valent aromatic group comprising an aromatic group represented by formula (AR) or a group in which a plurality of aromatic groups represented by formula (AR) linked by a single bond:

(AR)

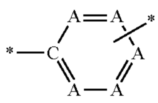

In formula (AR), A represents =C(R)— or =N— for forming an aromatic ring; and R represents a substituent. The number of nitrogen atoms as A is 0 to 3. * means a bonding hand. Incidentally, when the number of nitrogen atoms as A is 1 to 3, a plurality of R may be bonded to form a cyclic structure. In the above, the formula having two bonding hands * is shown as a preferred case, but the bonding hands may be three or more.

With regard to the n-valent aromatic group represented by La, n is preferably 2 to 6, more preferably 2 to 5, still more preferably 2 to 4, especially preferably 2 or 3, and most preferably 2.

It is preferred for the n-valent aromatic group represented by La to have 1 to 20 aromatic groups represented by formula (AR), more preferably 2 to 10, still more preferably 3 to 10, and especially preferably 4 to 8.

The nitrogen atoms as A are preferably the fewer. The nitrogen atom is preferably present as the atom at the ortho-position or para-position of the carbon atom shown in formula (AR).

The substituent represented by R has the same meaning with the substituent represented by $R^{115}$ to $R^{117}$, preferably an alkyl group, an aryl group, a heteroaryl group, a fluorine atom, and a cyano group are exemplified, preferably a fluorine atom and a cyano group, and more preferably a cyano group.

In the point of the reduction of voltage, a cyano group is especially preferred. As the aromatic group represented by La, it is preferred to have 1 or 2 cyano groups, and especially preferably 1 cyano group.

In the case of having 1 to 3 nitrogen atoms as A, a plurality of contiguous substituents represented by R may be bonded to form a cyclic structure such as an aromatic ring. That is, the aromatic ring in formula (AR) may be a condensed nitrogen-containing aromatic ring. However, it is preferred not to have a condensed cyclic structure from the viewpoint of light emission efficiency.

The n-valent aromatic group as La is especially preferably a group represented by the following formula (A). * means a bonding hand. In the following, the formula having two bonding hands * is shown as a preferred case, but the bonding hands may be three or more.

(A)

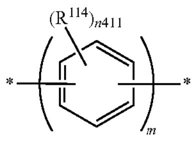

In formula (A), each of $R^{411}$ independently represents a substituent. Each of $n^{411}$ independently represents an integer of 0 to 4. m represents an integer of 1 or more, preferably an integer of 1 to 15, more preferably an integer of 2 to 10, and still more preferably an integer of 3 to 8. From the point of a sublimation property, m is preferably 10 or less.

The substituent represented by $R^{411}$ has the same meaning with the substituent represented by $R^{115}$ to $R^{117}$, preferably an alkyl group, an aryl group, a heteroaryl group, a fluorine atom, and a cyano group can be exemplified, and a fluorine atom and a cyano group are preferred.

$R^{411}$ on the contiguous benzene rings may be bonded to form a condensed aromatic heterocyclic structure (e.g., a thiophene ring, a furan ring). However, from the viewpoint of light emitting efficiency and synthesis suitability, it is preferred not to have a cyclic structure.

Each of $n^{411}$ independently represents an integer of 0 to 5, preferably 0 to 2, and more preferably 0 or 1.

This is for the reason that when $n^{411}$ is 2 or more, the dihedral angle with the linking group becomes large and comes to a primary factor of reduction of durability.

Linking number (m) of the group represented by formula (A) is preferably greater in the point of heat resistance and durability.

Linking of the group represented by formula (A) is preferably linking at the meta-position in the point of external quantum efficiency. This is, for example, for the reason that in the case where a green phosphorescent material is used as the dopant of a light-emitting layer, the excitation triplet energy is liable to be smaller than the dopant.

Incidentally, in the point of heat resistance and durability, linking at the para-position is preferred. However, linking at the para-position of the groups represented by formula (A) is preferably up to 3, and it is preferred that 4 or more groups represented by formula (A) are not linked at the para-position. This is, for example, for the reason that in the case where a green phosphorescent material is used as the dopant of a light-emitting layer, the excitation triplet energy is liable to be smaller than the dopant.

As the specific examples of the groups represented by formula (A), the following-shown groups and the groups obtained by combining a plurality of these groups can be exemplified.

In the following, * means a bonding hand. In the following, representative examples of the case of having bonding hands are shown, but in the case of forming an n-valent aromatic group as La, n *'s may be present irrespective of the following expression.

For example, when n forms a monovalent aromatic group in the following example, *'s of the second and up are groups to which hydrogen atoms are bonded. When n is 2 or more, the group in the parenthesis in formula (1) is bonded to n *'s, and hydrogen atoms are bonded to the remaining *.

L1

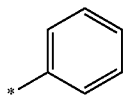

L2

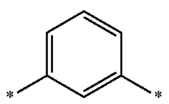

-continued

L3

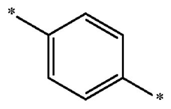

L4

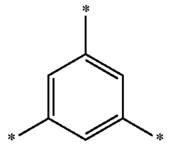

L5

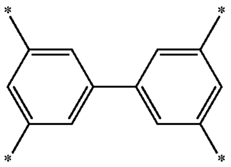

L6

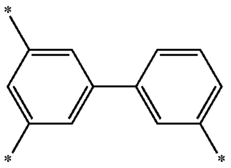

L7

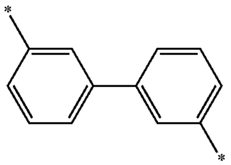

L8

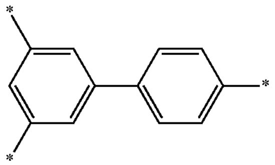

L9

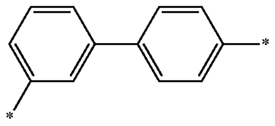

L10

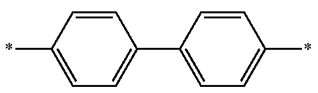

L11

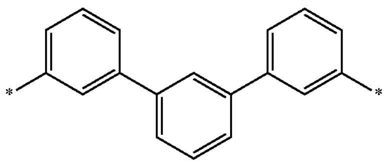

L12

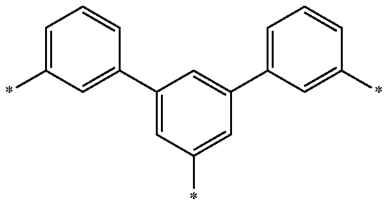

-continued

L13

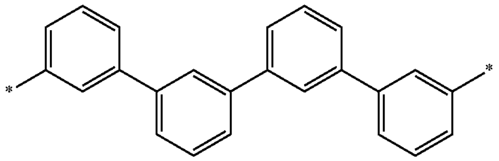

L14

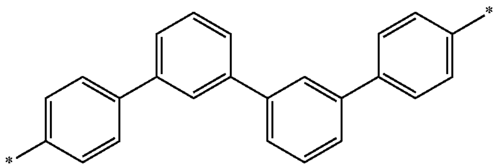

L15

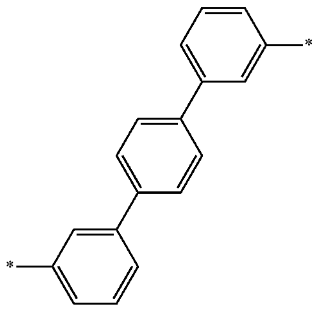

La is preferably an n-valent aromatic group having the structure of L7, L11, L13 or L15.

The compound represented by formula (1) is preferably a compound comprising a carbon atom, a hydrogen atom and an oxygen atom or a sulfur atom alone. Durability is improved by such a constitution.

The molecular weight of the compound represented by formula (1) is generally 400 or more and 1,500 or less, preferably 450 or more and 1,200 or less, more preferably 500 or more and 1,100 or less, and still more preferably 600 or more and 1,000 or less. The molecular weight of 400 or more is desired in the point of formation of a deposited film. The molecular weight of 450 or more is advantageous in formation of an amorphous thin film of a fine quality. When the molecular weight is 1,200 or less, solubility and a sublimation property are improved and advantageous in the improvement of purity of the compound.

Further, in formula (1), when n is 1, $R^{112}$ is a phenyl group and the aromatic group as La consists of one benzene ring alone, it is preferred that the benzene ring has a substituent in the point of forming a deposited film, and the groups belonging to substituent group A are exemplified as the examples of the substituents.

In the case where the compound represented by formula (1) is used as the host material of a light-emitting layer of an organic electroluminescence device or as the charge-transporting material of the layer contiguous to the light emitting layer, when the energy gap of the compound in a thin film state (the lowest excitation triplet energy ($T_1$) in a thin film state in the case where the light-emitting material is a phosphorescent material) is greater than that of the light-emitting material, quenching of light emission can be prevented, and so advantageous in the improvement of efficiency. On the other hand, from the viewpoint of chemical stability of the compound, energy gap and $T_1$ energy are preferably not too high.

$T^1$ energy of the compound represented by formula (1) in a film state is preferably 2.39 eV (55 kcal/mol) or more and 3.51 eV (80 kcal/mol) or less, and more preferably 2.52 eV (58 kcal/mol) or more and 3.04 eV (70 kcal/mol) or less. In particular, when a phosphorescent material is used as the light-emitting material, it is preferred that $T_1$ energy comes into the above range.

$T_1$ energy can be found from the short wavelength end of the light emission spectrum of phosphorescence of the thin film of a material. For example, a thin film is formed in a thickness of about 50 nm by vacuum deposition of a material on a cleaned quartz glass substrate, and the light emission spectrum of phosphorescence of the thin film is measured with F-7000 Hitachi fluorescence spectrophotometer (manufactured by Hitachi High Technologies Corporation) under a liquid nitrogen temperature. $T_1$ energy can be found by converting the rising wavelength on the short wavelength side of the obtained light emission spectrum into an energy unit.

In view of stable actuation of an organic electroluminescence device at a high temperature driving time and against calorification during driving of the device, the glass transition temperature (Tg) of the compound represented by formula (1) is preferably 100° C. or more and 400° C. or less, more preferably 120° C. or more and 400° C. or less, and still more preferably 140° C. or more and 400° C. or less.

If the purity of the compound represented by formula (1) is low, impurities function as trapping of charge transportation or deterioration of the device is accelerated, and so the purity of the compound represented by formula (1) is the higher the better. The purity can be measured by, for example, high performance liquid chromatography (HPLC). The area ratio of the compound represented by formula (1) detected at light absorption intensity of 254 nm is preferably 95.0% or more, more preferably 97.0% or more, especially preferably 99.0% or more, and most preferably 99.9% or more.

As is known by the carbazole-based materials described in WO 2008/117889, materials obtained by partially or entirely substituting the hydrogen atoms of the compound represented by formula (1) with a deuterium atom can also be used in the invention.

The specific examples of the compounds represented by formula (1) are shown below, but the invention is not restricted to these compounds.

Compound (1-1)

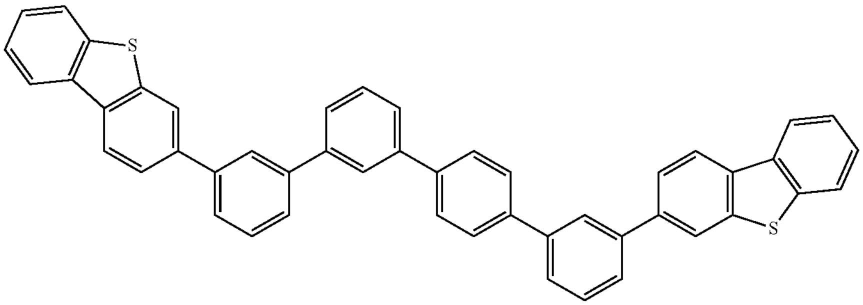

Compound (1-2)

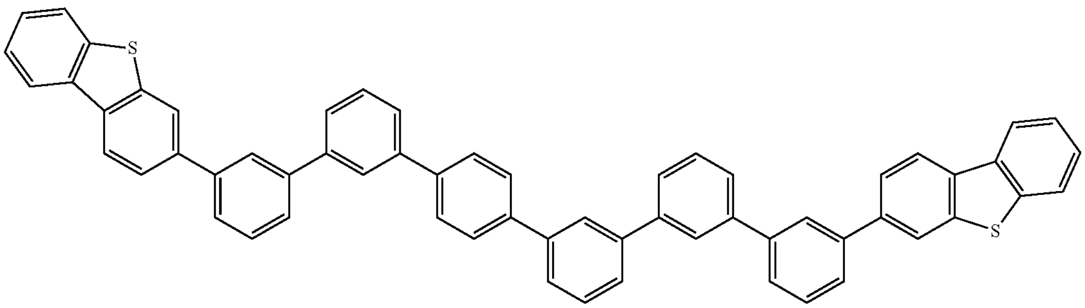

Compound (1-3)

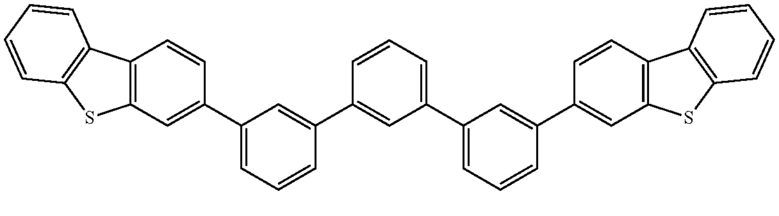

-continued
Compound (1-4)
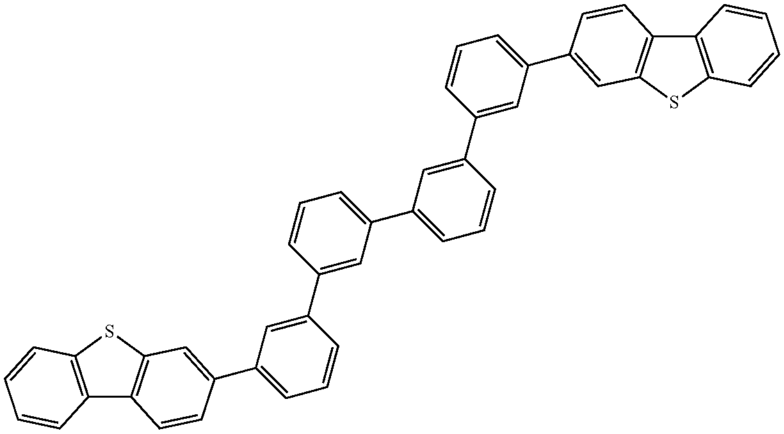
Compound (1-5)
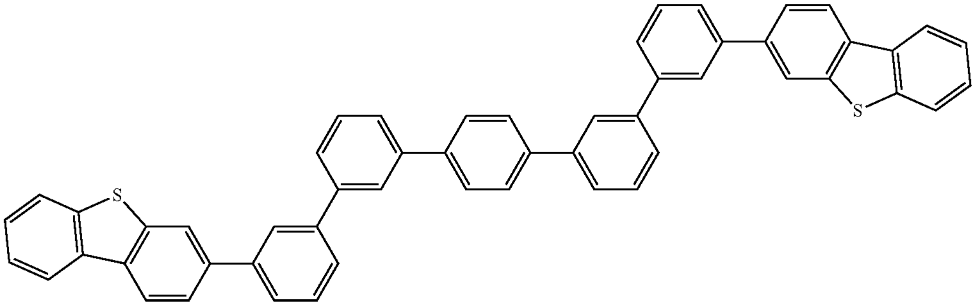
Compound (1-6)
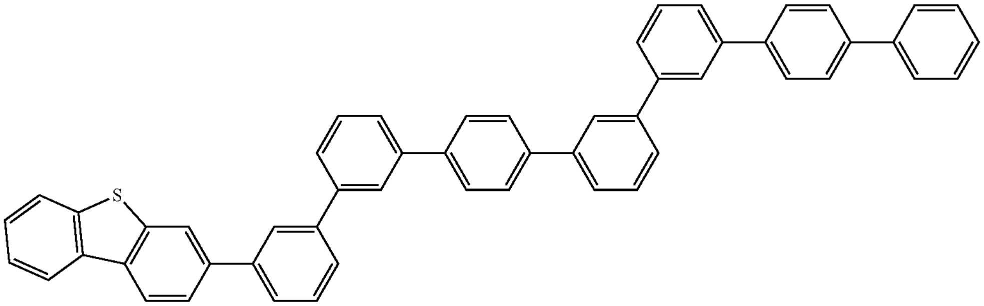
Compound (1-7)
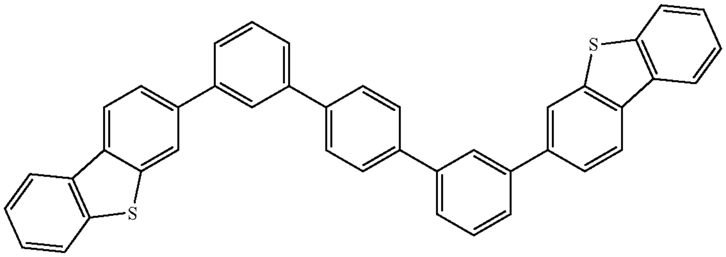
Compound (1-8)
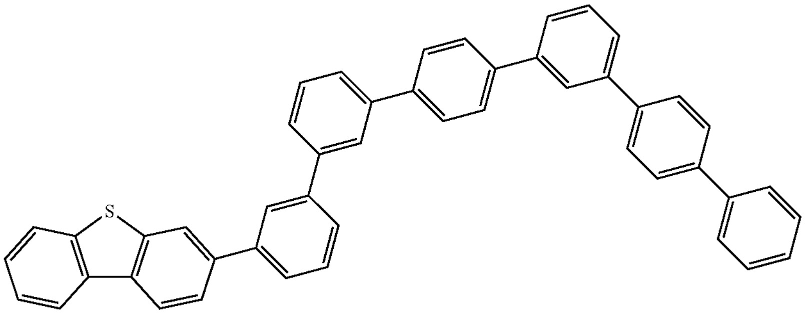

-continued
Compound (1-9)
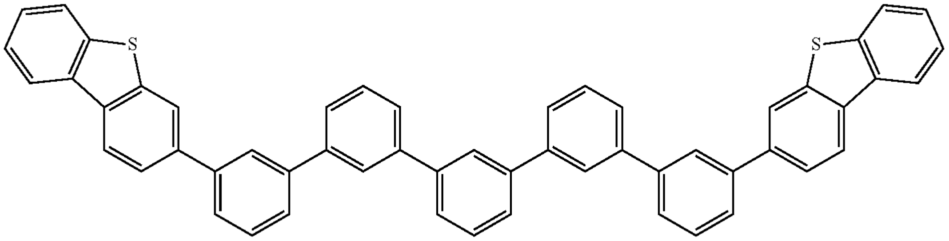
Compound (1-10)
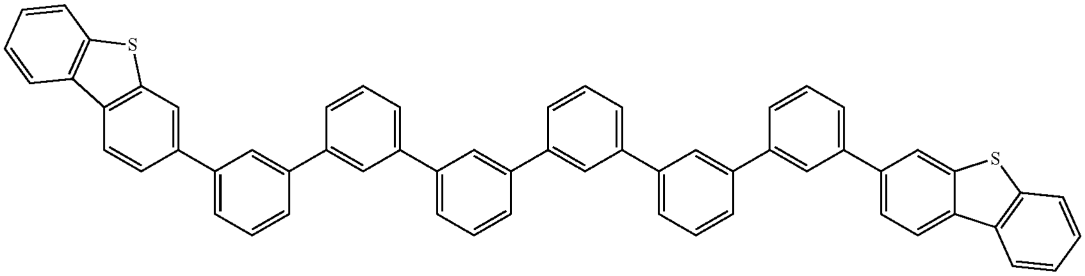
Compound (1-11)
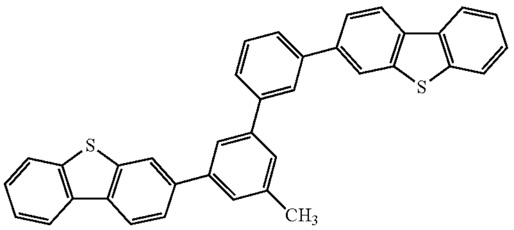
Compound (1-12)
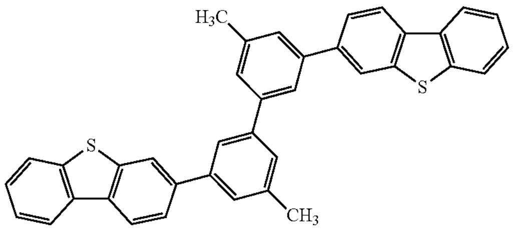
Compound (1-13)
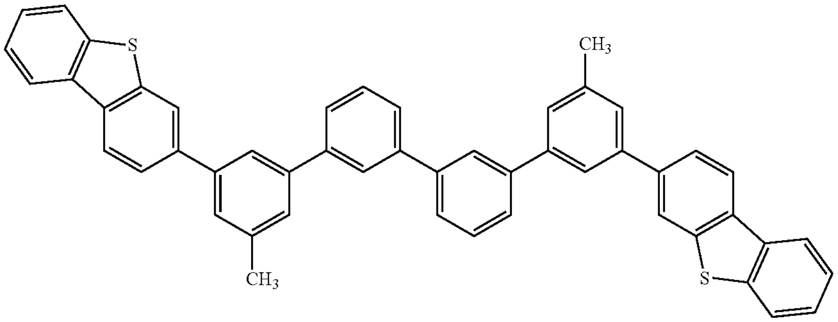
Compound (1-14)
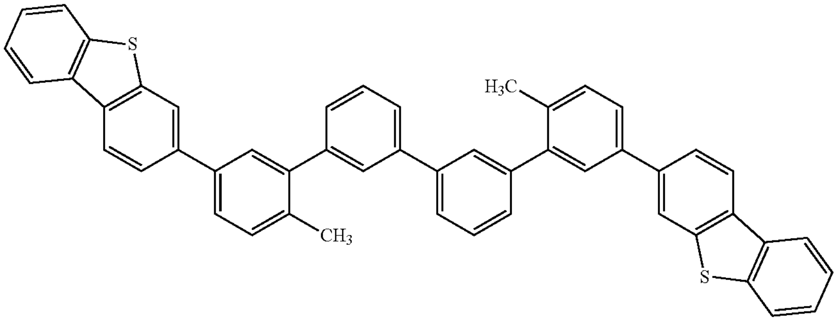

-continued
Compound (1-15)
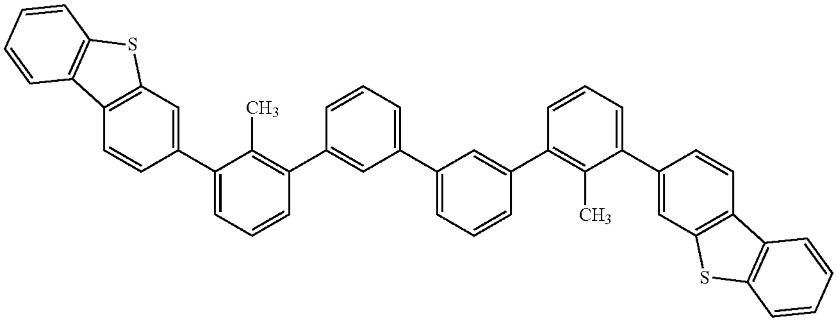
Compound (1-16)
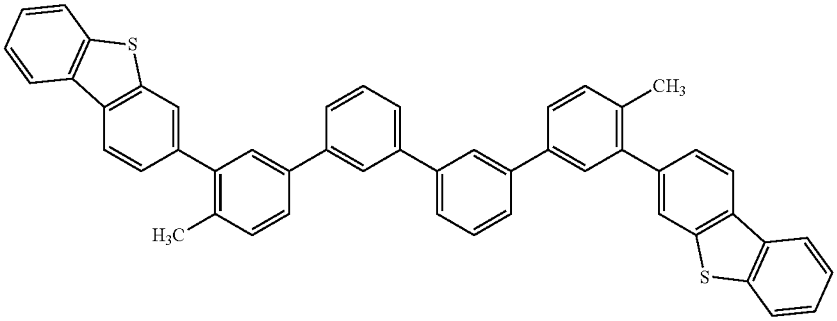
Compound (1-17)
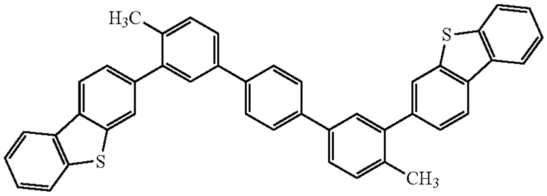
Compound (1-18)
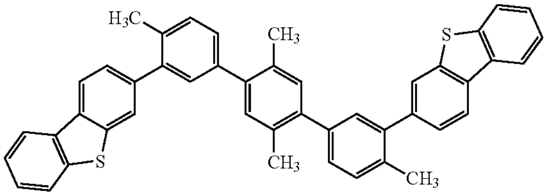
Compound (1-19)
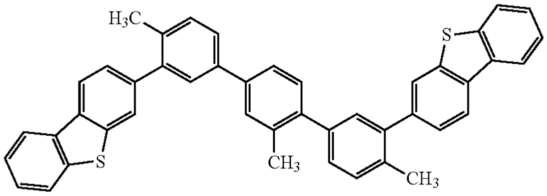
Compound (1-20)
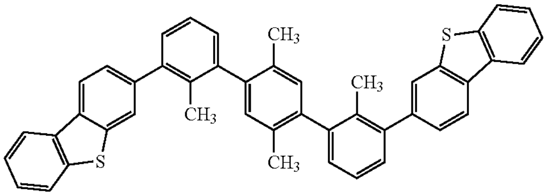
Compound (1-21)
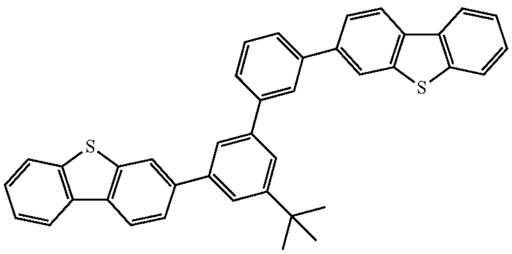
Compound (1-22)
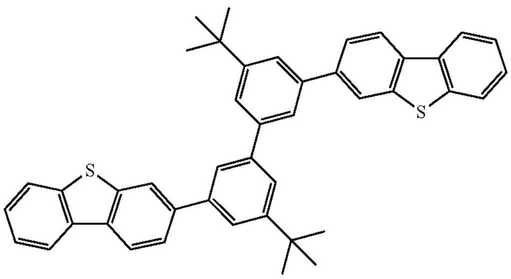

-continued
Compound (1-23)
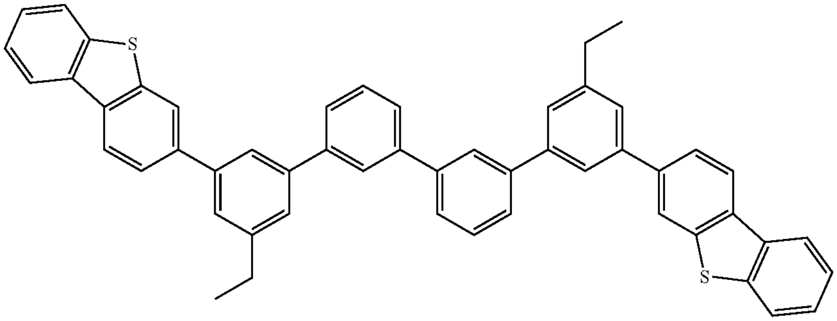
Compound (1-24)
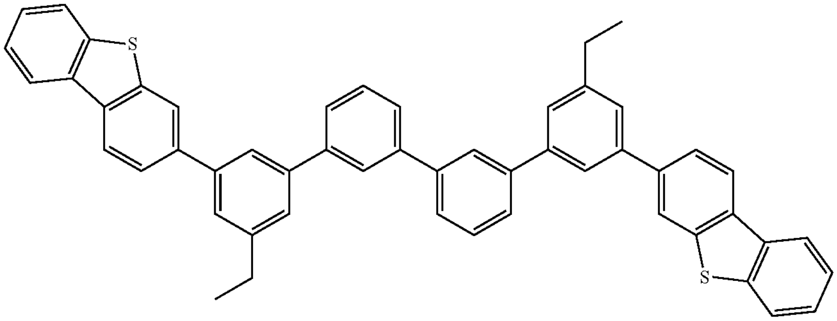
Compound (1-25)
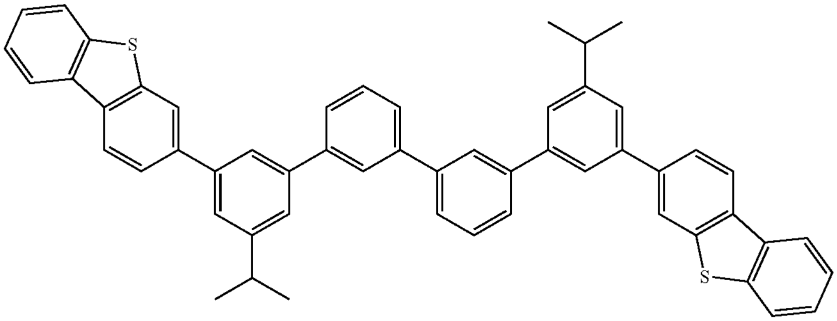
Compound (1-26)
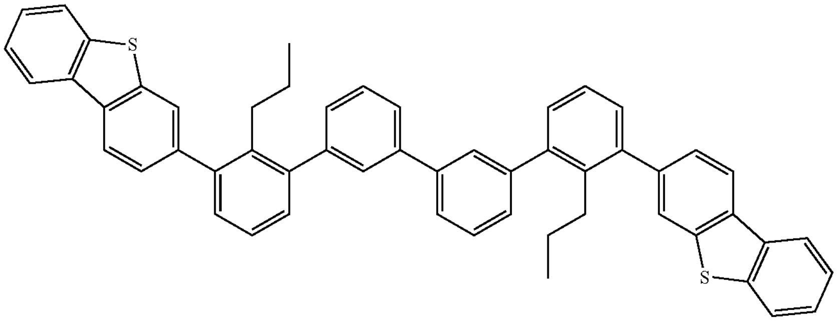
Compound (1-27)
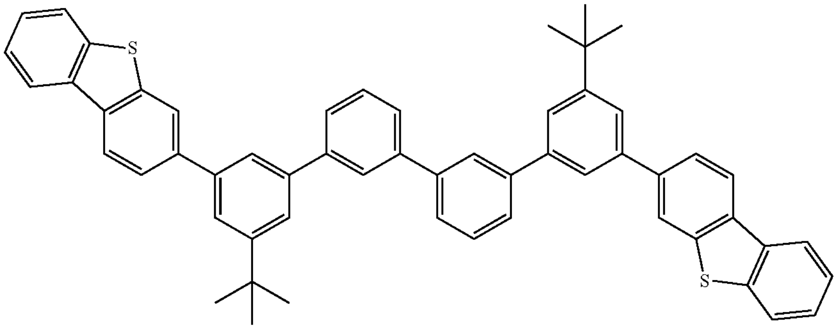

-continued
Compound (1-28)
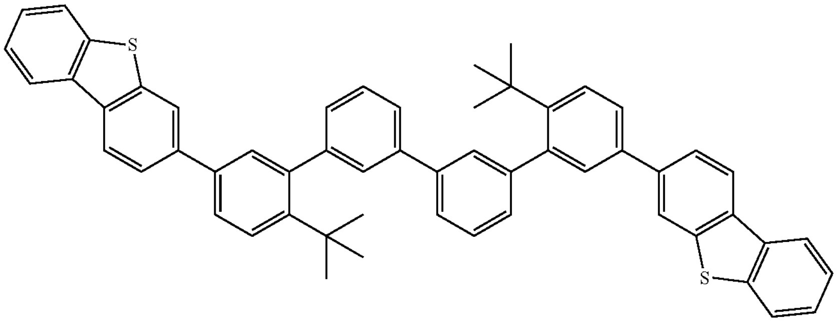
Compound (1-29)
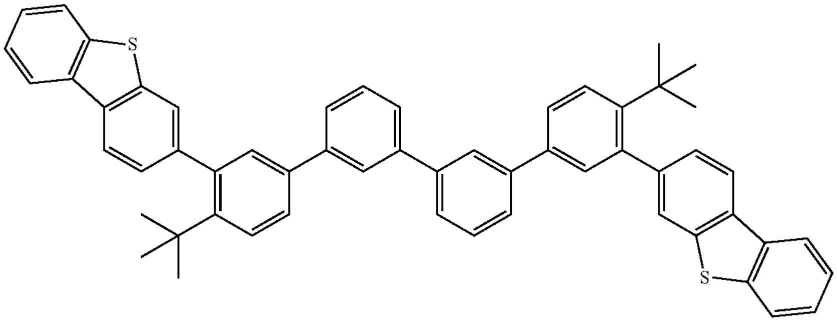
Compound (1-30)
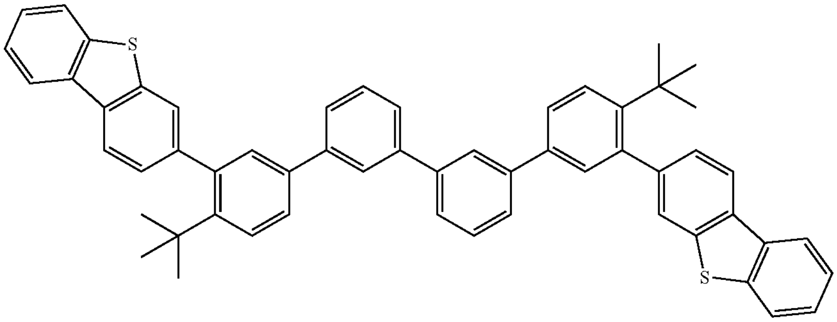
Compound (1-31)
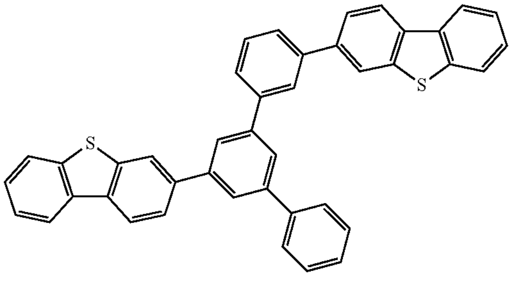
Compound (1-32)
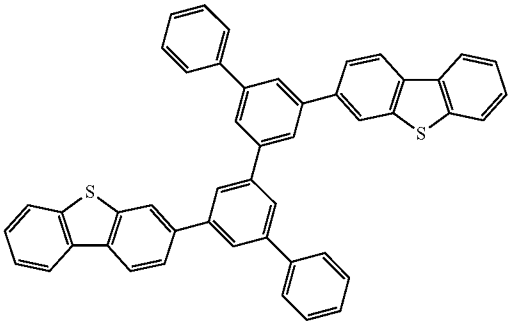

-continued
Compound (1-33)
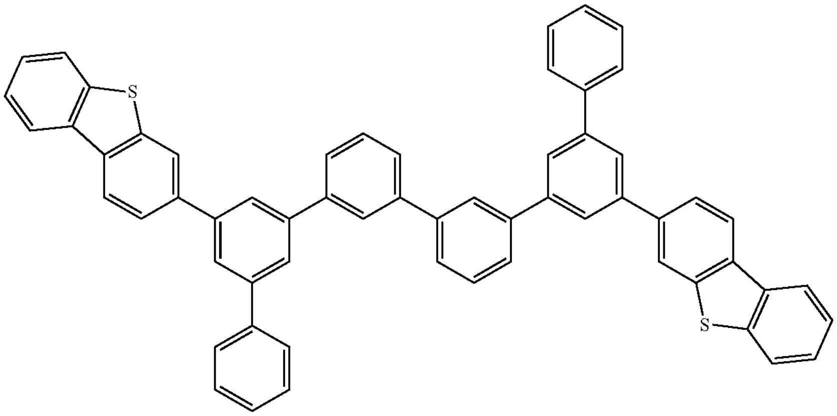
Compound (1-34)
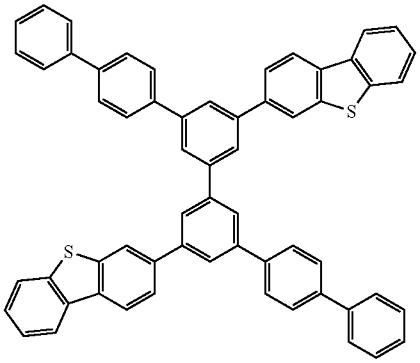
Compound (1-35)
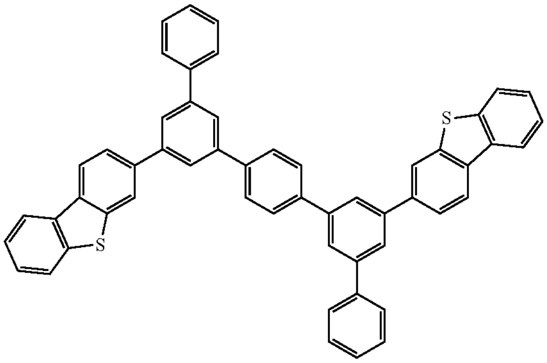
Compound (1-36)
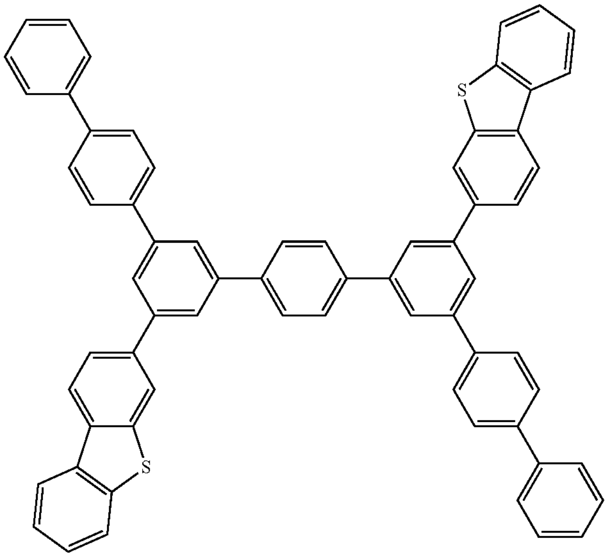

-continued
Compound (1-37)
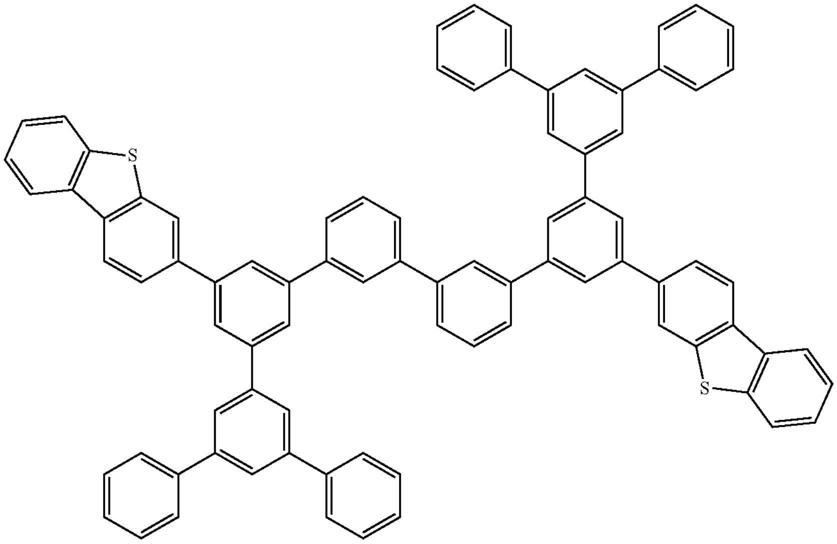
Compound (1-38)
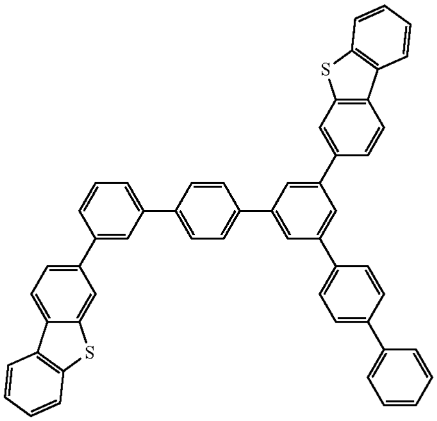
Compound (1-39)
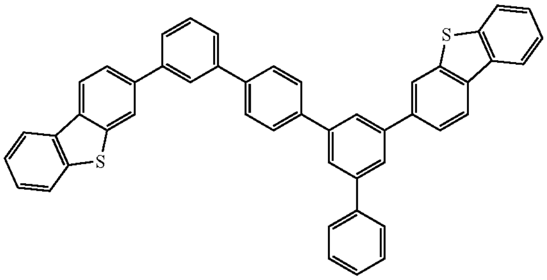
Compound (1-40)
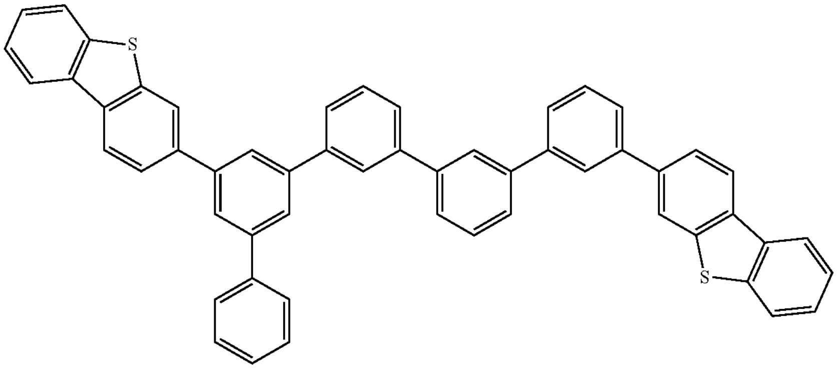

-continued
Compound (1-41)
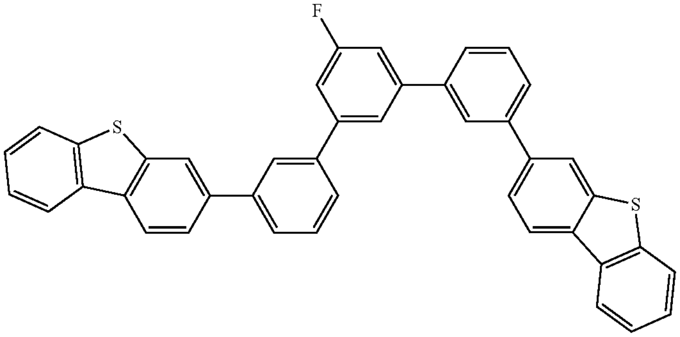
Compound (1-42)
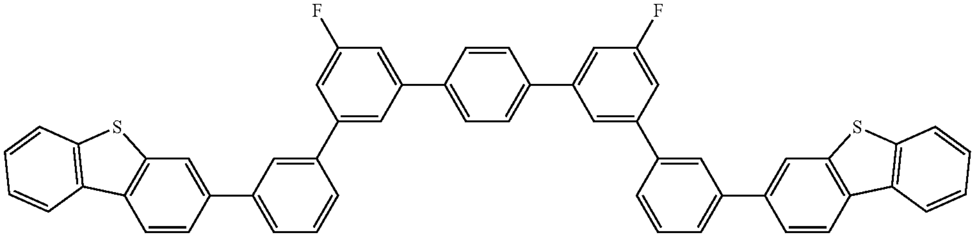
Compound (1-43)
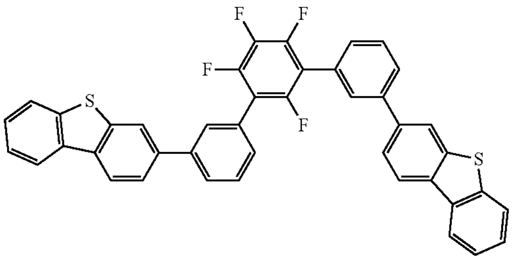
Compound (1-44)
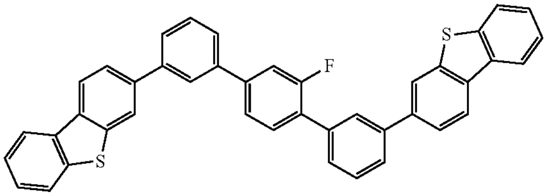
Compound (1-45)
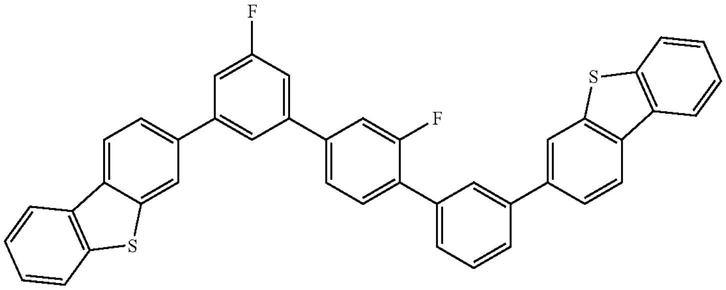
Compound (1-46)
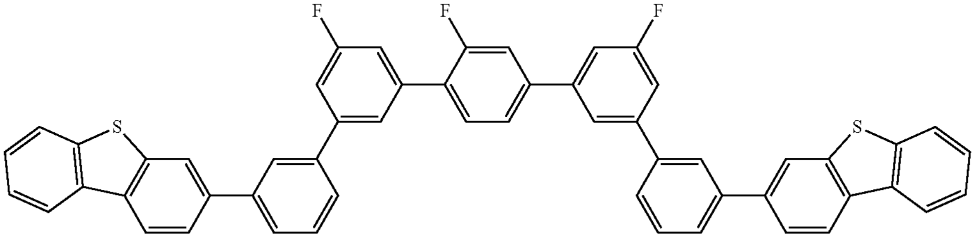

-continued
Compound (1-47)
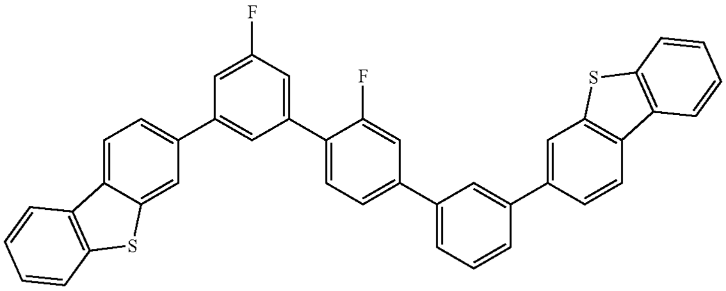
Compound (1-48)
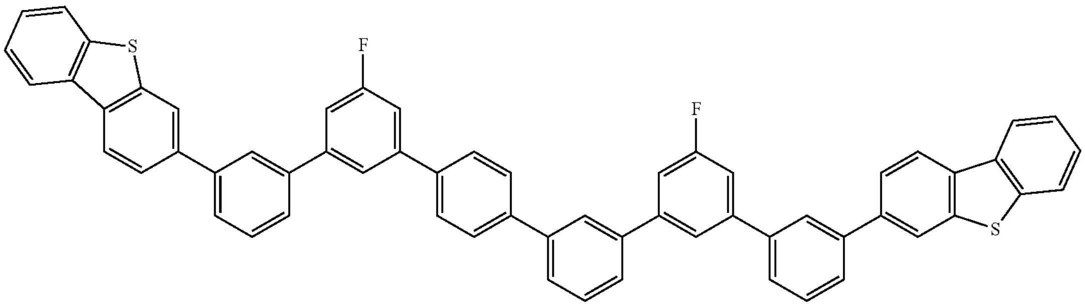
Compound (1-49)
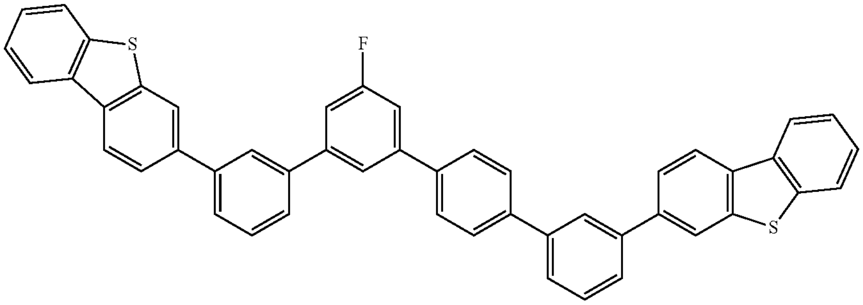
Compound (1-50)
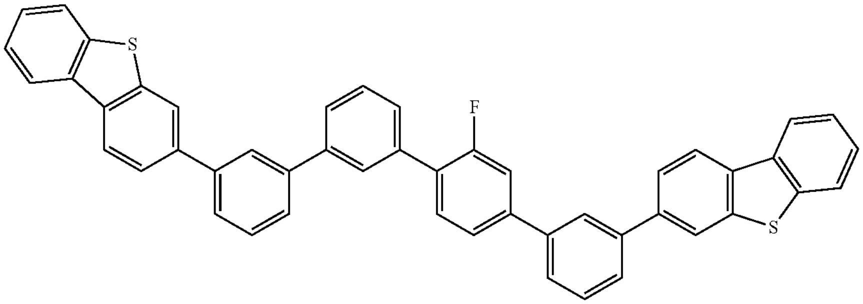

-continued
Compound (1-51)
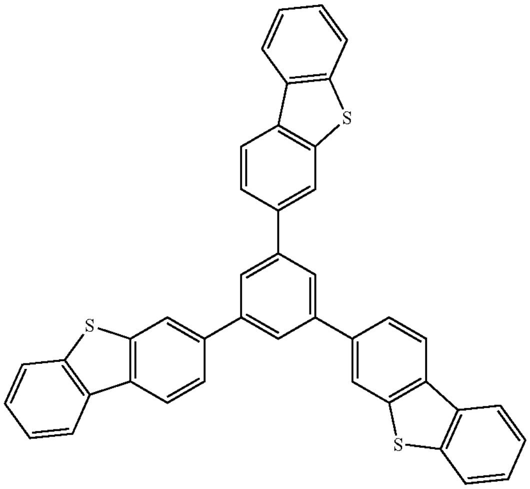
Compound (1-52)
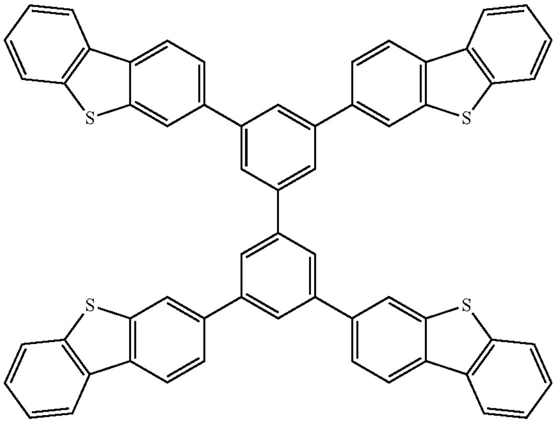
Compound (1-53)
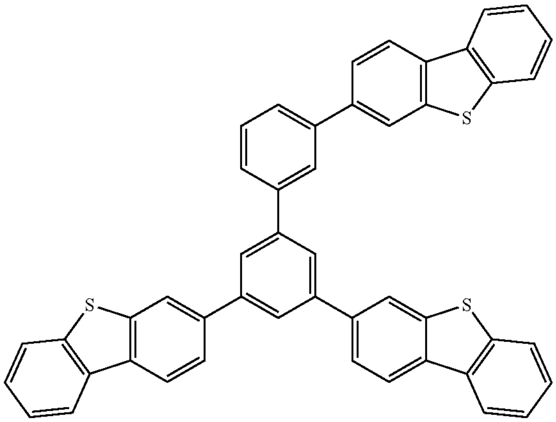
Compound (1-54)
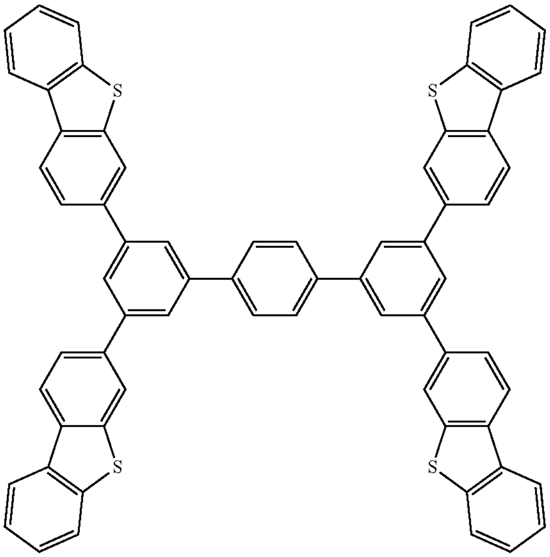
Compound (1-55)
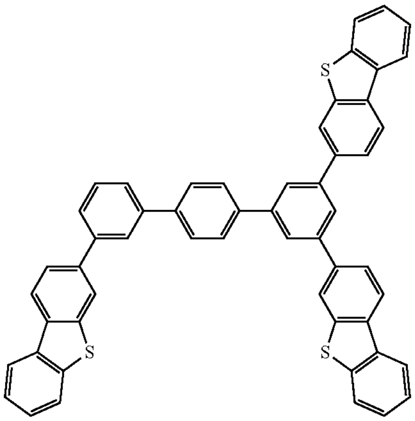
Compound (1-56)
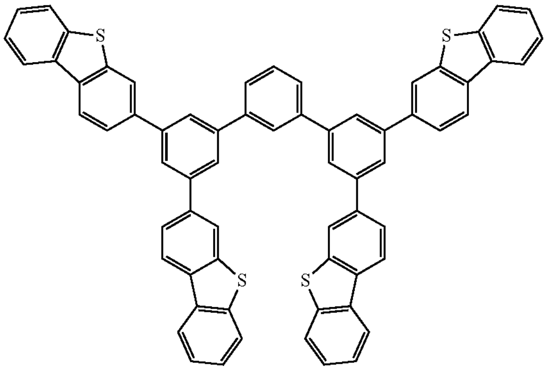

-continued
Compound (1-57)
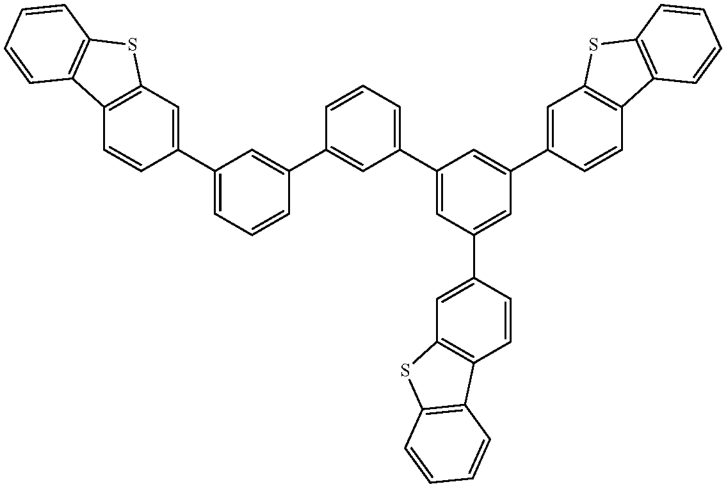
Compound (1-58)
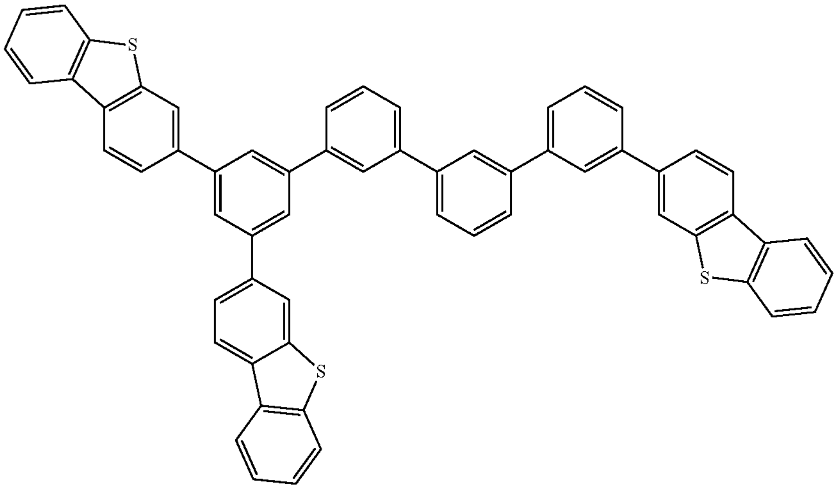
Compound (1-59)
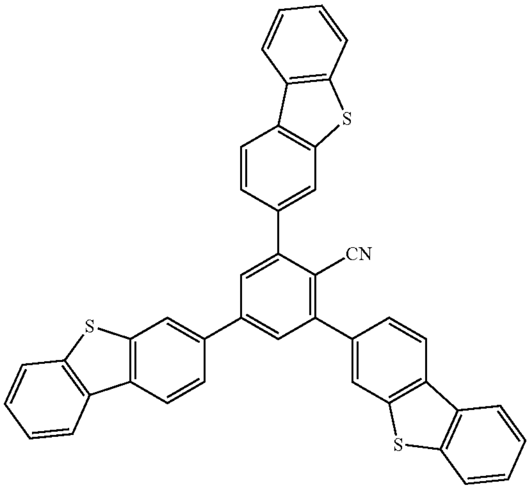
Compound (1-60)
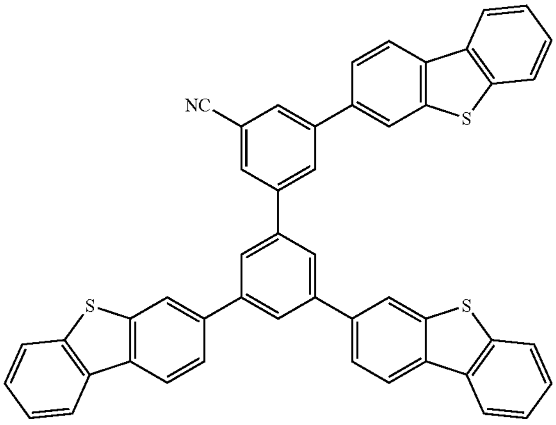

-continued
Compound (1-61)
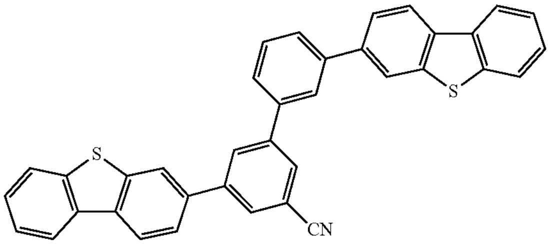
Compound (1-62)
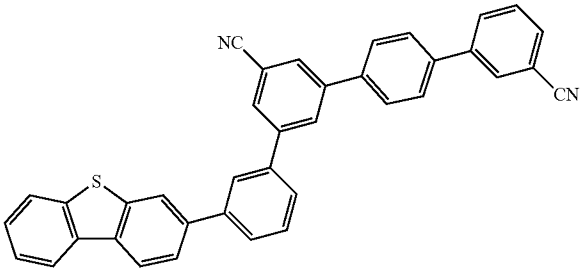
Compound (1-63)
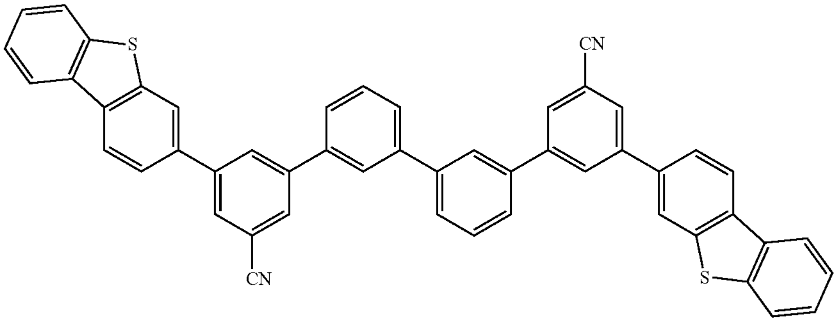
Compound (1-64)
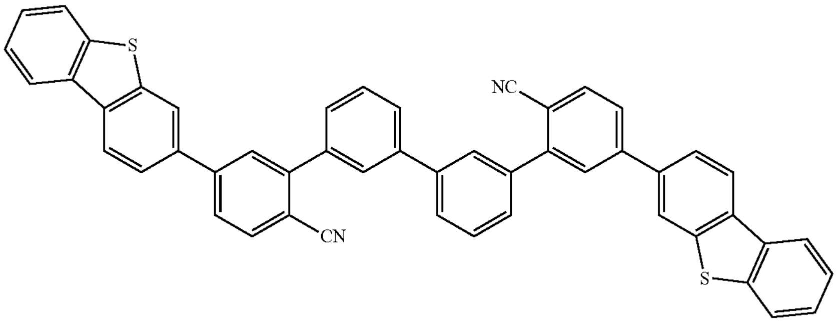
Compound (1-65)
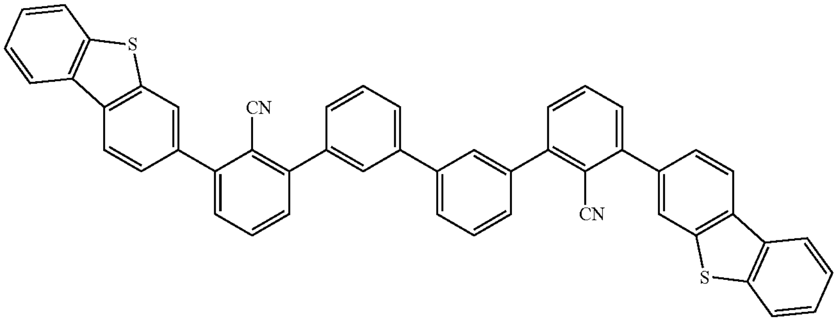
Compound (1-66)
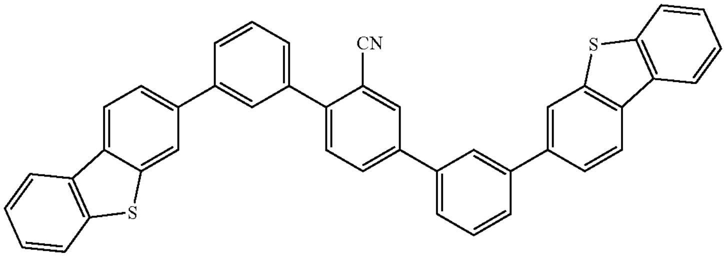

-continued
Compound (1-67)
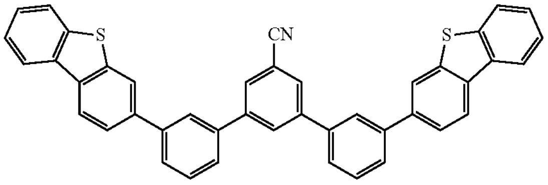
Compound (1-68)
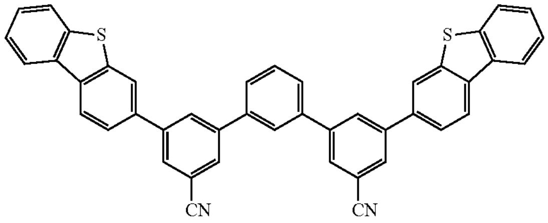
Compound (1-69)
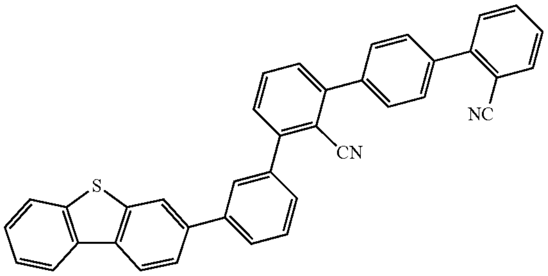
Compound (1-70)
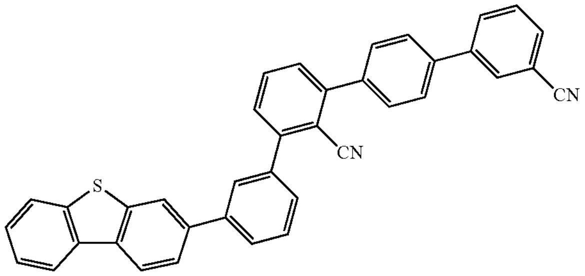
Compound (1-71)
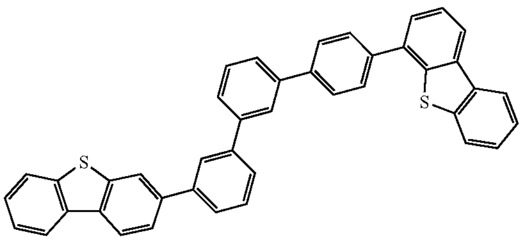
Compound (1-72)
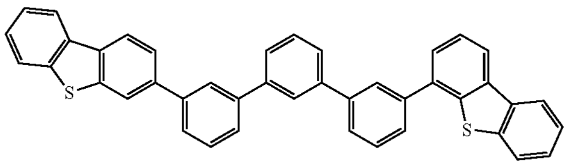
Compound (1-73)
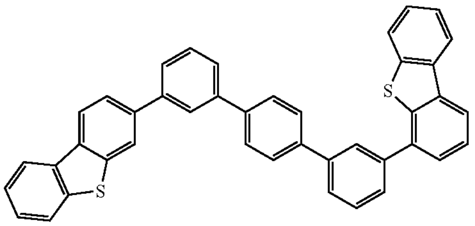
Compound (1-74)
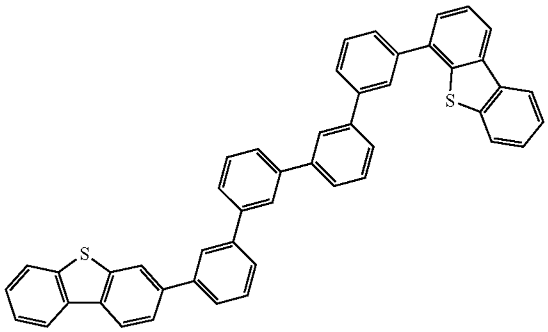
Compound (1-75)
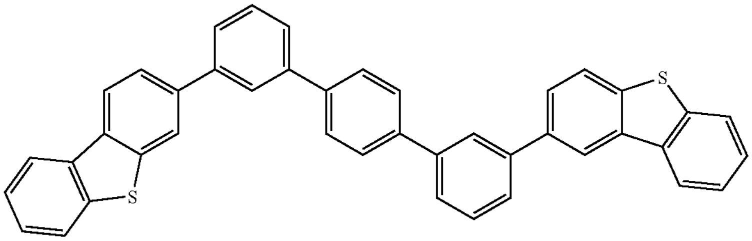

-continued
Compound (1-76)
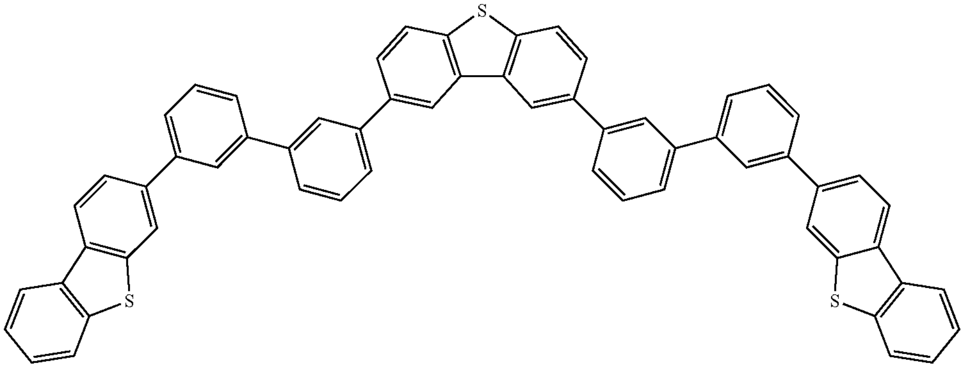
Compound (1-77)
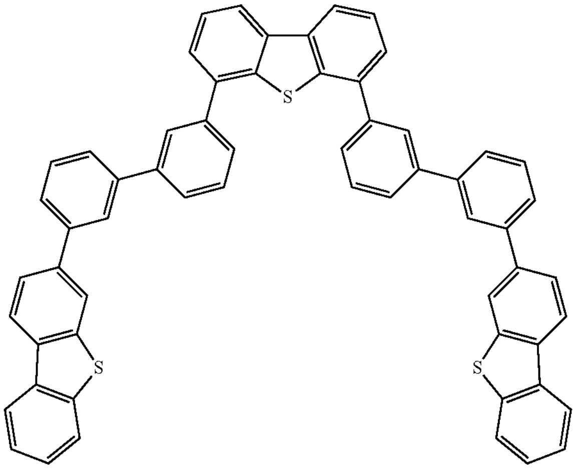
Compound (1-78)
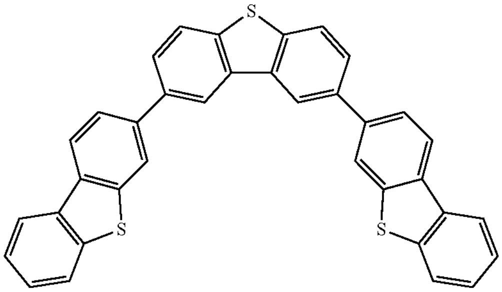
Compound (1-79)
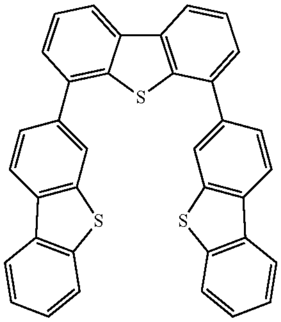
Compound (1-80)
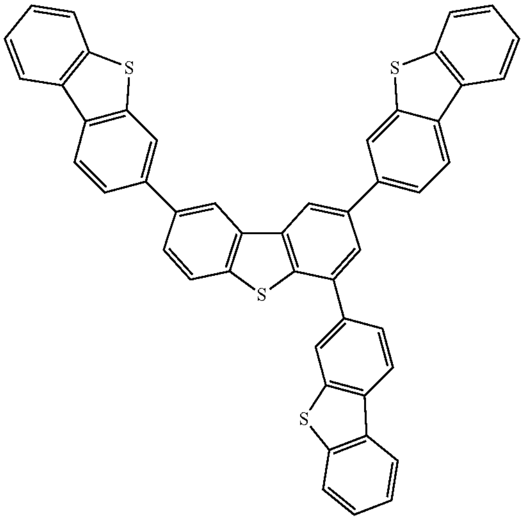

-continued
Compound (1-81)
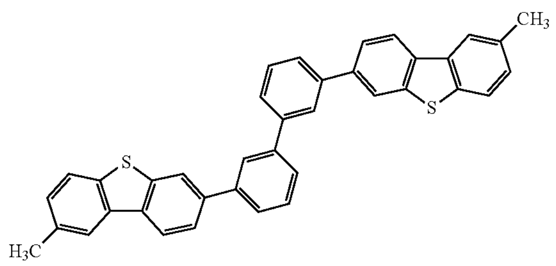
Compound (1-82)
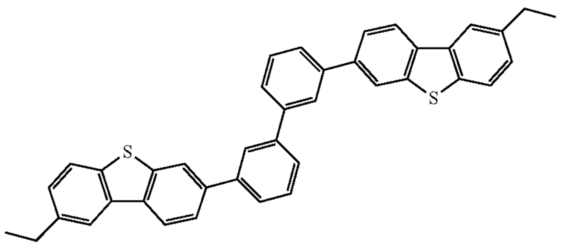
Compound (1-83)
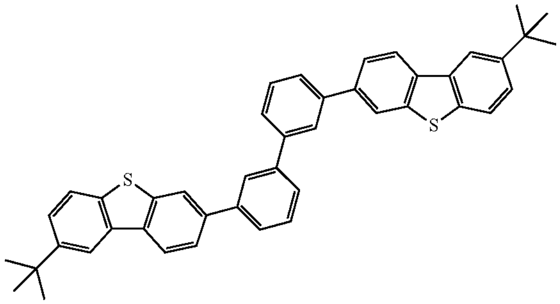
Compound (1-84)
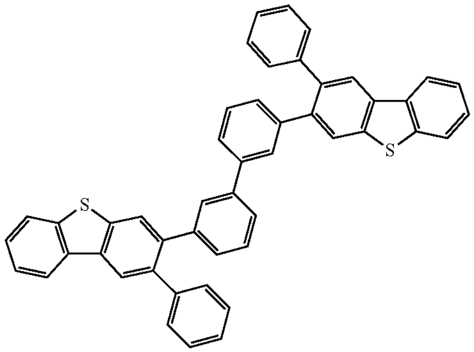
Compound (1-85)
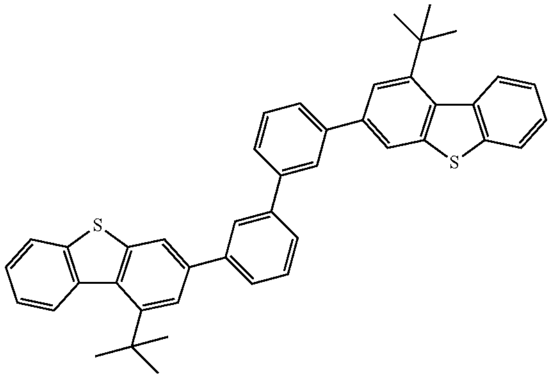
Compound (1-86)
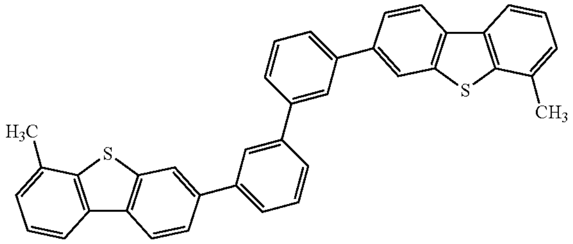
Compound (2-1)
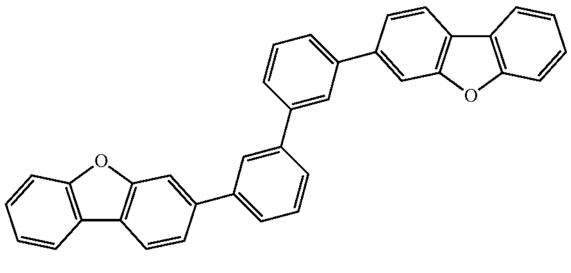
Compound (2-2)
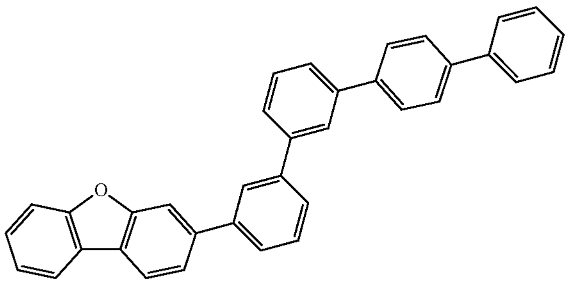
Compound (2-3)
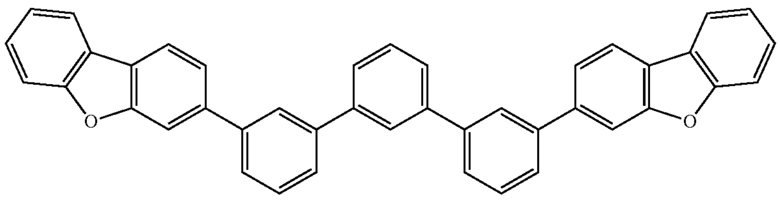

-continued
Compound (2-4)
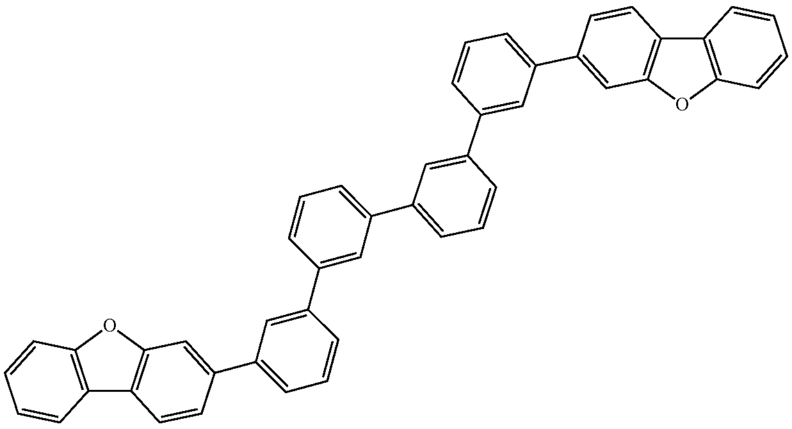
Compound (2-5)
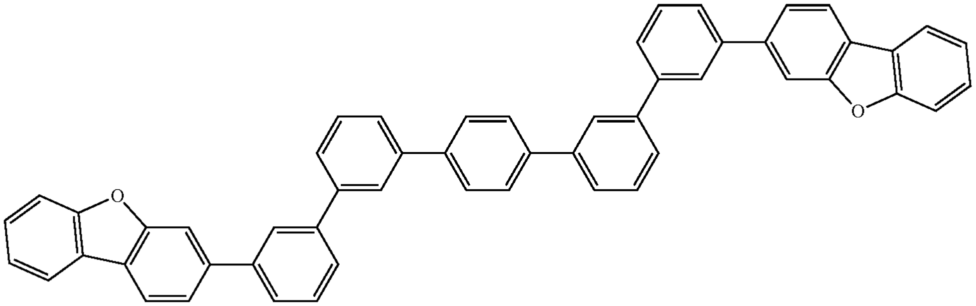
Compound (2-6)
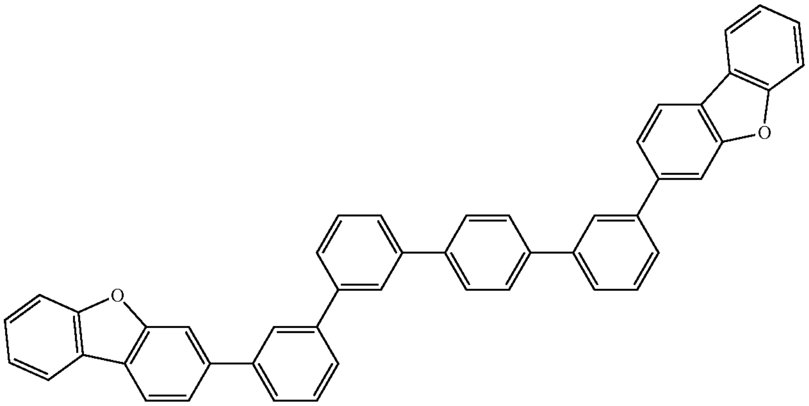
Compound (2-7)
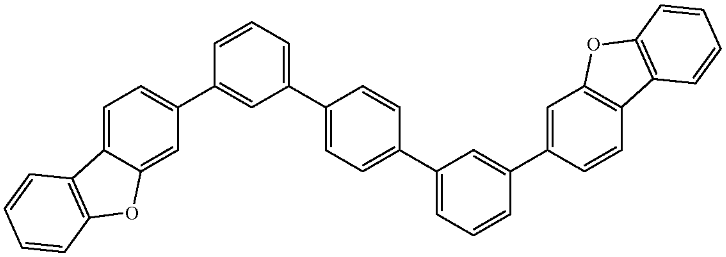

-continued
Compound (2-8)
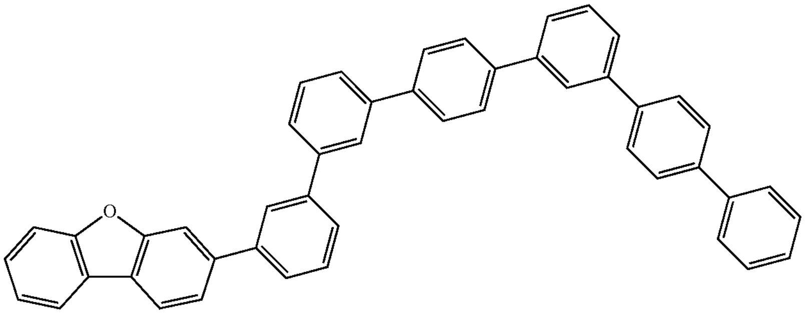
Compound (2-9)
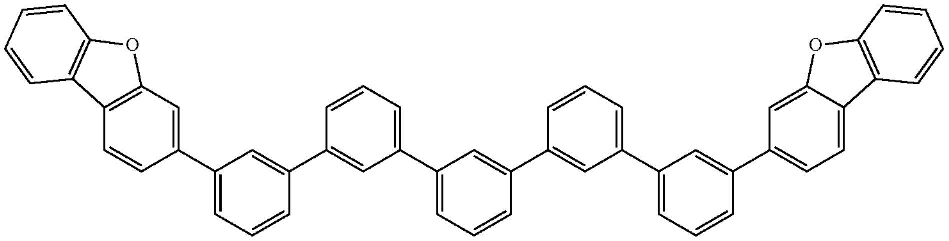
Compound (2-10)
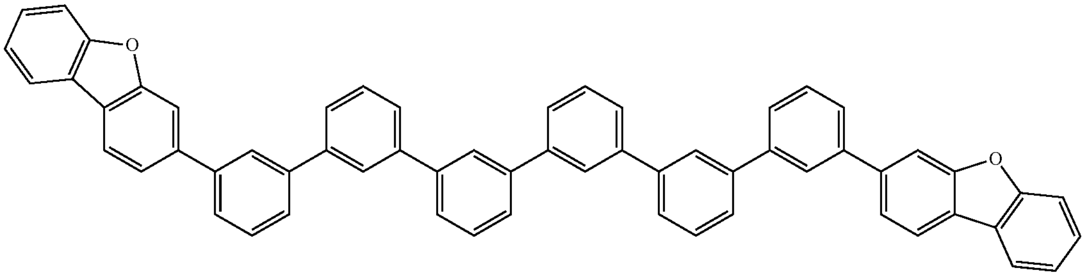
Compound (3-1)
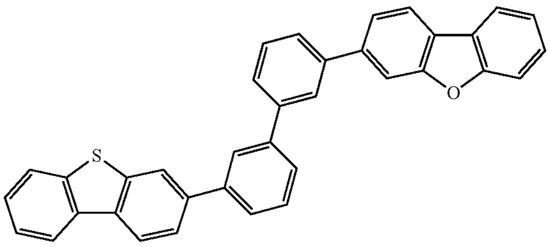
(Compound (3-2)
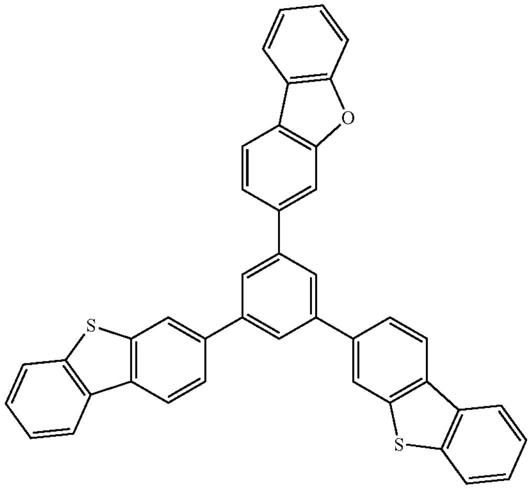
Compound (3-3)
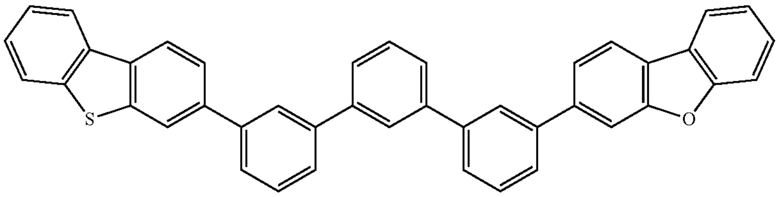

-continued
Compound (3-4)
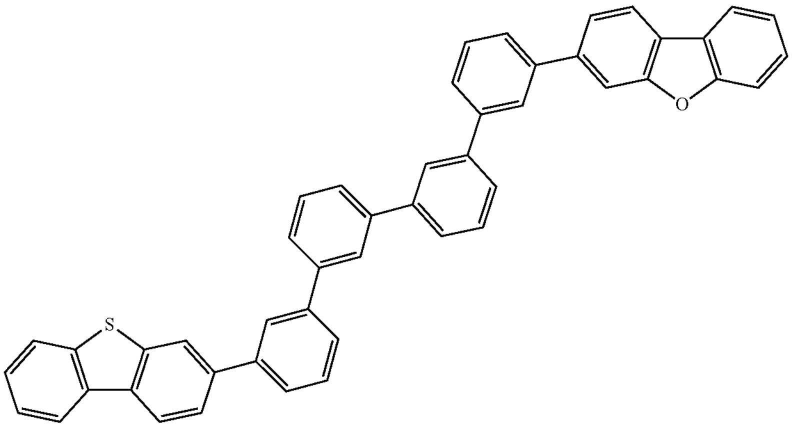
Compound (3-5)
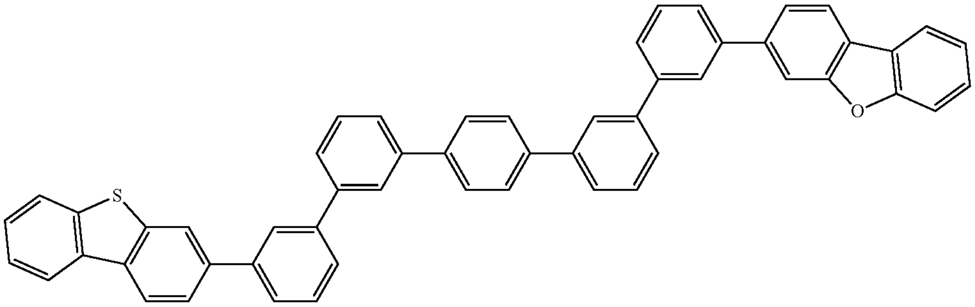
Compound (3-6)
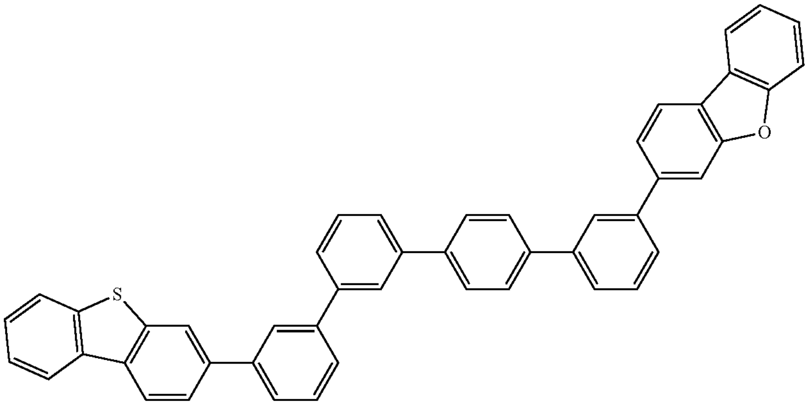
Compound (3-7)
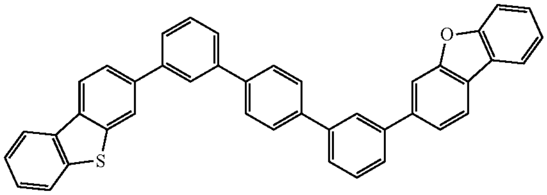
Compound (3-8)
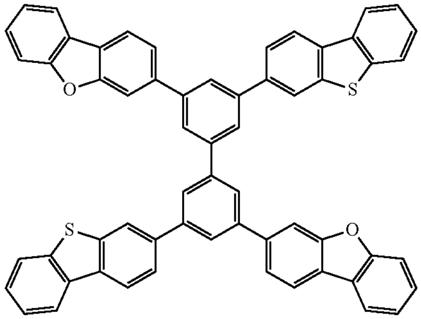

-continued
Compound (3-9)
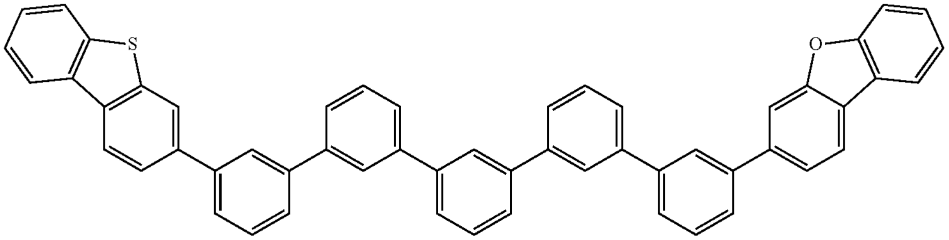
Compound (3-10)
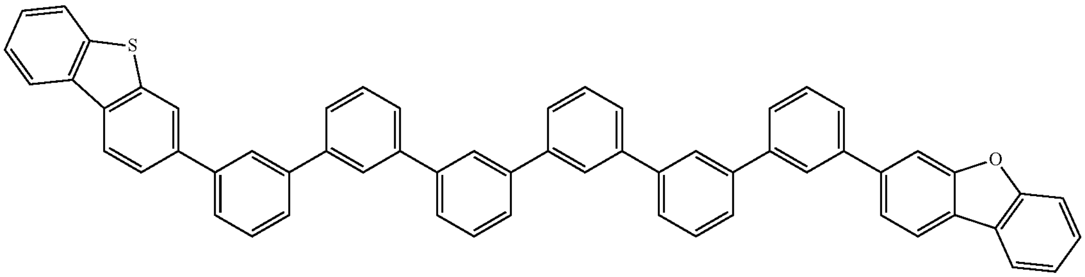
Compound (4-1)
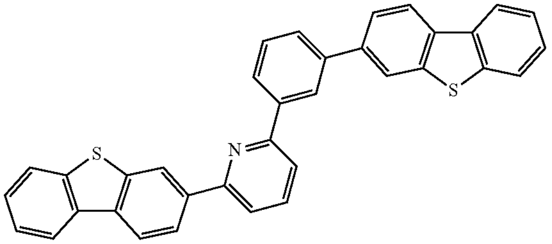
Compound (4-2)
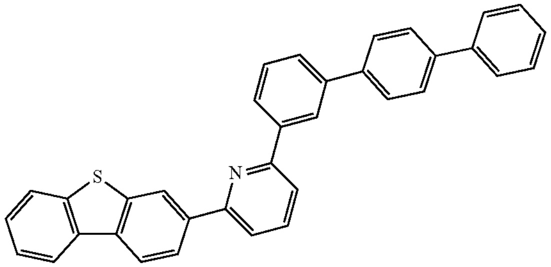
Compound (4-3)
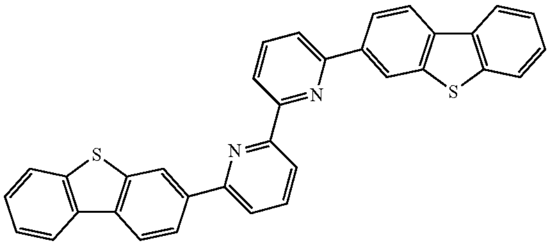
Compound (4-4)
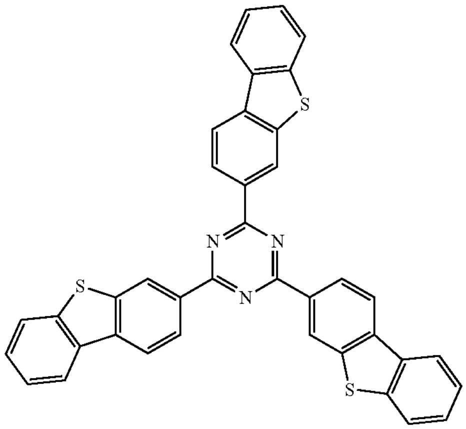

-continued
Compound (4-5)
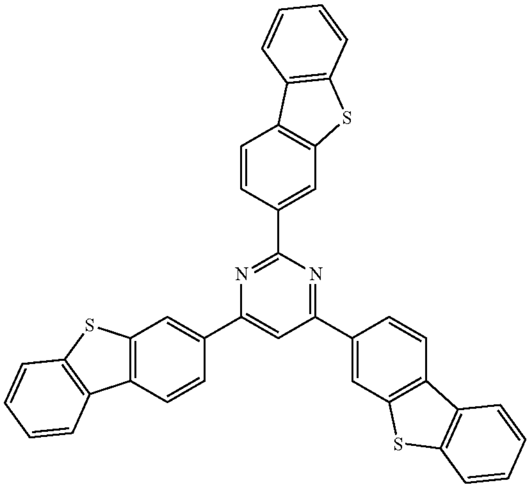
Compound (4-6)
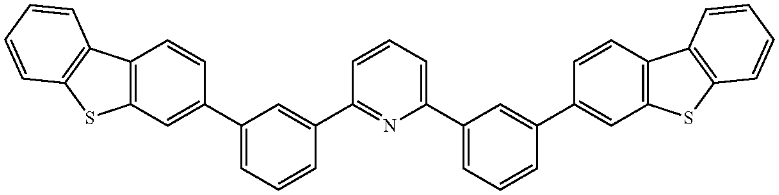
Compound (4-7)
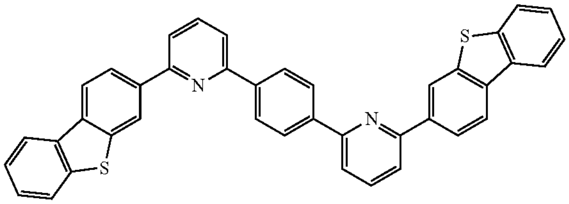
Compound (4-8)
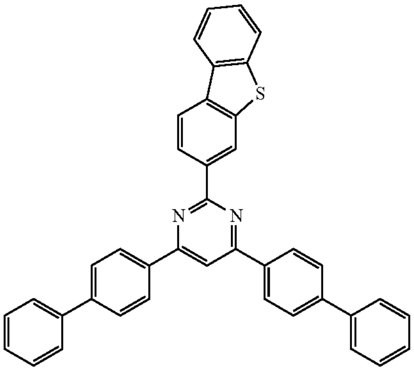
Compound (4-9)
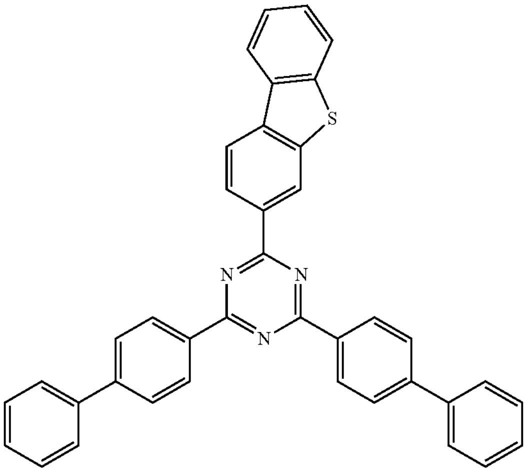

-continued
Compound (4-10)
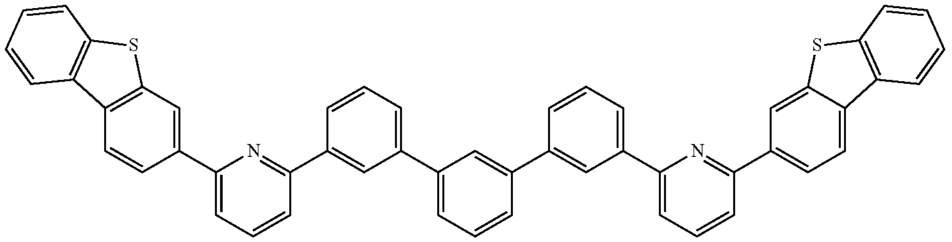
The compounds represented by the above formula (1) can be synthesized by the method to obtain the following intermediate (1) according to the method described, for example, in Tetrahedron, 58 (2002), pp. 1709 to 1718, or a similar method to obtain the following intermediate (2), as shown in the following scheme.
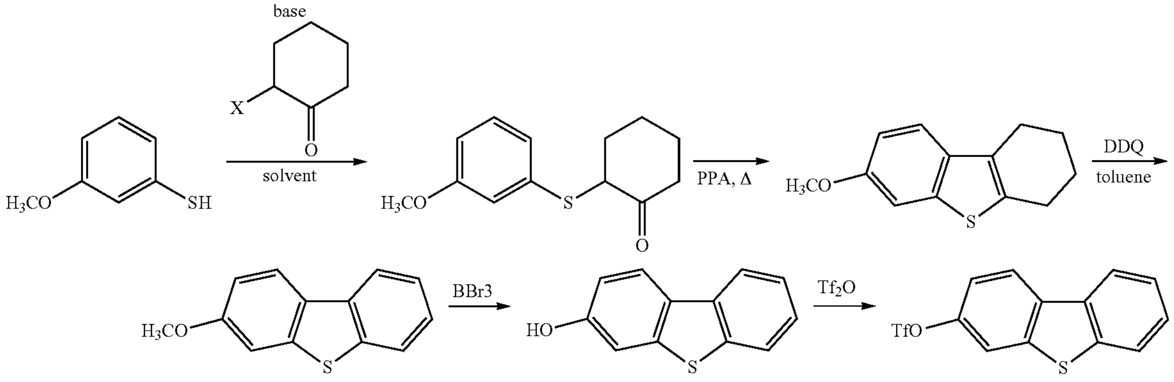
Intermediate (1)
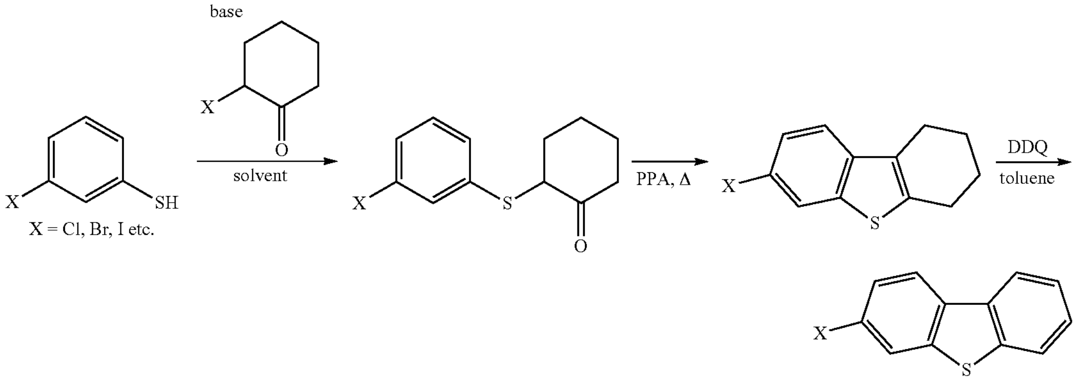
Intermediate (2)
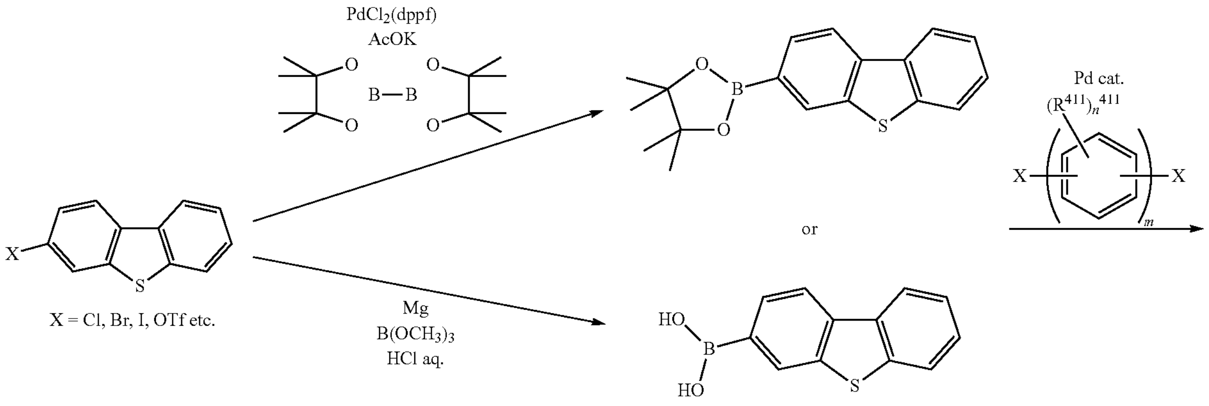

-continued

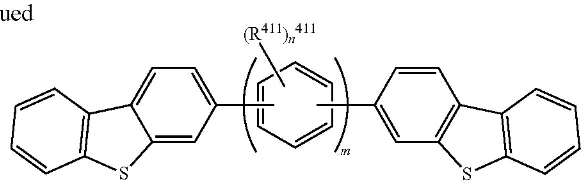

In the invention, the use of the compound represented by formula (1) is not restricted and the compound may be contained in any layer in the organic layers. The layers into which the compound represented by formula (1) is introduced are preferably any layer or two or more layers of a light-emitting layer, a layer between a light-emitting layer and the cathode, and a layer between a light-emitting layer and the anode, more preferably contained in any layer or two or more layers of a light-emitting layer, a hole-injecting layer, a hole-transporting layer, an electron-transporting layer, an electron-injecting layer, an exciton-blocking layer, and a charge-blocking layer, and still more preferably contained in any of a light-emitting layer, an electron-transporting layer and an electron-injecting layer.

In the invention, for still more restraining the reduction of light emitting efficiency after high temperature driving, it is preferred that the compound represented by formula (1) is contained in any of a light-emitting layer, an organic layer between a light-emitting layer and the cathode and contiguous to the light-emitting layer (the layer on the cathode side contiguous to the light-emitting layer), and an electron-injecting layer contiguous to the cathode on the light-emitting layer side, it is more preferred to be contained in any of a light-emitting layer and a layer on the cathode side contiguous to a light-emitting layer, and it is still more preferred to be contained in a light-emitting layer. Further, the compound represented by formula (1) may be contained in both layers of a light-emitting layer and a layer on the cathode side contiguous to a light-emitting layer.

When the compound represented by formula (1) is contained in a light-emitting layer, the content of the compound represented by formula (1) is preferably 0.1% by mass to 99% by mass to the gross mass of the light-emitting layer, more preferably 1% by mass to 97% by mass, and still more preferably 10% by mass to 96% by mass. When the compound represented by formula (1) is further contained in a layer other than the light-emitting layer, the content of the compound represented by formula (1) is preferably 70% by mass to 100% by mass to the gross mass of the layer other than the light-emitting layer, and more preferably 85% by mass to 100% by mass.

[Charge-Transporting Material Represented by Formula (1)]

The invention also relates to a charge-transporting material represented by formula (1).

[Use of Compound and Charge-Transporting Material Represented by Formula (1) of the Invention]

The compound and charge-transporting material represented by formula (1) of the invention can be preferably used in organic electronics elements, such as electrophotography, organic transistor, organic photoelectric conversion elements (use for energy conversion and use for sensor), and organic electroluminescence device, and it is especially preferred for use for organic electroluminescence device.

[Composition Containing the Compound Represented by Formula (1)]

The invention also relates to a composition containing the compound represented by formula (1) (a charge-transporting material). The content of the compound represented by formula (1) in the composition of the invention is preferably 30% by mass to 99% by mass to all the solids content in the composition, more preferably 50% by mass to 97% by mass, and still more preferably 70% by mass to 96% by mass. Other components which can be contained in the composition of the invention may be organic or inorganic, and the later-described host materials, fluorescent materials, phosphorescent materials, and materials exemplified as hydrocarbon materials are applicable, and preferred materials are host materials, phosphorescent materials and hydrocarbon materials.

The composition according to the invention can be formed into the organic layer of the organic electroluminescence device by a dry film-forming method such as a vacuum deposition method and a sputtering method, and a wet film-forming method such as a transfer method, and a printing method.

[Film Containing the Compound Represented by Formula (1)]

The invention also relates to a thin film containing the charge-transporting material represented by formula (1). The film (thin film) in the invention can be formed with the composition in the invention by a dry film-forming method such as a vacuum deposition method and a sputtering method, and a wet film-forming method such as such as a transfer method, and a printing method. The thickness of a thin film may be any thickness depending upon the purposes, but is preferably 0.1 nm to 1 mm, more preferably 0.5 nm to 1 μm, still more preferably 1 nm to 200 nm, and especially preferably 1 nm to 100 nm.

[Organic Electroluminescence Device]

The organic electroluminescence device according to the invention will be described in detail below.

The organic electroluminescence device in the invention is an organic electroluminescence device comprising a substrate having thereon a pair of electrodes of the anode and the cathode, and at least one organic layer including a light-emitting layer between the pair of electrodes, and the light-emitting layer contains at least one kind of phosphorescent material, and at least either one layer of the above at least one organic layer contains the compound represented by formula (1) of the invention.

From the nature of the luminescence device, it is preferred that at least one electrode of the pair of electrodes of the anode and cathode is transparent or translucent.

As the organic layers, a hole-injecting layer, a hole-transporting layer, a blocking layer (a hole-blocking layer, an exciton-blocking layer), and an electron transporting layer can be exemplified besides the light-emitting layer. Each of these organic layers may be comprised of a plurality of layers, and when a plurality of layers are provided, each layer may be formed of the same material or every layer may be formed of a different material.

An example of the constitution of the organic electroluminescence device according to the invention is shown in FIG. 1. Organic electroluminescence device 10 shown in FIG. 1 comprises substrate 2 having thereon organic layers including light-emitting layer 6 between a pair of electrode (anode 3 and cathode 9). As organic layers, hole-injecting layer 4, hole-transporting layer 5, light-emitting layer 6, hole-blocking layer 7, and electron-transporting layer 8 are laminated in this order from the side of anode 3.

<Constitution of Organic Layers>

The layer constitution of the organic layers is not especially restricted and the organic layers can be arbitrarily selected according to the use and purpose of the organic electroluminescence device, but the organic layers are preferably formed on the transparent electrode or the translucent electrode. In this case, the organic layers are formed on the front or on one side on the transparent electrode or the translucent electrode.

The shapes, sizes and thicknesses of organic layers are not especially restricted and these can be properly selected according to purposes.

As the specific layer constitutions, the following are exemplified but the invention is not restricted to these constitutions.

Anode/hole transporting layer/light emitting layer/electron transporting layer/cathode Anode/hole transporting layer/light emitting layer/blocking layer/electron transporting layer/cathode Anode/hole transporting layer/light emitting layer/blocking layer/electron transporting layer/electron injecting layer/cathode Anode/hole injecting layer/hole transporting layer/light emitting layer/blocking layer/electron transporting layer/cathode Anode/hole injecting layer/hole transporting layer/light emitting layer/electron transporting layer/electron injecting layer/cathode Anode/hole injecting layer/hole transporting layer/light emitting layer/blocking layer/electron transporting layer/electron injecting layer/cathode The constitutions of devices, substrates, cathodes and anodes of organic electroluminescence devices are described in detail in, e.g., JP-A-2008-270736, and the items described therein can be applied to the invention.

<Substrate>

The substrate for use in the invention is preferably a substrate that does not scatter or attenuate the light emitted from the organic layer. Organic materials are preferably excellent in heat resistance, dimensional stability, solvent resistance, an electric insulating property and a processing property <Anode>

The anode is generally sufficient to have the function as the electrode to supply holes to the organic layer. The shape, structure and size of the anode are not especially restricted, and materials can be properly selected from known materials of electrode in accordance with the intended use and purpose of the luminescence device. As described above, the anode is generally provided as a transparent anode.

<Cathode>

The cathode is generally sufficient to have the function as the electrode to inject electrons to the organic layer. The shape, structure and size of the cathode are not especially restricted, and materials can be properly selected from known materials of electrode in accordance with the intended use and purpose of the luminescence device.

<Organic Layers>

The organic layers in the invention are described below.

(Formation of Organic Layers)

In the organic electroluminescence device of the invention, each organic layer can be preferably formed by any of dry film-forming methods such as a vacuum deposition method, a sputtering method, and solution-coating methods such as a transfer method, a printing method, a spin coating method, a bar coating method, and the like.

(Light-Emitting Layer)

The light-emitting layer is a layer having functions to receive, at the time of electric field application, holes from the anode, hole-injecting layer or hole transporting layer, and receive electrons from the cathode, electron-injecting layer or electron-transporting layer, and offer the field of recombination of holes and electrons to emit light. The light-emitting layer in the organic electroluminescence device in the invention contains at least one kind of a phosphorescent material.

(Light-Emitting Material)

In the invention, in addition to the at least one kind of a phosphorescent material contained in the light-emitting layer, a fluorescent material and a phosphorescent material different from the phosphorescent material contained in the light-emitting layer can be used as the light-emitting material.

These fluorescent materials and phosphorescent materials are described in detail in JP-A-2008-270736, paragraphs [0100] to [0164], and JP-A-2007-266458, paragraphs [0088] to [0090], and the items described therein can be applied to the invention.

As the phosphorescent materials usable in the invention, phosphorescent compounds disclosed, for example, in U.S. Pat. No. 6,303,238B1, 6,097,147, WO 00/57676, WO 00/70655, WO 01/08230, WO 01/39234A2, WO 01/41512A1, WO 02/02714A2, WO 02/15645A1, WO 02/44189A1, WO 05/19373A2, JP-A-2001-247859, JP-A-2002-302671, JP-A-2002-117978, JP-A-2003-133074, JP-A-2002-235076, JP-A-2003-123982, JP-A-2002-170684, EP 1,211,257, JP-A-2002-226495, JP-A-2002-234894, JP-A-2001-247859, JP-A-2001-298470, JP-A-2002-173674, JP-A-2002-203678, JP-A-2002-203679, JP-A-2004-357791, JP-A-2006-256999, JP-A-2007-19462, JP-A-2007-84635, and JP-A-2007-96259 are exemplified. As further preferred light-emitting materials, phosphorescent metal complex compounds, such as an Ir complex, a Pt complex, a Cu complex, an Re complex, a W complex, an Rh complex, an Ru complex, a Pd complex, an Os complex, an Eu complex, a Tb complex, a Gd complex, a Dy complex, and a Ce complex are exemplified. As especially preferred light-emitting materials, an Ir complex, a Pt complex and an Re complex are exemplified. An Ir complex, a Pt complex and an Re complex including at least one coordination system of a metal-carbon bond, a metal-nitrogen bond, a metal-oxygen bond, and a metal-sulfur bond are preferred above all. Further, from the aspects of light emitting efficiency, driving durability and chromaticity, an Ir complex and a Pt complex are especially preferred, and an Ir complex is most preferred.

It is preferred that these phosphorescent metal complex compounds are contained in the light-emitting layer together with the compound represented by any of the above formulae (1) to (3).

As the phosphorescent material contained in the light-emitting layer, an iridium complex represented by the following formula (T-1), or a platinum complex represented by formula (C-1) which is described later is preferably used.

[Compound Represented by Formula (T-1)]

A compound represented by formula (T-1) is described below.

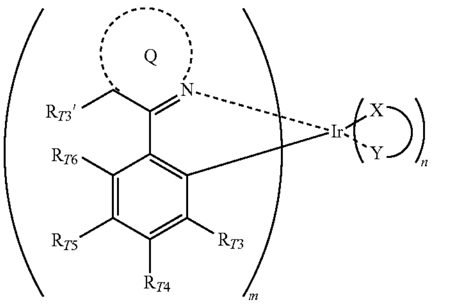

(T-1)

In formula (T-1), each of $R_{T3}'$, $R_{T3}$, $R_{T4}$, $R_{T5}$ and $R_{T6}$ independently represents a hydrogen atom or a substituent.

Contiguous arbitrary two of $R_{T3}$, $R_{T4}$, $R_{T5}$ and $R_{T6}$ may be bonded to each other to form a condensed 4- to 7-membered ring, and the condensed 4- to 7-membered ring is cycloalkyl, aryl or heteroaryl, and the condensed 4- to 7-membered ring may further have a substituent.

$R_{T3}'$ and $R_{T6}$ may be linked to form a ring by a linking group selected from —$C(R_T)_2$—$C(R_T)_2$", —$CR_T$=$CR_T$—, —$C(R_T)_2$—, —O—, —$NR_T$—, —O—$C(R_T)_2$—, —$NR_T$—$C(R_T)_2$— and —N=$CR_T$—, and each of $R_T$ independently represents a hydrogen atom, an alkyl group, an alkenyl group, an alkynyl group, an aryl group, or a heteroaryl group, and these groups may further have a substituent.

Ring Q represents a 5- or 6-membered aromatic heterocyclic ring comprising a nitrogen atom or a condensed aromatic heterocyclic ring comprising a nitrogen atom;

(X—Y) represents an auxiliary ligand, m represents an integer of 1 to 3, n represents an integer of 0 to 2, and m+n=3.

As each substituent represented by $R_{T3}'$, $R_{T3}$, $R_{T4}$, $R_{T5}$ and $R_{T6}$, the groups belonging to substituent group A can be exemplified, and preferably an alkyl group, an alkenyl group, an alkynyl group, —CN, a perfluoroalkyl group, a trifluorovinyl group, —$CO_2R_T$, —C(O)$R_T$, —$N(R_T)_2$, —$NO_2$, —$OR_T$, a fluorine atom, an aryl group or a heteroaryl group are exemplified, and may further have the following substituent T.

Substituent T represents a fluorine atom, —R', —OR', —$N(R')_2$, —SR', —C(O)R', —C(O)OR', —C(O)$N(R')_2$, —CN, —$NO_2$, —$SO_2$, —SOR', —$SO_2R'$, or —$SO_3R'$, and each of R' independently represents a hydrogen atom, an alkyl group, a perfluoroalkyl group, an alkenyl group, an alkynyl group, a heteroalkyl group, an aryl group or a heteroaryl group. As substituent T, an alkyl group, an alkoxy group, a fluorine atom, a cyano group and a dialkylamino group are preferred.

The alkyl group represented by $R_{T3}'$, $R_{T3}$, $R_{T4}$, $R_{T5}$ and $R_{T6}$ may have a substituent and may be saturated or unsaturated. As the groups which may be substituted, substituent T can be exemplified. The alkyl group represented by $R_{T3}'$, $R_{T3}$, $R_{T4}$, $R_{T5}$ and $R_{T6}$ is preferably an alkyl group having a total carbon atom number of 1 to 8, and more preferably an alkyl group having a total carbon atom number of 1 to 6, and, for example, a methyl group, an ethyl group, an i-propyl group and a t-butyl group are exemplified.

The cycloalkyl group represented by $R_{T3}'$, $R_{T3}$, $R_{T4}$, $R_{T5}$ and $R_{T6}$ may have a substituent and may be saturated or unsaturated. As the groups which may be substituted, substituent T can be exemplified. The cycloalkyl group represented by $R_{T3}'$, $R_{T3}$, $R_{T4}$, $R_{T5}$ and $R_{T6}$ is preferably a cycloalkyl group having a total carbon atom number of 4 to 7, and more preferably a cycloalkyl group having a total carbon atom number of 5 or 6, and, for example, a cyclopentyl group and a cyclohexyl group are exemplified.

The alkenyl group represented by $R_{T3}'$, $R_{T3}$, $R_{T4}$, $R_{T5}$ and $R_{T6}$ is preferably an alkenyl group having 2 to 30 carbon atoms, more preferably having 2 to 20 carbon atoms, and especially preferably having 2 to 10 carbon atoms, and, for example, vinyl, allyl, 1-propenyl, 1-isopropenyl, 1-butenyl, 2-butenyl and 3-pentenyl are exemplified.

The alkynyl group represented by $R_{T3}'$, $R_{T3}$, $R_{T4}$, $R_{T5}$ and $R_{T6}$ is preferably an alkynyl group having 2 to 30 carbon atoms, more preferably 2 to 20 carbon atoms, and especially preferably 2 to 10 carbon atoms, and, for example, an ethynyl group, a propargyl group, a 1-propynyl group and a 3-pentynyl group are exemplified.

The aryl group represented by $R_{T3}'$, $R_{T3}$, $R_{T4}$, $R_{T5}$ and $R_{T6}$ is preferably a substituted or unsubstituted aryl group having 6 to 30 carbon atoms, and, for example, a phenyl group, a tolyl group and a naphthyl group are exemplified.

The heteroaryl group represented by $R_{T3}'$, $R_{T3}$, $R_{T4}$, $R_{T5}$ and $R_{T6}$ is preferably a heteroaryl group having 5 to 8 carbon atoms, and more preferably a substituted or unsubstituted 5- or 6-membered heteroaryl group, and, for example, a pyridyl group, a pyrazinyl group, a pyridazinyl group, a pyrimidinyl group, a triazinyl group, a quinolinyl group, an isoquinolinyl group, a quinazolinyl group, a cinnolinyl group, a phthalazinyl group, a quinoxalinyl group, a pyrrolyl group, an indolyl group, a furyl group, a benzofuryl group, a thienyl group, a benzothienyl group, a pyrazolyl group, an imidazolyl group, a benzimidazolyl group, a triazolyl group, an oxazolyl group, a benzoxazolyl group, a thiazolyl group, a benzothiazolyl group, an isothiazolyl group, a benzisothiazolyl group, a thiadiazolyl group, an isoxazolyl group, a benzisoxazolyl group, a pyrrolidinyl group, a piperidinyl group, a piperazinyl group, an imidazolidinyl group, a thiazolinyl group, a sulforanyl group, a carbazolyl group, a dibenzofuryl group, a dibenzothienyl group, and a pyridoindolyl group are exemplified. The preferred examples include a pyridyl group, a pyrimidinyl group, an imidazolyl group, and a thienyl group, and more preferred examples are a pyridyl group and a pyrimidinyl group.

Each of $R_{T3}'$, $R_{T3}$, $R_{T4}$, $R_{T5}$ and $R_{T6}$ preferably represents a hydrogen atom, an alkyl group, a cyano group, a trifluoromethyl group, a perfluoroalkyl group, a dialkylamino group, a fluorine atom, an aryl group or a heteroaryl group, more preferably represents a hydrogen atom, an alkyl group, a cyano group, a trifluoromethyl group, a fluorine atom, or an aryl group, and still more preferably represents a hydrogen atom, an alkyl group or an aryl group.

Contiguous arbitrary two of $R_{T3}$, $R_{T4}$, $R_{T5}$ and $R_{T6}$ may be bonded to each other to form a condensed 4- to 7-membered ring. It is preferred that $R_{T3}$ and $R_{T4}$ are bonded to each other to form a condensed 4- to 7-membered ring. The condensed 4- to 7-membered ring is cycloalkyl, aryl or heteroaryl, and the condensed 4- to 7-membered ring may further have a substituent, preferably may have substituent T. The definitions and preferred ranges of the cycloalkyl, aryl and heteroaryl to be formed are the same as those defined as to the cycloalkyl group, aryl group and heteroaryl group in $R_{T3}'$, $R_{T3}$, $R_{T4}$, $R_{T5}$ and $R_{T6}$.

As the aromatic heterocyclic rings represented by Q, a pyridine ring, a pyrazine ring, a pyrimidine ring, a pyrazole ring, an imidazole ring, a triazole ring, an oxazole ring, an oxadiazole ring, a thiazole ring, and a thiadiazole ring are exemplified, preferably a pyridine ring and a pyrazine ring, and more preferably a pyridine ring.

As the condensed aromatic heterocyclic rings represented by Q, a quinoline ring, an isoquinoline ring, and a quinoxaline ring are exemplified, preferably a quinoline ring and an isoquinoline ring, and more preferably a quinoline ring.

m is preferably 1 to 3, and more preferably 2 or 3. That is, n is preferably 0 or 1. The kind of the ligand in the complex is preferably composed of one kind or two kinds, and more preferably composed of one kind. That the ligand is composed of two kinds is also preferred from the viewpoint of easiness of synthesis in introducing a reactive group into the complex molecule.

The metal complex represented by formula (T-1) may be composed by including a combination of a ligand represented by the following formula (T-1-A) in formula (T-1) or the tautomer thereof, and a ligand represented by (X—Y) or the tautomer thereof, alternatively all the ligands of the metal complex are composed of a ligand represented by the following formula (T-1-A) or the tautomer thereof alone.

(T-1-A)

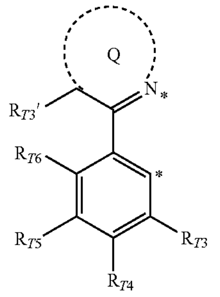

In formula (T-1-A), $R_{T3}'$, $R_{T3}$, $R_{T4}$, $R_{T5}$, $R_{T6}$ and Q have the same meaning with $R_{T3}'$, $R_{T3}$, $R_{T4}$, $R_{T5}$, $R_{T6}$ and Q in formula (T-1) respectively, and * represents the position of coordination to iridium.

If necessary, ligands conventionally well known in the industry as what are called ligands for use in forming metal complexes (also referred to as ligand compounds) may be used as the ligand represented by (X—Y).

As conventionally known ligands for use in metal complexes, various kinds of ligands are known. For example, the ligands as described in H. Yersin, Photochemistry and Photophysics of Coordination Compounds, published by Springer Verlag (1987), Akio Yamamoto, Yuki Kinzoku Kagaku—Kiso to Ouyou—(Organometallic Chemistry—Fundamentals and Applications—), Shokabo Publishing Co., Ltd. (1982) (e.g., halogen ligands (preferably chlorine ligands), nitrogen-containing heteroaryl ligands (e.g., bipyridyl, phenanthroline and the like), diketone ligands (e.g., acetylacetone and the like)) are exemplified. As the ligands represented by (X—Y), diketones or picolinic acid derivatives are preferred. In the light of the stability of complex and capability of high light-emitting efficiency, the following acetylacetonate (acac) is most preferred.

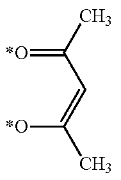

acac

In the above, * represents the position of coordination to iridium.

The specific examples of the ligands represented by (X—Y) are shown below, but the invention is not limited thereto.

(I-1)

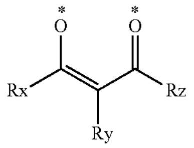

(I-2)

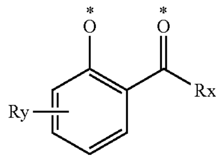

(I-3)

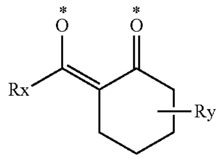

(I-4)

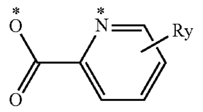

(I-5)

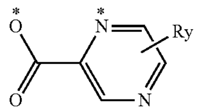

(I-6)

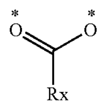

(I-7)

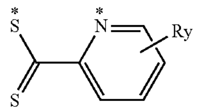

(I-8)

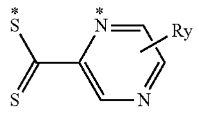

-continued (I-9)

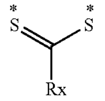

(I-10)

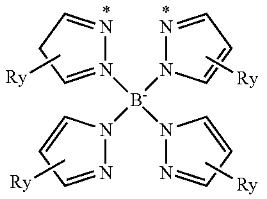

(I-11)

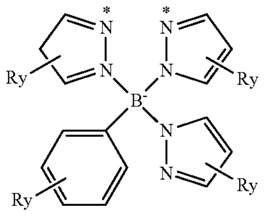

(I-12)

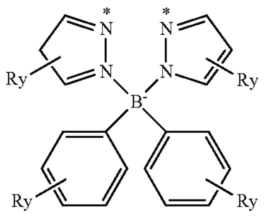

(I-13)

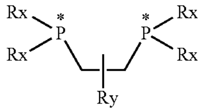

(I-14)

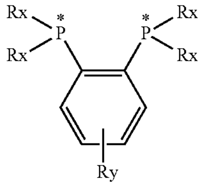

In the examples of the ligands represented by (X—Y), * represents the position of coordination to iridium in formula (T-1). Each of Rx, Ry and Rz independently represents a hydrogen atom or a substituent. As the substituents, substituents selected from the above substituent group A are exemplified. Preferably each of Rx and Rz independently represents any of an alkyl group, a perfluoroalkyl group, a fluorine atom, and an aryl group, more preferably an alkyl group having 1 to 4 carbon atoms, a perfluoroalkyl group having 1 to 4 carbon atoms, a fluorine atom, or a phenyl group which may be substituted, and most preferably a methyl group, an ethyl group, a trifluoromethyl group, a fluorine atom, or a phenyl group. Ry preferably represents any of a hydrogen atom, an alkyl group, a perfluoroalkyl group, a fluorine atom, and an aryl group, more preferably a hydrogen atom, an alkyl group having 1 to 4 carbon atoms, or a phenyl group which may be substituted, and most preferably either a hydrogen atom or a methyl group. Since these ligands are considered not to be the site to transport electric charge in a device or the site where electrons are converged by excitation, it is enough for Rx, Ry and Rz to be chemically stable substituents, and so the invention is not affected.

In the above specific examples of ligands, formulae (1-1), (1-4) and (1-5) are preferred for easiness of synthesis of complexes, and (1-1) is most preferred. The complexes having these ligands can be synthesized similarly to known synthesis examples by using the corresponding ligand precursors. For example, a complex can be synthesized according to the method shown below similarly to the method disclosed in WO 2009/073245, p. 46, by using commercially available difluoroacetylacetone.

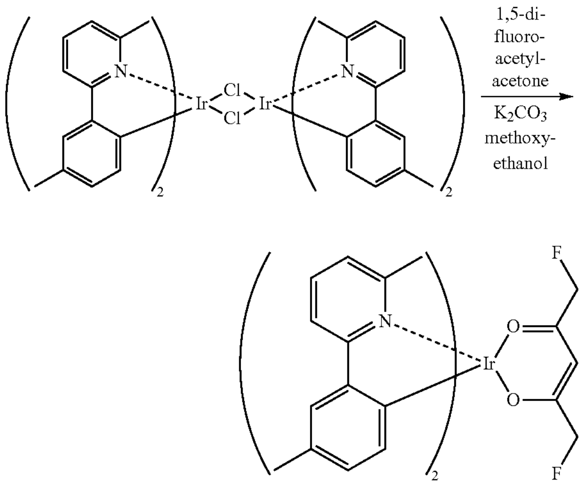

The monoanionic ligand shown in the following formula (I-15) can also be used as a ligand.

(I-15)

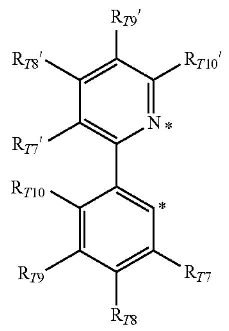

$R_{T7}$ to $R_{T10}$ in formula (I-15) have the same meaning with $R_{T3}$ to $R_{T6}$ in formula (T-1), and preferred range is also the same. $R_{T7}'$ to $R_{T10}'$ have the same meaning with $R_{T3}'$, and preferred range is also the same with the preferred range of $R_{T3}'$. * represents the position of coordination to iridium.

The compound represented by formula (T-1) is preferably a compound represented by the following formula (T-2).

(T-2)

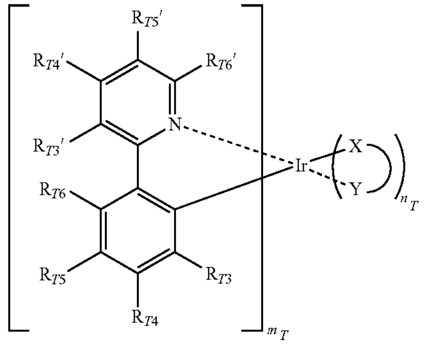

In formula (T-2), each of $R_{T3}$' to $R_{T6}$' and $R_{T3}$ to $R_{T6}$ independently represents a hydrogen atom, an alkyl group, an alkenyl group, an alkynyl group, —CN, a perfluoroalkyl group, a trifluorovinyl group, —$CO_2R_T$, —C(O)$R_T$, —$N(R_T)_2$, —$NO_2$, —ORT, a fluorine atom, an aryl group, or a heteroaryl group, and they may further have substituent T.

Contiguous arbitrary two of $R_{T3}$, $R_{T4}$, $R_{T5}$ and $R_{T6}$ may be bonded to each other to form a condensed 4- to 7-membered ring, and the condensed 4- to 7-membered ring may further have substituent T.

$R_{T3}$' and $R_{T6}$ may be linked to form a ring by a linking group selected from —$C(R_T)_2$—$C(R_T)_2$—, —$CR_T$═$CR_T$—, —$C(R_T)_2$—, —O—, —$NR_T$—, —O—$C(R_T)_2$—, —$NR_T$—$C(R_T)_2$— and —N═$CR_T$—.

Each of $R_T$ independently represents a hydrogen atom, an alkyl group, an alkenyl group, an alkynyl group, a heteroalkyl group, an aryl group, or a heteroaryl group, and these groups may further have substituent T.

Each of substituent T independently represents a fluorine atom, —R', —OR', —N(R')$_2$, —SR', —C(O)R', —C(O)OR', —C(O)N(R')$_2$, —CN, —$NO_2$, —$SO_2$, —SOR', —$SO_2$R', or —$SO_3$R', and each of R' independently represents a hydrogen atom, an alkyl group, a perfluoroalkyl group, an alkenyl group, an alkynyl group, a heteroalkyl group, an aryl group or a heteroaryl group.

(X—Y) represents a ligand. $m_T$ represents an integer of 1 to 3, $n_T$ represents an integer of 0 to 2, and $m_T+n_T=3$.

Each preferred range of $R_{T3}$', $R_{T3}$ to $R_{T6}$, (X—Y), $m_T$ and $n_T$ in formula (T-2) is the same with the preferred range of each of $R_{T3}$', $R_{T3}$ to $R_{T6}$, (X—Y), m and n in formula (T-1).

$R_{T4}$' preferably represents a hydrogen atom, an alkyl group, an aryl group or a fluorine atom, and more preferably represents a hydrogen atom.

It is preferred that each of $R_{T5}$' and $R_{T6}$' represents a hydrogen atom, or $R_{T5}$' and $R_{T6}$' are bonded to each other to form a condensed 4- to 7-membered cyclic group. The condensed 4- to 7-membered cyclic group is more preferably cycloalkyl, cycloheteroalkyl, aryl or heteroaryl, and still more preferably aryl.

As substituent T in $R_{T4}$' to $R_{T6}$', an alkyl group, an alkoxy group, a fluorine atom, a cyano group, an alkylamino group, and a diarylamino group are preferred, and an alkyl group is more preferred.

One preferred embodiment of the compound represented by formula (T-2) is a case where contiguous arbitrary two of $R_{T3}$', $R_{T4}$', $R_{T5}$', $R_{T6}$', $R_{T3}$, $R_{T4}$, $R_{T5}$ and $R_{T6}$ are not bonded to form a condensed ring.

One preferred embodiment of the compound represented by formula (T-2) is a compound represented by the following formula (T-3).

(T-3)

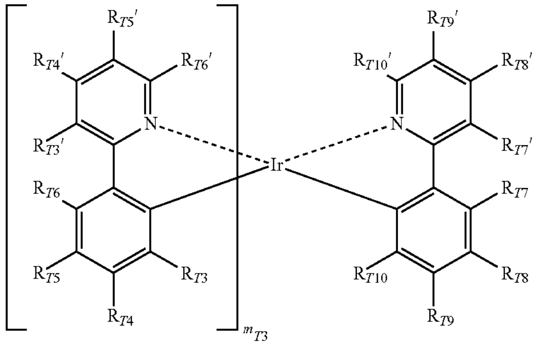

$R_{T3}$' to $R_{T6}$' and $R_{T3}$ to $R_{T6}$ in formula (T-3) have the same meaning with $R_{T3}$' to $R_{T6}$' and $R_{T3}$ to $R_{T6}$ in formula (T-2) respectively, and preferred range is also the same.

$m_{T3}$ represents 2.

$R_{T7}$ to $R_{T10}$ have the same meaning with $R_{T3}$ to $R_{T6}$ and preferred range is also the same. $R_{T7}$' to $R_{T10}$' have the same meaning with $R_{T3}$' to $R_{T6}$' and preferred range is also the same.

Another preferred embodiment of the compound represented by formula (T-2) is a compound represented by the following formula (T-4).

(T-4)

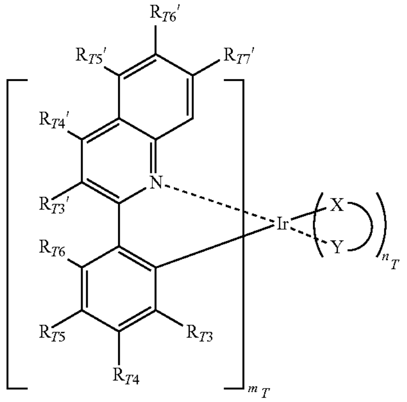

$R_{T3}$' to $R_{T7}$', $R_{T3}$ to $R_{T6}$, (X—Y), $m_T$ and $n_T$ in formula (T-4) have the same meaning with $R_{T3}$' to $R_{T6}$', $R_{T3}$ to $R_{T6}$, (X—Y), $m_T$ and $n_T$ in formula (T-2), and preferred range is also the same. The case in which from zero to two of $R_{T3}$' to $R_{T7}$' and $R_{T3}$ to $R_{T6}$ represent an alkyl group or a phenyl group and the remainder represent a hydrogen atom is especially preferred. The case in which one or two of $R_{T3}$' to $R_{T6}$' and $R_{T3}$ to $R_{T6}$ represent an alkyl group and all of the remainder represent a hydrogen atom is still more preferred.

Another preferred embodiment of the compound represented by formula (T-2) is a compound represented by the following formula (T-5).

(T-5)

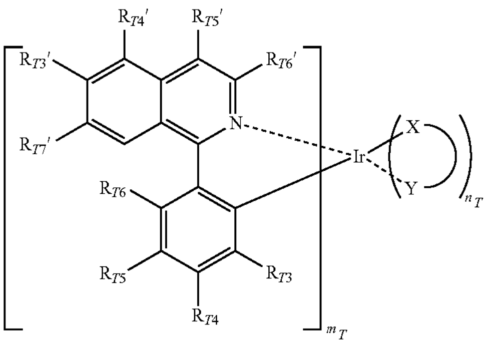

$R_{T3}$' to $R_{T7}$', $R_{T3}$ to $R_{T6}$, (X—Y), $m_T$ and $n_T$ in formula (T-5) have the same meaning with $R_{T3}$' to $R_{T6}$', $R_{T3}$ to $R_{T6}$, (X—Y), $m_T$ and $n_T$ in formula (T-2) respectively, and preferred range is also the same.

Another preferred embodiment of the compound represented by formula (T-1) is a compound represented by the following formula (T-6).

(T-6)

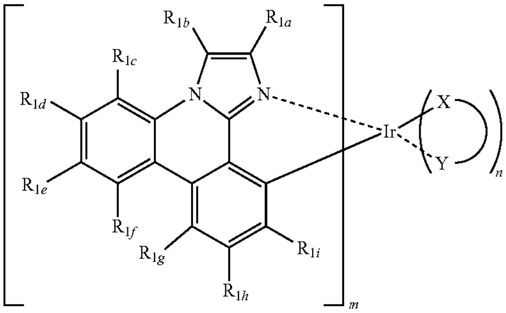

In formula (T-6), the definition and preferred range of $R_{1a}$ to $R_{1i}$ are the same with those of $R_{T3}$ to $R_{T6}$ in formula (T-1). The case where from zero to two of $R_{1a}$ to $R_{1i}$ represent an alkyl group or an aryl group and all of the remainder represent a hydrogen atom is especially preferred. The definition and preferred range of (X—Y), m and n are the same with (X—Y), m and n in formula (T-1).

The preferred specific examples of the compounds represented by formula (T-1) are shown below, but the invention is not restricted thereto.

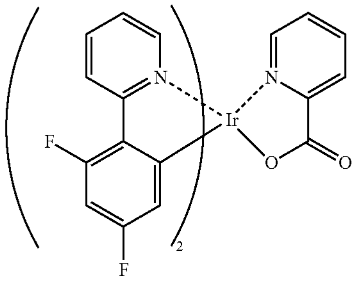

-continued

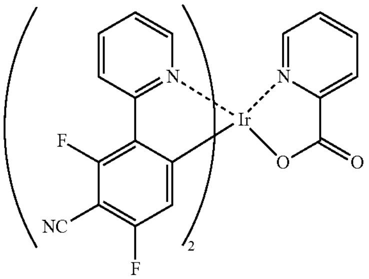

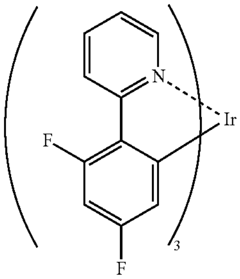

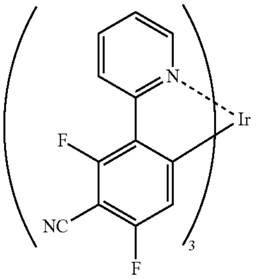

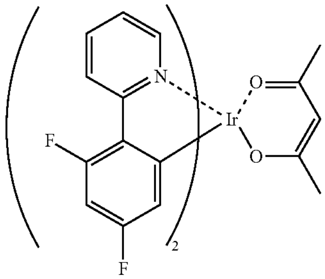

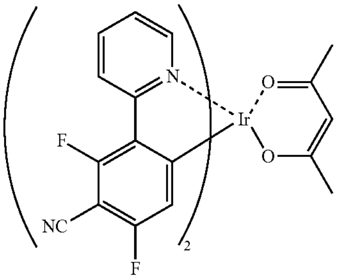

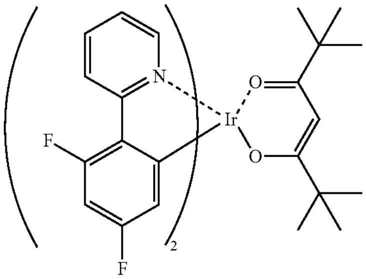

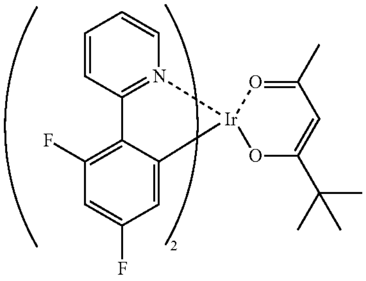

-continued
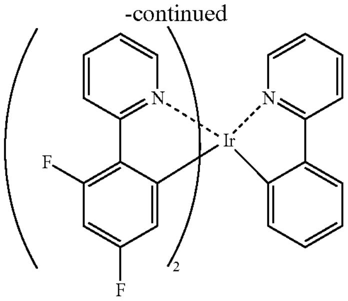
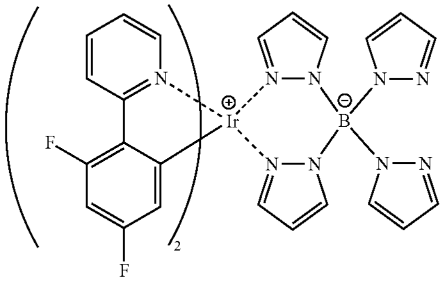
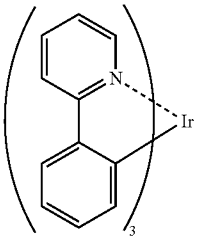
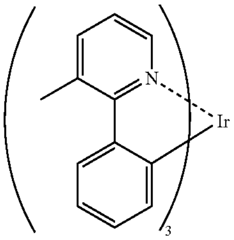
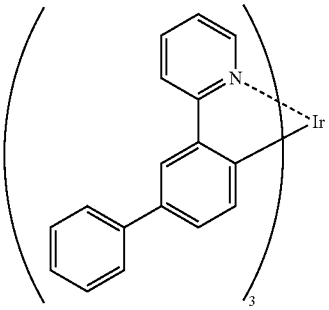
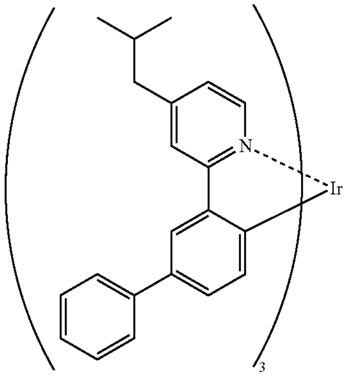
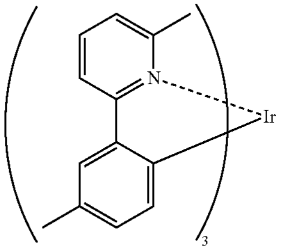
-continued
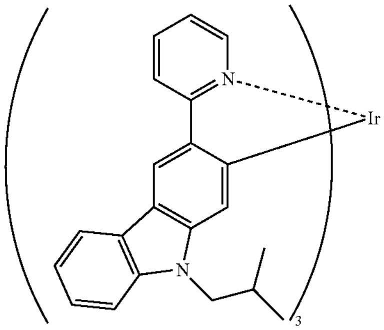
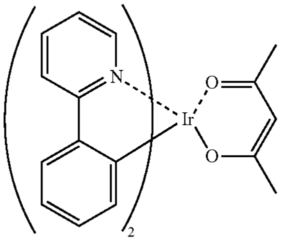
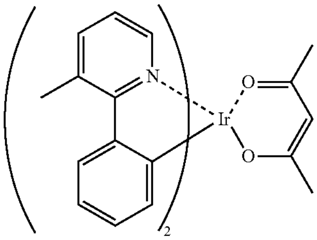
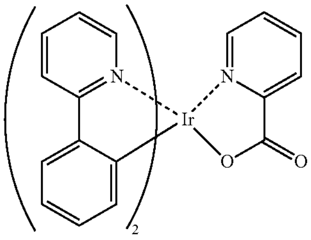
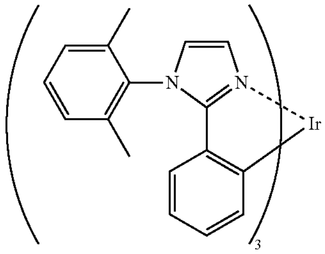
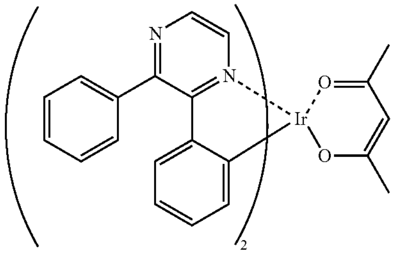

-continued
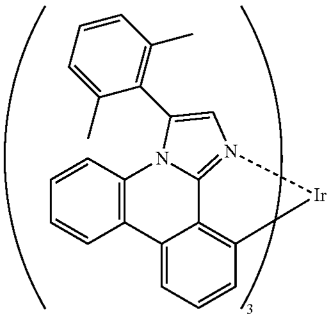
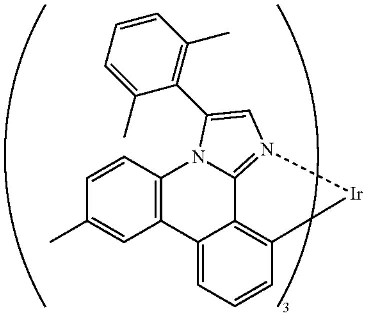
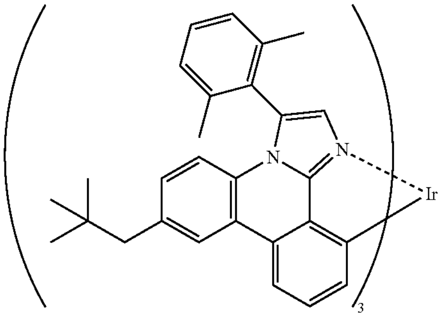
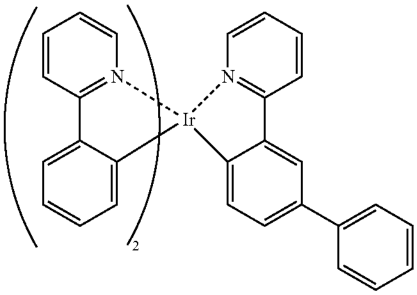
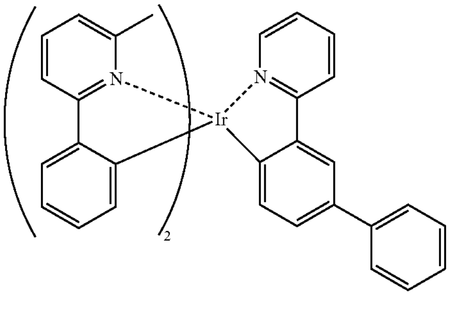
-continued
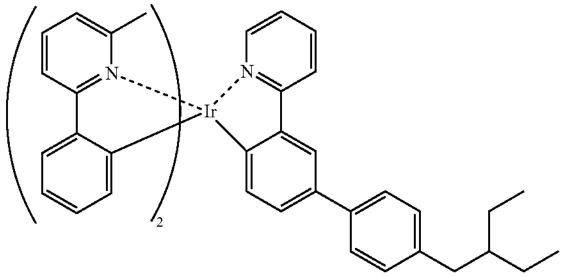
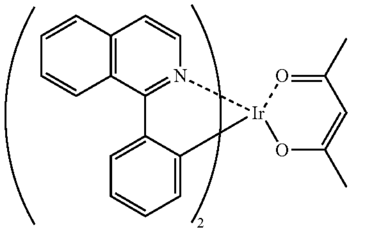
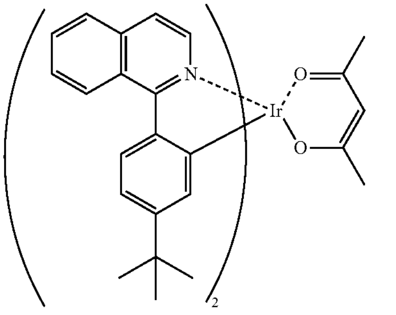
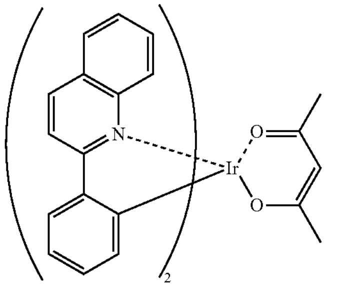
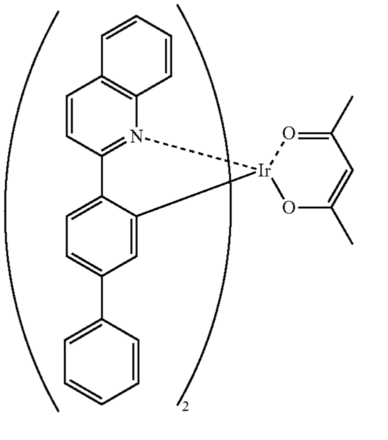

-continued

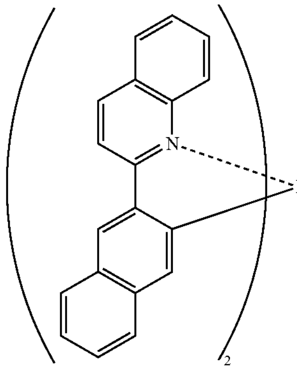

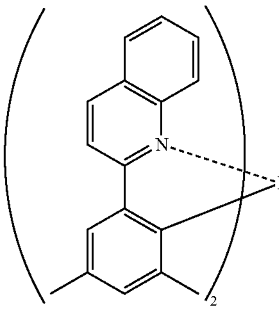

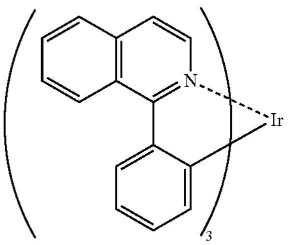

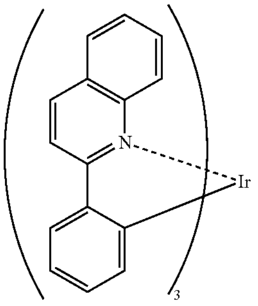

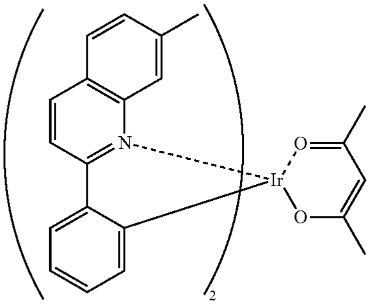

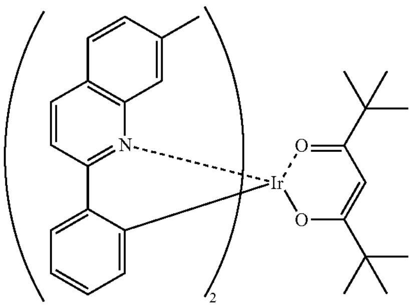

-continued

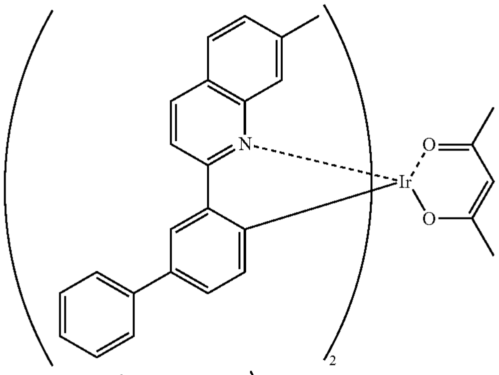

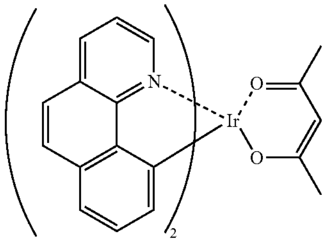

The compounds exemplified as the compounds represented by formula (T-1) can be synthesized by various methods, for example, by the methods disclosed in JP-A-2009-99783 and U.S. Pat. No. 7,279,232. After synthesis and purification by column chromatography and recrystallization, it is preferred to perform purification by sublimation purification. Not only organic impurities can be separated but also inorganic salts and residual solvents can be effectively removed by sublimation purification.

The compound represented by formula (T-1) is contained in a light-emitting layer but the use is not restricted, and the compound may further be contained in any layer of organic layers.

As iridium complex, other than the compound represented by formula (T-1), a compound represented by the following formula (T-7) and a compound having carbene as the ligand can also be preferably used.

(T-7)

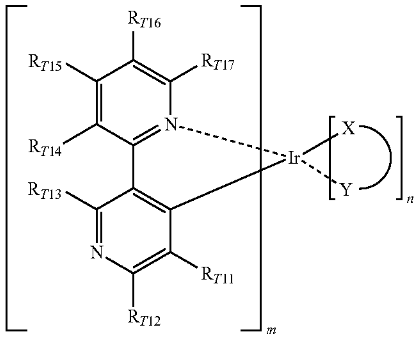

In formula (T-7), $R_{T11}$ to $R_{T17}$ have the same meaning with $R_{T3}$ to $R_{T6}$ in formula (T-2) and preferred range is also the same. (X—Y), n and m have the same meaning with (X—Y), $n_T$ and $m_T$ in formula (T-2) respectively and preferred range is also the same.

The preferred specific examples thereof are shown below, but the invention is not restricted thereto.

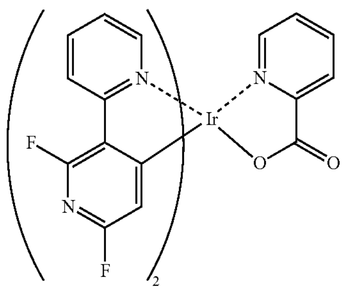

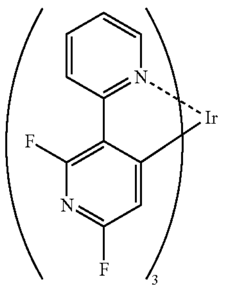

-continued

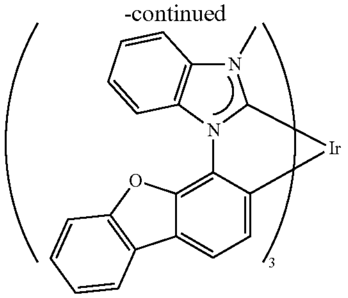

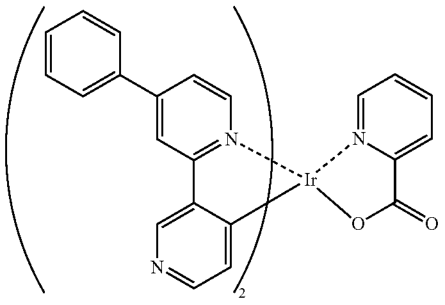

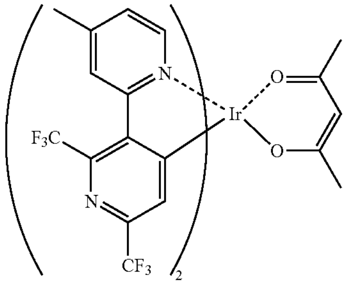

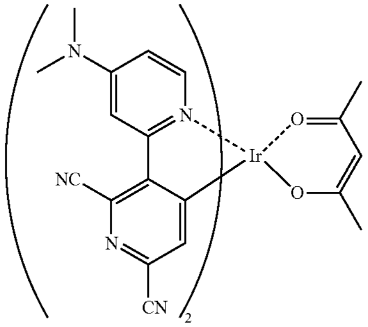

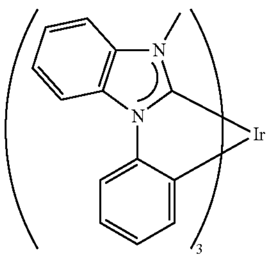

A light-emitting material is contained in a light-emitting layer generally in an amount of 0.1% by mass to 50% by mass based on the gross compound mass for forming the light-emitting layer, but the content is preferably 1% by mass to 50% by mass from the viewpoint of durability and external quantum efficiency, and more preferably 2% by mass to 40% by mass.

The thickness of a light-emitting layer is not especially limited but is usually preferably 2 nm to 500 nm, and more preferably 3 nm to 200 nm in the point of external quantum efficiency, and still more preferably 5 nm to 100 nm.

The light-emitting layer in the device of the invention may be a mixed layer comprising a host material and a light-emitting material. The light-emitting material may be a fluorescent material or may be a phosphorescent material, and a dopant may consist of one kind or two or more kinds. The host material is preferably a charge transporting material. The host material may consist of one kind or two or more kinds and, for example, constitution comprising the mixture of an electron-transporting host material and a hole-transporting host material can be exemplified. Further, a material which does not have a charge-transporting property and does not emit light may be contained in the light-emitting layer.

Further, the light-emitting layer may take a single layer structure or may take a multilayer structure of two or more layers. In addition, each light-emitting layer may emit light of a different luminescent color.

In the invention, the compound represented by formula (T-1) is contained in the light-emitting layer for the purpose of improving light emitting efficiency and durability (in particular, durability at the time of high temperature driving), but the use is not limited and may be contained in any layer of the organic layers in addition to the light-emitting layer. As the layers into which the compound represented by formula (T-1) is introduced, besides the light-emitting layer, it is preferred that the compound is introduced to any one or two or more layers of a hole-injecting layer, a hole-transporting layer, an electron-transporting layer, an electron-injecting layer, an exciton-blocking layer, and a charge-blocking layer.

[Composition Containing the Compound Represented by Formula (1) and the Compound Represented by Formula (T-1)]

The invention also relates to a composition containing the compound represented by formula (1) and the compound represented by formula (T-1).

The content of the compound represented by formula (1) in the composition of the invention is preferably 50% by mass to 99% by mass, and more preferably 70% by mass to 95% by mass.

The content of the compound represented by formula (T-1) in the composition of the invention is preferably 1% by mass to 30% by mass, and more preferably 5% by mass to 20% by mass.

The components which may be contained in the composition of the invention may be organic or inorganic, and as organic materials, the later-described host materials, and materials exemplified as fluorescent materials and phosphorescent materials are applicable.

The composition of the invention can be formed into the organic layer of the organic electroluminescence device by a dry film-forming method such as a vacuum deposition method and a sputtering method, and a transfer method, a printing method, and the like.

In the next place, formula (C-1) is described below.

(C-1)

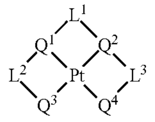

In formula (C-1), each of $Q^1$, $Q^2$, $Q^3$ and $Q^4$ independently represents a ligand to coordinate to Pt. Each of $L^1$, $L^2$ and $L^3$ independently represents a single bond or a divalent linking group.

Formula (C-1) is explained.

Each of $Q^1$, $Q^2$, $Q^3$ and $Q^4$ independently represents a ligand to coordinate to Pt. At this time, bonding of $Q^1$, $Q^2$, $Q^3$ and $Q^4$ to Pt may be any bonding via a covalent bond, an ionic bond or a coordinate bond. As the atoms in $Q^1$, $Q^2$, $Q^3$ and $Q^4$ to be bonded to Pt, a carbon atom, a nitrogen atom, an oxygen atom, a sulfur atom and a phosphorus atom are preferred, and it is preferred that at least one atom of the atoms in $Q^1$, $Q^2$, $Q^3$ and $Q^4$ to be bonded to Pt is a carbon atom, more preferably two atoms are carbon atoms, and especially preferably two are carbon atoms and two are nitrogen atoms.

$Q^1$, $Q^2$, $Q^3$ and $Q^4$ to be bonded to Pt via a carbon atom may be an anionic ligand or a neutral ligand. The examples of anionic ligands include a vinyl ligand, an aromatic hydrocarbon cyclic ligand (e.g., a benzene ligand, a naphthalene ligand, an anthracene ligand, a phenanthrene ligand, etc.), a heterocyclic ligand (e.g., a furan ligand, a thiophene ligand, a pyridine ligand, a pyrazine ligand, a pyrimidine ligand, a pyridazine ligand, a triazine ligand, a thiazole ligand, an oxazole ligand, a pyrrole ligand, an imidazole ligand, a pyrazole ligand, a triazole ligand, and a condensed ring containing any of these ligands (e.g., a quinoline ligand and a benzothiazole ligand)). As the neutral ligand, a carbene ligand is exemplified.

$Q^1$, $Q^2$, $Q^3$ and $Q^4$ to be bonded to Pt via a nitrogen atom may be a neutral ligand or an anionic ligand. The examples of neutral ligands include a nitrogen-containing aromatic heterocyclic ligand (e.g., a pyridine ligand, a pyrazine ligand, a pyrimidine ligand, a pyridazine ligand, a triazine ligand, an imidazole ligand, a pyrazole ligand, a triazole ligand, an oxazole ligand, a thiazole ligand, and a condensed ring containing any of these ligands (e.g., a quinoline ligand and a benzimidazole ligand)), an amine ligand, a nitrile ligand, and an imine ligand. As the anionic ligands, an amino ligand, an imino ligand, and a nitrogen-containing aromatic heterocyclic ligand (e.g., a pyrrole ligand, an imidazole ligand, a triazole ligand, and a condensed ring containing any of these ligands (e.g., an indole ligand and a benzimidazole ligand)) are exemplified.

$Q^1$, $Q^2$, $Q^3$ and $Q^4$ to be bonded to Pt via an oxygen atom may be a neutral ligand or an anionic ligand. As the neutral ligands, an ether ligand, a ketone ligand, an ester ligand, an amide ligand, an oxygen-containing heterocyclic ligand (e.g., a furan ligand, an oxazole ligand, and a condensed ring containing any of these ligands (e.g., a benzoxazole ligand, etc.)) are exemplified. As the anionic ligands, an alkoxy ligand, an aryloxy ligand, a heteroaryloxy ligand, an acyloxy ligand, and a silyloxy ligand are exemplified.

$Q^1$, $Q^2$, $Q^3$ and $Q^4$ to be bonded to Pt via a sulfur atom may be a neutral ligand or an anionic ligand. As the neutral ligands, a thioether ligand, a thioketone ligand, a thioester ligand, a thioamide ligand, a sulfur-containing heterocyclic ligand (e.g., a thiophene ligand, a thiazole ligand, and a condensed ring containing any of these ligands (e.g., a benzothiazole ligand, etc.)) are exemplified. As the anionic ligands, an alkylmercapto ligand, an arylmercapto ligand, and a heteroarylmercapto ligand are exemplified.

$Q^1$, $Q^2$, $Q^3$ and $Q^4$ to be bonded to Pt via a phosphorus atom may be a neutral ligand or an anionic ligand. As the neutral ligands, a phosphine ligand, a phosphate ligand, a phosphite ligand, and a phosphorus-containing heterocyclic ligand (e.g., a phosphinine ligand) are exemplified. As the anionic ligands, a phosphino ligand, a phosphinyl ligand, and a phosphoryl ligand are exemplified.

Each of the groups represented by $Q^1$, $Q^2$, $Q^3$ and $Q^4$ may have a substituent, and the above-described substituent group A is properly applicable as the substituents. Substituents may be linked to each other (when $Q^3$ and $Q^4$ are linked, it becomes a Pt complex of a cyclic tetradentate ligand).

Each of the groups represented by $Q^1$, $Q^2$, $Q^3$ and $Q^4$ preferably represents an aromatic hydrocarbon cyclic ligand to be bonded to Pt via a carbon atom, an aromatic heterocyclic ligand to be bonded to Pt via a carbon atom, a nitrogen-containing aromatic heterocyclic ligand to be bonded to Pt via a nitrogen atom, an acyloxy ligand, an alkyloxy ligand, an aryloxy ligand, a heteroaryloxy ligand, or a silyloxy ligand, more preferably an aromatic hydrocarbon cyclic ligand to be bonded to Pt via a carbon atom, an aromatic heterocyclic ligand to be bonded to Pt via a carbon atom, a nitrogen-containing aromatic heterocyclic ligand to be bonded to Pt via a nitrogen atom, an acyloxy ligand, or an aryloxy ligand, and still more preferably an aromatic hydrocarbon cyclic ligand to be bonded to Pt via a carbon atom, an aromatic heterocyclic ligand to be bonded to Pt via a carbon atom, a nitrogen-containing aromatic heterocyclic ligand to be bonded to Pt via a nitrogen atom, or an acyloxy ligand.

Each of $L^1$, $L^2$ and $L^3$ represents a single bond or a divalent linking group. The examples of the divalent linking groups represented by $L^1$, $L^2$ and $L^3$ include an alkylene group (e.g., methylene, ethylene, propylene, and the like), an arylene group (e.g., phenylene, naphthalenediyl), a heteroarylene group (e.g., pyridinediyl, thiophenediyl, and the like), an imino group ($—NR_L—$), (e.g., a phenylimino group and the like), an oxy group (—O—), a thio group (—S—), a phosphinidene group ($—PR_L—$) (e.g., a phenylphosphinidene group, and the like), a silylene group ($—SiR_LR_L'—$) (e.g., a dimethylsilylene group, a diphenylsilylene group, and the like), and a combination of these groups. As $R_L$ and $R_L'$, an alkyl group and an aryl group are exemplified. These linking groups may further have a substituent, and the above-described substituent group A is properly applicable as the substituents.

From the viewpoint of stability of the complex and light-emitting quantum yield, each of $L^1$, $L^2$ and $L^3$ preferably represents a single bond, an alkylene group, an arylene group, a heteroarylene group, an imino group, an oxy group, a thio group, or a silylene group, more preferably a single bond, an alkylene group, an arylene group, or an imino group, still more preferably a single bond, an alkylene group, or an arylene group, still further preferably a single bond, a methylene group or a phenylene group, still yet preferably a single bond or a di-substituted methylene group, still more yet preferably a single bond, a dimethylmethylene group, a diethylmethylene group, a diisobutylmethylene group, a dibenzylmethylene group, an ethylmethylmethylene group, a methylpropylmethylene group, an isobutylmethylmethylene group, a diphenylmethylene group, a methylphenylmethylene group, a cyclohexanediyl group, a cyclopentanediyl group, a fluorenediyl group, or a fluoromethylmethylene group, and especially preferably a single bond, a dimethylmethylene group, a diphenylmethylene group, or a cyclohexanediyl group.

The platinum complex represented by formula (C-1) is more preferably represented by the following formula (C-2).

(C-2)

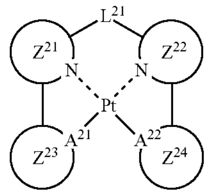

In formula (C-2), $L^{21}$ represents a single bond or a divalent linking group. Each of $A^{21}$ and $A^{22}$ independently represents a carbon atom or a nitrogen atom. Each of $Z^{21}$ and $Z^{22}$ independently represents a nitrogen-containing heterocyclic ring. Each of $Z^{23}$ and $Z^{24}$ independently represents a benzene ring or an aromatic heterocyclic ring.

Formula (C-2) is described below.

$L^{21}$ has the same meaning with $L^1$ in formula (C-1) and the preferred range is also the same.

Each of $A^{21}$ and $A^{22}$ independently represents a carbon atom or a nitrogen atom. At least either $A^{21}$ or $A^{22}$ preferably represents a carbon atom, and more preferably both $A^{21}$ and $A^{22}$ represent a carbon atom from the viewpoint of stability of the complex and light-emitting quantum yield.

Each of $Z^{21}$ and $Z^{22}$ independently represents a nitrogen-containing aromatic heterocyclic ring. As the nitrogen-containing aromatic heterocyclic rings represented by $Z^{21}$ and $Z^{22}$, a pyridine ring, a pyrimidine ring, a pyrazine ring, a triazine ring, an imidazole ring, a pyrazole ring, an oxazole ring, a thiazole ring, a triazole ring, an oxadiazole ring, and a thiadiazole ring are exemplified. From the viewpoint of stability of the complex, control of light emitting wavelength and light-emitting quantum yield, the rings represented by $Z^{21}$ and $Z^{22}$ are preferably a pyridine ring, a pyrazine ring, an imidazole ring, and a pyrazole ring, more preferably a pyridine ring, an imidazole ring, and a pyrazole ring, still more preferably a pyridine ring and a pyrazole ring, and especially preferably a pyridine ring.

The nitrogen-containing aromatic heterocyclic ring represented by $Z^{21}$ and $Z^{22}$ may have a substituent. The above substituent group A is applicable as the substituent on a carbon atom and the above substituent group B is applicable as the substituent on a nitrogen atom. As the substituent on a carbon atom, an alkyl group, a perfluoroalkyl group, an aryl group, an aromatic heterocyclic group, a dialkylamino group, a diarylamino group, an alkoxy group, a cyano group or a halogen atom is preferred. The substituent is arbitrarily selected for controlling light emitting wavelength and electric potential. For shortening the wavelength, an electron donating group, a fluorine atom, or an aromatic cyclic group is preferred and, for example, an alkyl group, a dialkylamino group, an alkoxy group, a fluorine atom, an aryl group or an aromatic heterocyclic group is selected. For lengthening the wavelength, an electron withdrawing group is preferred and, for example, a cyano group or a perfluoroalkyl group is selected. As the substituent on a nitrogen atom, an alkyl group, an aryl group, or an aromatic heterocyclic group is preferred, and from the aspect of stability of the complex, an alkyl group or an aryl group is preferred. These substituents may be linked to each other to form a condensed ring. As the rings to be formed, a benzene ring, a pyridine ring, a pyrazine ring, a pyridazine ring, a pyrimidine ring, an imidazole ring, an oxazole ring, a thiazole ring, a pyrazole ring, a thiophene ring, and a furan ring are exemplified.

Each of $Z^{23}$ and $Z^{24}$ independently represents a benzene ring or an aromatic heterocyclic ring. As the nitrogen-containing aromatic heterocyclic ring represented by $Z^{23}$ and $Z^{24}$, a pyridine ring, a pyrimidine ring, a pyrazine ring, a pyridazine ring, a triazine ring, an imidazole ring, a pyrazole ring, an oxazole ring, a thiazole ring, a triazole ring, an oxadiazole ring, a thiadiazole ring, a thiophene ring, and a furan ring are exemplified. From the viewpoint of stability of the complex, control of light emitting wavelength and light-emitting quantum yield, the rings represented by $Z^{23}$ and $Z^{24}$ are preferably a benzene ring, a pyridine ring, a pyrazine ring, an imidazole ring, a pyrazole ring, and a thiophene ring, more preferably a benzene ring, a pyridine ring and a pyrazole ring, and still more preferably a benzene ring and a pyridine ring.

The benzene ring and nitrogen-containing aromatic heterocyclic ring represented by $Z^{23}$ and $Z^{24}$ may have a substituent. The above substituent group A is applicable as the substituent on a carbon atom and the above substituent group B is applicable as the substituent on a nitrogen atom. As the substituent on a carbon atom, an alkyl group, a perfluoroalkyl group, an aryl group, an aromatic heterocyclic group, a dialkylamino group, a diarylamino group, an alkoxy group, a cyano group or a halogen atom is preferred. The substituent is arbitrarily selected for controlling light emitting wavelength and electric potential. For lengthening the wavelength, an electron donating group or an aromatic cyclic group is preferred and, for example, an alkyl group, a dialkylamino group, an alkoxy group, an aryl group or an aromatic heterocyclic group is selected. For shortening the wavelength, an electron withdrawing group is preferred and, for example, a fluorine atom, a cyano group or a perfluoroalkyl group is selected. As the substituent on a nitrogen atom, an alkyl group, an aryl group, or an aromatic heterocyclic group is preferred, and from the aspect of stability of the complex, an alkyl group or an aryl group is preferred. These substituents may be linked to each other to form a condensed ring. As the rings to be formed, a benzene ring, a pyridine ring, a pyrazine ring, a pyridazine ring, a pyrimidine ring, an imidazole ring, an oxazole ring, a thiazole ring, a pyrazole ring, a thiophene ring, and a furan ring are exemplified.

The platinum complex represented by formula (C-2) is more preferably represented by the following formula (C-3).

(C-3)

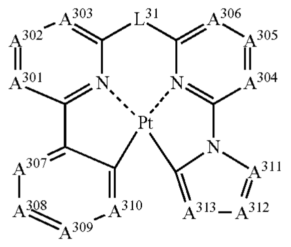

In formula (C-3), each of $A^{301}$ to $A^{313}$ independently represents C—R or a nitrogen atom. R represents a hydrogen atom or a substituent. $L^{31}$ represents a single bond or a divalent linking group.

Formula (C-3) is described below.

$L^{31}$ has the same meaning with $L^{21}$ in formula (C-2) and the preferred range is also the same.

Each of $A^{301}$ to $A^{306}$ independently represents C—R or a nitrogen atom. R represents a hydrogen atom or a substituent. As the substituent represented by R, those enumerated above as substituent group A can be applied. Each of $A^{301}$ to $A^{306}$ preferably represents C—R, and R's may be linked to each other to form a ring. When each of $A^{301}$ to $A^{306}$ represents C—R, each R of $A^{302}$ and $A^{305}$ preferably represents a hydrogen atom, an alkyl group, an aryl group, an amino group, an alkoxy group, an aryloxy group, a fluorine atom, or a cyano group, more preferably a hydrogen atom, an amino group, an alkoxy group, an aryloxy group, or a fluorine atom, and especially preferably a hydrogen atom or a fluorine atom. Each R of $A^{301}$, $A^{303}$, $A^{304}$ and $A^{306}$ preferably represents a hydrogen atom, an alkyl group, an aryl group, an amino group, an alkoxy group, an aryloxy group, a fluorine atom, or a cyano group, more preferably a hydrogen atom, an amino group, an alkoxy group, an aryloxy group, or a fluorine atom, and especially preferably a hydrogen atom.

Each of $A^{307}$, $A^{308}$, $A^{309}$ and $A^{310}$ independently represents C—R or a nitrogen atom. R represents a hydrogen atom or a substituent. Those enumerated above as substituent group A can be applied to the substituent represented by R. When each of $A^{307}$, $A^{308}$, $A^{309}$ and $A^{310}$ represents C—R, each R preferably represents a hydrogen atom, an alkyl group, a perfluoroalkyl group, an aryl group, an aromatic heterocyclic group, a dialkylamino group, a diarylamino group, an alkyloxy group, a cyano group, or a halogen atom, more preferably a hydrogen atom, an alkyl group, a perfluoroalkyl group, an aryl group, a dialkylamino group, a cyano group, or a fluorine atom, and still more preferably a hydrogen atom, an alkyl group, a trifluoromethyl group, or a fluorine atom. If possible, substituents may be linked to each other to form a condensed ring structure. When light emitting wavelength is shifted to the shorter wavelength side, it is preferred that $A^{308}$ represents a nitrogen atom.

When $A^{307}$, $A^{308}$, $A^{309}$ and $A^{310}$ are selected as described above, as the 6-membered ring formed by two carbon atoms and $A^{307}$, $A^{308}$, $A^{309}$ and $A^{310}$, a pyridine ring, a pyrazine ring, a pyrimidine ring, a pyridazine ring, and a triazine ring are exemplified, preferably a pyridine ring, a pyrazine ring, a pyrimidine ring, and a pyridazine ring, and especially preferably a pyridine ring. By the 6-membered ring being a pyridine ring, a pyrazine ring, a pyrimidine ring, or a pyridazine ring (especially preferably a pyridine ring), as compared with a benzene ring, acidity of the hydrogen atom present at the position for forming a metal-carbon bond is improved, and so advantageous in that a metal complex can be more easily formed.

Each of $A^{311}$, $A^{312}$ and $A^{313}$ independently represents C—R or a nitrogen atom. R represents a hydrogen atom or a substituent. Those enumerated above as substituent group A can be applied to the substituents represented by R. When each of $A^{311}$, $A^{312}$ and $A^{313}$ represents C—R, each R preferably represents a hydrogen atom, an alkyl group, a perfluoroalkyl group, an aryl group, an aromatic heterocyclic group, a dialkylamino group, a diarylamino group, an alkyloxy group, a cyano group, or a halogen atom, more preferably a hydrogen atom, an alkyl group, a perfluoroalkyl group, an aryl group, a dialkylamino group, a cyano group, or a fluorine atom, and still more preferably a hydrogen atom, an alkyl group, a trifluoromethyl group, or a fluorine atom. If possible, substituents may be linked to each other to form a condensed ring structure.

As the 5-membered ring formed by $A^{311}$, $A^{312}$, $A^{313}$, one nitrogen atom and one carbon atom, a pyrrole ring, a pyrazole ring, an imidazole ring, a furan ring and a thiophene ring are exemplified, and more preferably a pyrrole ring, a pyrazole ring, and an imidazole ring, and more preferably a pyrrole ring and a pyrazole ring. By the 5-membered ring being a pyrrole ring, a pyrazole ring, an imidazole ring (more preferably a pyrrole ring, a pyrazole ring), stability of the metal complex is improved, and so advantageous.

The platinum complex represented by formula (C-2) is more preferably represented by the following formula (C-4).

(C-4)

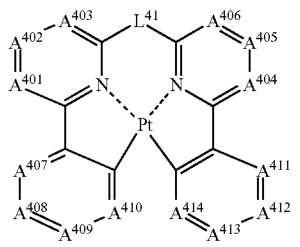

In formula (C-4), each of $A^{401}$ to $A^{414}$ independently represents C—R or a nitrogen atom. R represents a hydrogen atom or a substituent. $L^{41}$ represents a single bond or a divalent linking group.

Formula (C-4) is described below.

Each of $A^{401}$ to $A^{414}$ independently represents C—R or a nitrogen atom. R represents a hydrogen atom or a substituent. $A^{401}$ to $A^{406}$ and $L^{41}$ respectively have the same meanings with $A^{301}$ to $A^{306}$ and $L^{31}$ in formula (C-3) and preferred ranges are also the same.

As $A^{407}$ to $A^{414}$, in each of $A^{407}$ to $A^{410}$ and $A^{411}$ to $A^{414}$, the number of nitrogen atoms is preferably 0 to 2, and more preferably 0 or 1. When light emitting wavelength is shifted to the shorter wavelength side, it is preferred that $A^{408}$ or $A^{412}$ represents a nitrogen atom, and it is more preferred that both $A^{408}$ and $A^{412}$ represent a nitrogen atom.

When each of $A^{407}$ to $A^{414}$ represents C—R, each R of $A^{408}$ and $A^{412}$ preferably represents a hydrogen atom, an alkyl group, a perfluoroalkyl group, an aryl group, an amino group, an alkoxy group, an aryloxy group, a fluorine atom, or a cyano group, more preferably a hydrogen atom, a perfluoroalkyl group, an alkyl group, an aryl group, a fluorine atom, or a cyano group, and especially preferably a hydrogen atom, a perfluoroalkyl group, or a cyano group. Each R of $A^{407}$, $A^{409}$, $A^{411}$ and $A^{413}$ preferably represents a hydrogen atom, an alkyl group, a perfluoroalkyl group, an aryl group, an amino group, an alkoxy group, an aryloxy group, a fluorine atom, or a cyano group, more preferably a hydrogen atom, a perfluoroalkyl group, a fluorine atom, or a cyano group, and especially preferably a hydrogen atom or a fluorine atom. Each R of $A^{410}$ and $A^{414}$ preferably represents a hydrogen atom or a fluorine atom, and more preferably a hydrogen atom. When any of $A^{407}$ to $A^{409}$ and $A^{411}$ to $A^{413}$ represents C—R, R's may be linked to each other to form a ring.

The platinum complex represented by formula (C-1) is more preferably represented by the following formula (C-5).

(C-5)

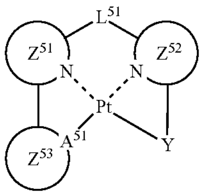

In formula (C-5), $L^{51}$ represents a single bond or a divalent linking group. Each of $A^{51}$ independently represents a carbon atom or a nitrogen atom. Each of $Z^{51}$ and $Z^{52}$ independently represents a nitrogen-containing aromatic heterocyclic ring. Each of $Z^{53}$ independently represents a benzene ring or an aromatic heterocyclic ring. Y represents an anionic acyclic ligand bonding to Pt.

Formula (C-5) is described.

$L^{51}$ has the same meaning with $L^1$ in formula (C-1) and the preferred range is also the same.

$A^{51}$ represents a carbon atom or a nitrogen atom. From the stability of the complex and light-emitting quantum yield, $A^{51}$ preferably represents a carbon atom.

$Z^{51}$ and $Z^{52}$ have the same meaning with $Z^{21}$ and $Z^{22}$ in formula (C-2) and the preferred range is also the same. $Z^{53}$ has the same meaning with $Z^{23}$ in formula (C-2) and the preferred range is also the same.

Y represents an anionic acyclic ligand bonding to Pt. The acyclic ligand is a ligand in which the atom bonding to Pt does not form a ring in a state of a ligand. As the atoms in Y bonding to Pt, a carbon atom, a nitrogen atom, an oxygen atom, and a sulfur atom are preferred, more preferably a nitrogen atom and an oxygen atom, and most preferably an oxygen atom. As Y bonding to Pt via a carbon atom, a vinyl ligand is exemplified. As Y bonding to Pt via a nitrogen atom, an amino ligand and an imino ligand are exemplified. As Y bonding to Pt via an oxygen atom, an alkoxy ligand, an aryloxy ligand, a heteroaryloxy ligand, an acyloxy ligand, a silyloxy ligand, a carboxyl ligand, a phosphoric acid ligand, and a sulfonic acid ligand are exemplified. As Y bonding to Pt via a sulfur atom, an alkylmercapto ligand, an arylmercapto ligand, a heteroarylmercapto ligand, and a thiocarboxylic acid ligand are exemplified.

The ligand represented by Y may have a substituent, and the substituents described above as substituent group A are arbitrarily applied. The substituents may be linked to each other.

The ligand represented by Y is preferably a ligand bonding to Pt via an oxygen atom, more preferably an acyloxy ligand, an alkyloxy ligand, an aryloxy ligand, a heteroaryloxy ligand, or a silyloxy ligand, and still more preferably an acyloxy ligand.

The platinum complex represented by formula (C-5) is more preferably represented by the following formula (C-6).

(C-6)

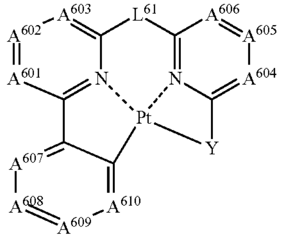

In formula (C-6), each of $A^{601}$ to $A^{610}$ independently represents C—R or a nitrogen atom. R represents a hydrogen atom or a substituent. $L^{61}$ represents a single bond or a divalent linking group. Y represents an anionic acyclic ligand bonding to Pt.

Formula (C-6) is described.

$L^{61}$ has the same meaning with that of $L^{51}$ in formula (C-5) and the preferred range is also the same. $A^{601}$ to $A^{610}$ respectively have the same meanings with $A^{301}$ to $A^{310}$ in formula (C-3) and the preferred ranges are also the same. Y has the same meaning as in formula (C-5) and the preferred range is also the same.

As the platinum complexes represented by formula (C-1), specifically the following compounds are exemplified: the compounds described in JP-A-2005-310733, paragraphs [0143] to [0152], [0157] to [0158], [0162] to [0168], the compounds described in JP-A-2006-256999, paragraphs [0065] to [0083], the compounds described in JP-A-2006-93542, paragraphs [0065] to [0090], the compounds described in JP-A-2007-73891, paragraphs [0063] to [0071], the compounds described in JP-A-2007-324309, paragraphs [0079] to [0083], the compounds described in JP-A-2006-93542, paragraphs [0065] to [0090], JP-A-2007-96255, paragraphs [0055] to [0071], and the compounds described in JP-A-2006-313796, paragraphs [0043] to [0046]. More specifically, the following shown platinum complexes are exemplified, but the invention is not restricted thereto.

Pt-1

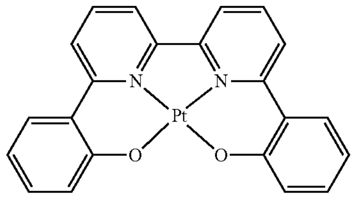

Pt-2

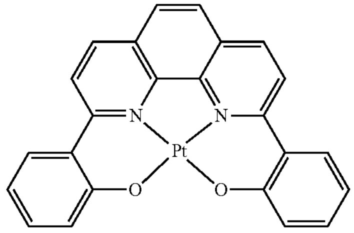

-continued
Pt-3
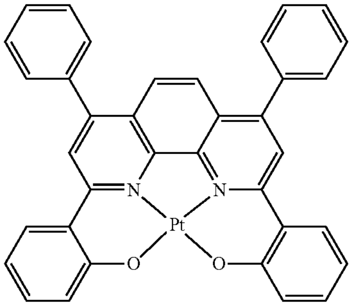
Pt-4
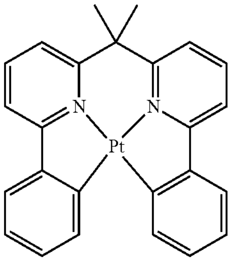
Pt-5
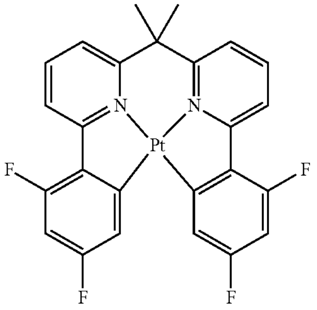
Pt-6
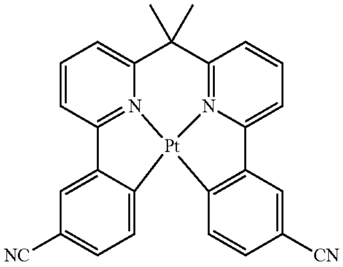
Pt-7
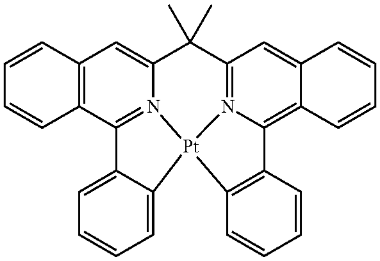
-continued
Pt-8
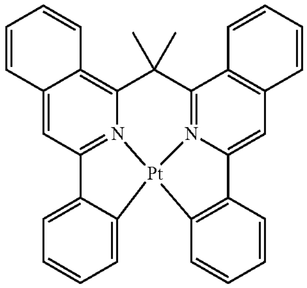
Pt-9
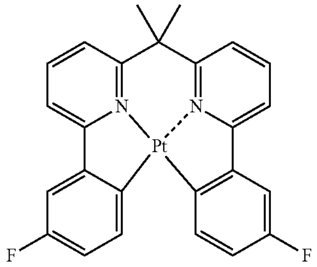
Pt-10
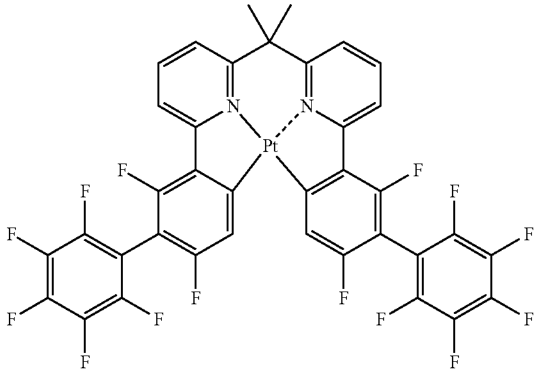
Pt-11
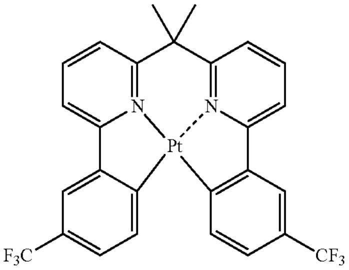
Pt-12
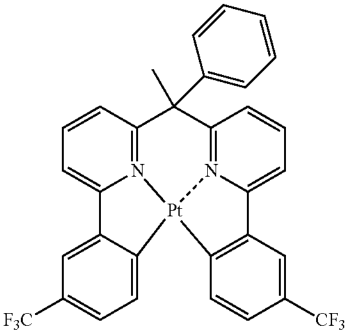

-continued
Pt-13
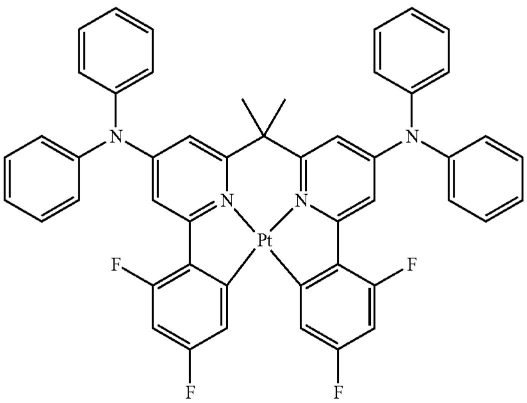
Pt-14
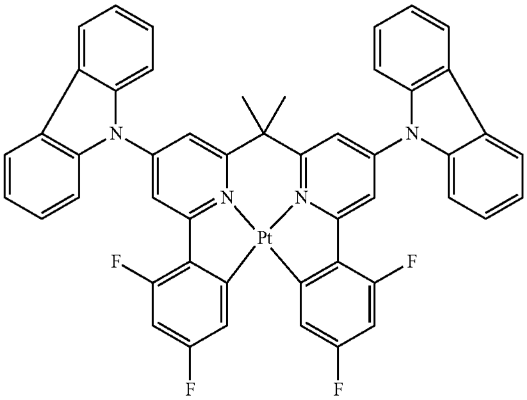
Pt-15
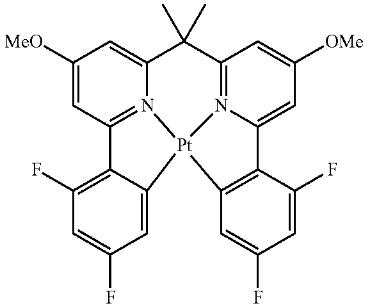
Pt-16
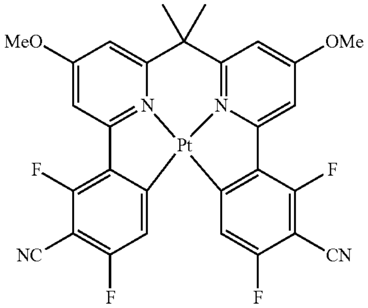
-continued
Pt-17
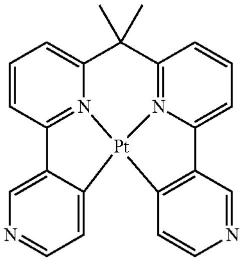
Pt-18
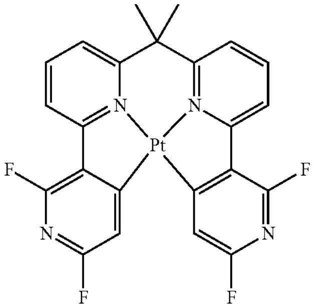
Pt-19
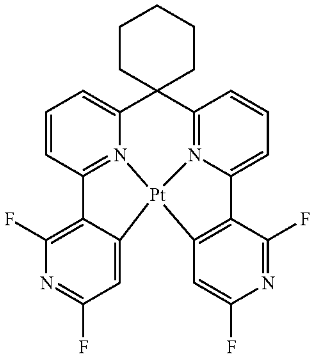
Pt-20
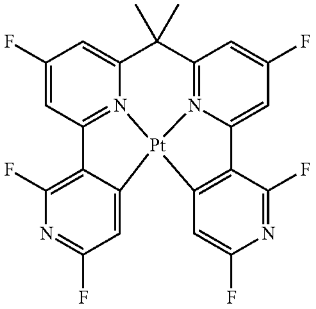
Pt-21
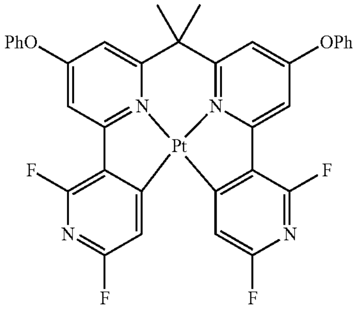

Pt-22
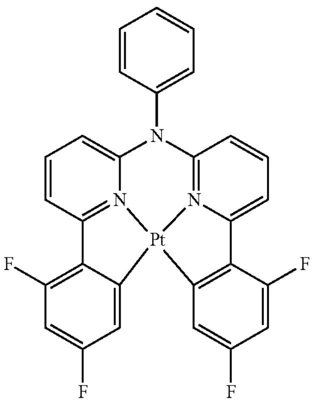
Pt-23
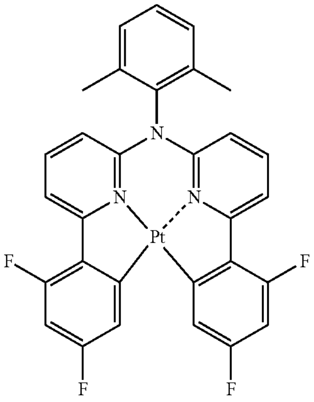
Pt-24
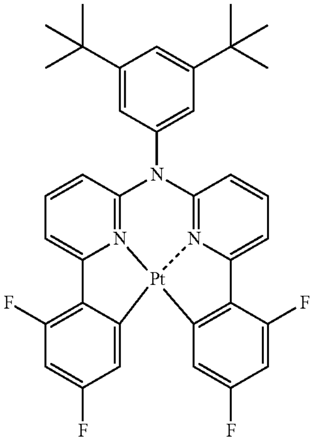
Pt-25
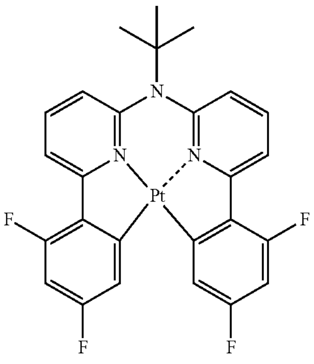
Pt-26
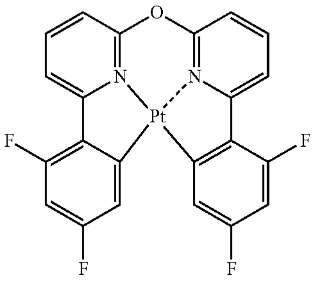
Pt-27
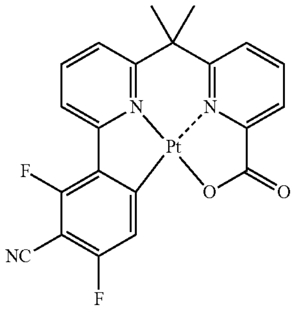
Pt-28
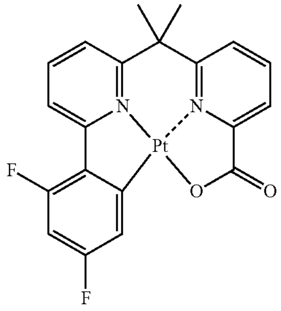
Pt-29
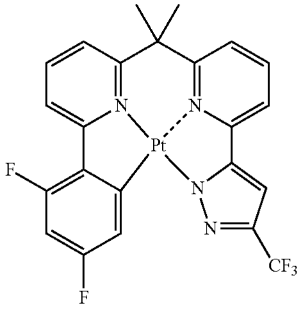
Pt-30
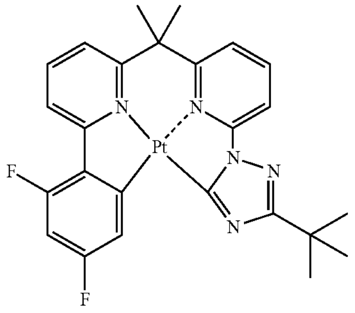

-continued
Pt-31
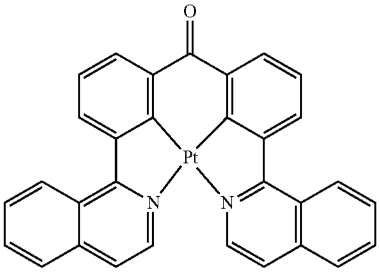
Pt-32
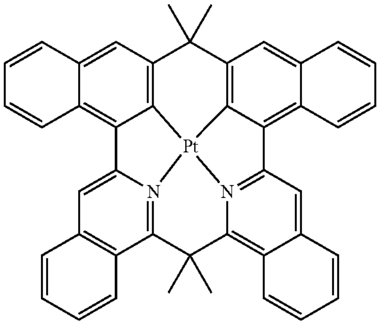
Pt-33
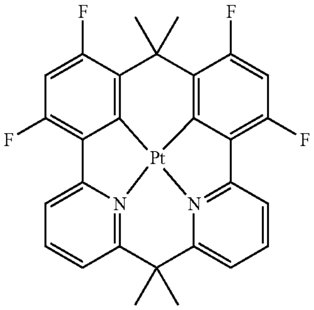
Pt-34
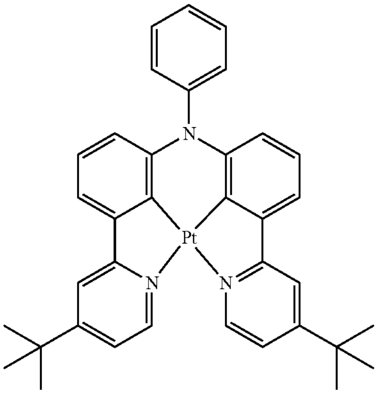
Pt-35
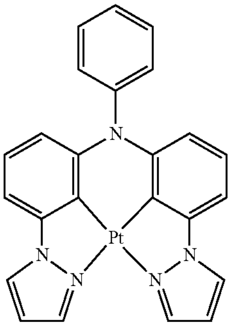
-continued
Pt-36
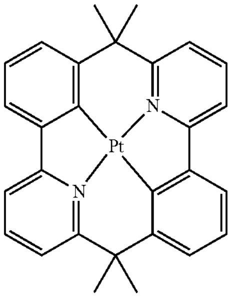
Pt-37
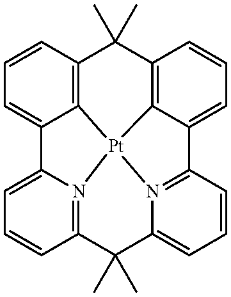
Pt-38
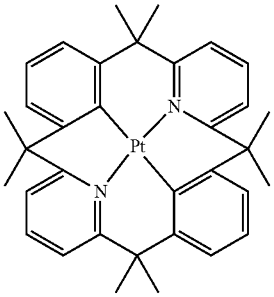
Pt-39
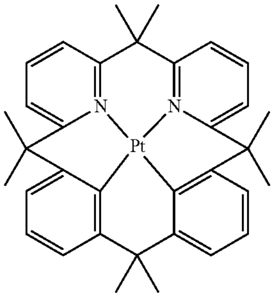
Pt-40
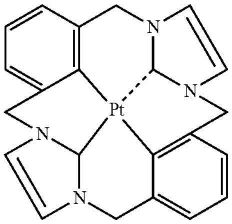

-continued
Pt-41
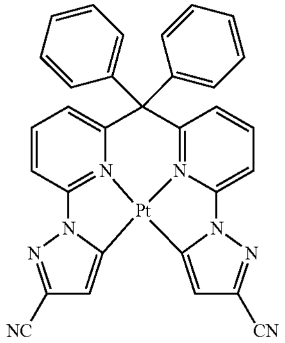
Pt-42
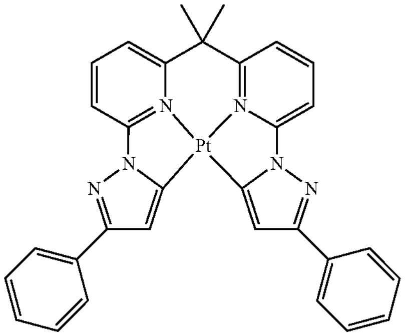
Pt-43
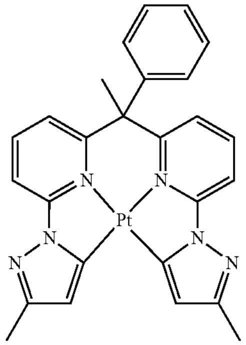
Pt-44
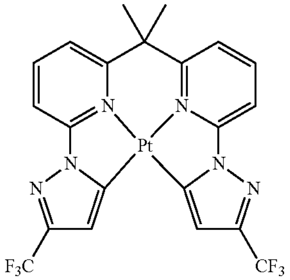
Pt-45
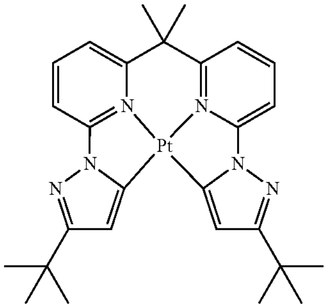
-continued
Pt-46
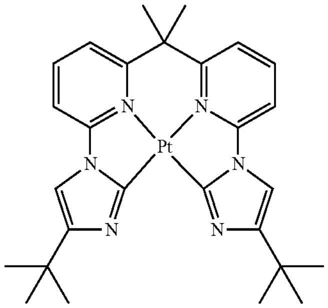
Pt-47
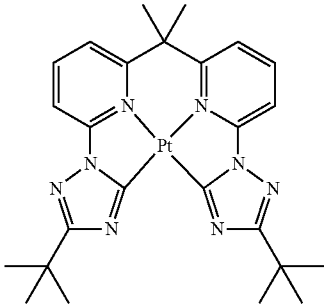
Pt-48
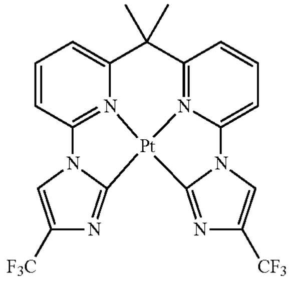
Pt-49
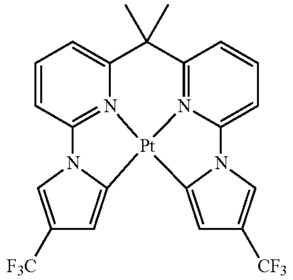
Pt-50
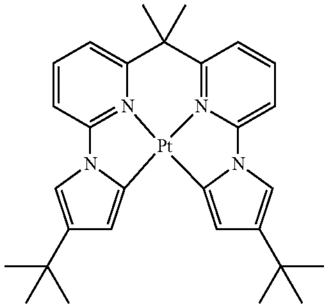

-continued
Pt-51
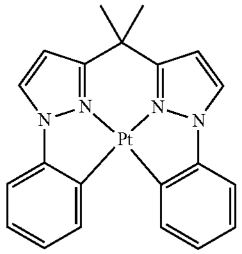
Pt-52
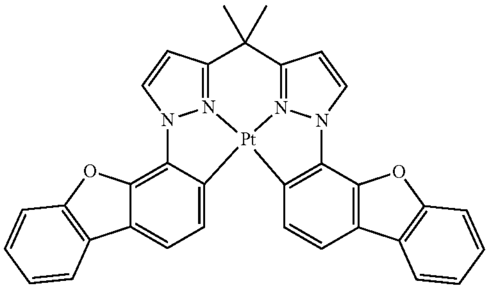
Pt-53
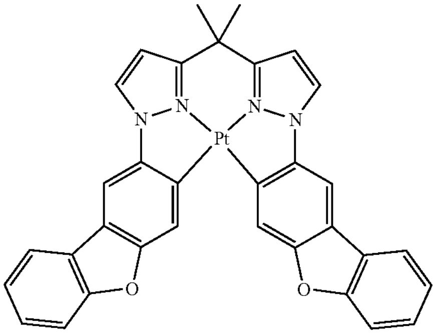
Pt-54
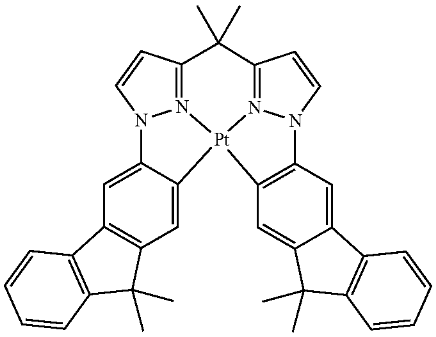
Pt-55
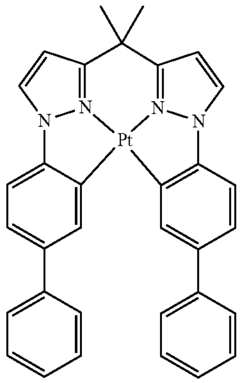
-continued
Pt-56
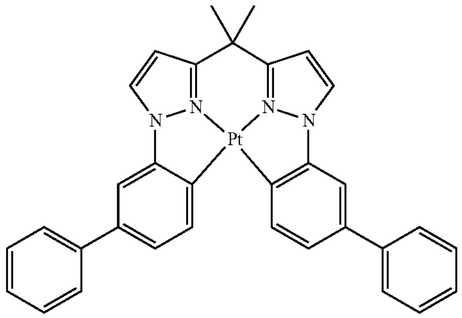
Pt-57
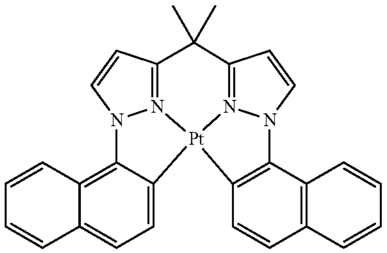
Pt-58
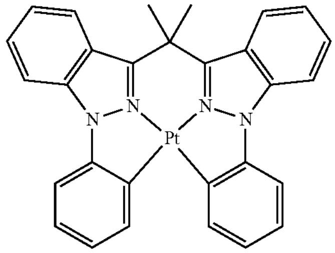
Pt-59
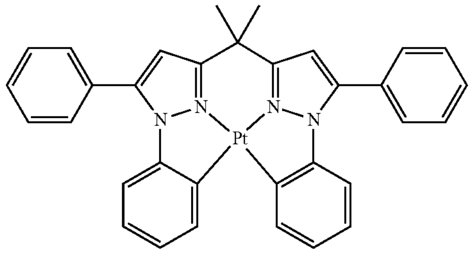
Pt-60
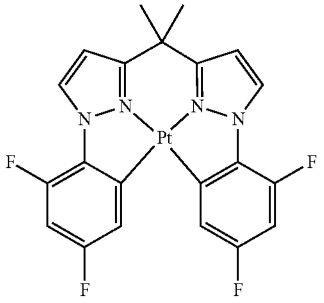

-continued

Pt-61

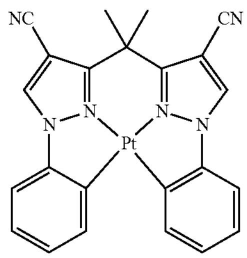

Pt-62

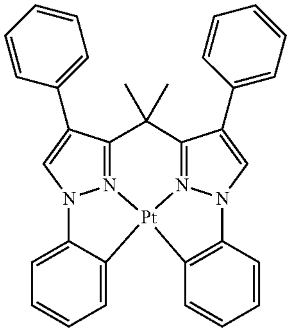

Pt-63

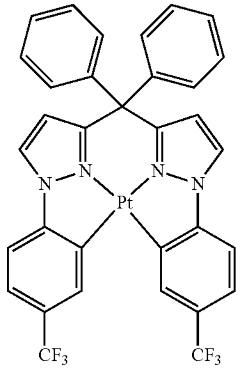

Pt-64

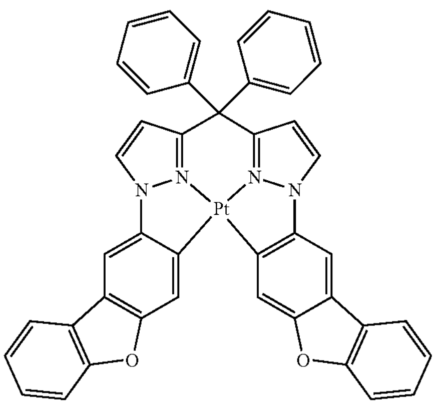

-continued

Pt-65

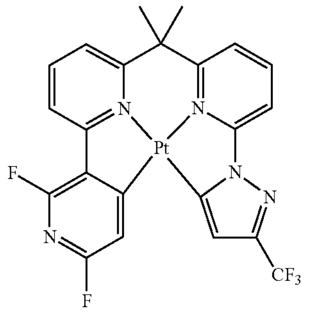

Pt-66

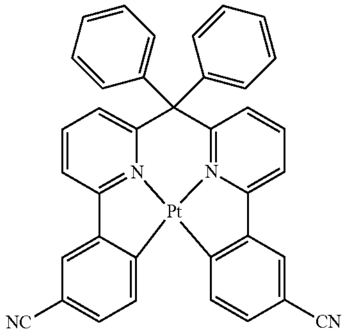

Pt-67

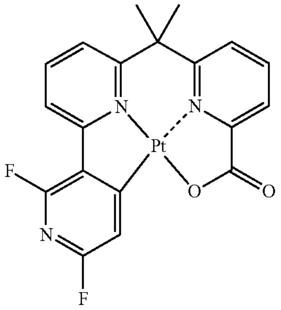

The platinum complex compounds represented by formula (C-1) can be synthesized by various methods, for example, the method described in G. R. Newkome et al., Journal of Organic Chemistry, 53, 786, (1988), page 789, left column, line 53 to right column, line 7, the method described in page 790, left column, line 18 to line 38, the method described in page 790, right column, line 19 to line 30, and combinations of these methods, and the method described in H. Lexy et al., Chemische Berichte, 113, 2749 (1980), page 2752, line 26 to line 35 can be used.

For example, the platinum complex compounds represented by formula (C-1) can be obtained at room temperature or lower or by heating a ligand or the dissociation product thereof and a metal compound (other than ordinary heating, a method of heating with a microwave is also effective) in the presence of a solvent (e.g., a halogen solvent, an alcohol solvent, an ether solvent, an ester solvent, a ketone solvent, a nitrile solvent, an amide solvent, a sulfone solvent, a sulfoxide solvent, and water can be exemplified) or in the absence of a solvent, in the presence of a base (various organic and inorganic bases, e.g., sodium methoxide, potassium t-butoxide, triethylamine, potassium carbonate can be exemplified) or in the absence of a base.

The content of the compound represented by formula (C-1) in the light-emitting layer of the invention is preferably 1% by mass to 30% by mass, more preferably 3% by mass to 25% by mass, and still more preferably 5% by mass to 20% by mass.

(Host Material)

The host material is a compound primarily bearing injection and transportation of charge in a light-emitting layer, which is a compound that does not substantially emit light. The terms "does not substantially emit light" here mean that the quantum of light emission from the compound that does not substantially emit light is preferably 5% or less of the total quantum of light emission of the device as a whole, more preferably 3% or less, and still more preferably 1% or less.

As host materials, the compound represented by any of formulae (1) to (3) can be used.

As the host materials which can be used in the invention, the following compounds can be exemplified.

For example, pyrrole, indole, carbazole, azaindole, azacarbazole, triazole, oxazole, oxadiazole, pyrazole, imidazole, thiophene, polyarylalkane, pyrazoline, pyrazolone, phenylenediamine, arylamine, amino-substituted chalcone, styrylanthracene, fluorenone, hydrazone, stilbene, silazane, aromatic tertiary amine compounds, styrylamine compounds, porphyrin-based compounds, polysilane-based compounds, poly(N-vinylcarbazole), aniline-based copolymers, thiophene oligomers, conductive polymeric oligomers such as polythiophene, etc., organic silane, a carbon film, pyridine, pyrimidine, triazine, imidazole, pyrazole, triazole, oxazole, oxadiazole, fluorenone, anthraquinodimethane, anthrone, diphenylquinone, thiopyran dioxide, carbodiimide, fluorenylidenemethane, distyrylpyrazine, fluorine-substituted aromatic compounds, heterocyclic ring tetracarboxylic anhydride such as naphthaleneperylene, phthalocyanine, various kinds of metal complexes represented by metal complex of 8-quinolinol derivative, metal phthalocyanine, and metal complexes having benzoxazole or benzothiazole as a ligand, and derivatives thereof (which may have a substituent or a condensed ring) can be exemplified.

Host materials which can be used in combination in the invention may be a hole-transporting host material or an electron-transporting host material, but a hole-transporting host material can be used.

In the invention, it is preferred for the light-emitting layer to contain a host material. The host material is preferably a compound represented by the following formula (4-1) or (4-2).

In the invention, it is more preferred for the light-emitting layer to contain at least one or more compounds represented by formula (4-1) or (4-2).

When the compound represented by formula (4-1) or (4-2) is contained in the light-emitting layer, it is preferred that the compound represented by formula (4-1) or (4-2) is contained in the light-emitting layer in an amount of 30% by mass to 100% by mass, more preferably 40% by mass to 100% by mass, and especially preferably 50% by mass to 100% by mass. When the compound represented by formula (4-1) or (4-2) is contained in two or more organic layers; it is preferred to contain the compound in each layer in the above range.

The compound represented by formula (4-1) or (4-2) may be contained in any organic layer one kind alone, or the compound represented by formula (4-1) or (4-2) may be used in combination in a proper rate.

Formula (4-1)

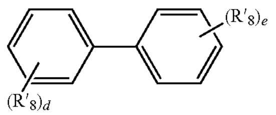

Formula (4-2)

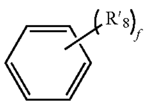

In formulae (4-1) and (4-2), each of d and e represents an integer of 0 to 3, and at least either one is 1 or more. f represents an integer of 1 to 4. Each of $R'_8$ independently represents a substituent. When d, e and f represent 2 or more, $R'_8$ may be different or the same. At least one of $R'_8$ is a carbazole represented by the following formula (5).

(5)

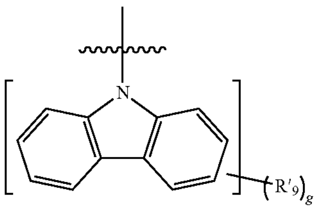

In formula (5), each of $R'_9$ independently represents a substituent. g is an integer of 0 to 8.

Each of $R'_8$ independently represents a substituent, specifically a halogen atom, an alkoxy group, a cyano group, a nitro group, an alkyl group, an aryl group, a heterocyclic group, or the substituent represented by formula (5). When $R'_8$ does not represent formula (5), $R'_8$ preferably represents an alkyl group having 10 or less carbon atoms, or a substituted or unsubstituted aryl group having 10 or less carbon atoms, and more preferably an alkyl group having 6 or less carbon atoms.

Each of $R'_9$ independently represents a substituent, specifically a halogen atom, an alkoxy group, a cyano group, a nitro group, an alkyl group, an aryl group, or a heterocyclic group, preferably an alkyl group having 10 or less carbon atoms, or a substituted or unsubstituted aryl group having 10 or less carbon atoms, and more preferably an alkyl group having 6 or less carbon atoms.

g represents an integer of 0 to 8, and not for shielding the structure of the carbazole of bearing charge transportation too much, g is preferably 0 to 4. Further, from the viewpoint of easiness of synthesis, when the carbazole has a substituent, it is preferred to have a substituent symmetrically about the nitrogen atom.

In formula (4-1), for maintaining the charge transporting performance, the sum of d and e is preferably 2 or more. It is also preferred for $R'_8$ to be substituted at the meta-position to the other benzene ring. This is for the reason that steric hindrance of the contiguous substituents is great and the bonding is susceptible to cleavage and durability lowers when the position of substitution is the ortho-position. Further, molecular shape approaches a stiff rod-state by para-substitution and liable to be crystallized, and so deterioration of the device easily occurs at a high temperature condition. Specifically, a compound having the following structure is preferred.

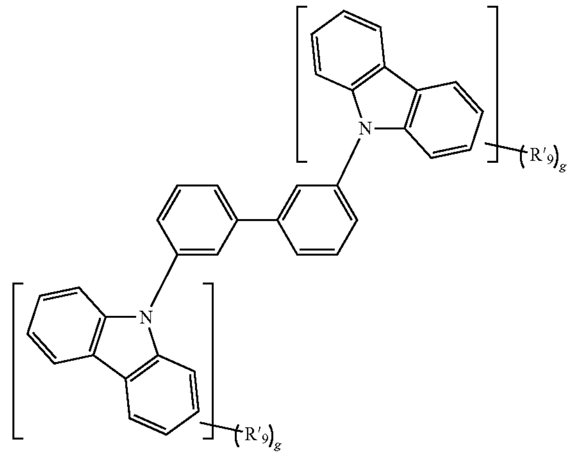

In formula (4-2), for maintaining the charge transporting performance, f is preferably 2 or more. When f is 2 or 3, from the similar viewpoint, it is preferred that $R'_8$ are substituted at the meta-position to each other. Specifically, a compound having the following structure is preferred.

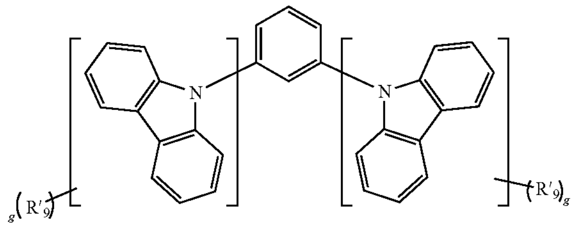

When formulae (4-1) and (4-2) have hydrogen atoms, the isotopes of hydrogen atoms (deuterium atoms and the like) are also included. In such a case, all the hydrogen atoms in the compounds may be substituted with hydrogen isotopes, or the compound may be mixtures partially containing hydrogen isotopes. A preferred case is formula (5) in which $R'_9$ is substituted with a deuterium, and especially preferably the following structure is exemplified.

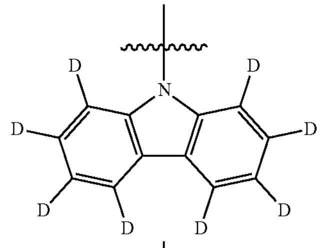

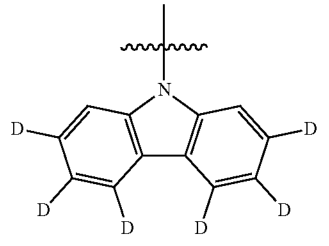

-continued

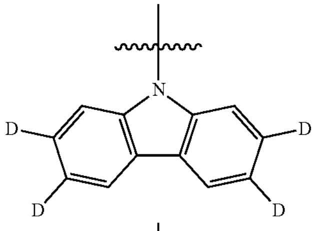

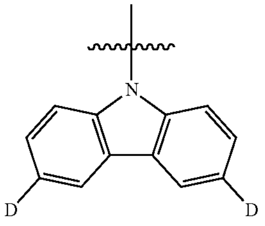

Further, the atoms constituting the substituent contain also the isotopes thereof.

The compounds represented by formula (4-1) and formula (4-2) can be synthesized by combining various known synthesis methods. Most generally, concerning the carbazole compounds, synthesis by dehydrogenation aromatization after aza-Cope rearrangement of the condensation product of aryl hydrazine and cyclohexane derivative (L. F. Tieze, Th. Eicher, translated by Takano and Ogasawara, Precision Organic Syntheses, p. 339, published by Nanko-Do) is exemplified. Further, concerning the coupling reaction of the obtained carbazole compound and an aryl halide compound using a palladium catalyst, the methods described in Tetrahedron Letters, Vol. 39, p. 617 (1998), ibid., Vol. 39, p. 2367 (1998), and ibid., Vol. 40, p. 6393 (1999) are exemplified. The reaction temperature and reaction time are not especially restricted and the conditions in the above documents are applied. Concerning some compounds, such as mCP, commercially available products can be preferably used.

It is preferred that the thin layer of the compound represented by formula (4-1) or (4-2) is formed according to a vacuum deposition process, but a wet process such as solution coating can also be preferably used. The molecular weight of the compound is preferably 2,000 or less in view of deposition suitability and solubility, more preferably 1,200 or less, and especially preferably 800 or less. Further, in the point of vacuum deposition suitability, too small a molecular weight is accompanied by small vapor pressure and transition from a vapor phase to a solid phase does not occur and it becomes difficult to form an organic layer. Accordingly, the molecular weight is preferably 250 or more, and especially preferably 300 or more.

Compounds having the structures shown below, or compounds obtained by substituting one or more hydrogen atoms of the following compounds with deuterium atoms are preferably used as the compounds of formulae (4-1) and (4-2). $R'_9$ in the following-shown structure has the same meaning with $R'_9$ in formula (5), and $R'_8$ has the same meaning with $R'_8$ in formula (4-1).

-continued
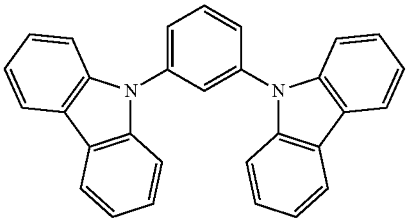
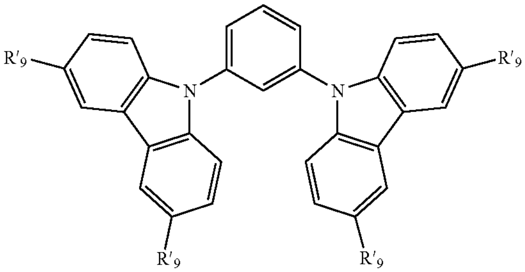
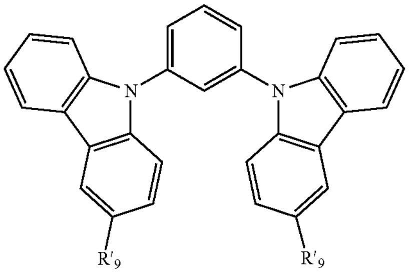
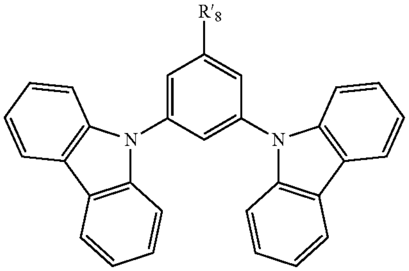
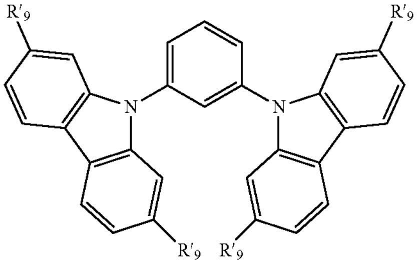
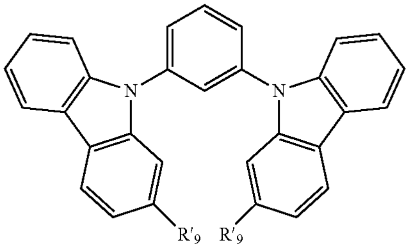
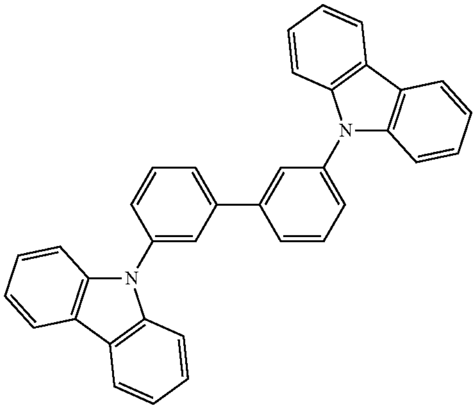
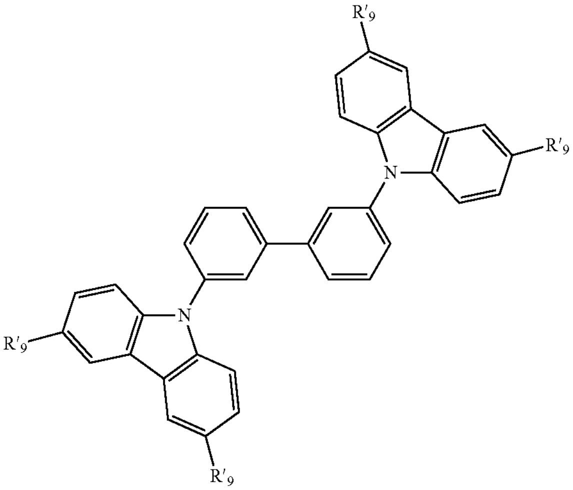
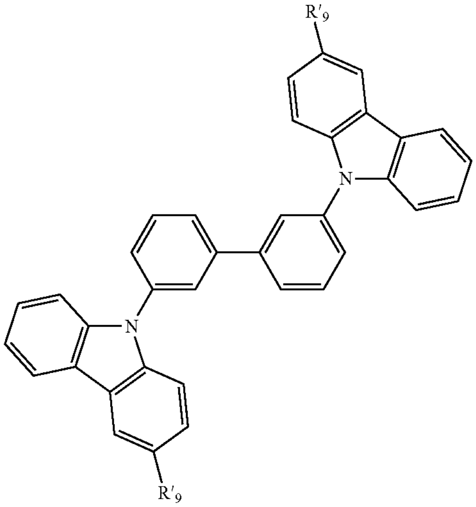

-continued
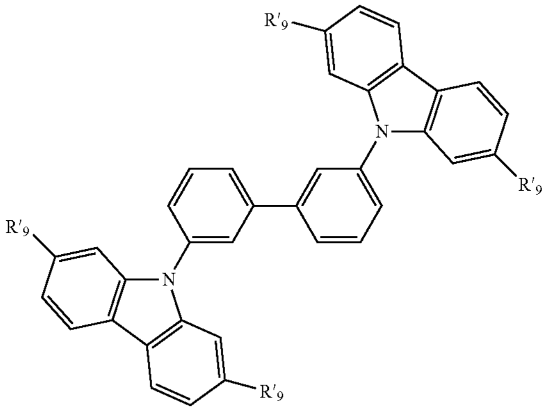
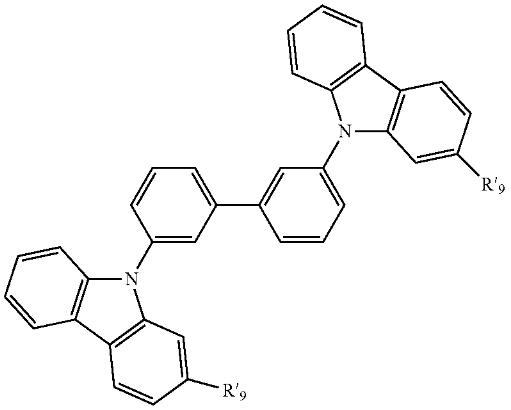
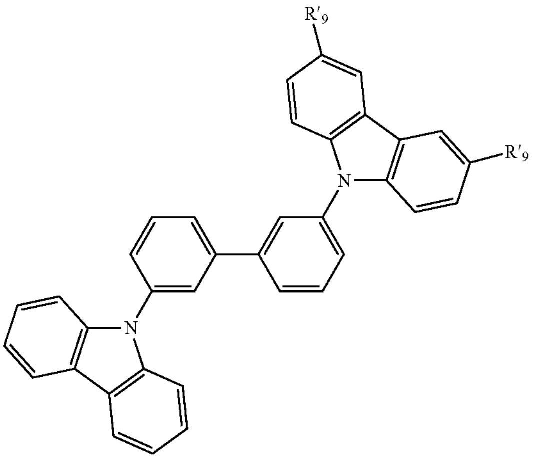
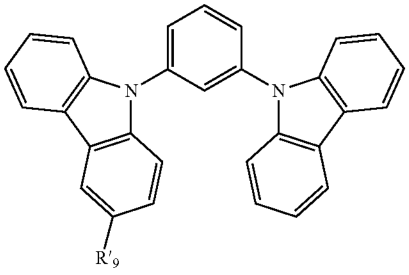
-continued
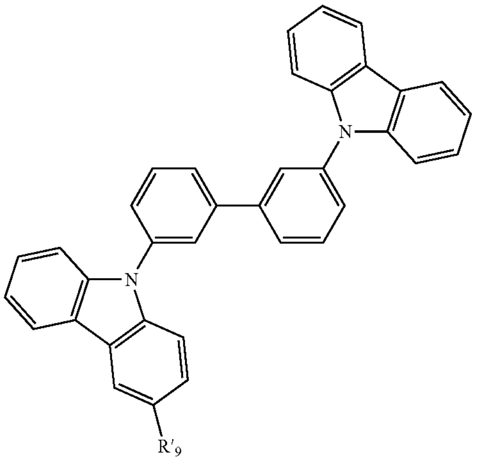
The specific examples of the compounds represented by formulae (4-1) and (4-2) are shown below, but the invention is not restricted thereto.
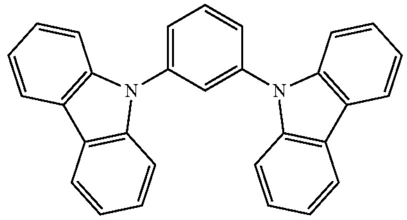
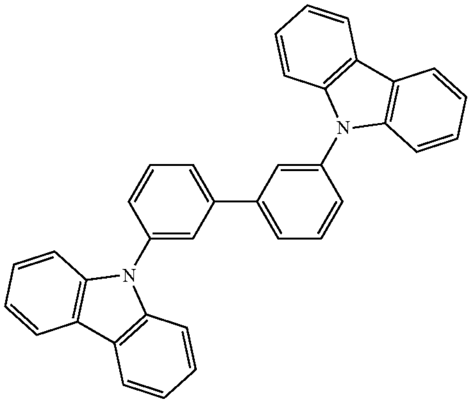
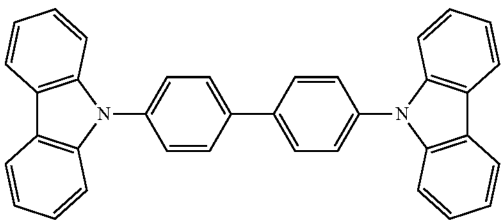

-continued
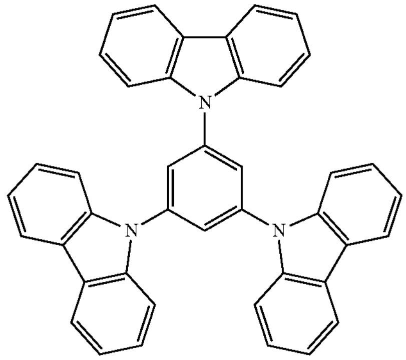
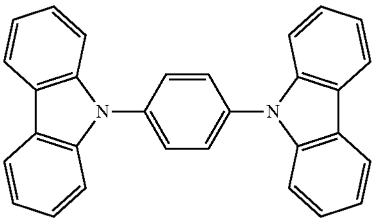
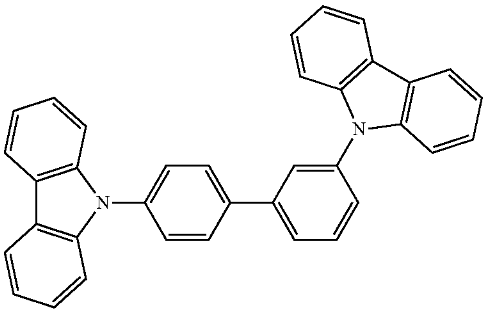
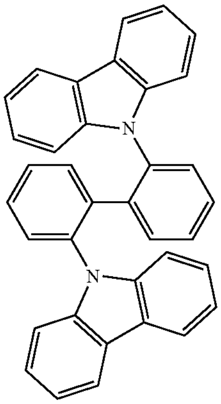
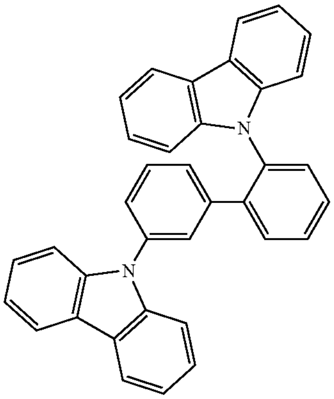
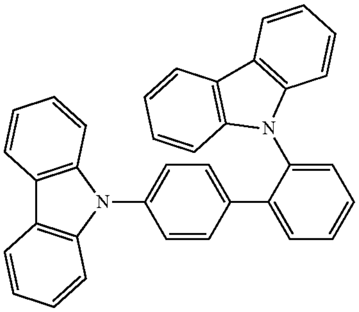
-continued
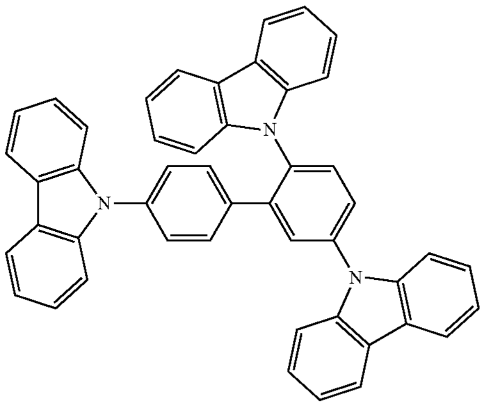
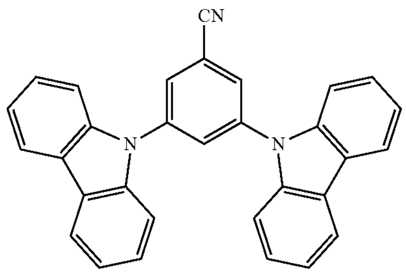
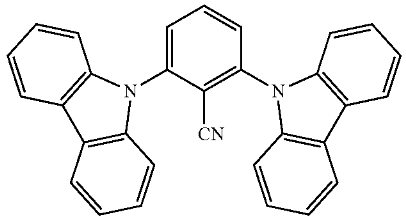
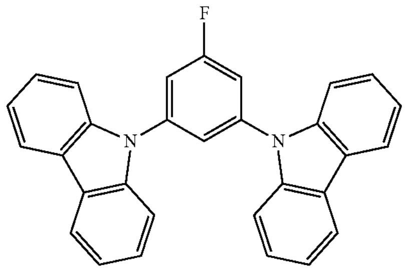
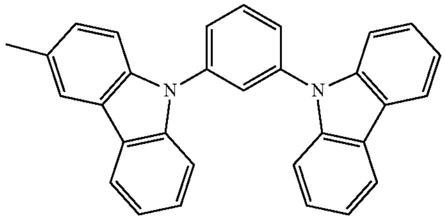
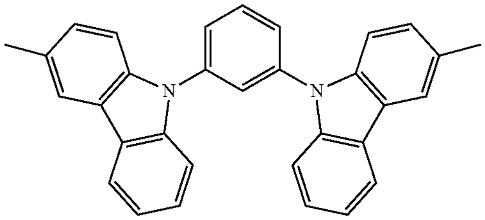

-continued
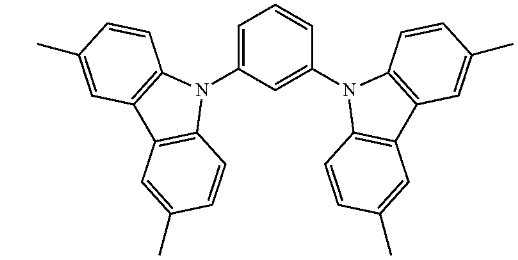
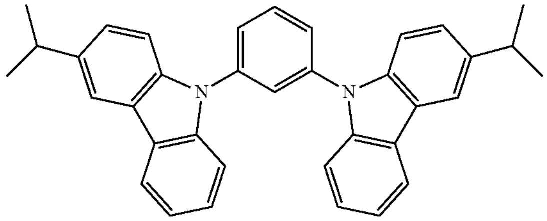
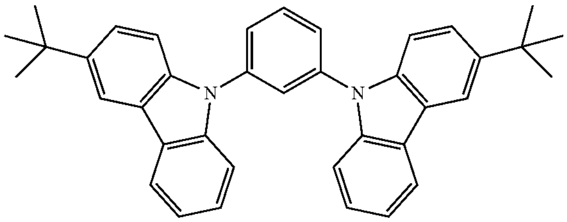
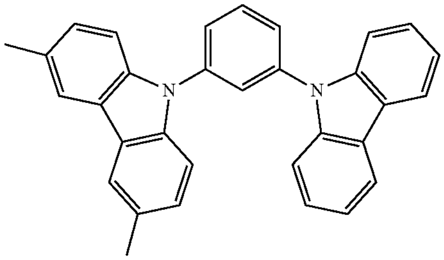
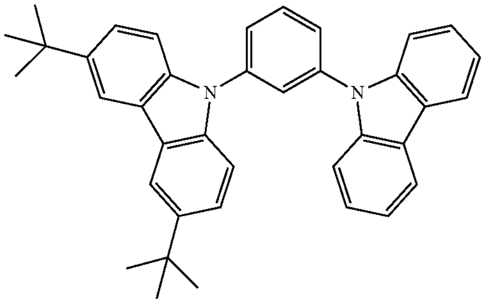
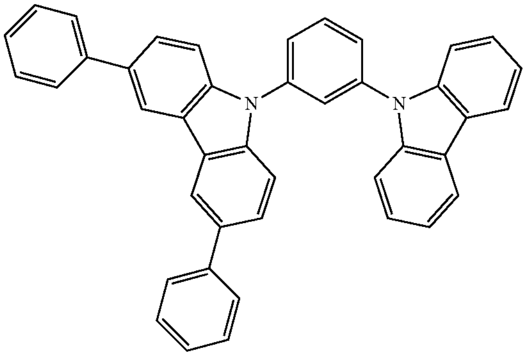
-continued
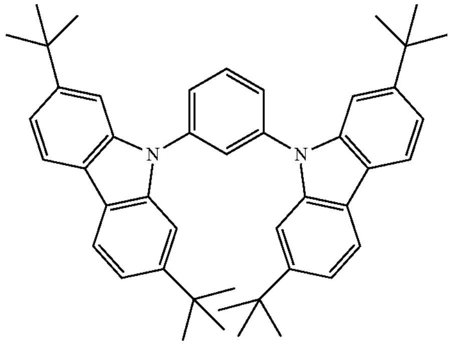
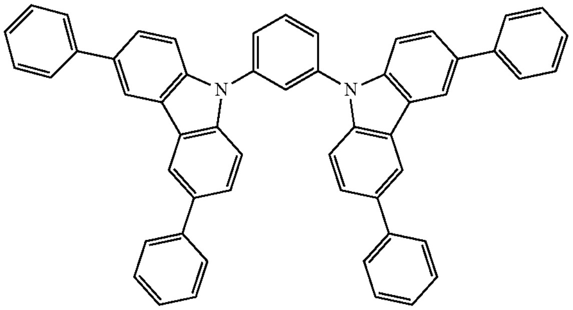
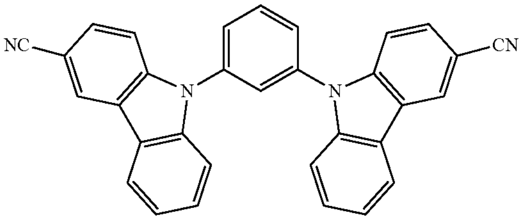
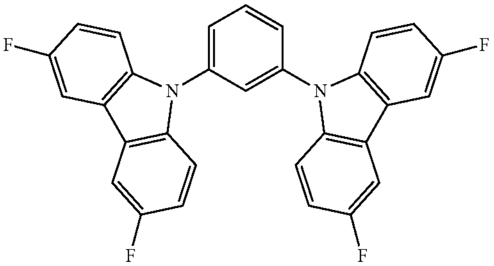
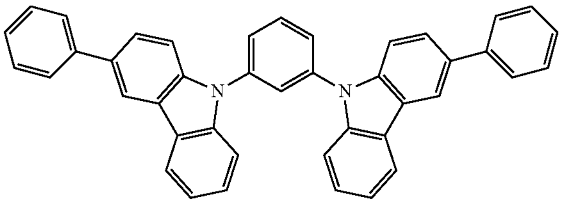
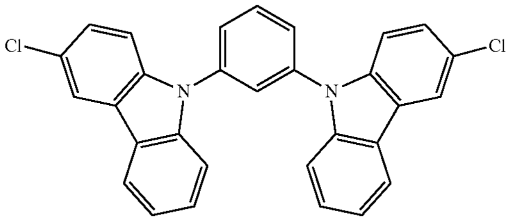

-continued
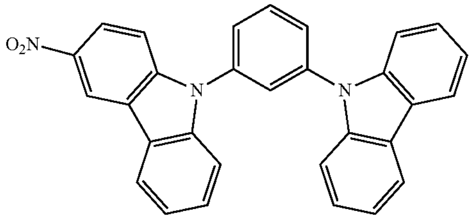
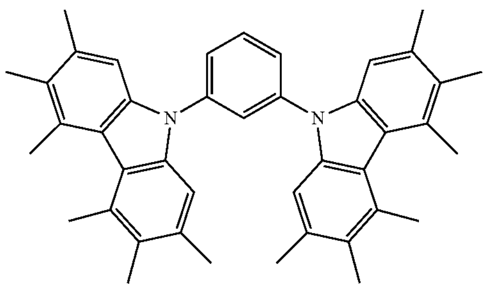
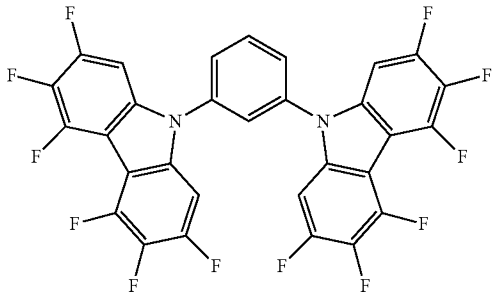
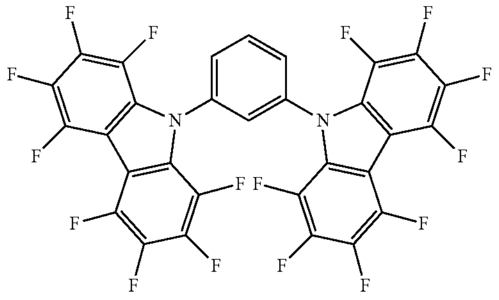
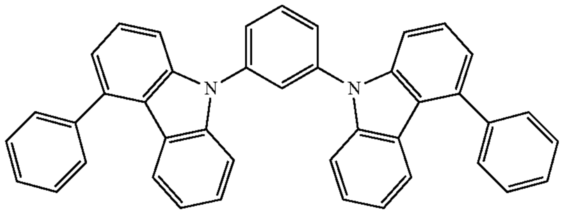
-continued
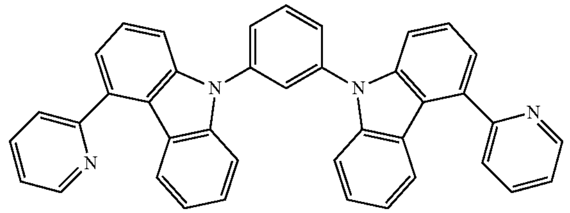
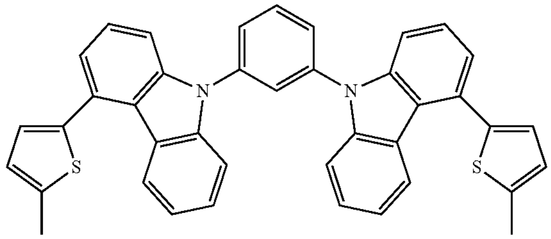
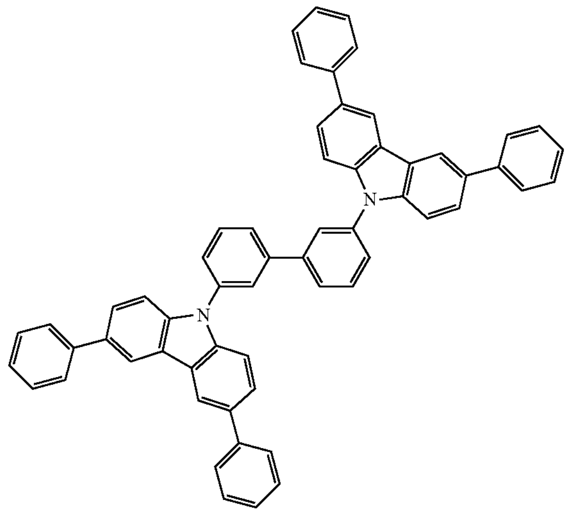
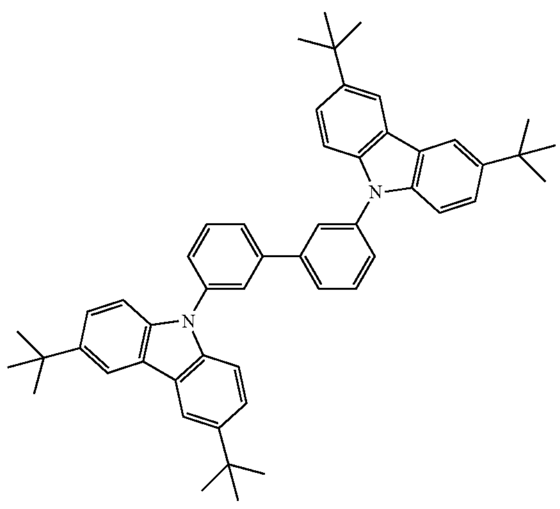

-continued
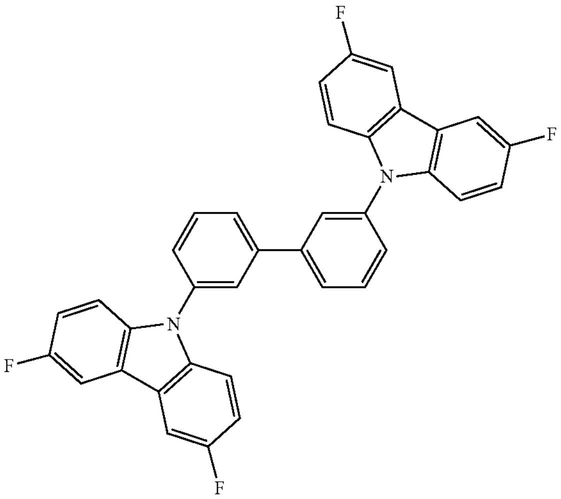
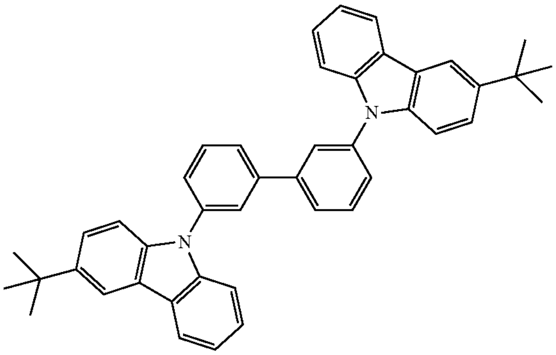
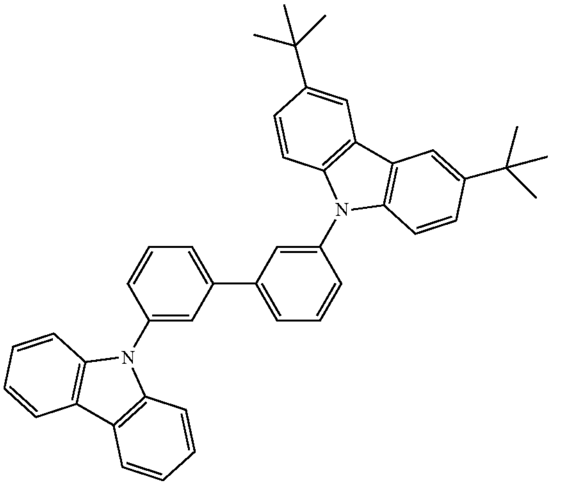
-continued
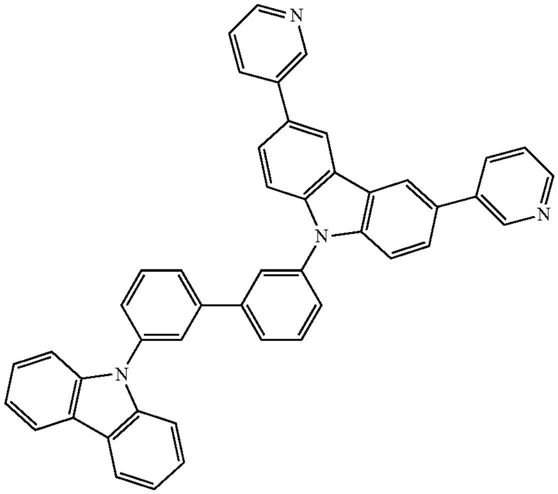
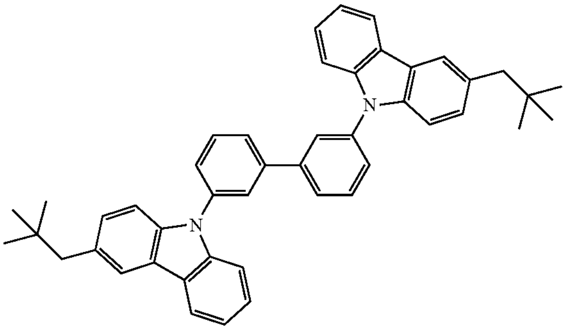
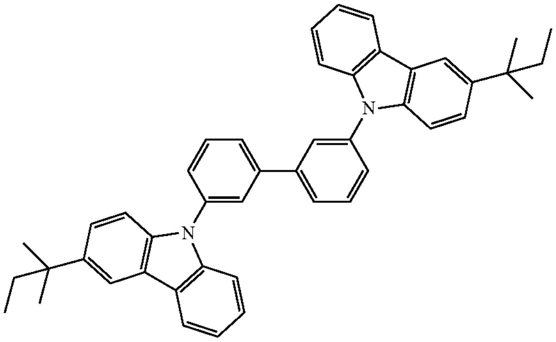
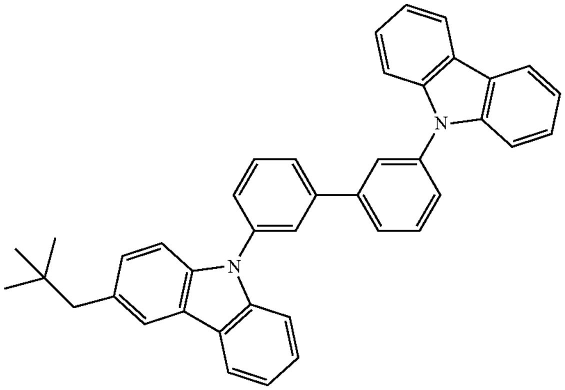

-continued
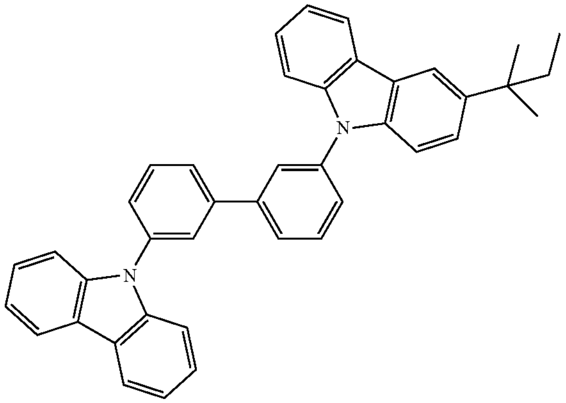
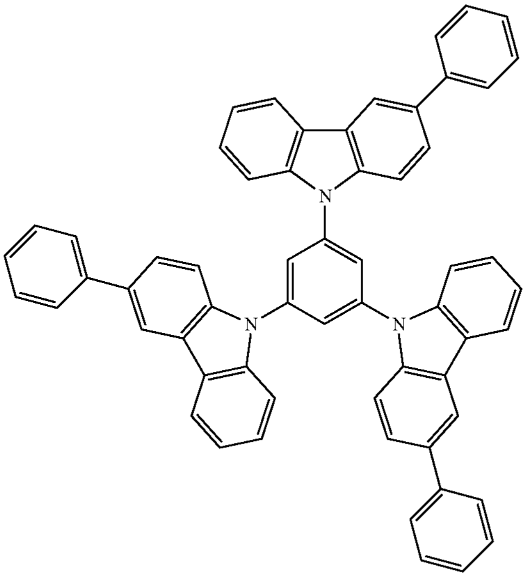
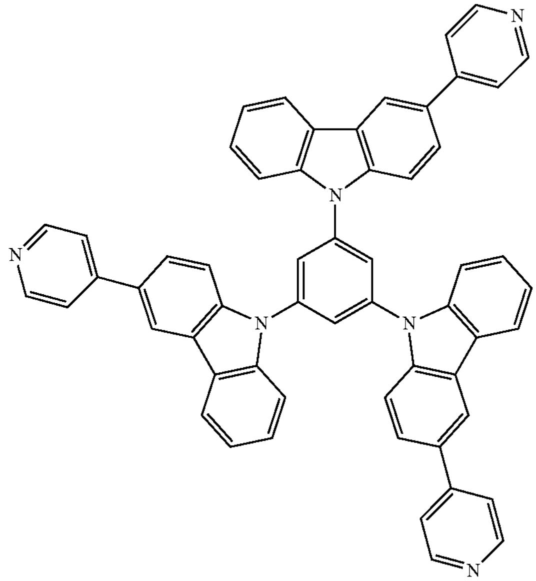
-continued
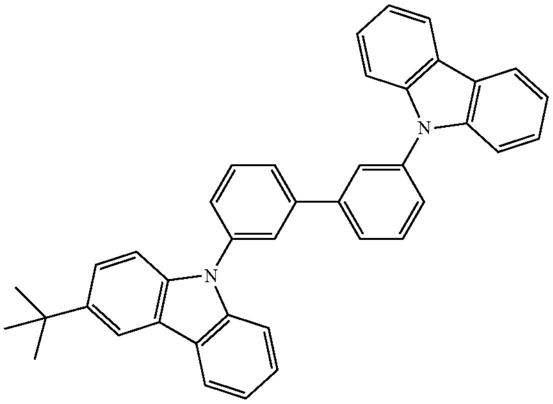
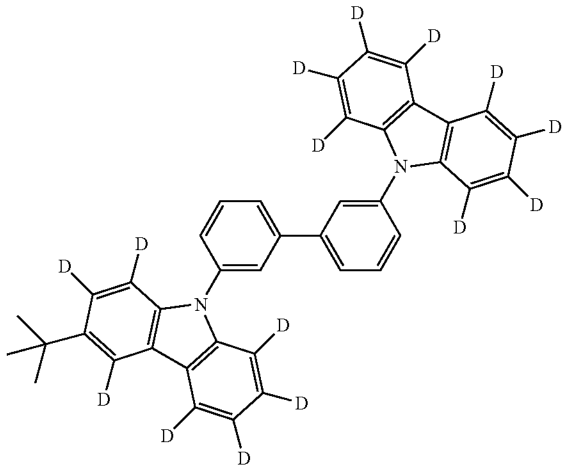
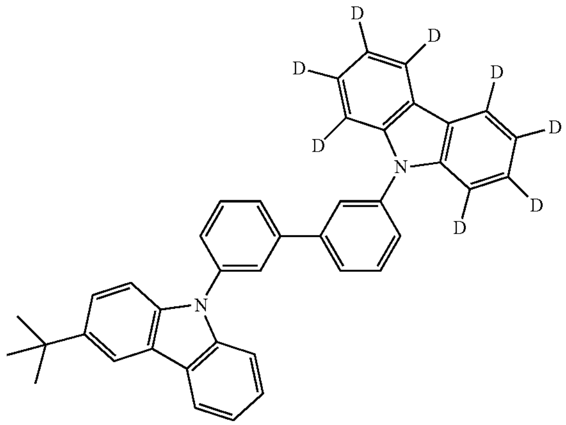
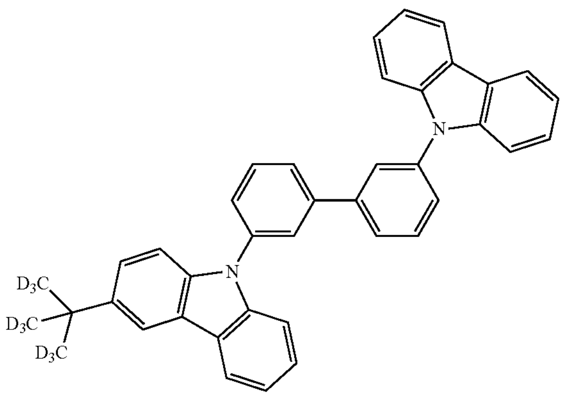

-continued
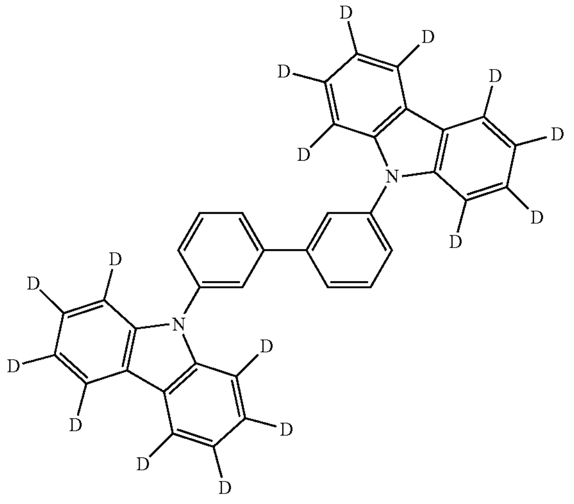
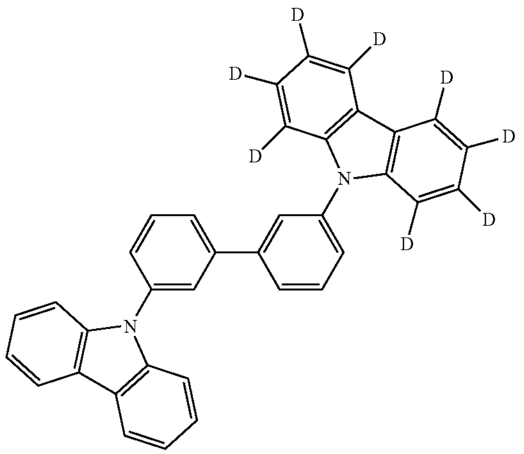
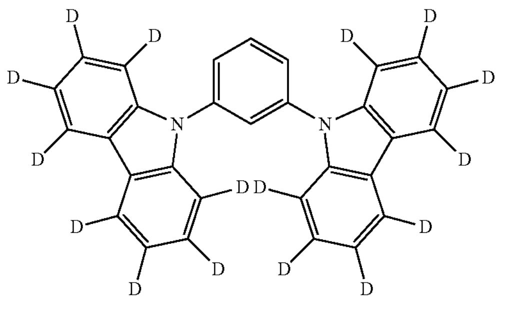
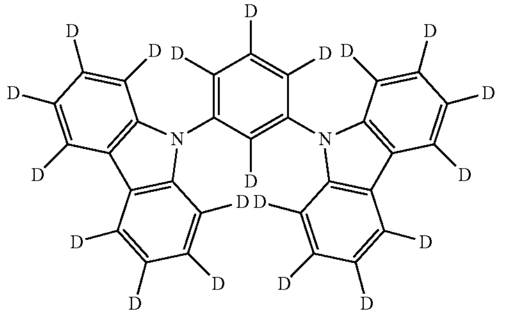
-continued
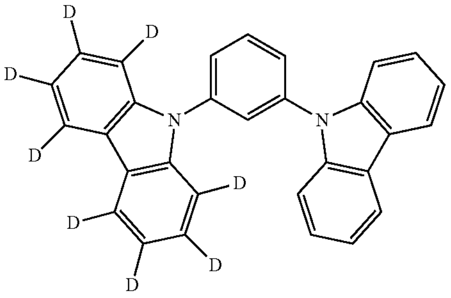
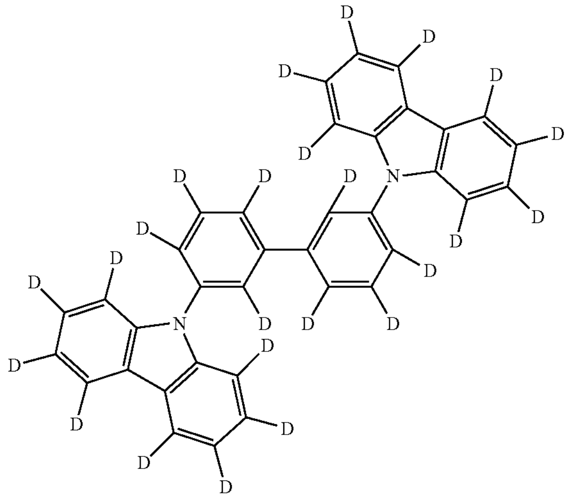
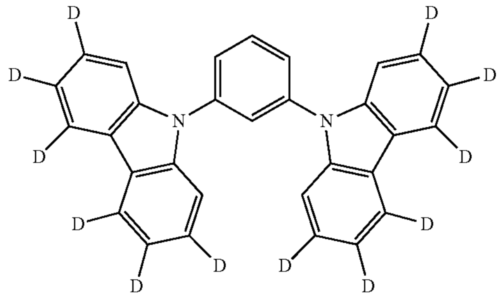
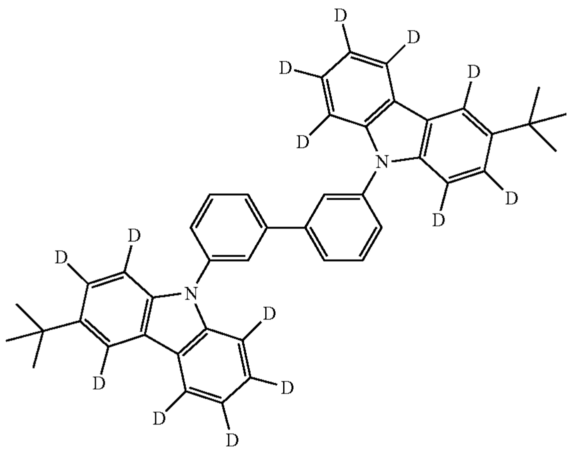

-continued

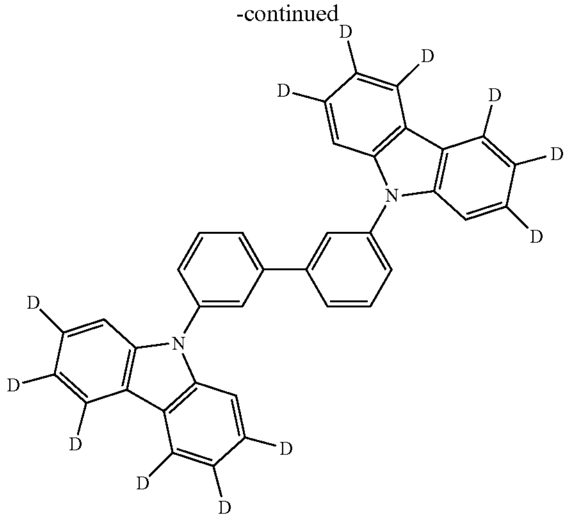

In the light-emitting layer, in the points of color purity, light emitting efficiency and driving durability, it is preferred that the lowest excitation triplet energy ($T_1$ energy) of the host material is higher than $T_1$ energy of the phosphorescent material. It is more preferred that $T_1$ of the host material is higher than $T_1$ of the phosphorescent material by 0.1 eV or more, more preferably higher by 0.2 eV or more, and still more preferably higher than by 0.3 eV or more.

If $T_1$ of the host material is smaller than $T_1$ of the phosphorescent material, light emission is quenched. Therefore, the host material is required to have higher $T_1$ than that of the phosphorescent material. Further, even when $T_1$ of the host material is higher than $T_1$ of the phosphorescent material, in the case where the difference in $T_1$ between both materials is small, reverse energy transfer from the phosphorescent material to the host material partially occurs, which causes efficiency reduction and durability reduction. Accordingly, a host material having sufficiently high $T_1$, chemical stability, and high carrier injection and transporting properties is required.

Although the content of the host compound in the invention is not especially restricted, but from the point of light emitting efficiency and driving voltage, the content is preferably 15% by mass or more and 95% by mass or less on the basis of the gross mass of the compounds for forming the light-emitting layer. When the light-emitting layer contains two or more kinds of host compounds containing a compound represented by any of formulae (1) to (3), the content of the compound represented by any of formulae (1) to (3) is preferably 50% by mass or more and 99% by mass or less in all the host compounds.

(Compound Represented by Formula (M-1))

The organic electroluminescence device in the invention comprises a pair of electrodes including the anode, and it is preferred to include at least one organic layer between the light-emitting layer and the anode, and it is preferred to contain at least one kind of a compound represented by the following formula (M-1) in the organic layer.

A compound represented by formula (M-1) is more preferably contained in an organic layer between the light-emitting layer and the anode and contiguous to the light-emitting layer, but the use is not restricted and may be contained in any layer of the organic layers. A compound represented by formula (M-1) of the invention can be contained in any layer or two or more layers of the light-emitting layer, a hole-injecting layer, a hole-transporting layer, an electron-transporting layer, an electron-injecting layer, an exciton-blocking layer, and a charge blocking layer.

The organic layer between the light-emitting layer and the anode and contiguous to the light-emitting layer in which a compound represented by formula (M-1) is contained is more preferably a hole-transporting layer.

(M-1)

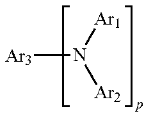

In formula (M-1), each of $Ar_1$ and $Ar_2$ independently represents alkyl, aryl, heteroaryl, arylamino, alkylamino, morpholino, thiomorpholino, 5- or 6-membered heterocycloalkyl containing 1 or more heteroatoms selected from N, O and S, or cycloalkyl, and they may further have substituent Z. Further, $Ar_1$ and $Ar_2$ may be bonded via a single bond, alkylene or alkenylene (irrespective of the presence of a condensed ring) to form a condensed 5- to 9-membered ring.

$Ar_3$ represents p-valent alkyl, aryl, heteroaryl or arylamino, and may further have substituent Z.

Each of substituent Z independently represents a halogen atom, —R", —OR", —N(R")$_2$, —SR", —C(O)R", —C(O)OR", —C(O)N(R")$_2$, —CN, —$NO_2$, —$SO_2$, —SOR", —$SO_2$R", or —$SO_3$R". Each of R" independently represents a hydrogen atom, an alkyl group, a perhaloalkyl group, an alkenyl group, an alkynyl group, an aryl group, or a heteroaryl group.

p represents an integer of 1 to 4, and when p is 2 or more, $Ar_1$ and $Ar_2$ may be the same with or different from each other.

The compound represented by formula (M-1) is preferably represented by the following formula (M-2).

(M-2)

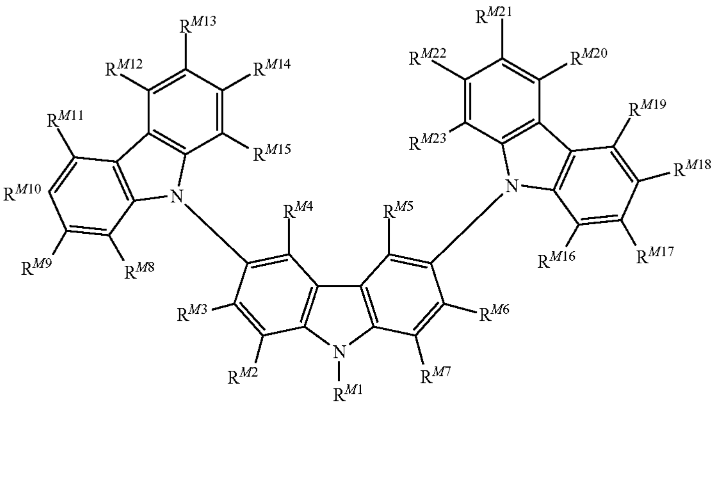

In formula (M-2), $R^{M1}$ represents an alkyl group, an aryl group or a heteroaryl group.

Each of $R^{M2}$ to $R^{M23}$ independently represents a hydrogen atom, an alkyl group, an aryl group, a heteroaryl group, an alkoxy group, an aryloxy group, an amino group, a silyl group, a cyano group, a nitro group or a fluorine atom.

In formula (M-2), $R^{M1}$ represents an alkyl group (preferably having 1 to 8 carbon atoms), an aryl group (preferably having 6 to 30 carbon atoms) or a heteroaryl group (preferably having 4 to 12 carbon atoms). These groups may have substituent Z. $R^{M1}$ preferably represents an aryl group or a heteroaryl group, and more preferably an aryl group. As preferred examples of the substituents at the time when the aryl group represented by $R^{M1}$ has a substituent, an alkyl group, a halogen atom, a cyano group, an aryl group, and an alkoxy group are exemplified, an alkyl group, a halogen atom, a cyano group, and an aryl group are more preferred, and an alkyl group, a cyano group and an aryl group are still more preferred. The aryl group represented by $R^{M1}$ is preferably a phenyl group which may have substituent Z, and more preferably a phenyl group which may have an alkyl group or a cyano group.

Each of $R^{M2}$ to $R^{M23}$ independently represents a hydrogen atom, an alkyl group (preferably having 1 to 8 carbon atoms), an aryl group (preferably having 6 to 30 carbon atoms), a heteroaryl group (preferably having 4 to 12 carbon atoms), an alkoxy group (preferably having 1 to 8 carbon atoms), an aryloxy group (preferably having 6 to 30 carbon atoms), an amino group (preferably having 0 to 24 carbon atoms), a silyl group (preferably having 0 to 18 carbon atoms), a cyano group, a nitro group or a fluorine atom, and these groups may have substituent Z.

Each of $R^{M2}$, $R^{M7}$, $R^{M8}$, $R^{M15}$, $R^{M16}$ and $R^{M23}$ preferably represents a hydrogen atom, or an alkyl group or an aryl group which may have substituent Z, and more preferably a hydrogen atom.

Each of $R^{M4}$, $R^{M5}$, $R^{M11}$, $R^{M12}$, $R^{M19}$, and $R^{M20}$ preferably represents a hydrogen atom, an alkyl group or an aryl group which may have substituent Z, or a fluorine atom, and more preferably a hydrogen atom.

Each of $R^{M3}$, $R^{M9}$, $R^{M14}$, $R^{M17}$ and $R^{M22}$ preferably represents a hydrogen atom, an alkyl group or an aryl group which may have substituent Z, a fluorine atom, or a cyano group, and more preferably a hydrogen atom, or an alkyl group which may have substituent Z, and more preferably a hydrogen atom.

Each of $R^{M10}$, $R^{M13}$, $R^{M18}$ and $R^{M21}$ preferably represents a hydrogen atom, an alkyl group, an aryl group, a heteroaryl group or an amino group which may have substituent Z, a nitro group, a fluorine atom, or a cyano group, more preferably a hydrogen atom, an alkyl group or an aryl group which may have substituent Z, a nitro group, a fluorine atom, or a cyano group, and still more preferably a hydrogen atom, or an alkyl group which may have substituent Z. As the example of the substituent at the time when the alkyl group has a substituent, a fluorine atom is preferred, and the carbon atom number of the alkyl group which may have substituent Z is 1 to 6, and more preferably 1 to 4.

The compound represented by formula (M-1) is preferably represented by the following formula (M-3).

(M-3)

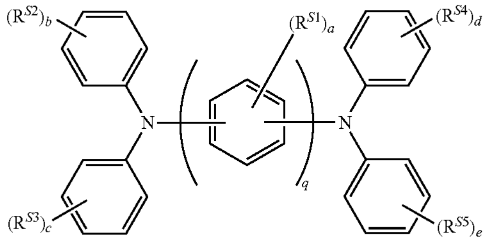

In formula (M-3), each of $R^{S1}$ to $R^{S5}$ independently represents an alkyl group, a cyaloalkyl group, an alkenyl group, an alkynyl group, —CN, a perfluoroalkyl group, a trifluorovinyl group, —$CO_2R$, —C(O)R, —$NR_2$, —$NO_2$, —OR, a halogen atom, an aryl group, or a heteroaryl group, which may further have substituent Z. Each of R independently represents a hydrogen atom, an alkyl group, a perhaloalkyl group, an alkenyl group, an alkynyl group, an aryl group, or a heteroaryl group. When a plurality of $R^{S1}$ to $R^{S5}$ are present, they may be bonded to each other to form a ring, and may further have substituent Z.

a represents an integer of 0 to 4, and when a plurality of $R^{S1}$ are present, they may be the same with or different from each other, and may be bonded to each other to form a ring. Each of b to e independently represents an integer of 0 to 5, and when a plurality of $R^{S2}$ to $R^{S5}$ are present, they may be the same with or different from each other, and optional two may be bonded to each other to form a ring.

q represents an integer of 1 to 5, and when q is 2 or more, a plurality of $R^{S1}$ may be the same with or different from each other, and they may be bonded to each other to form a ring.

The alkyl group may have a substituent, may be saturated or unsaturated, and as the group which may be substituted, the above substituent Z can be exemplified. The alkyl group represented by each of $R^{S1}$ to $R^{S5}$ is an alkyl group having 1 to 8 carbon atoms in total, and more preferably an alkyl group having 1 to 6 carbon atoms in total, and, e.g., a methyl group, an ethyl group, an i-propyl group, a cyclohexyl group, and a t-butyl group can be exemplified.

The cycloalkyl group may have a substituent, may be saturated or unsaturated, and as the group which may be substituted, the above substituent Z can be exemplified. The cycloalkyl group represented by each of $R^{S1}$ to $R^{S5}$ is preferably a cycloalkyl group having 4 to 7 carbon atoms in total, and more preferably a cycloalkyl group having 5 to 6 carbon atoms in total, and, e.g., a cyclopentyl group and a cyclohexyl group can be exemplified.

The alkenyl group represented by each of $R^{S1}$ to $R^{S5}$ is preferably an alkenyl group having 2 to 30 carbon atoms, more preferably 2 to 20 carbon atoms, and especially preferably 2 to 10 carbon atoms, and, e.g., vinyl, allyl, 1-propenyl, 1-isopropenyl, 1-butenyl, 2-butenyl and 3-pentenyl are exemplified.

The alkynyl group represented by each of $R^{S1}$ to $R^{S5}$ is preferably an alkynyl group having 2 to 30 carbon atoms, more preferably 2 to 20 carbon atoms, and especially preferably 2 to 10 carbon atoms, and, e.g., ethynyl, propargyl, 1-propynyl, and 3-pentynyl are exemplified.

As the perfluoroalkyl group represented by each of $R^{S1}$ to $R^{S5}$, the groups obtained by substituting all the hydrogen atoms of the above alkyl groups with fluorine atoms can be exemplified.

The aryl group represented by each of $R^{S1}$ to $R^{S5}$ is preferably a substituted or unsubstituted aryl group having 6 to 30 carbon atoms, and, e.g., a phenyl group, a tolyl group, a biphenyl group and a terphenyl group can be exemplified.

The heteroaryl group represented by each of $R^{S1}$ to $R^{S5}$ is preferably a heteroaryl group having 5 to 8 carbon atoms, and more preferably a substituted or unsubstituted 5- or 6-membered heteroaryl group, and, for example, a pyridyl group, a pyrazinyl group, a pyridazinyl group, a pyrimidinyl group, a triazinyl group, a quinolinyl group, an isoquinolinyl group, a quinazolinyl group, a cinnolinyl group, a phthalazinyl group, a quinoxalinyl group, a pyrrolyl group, an indolyl group, a furyl group, a benzofuryl group, a thienyl group, a benzothienyl group, a pyrazolyl group, an imidazolyl group, a benzimidazolyl group, a triazolyl group, an oxazolyl group, a benzoxazolyl group, a thiazolyl group, a benzothiazolyl group, an isothiazolyl group, a benzisothiazolyl group, a thiadiazolyl group, an isoxazolyl group, a benzisoxazolyl group, a pyrrolidinyl group, a piperidinyl group, a piperazinyl group, an imidazolidinyl group, a thiazolinyl group, a sulforanyl group, a carbazolyl group, a dibenzofuryl group, a dibenzothienyl group, and a pyridoindolyl group are exemplified. The preferred examples include a pyridyl group, a pyrimidinyl group, an imidazolyl group, and a thienyl group, and more preferred examples are a pyridyl group and a pyrimidinyl group.

Each of $R^{S1}$ to $R^{S5}$ preferably represents a hydrogen atom, an alkyl group, a cyano group, a trifluoromethyl group, a perfluoroalkyl group, a dialkylamino group, a fluoro group, an aryl group or a heteroaryl group, more preferably represents a hydrogen atom, an alkyl group, a cyano group, a trifluoromethyl group, a fluoro group, or an aryl group, and still more preferably represents a hydrogen atom, an alkyl group or an aryl group. As substituent Z, an alkyl group, an alkoxy group, a fluoro group, a cyano group, and a dialkylamino group are preferred, and a hydrogen atom and an alkyl group are more preferred.

Optional two of $R^{S1}$ to $R^{S5}$ may be bonded to each other to form a condensed 4- to 7-membered ring. The condensed 4- to 7-membered ring is cycloalkyl, aryl or heteroaryl, and the condensed 4- to 7-membered ring may further have substituent Z. The definitions and preferred ranges of the cycloalkyl, aryl and heteroaryl to be formed are the same as those defined as to the cycloalkyl group, aryl group and heteroaryl group in $R^{S1}$ to $R^{S5}$.

When the compound represented by formula (M-1) is used in the hole-transporting layer, the compound represented by formula (M-1) is preferably contained in an amount of 50% by mass to 100% by mass, more preferably 80% by mass to 100% by mass, and especially preferably 95% by mass to 100% by mass.

When the compound represented by formula (M-1) is contained in two or more organic layers, it is preferred to contain the compound in each layer in the above range.

The compound represented by formula (M-1) may be contained in any organic layer one kind alone, or the compound represented by formula (M-1) may be used in combination in a proper rate.

The thickness of the hole-transporting layer containing the compound represented by formula (M-1) is preferably 1 nm to 500 nm, more preferably 3 nm to 200 nm, and still more preferably 5 nm to 100 nm. It is preferred to provide the hole-transporting layer in contiguous to the light-emitting layer.

The hole-transporting layer may take a single layer structure comprising one or two or more kinds of the above-described materials or may take a multilayer structure of two or more layers of the same composition or different compositions.

The lowest excitation triplet energy ($T_1$) in a thin film state of the compound represented by formula (M-1) is preferably 2.52 eV (58 kcal/mol) or more and 3.47 eV (80 kcal/mol) or less, more preferably 2.60 eV (60 kcal/mol) or more and 3.25 eV (75 kcal/mol) or less, and still more preferably 2.69 eV (62 kcal/mol) or more and 3.04 eV (70 kcal/mol) or less.

The hydrogen atoms for constituting formula (M-1) also include the isotopes of hydrogen atoms (deuterium atoms and the like). In such a case, all the hydrogen atoms in the compound may be substituted with hydrogen isotopes, or the compound may be mixtures partially containing hydrogen isotopes.

The compounds represented by formula (M-1) can be synthesized by combining various known synthesis methods. Most generally, concerning the carbazole compounds, synthesis by dehydrogenation aromatization after aza-Cope rearrangement of the condensation product of aryl hydrazine and cyclohexane derivative (L. F. Tieze, Th. Eicher, translated by Takano and Ogasawara, Precision Organic Syntheses, p. 339, published by Nanko-Do) is exemplified. Further, concerning the coupling reaction of the obtained carbazole compound and an aryl halide compound using a palladium catalyst, the methods described in Tetrahedron Letters, Vol. 39, p. 617 (1998), ibid., Vol. 39, p. 2367 (1998), and ibid., Vol. 40, p. 6393 (1999) are exemplified. The reaction temperature and reaction time are not especially restricted and the conditions in the above documents are applied.

It is preferred that the thin layer of the compound represented by formula (M-1) is formed according to a vacuum deposition process, but a wet process such as solution coating can also be preferably used. The molecular weight of the compound is preferably 2,000 or less in view of deposition suitability and solubility, more preferably 1,200 or less, and especially preferably 800 or less. Further, in the point of vacuum deposition suitability, too small a molecular weight is accompanied by small vapor pressure and transition from a vapor phase to a solid phase does not occur and it becomes difficult to form an organic layer. Accordingly, the molecular weight is preferably 250 or more, and especially preferably 300 or more.

The specific examples of the compounds represented by formula (M-1) are shown below, but the invention is not restricted thereto.

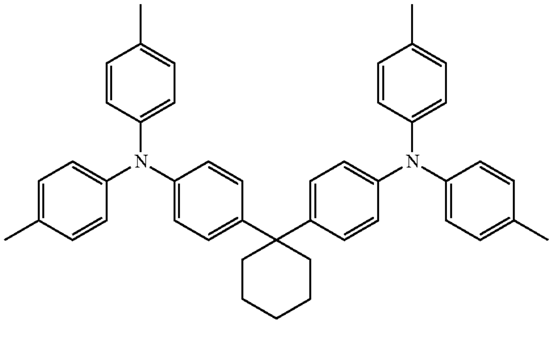

-continued
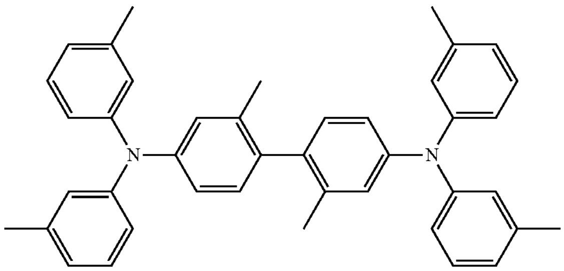
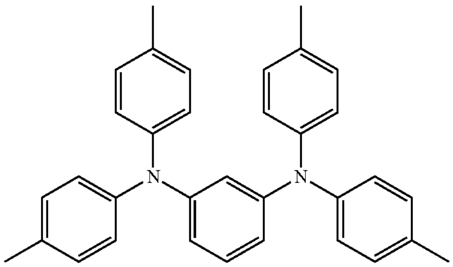
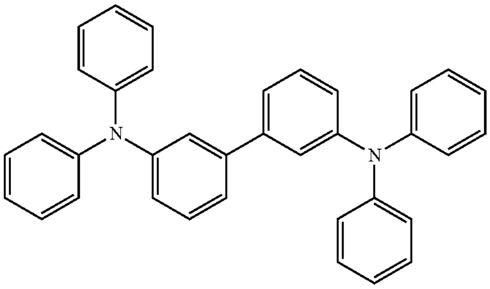
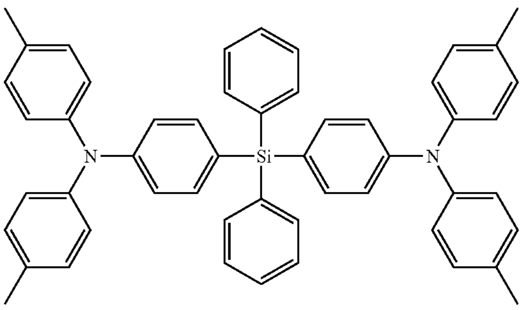
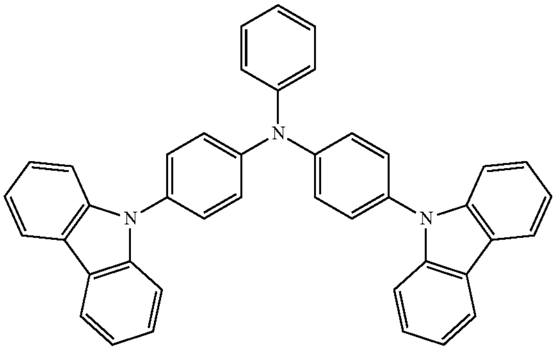
-continued
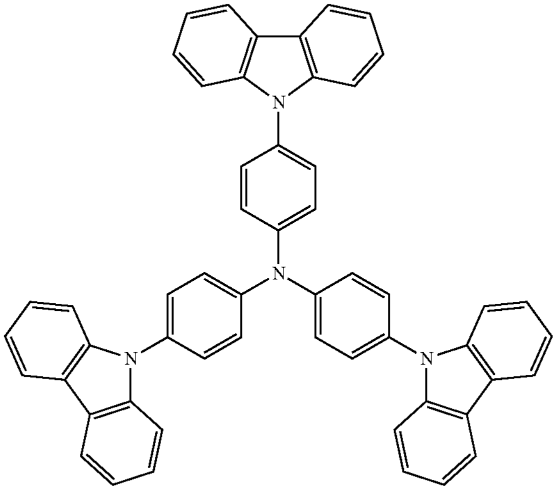
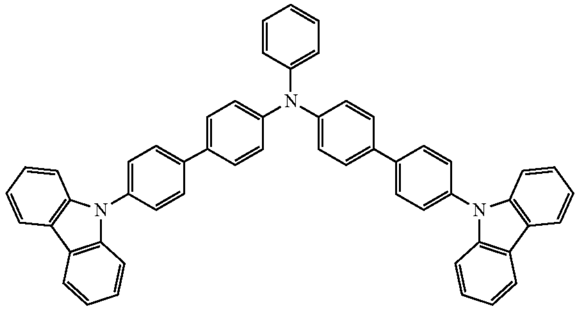
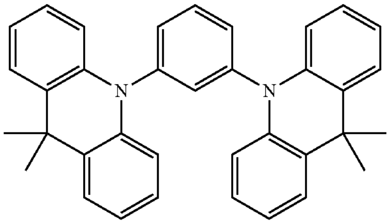
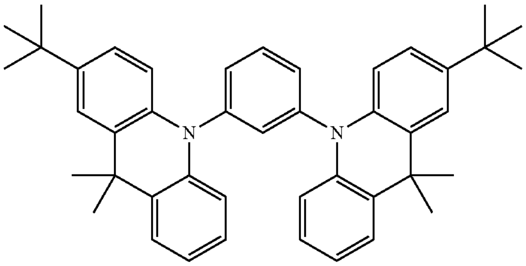
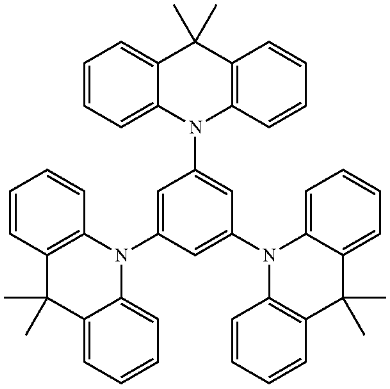

-continued
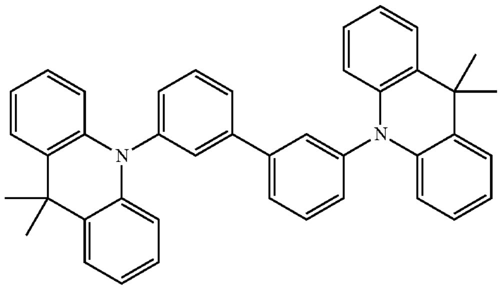
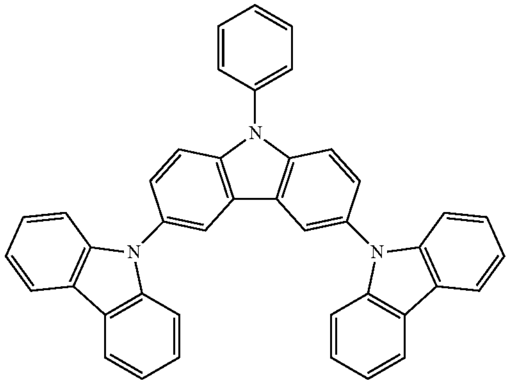
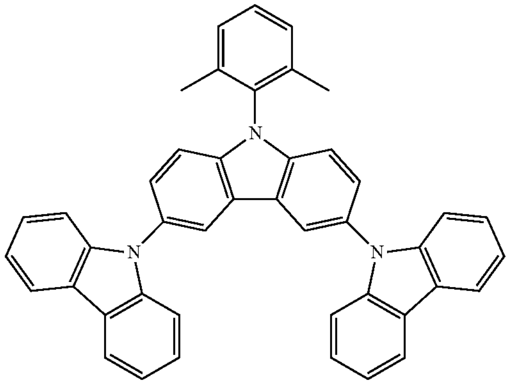
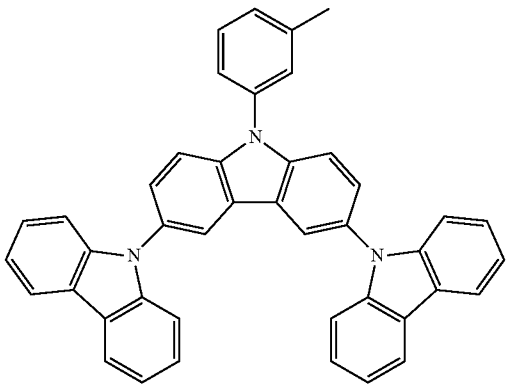
-continued
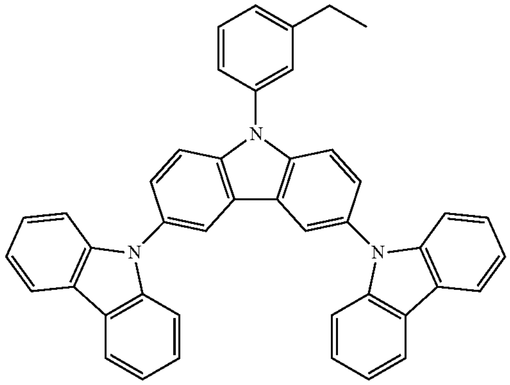
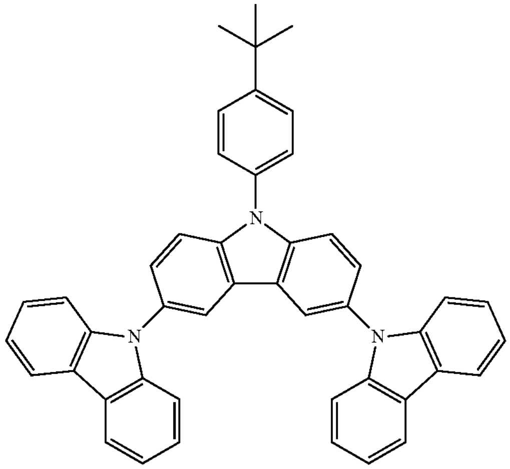
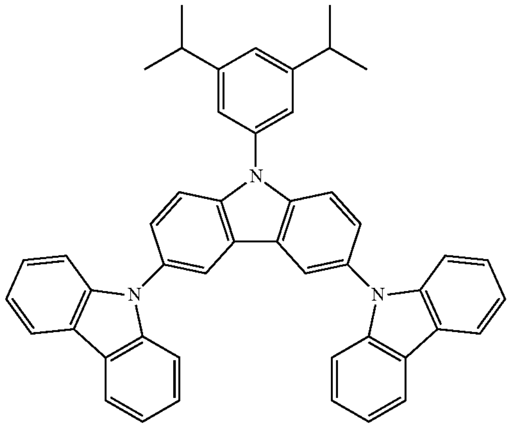
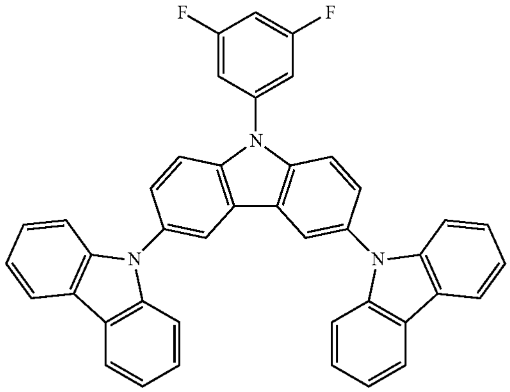

-continued
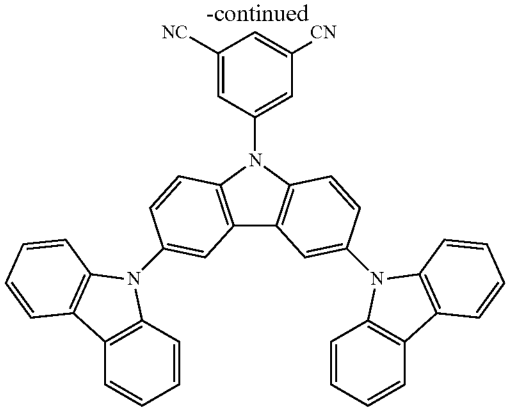
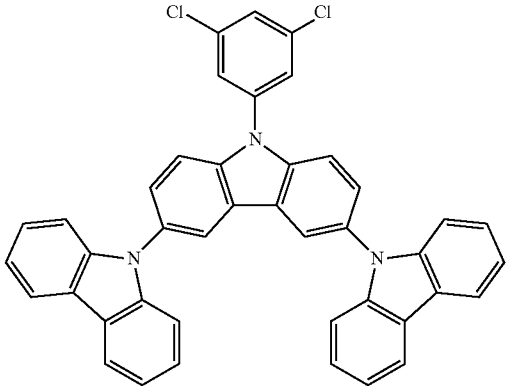
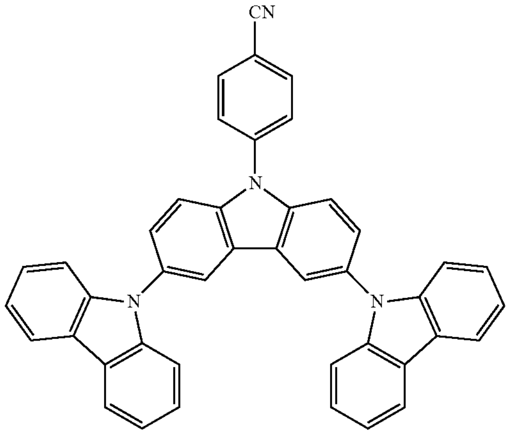
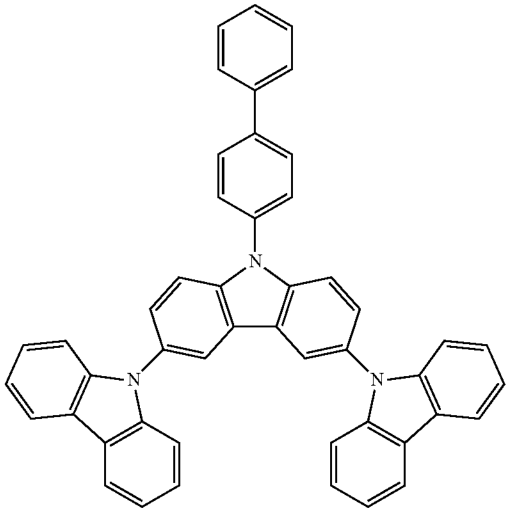
-continued
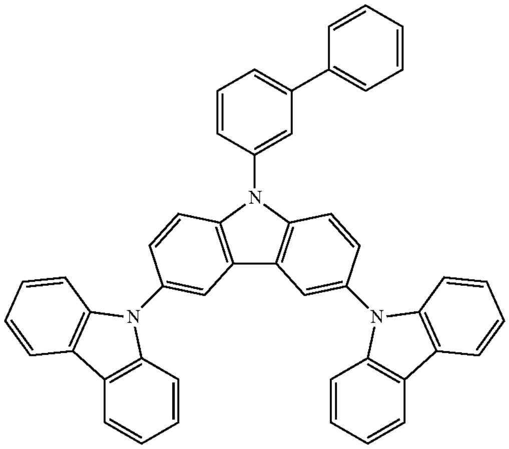
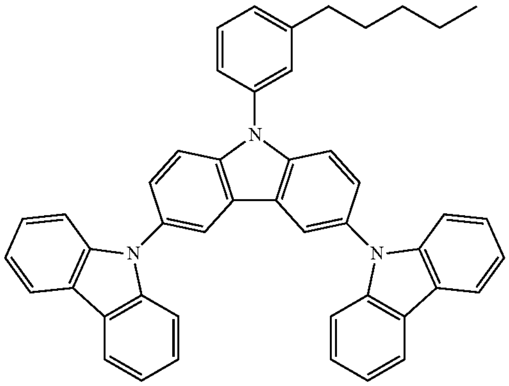
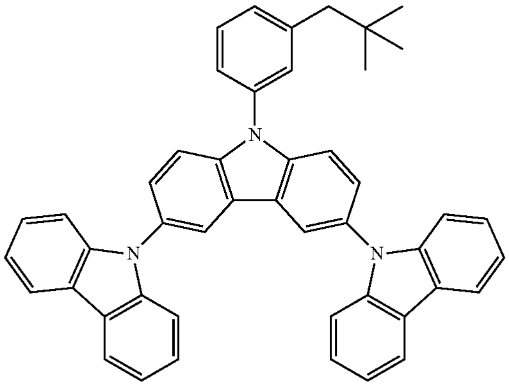
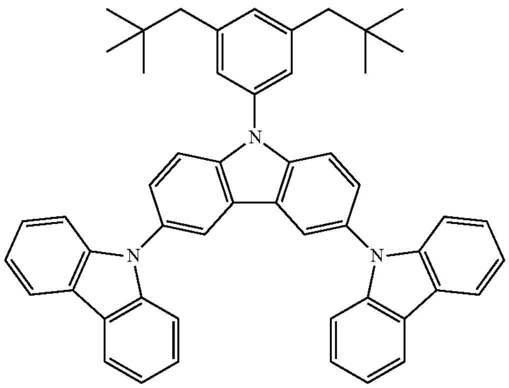

-continued
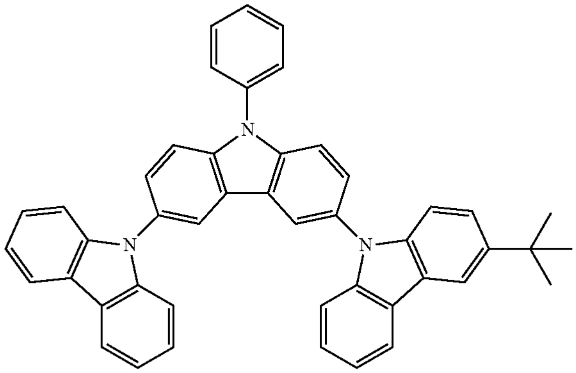
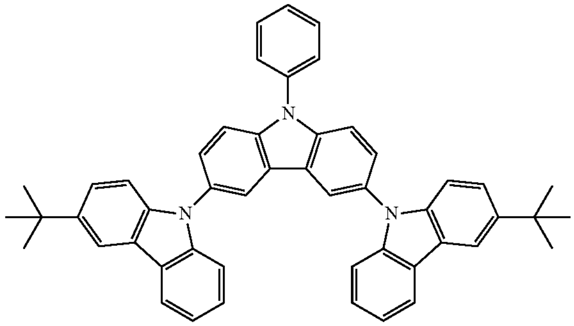
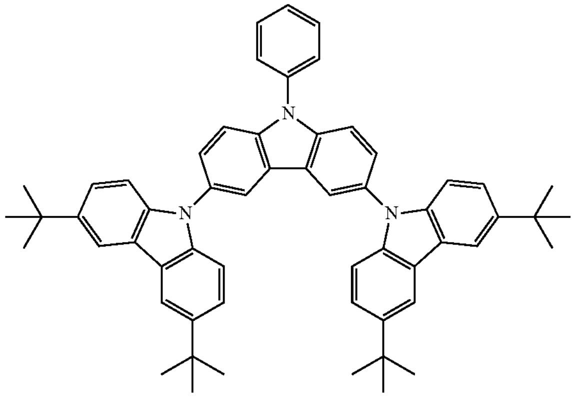
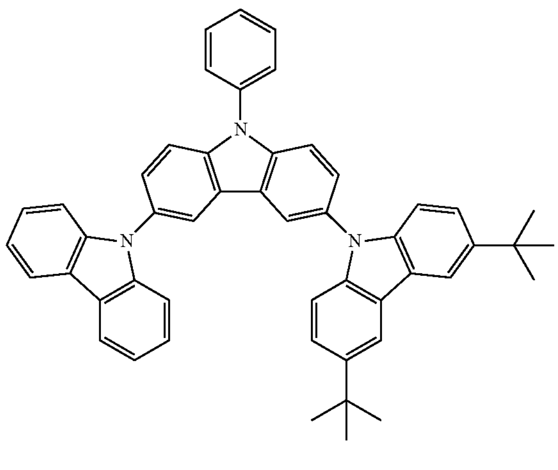
-continued
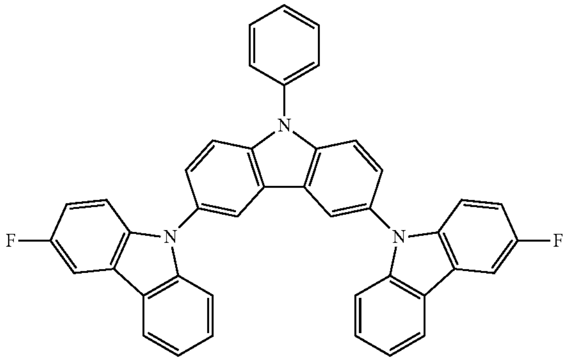
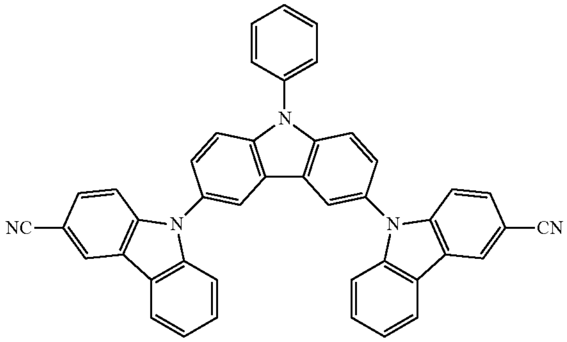
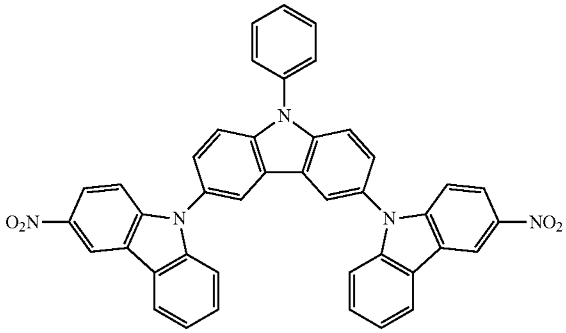
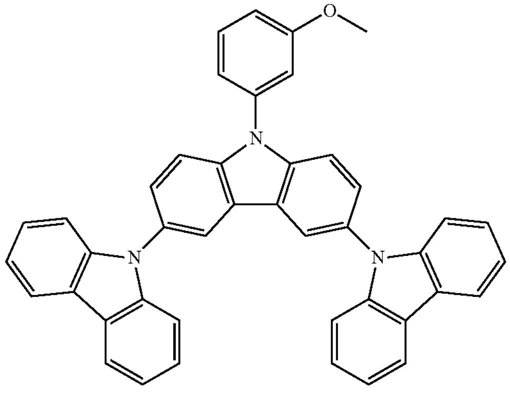

-continued
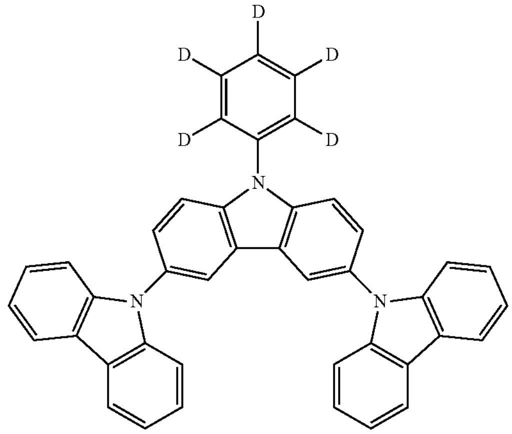
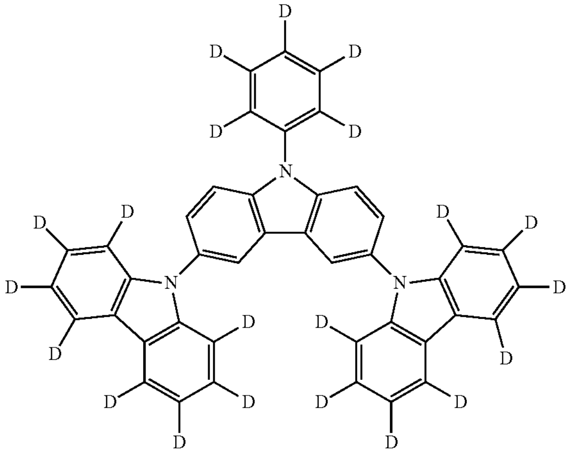
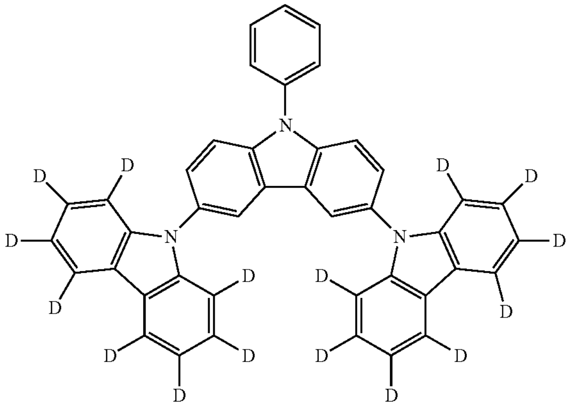
-continued
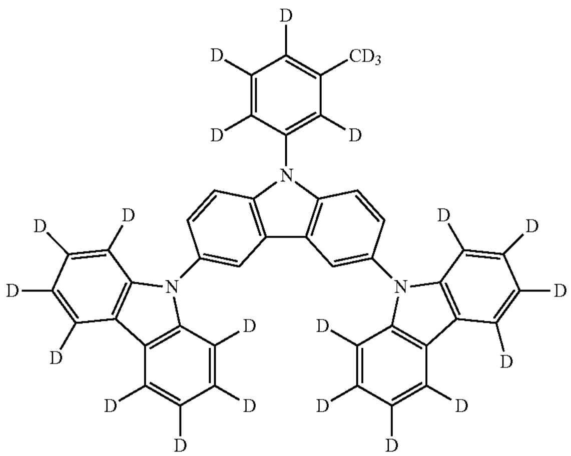
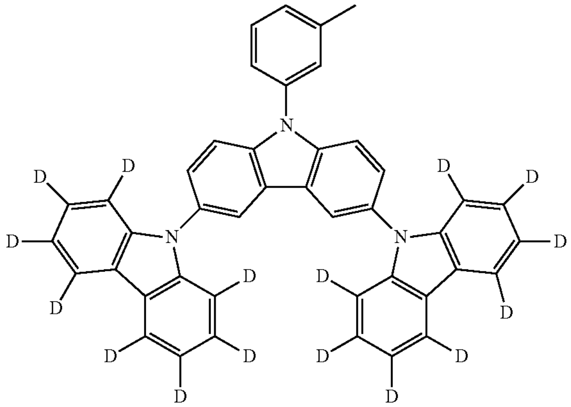
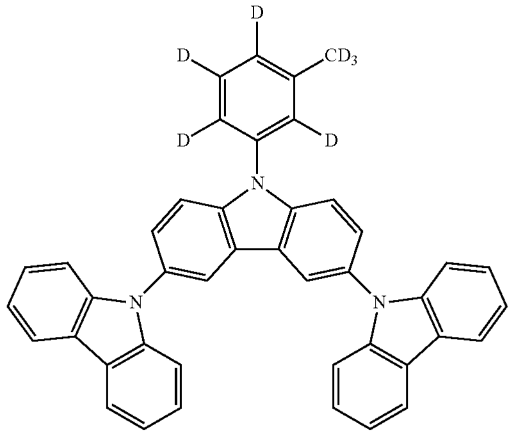
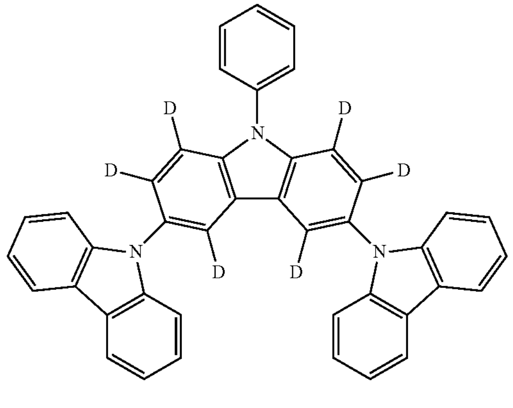 [SMILES: [2H]c1c(-n2c3ccccc3c3ccccc32)c([2H])c2c3c([2H])c(-n4c5ccccc5c5ccccc54)c([2H])c([2H])c3n(-c3ccccc3)c2c1[2H]]

[Aromatic Hydrocarbon Compound]

The organic electroluminescence device in the invention comprises a pair of electrodes including the anode, and it is preferred to include at least one organic layer between the light-emitting layer and the anode, and it is preferred to contain an aromatic hydrocarbon compound in the organic layer.

The aromatic hydrocarbon compound is more preferably contained in an organic layer between the light-emitting layer and the anode and contiguous to the light-emitting layer, but the use is not restricted and may be contained in any layer of the organic layers. The aromatic hydrocarbon compound of the invention can be contained in any layer or two or more layers of the light-emitting layer, a hole-injecting layer, a hole-transporting layer, an electron-transporting layer, an electron-injecting layer, an exciton-blocking layer, and a charge blocking layer.

The organic layer between the light-emitting layer and the anode and contiguous to the light-emitting layer in which the aromatic hydrocarbon compound is contained is preferably a charge blocking layer or an electron-transporting layer, and more preferably an electron-transporting layer.

The aromatic hydrocarbon compound is preferably composed of carbon atoms and hydrogen atoms alone in view of easiness of synthesis.

When the aromatic hydrocarbon compound is contained in the layers other than the light-emitting layer, the content is preferably 70% by mass to 100% by mass, and more preferably 85% by mass to 100% by mass. When the aromatic hydrocarbon compound is contained in the light-emitting layer, the content is preferably 0.1% by mass to 99% by mass to the gross mass of the light-emitting layer, more preferably 1% by mass to 95% by mass, and still more preferably 10% by mass to 95% by mass.

It is preferred to use a hydrocarbon compound comprising carbon atoms and hydrogen atoms alone, having a molecular weight in the range of 400 to 1,200, and condensed polycyclic structure of the total carbon atom number of 13 to 22. As the condensed polycyclic structure of the total carbon atom number of 13 to 22, any of fluorene, anthracene, phenanthrene, tethracene, chrysene, pentacene, pyrene, perylene, and triphenylene is preferred, fluorene, triphenylene and phenanthrene are more preferred in view of $T_1$, triphenylene is more preferred from the point of compound stability and charge injecting and transporting properties, and a compound represented by the following formula (Tp-1) is especially preferred.

The hydrocarbon compound represented by formula (Tp-1) has a molecular weight of preferably in the range of 400 to 1,200, more preferably 400 to 1,000, and still more preferably 400 to 800. When the molecular weight is 400 or more, an amorphous film of fine quality can be formed, while when the molecular weight is 1,200 or less, good solubility in a solvent is obtained, and preferred in the aspect of sublimation and vacuum deposition suitability.

The use of the hydrocarbon compound represented by formula (Tp-1) is not restricted, and may be contained not only in the organic layer contiguous to the light-emitting layer but also in any layer of the organic layers.

(Tp-1)

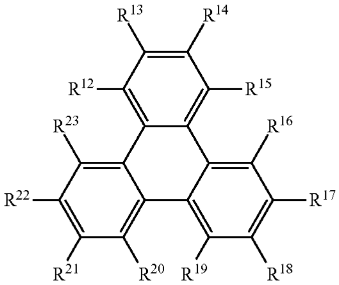

In formula (Tp-1), each of $R^{12}$ to $R^{23}$ independently represents a hydrogen atom, an alkyl group, or a phenyl group, a fluorenyl group, a naphthyl group, or a triphenylenyl group (these groups may be substituted with an alkyl group, a phenyl group, a fluorenyl group, a naphthyl group or a triphenylenyl group), provided that all of $R^{12}$ to $R^{23}$ do not represent a hydrogen atom.

As the alkyl group represented by each of $R^{12}$ to $R^{23}$, for example, a methyl group, an ethyl group, an isopropyl group, an n-butyl group, a tert-butyl group, an n-octyl group, an n-decyl group, an n-hexadecyl group, a cyclopropyl group, a cyclopentyl group, and a cyclohexyl group are exemplified, each of which may be substituted or unsubstituted, preferably a methyl group, an ethyl group, an isopropyl group, a tert-butyl group, and a cyclohexyl group, and more preferably a methyl group, an ethyl group, and a tert-butyl group.

Each of $R^{12}$ to $R^{23}$ preferably represents an alkyl group having 1 to 4 carbon atoms, or a phenyl group, a fluorenyl group, a naphthyl group, or a triphenylenyl group (these groups may further be substituted with an alkyl group, a phenyl group, a fluorenyl group, a naphthyl group, or a triphenylenyl group), each of which may be substituted with an alkyl group having 1 to 4 carbon atoms, a phenyl group, a fluorenyl group, a naphthyl group, or a triphenylenyl group.

A benzene ring which may be substituted with a phenyl group, a fluorenyl group, a naphthyl group or a triphenylenyl group (these groups may further be substituted with an alkyl group, a phenyl group, a fluorenyl group, a naphthyl group or a triphenylenyl group) is especially preferred.

The total number of aryl rings in formula (Tp-1) is preferably 2 to 8, and more preferably 3 to 5. When the number of the aryl rings is in this range, an amorphous film of fine quality can be formed, and solubility in a solvent, sublimation and vacuum deposition suitability are improved.

Each of $R^{12}$ to $R^{23}$ independently preferably has total carbon atoms of 20 to 50, and more preferably total carbon atoms of 20 to 36. In this range of total carbon atoms, an amorphous film of fine quality can be formed, and solubility in a solvent, sublimation and vacuum deposition suitability are improved.

In one embodiment of the invention, the hydrocarbon compound represented by formula (Tp-1) is preferably a hydrocarbon compound represented by the following formula (Tp-2).

(Tp-2)

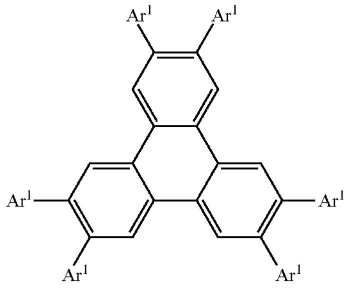

In formula (Tp-2), a plurality of $Ar^1$ are the same with each other and represent a phenyl group, a fluorenyl group, a naphthyl group, or a triphenylenyl group which may be substituted with an alkyl group, a phenyl group, a fluorenyl group, a naphthyl group, or a triphenylenyl group.

The alkyl group, and the phenyl group, fluorenyl group, naphthyl group and triphenylenyl group represented by $Ar^1$, which may be substituted with an alkyl group, a phenyl group, a fluorenyl group, a naphthyl group or a triphenylenyl group, are the same with those described in $R^{12}$ to $R^{23}$ and preferred ranges are also the same.

In another embodiment of the invention, the hydrocarbon compound represented by formula (Tp-1) is preferably a hydrocarbon compound represented by the following formula (Tp-3).

Formula (Tp-3)

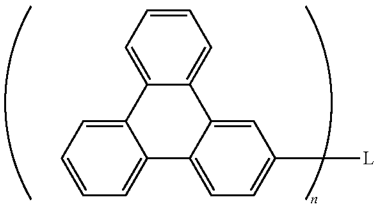

In formula (Tp-3), L represents a phenyl group, a fluorenyl group, a naphthyl group, or a triphenylenyl group which may be substituted with an alkyl group, a phenyl group, a fluorenyl group, a naphthyl group or a triphenylenyl group, or an n-valent linking group obtained by combining these groups. n represents an integer of 1 to 6.

The alkyl group, phenyl group, fluorenyl group, naphthyl group, or triphenylenyl group forming the n-valent linking group represented by L has the same meaning as described in $R^{12}$ to $R^{23}$.

L preferably represents a benzene ring or a fluorene ring which may be substituted with an alkyl group or a benzene ring, or an n-valent linking group obtained by combining these groups.

The preferred specific examples of L are shown below, but the invention is not restricted thereto. In the specific examples, L bonds to a triphenylen ring via *.

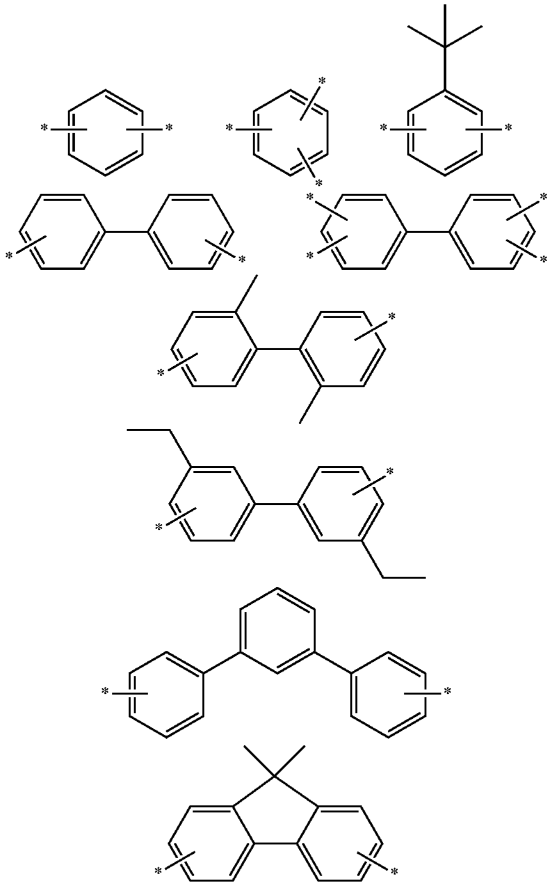

n is preferably 1 to 5, and more preferably 1 to 4.

In another embodiment of the invention, the hydrocarbon compound represented by formula (Tp-1) is preferably a hydrocarbon compound represented by the following formula (Tp-4).

(Tp-4)

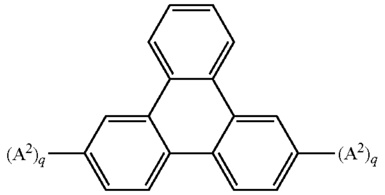

In formula (Tp-4), a plurality of $Ar^2$ are the same with each other, and $Ar^2$ represent a group substituted with an alkyl group, a phenyl group, a naphthyl group, or a triphenylenyl group, or a group obtained by combining these groups. Each of p and q independently represents 0 or 1, provided that p and q do not represent 0 at the same time. When each of p and q represents 0, $Ar^2$ represents a hydrogen atom.

$Ar^2$ preferably represents a group obtained by combining an alkyl group having 1 to 4 carbon atoms, a phenyl group, a naphthyl group, and a triphenylenyl group, and more preferably a group obtained by combining a methyl group, a t-butyl group, a phenyl group and a triphenylenyl group.

$Ar^2$ is especially preferably a benzene ring whose meta-position is substituted with an alkyl group having 1 to 4 carbon atoms, a phenyl group, a naphthyl group, a triphenylenyl group, or a group obtained by combining these groups.

In the case where the hydrocarbon compound according to the invention is used as the host material of the light-emitting layer of the organic electroluminescence device or as the charge-transporting material of the layer contiguous to the light emitting layer, when the energy gap of the hydrocarbon compound in a film state (the lowest excitation triplet energy ($T_1$) in a film state in the case where the light-emitting material is a phosphorescent material) is greater than that of the light-emitting material, quenching of light emission can be prevented, and so advantageous in the improvement of efficiency. On the other hand, from the viewpoint of chemical stability of the hydrocarbon compound, energy gap and $T_1$ energy are preferably not too high. $T^1$ energy of the hydrocarbon compound represented by formula (Tp-1) in a film state is preferably 52 kcal/mol or more and 80 kcal/mol or less, more preferably 55 kcal/mol or more and 68 kcal/mol or less, and still more preferably 58 kcal/mol or more and 63 kcal/mol or less. In particular, when a phosphorescent material is used as the light-emitting material, it is preferred that $T_1$ energy comes into the above range.

$T_1$ energy can be found by the same method as in the description of formula (1).

From the aspect of driving the organic electroluminescence device stably at high temperature driving time or to the calorification during driving of the device, the glass transition temperature (Tg) of the hydrocarbon compound of the invention is preferably 80° C. or more and 400° C. or less, more preferably 100° C. or more and 400° C. or less, and still more preferably 120° C. or more and 400° C. or less.

The specific examples of the hydrocarbon compounds according to the invention are shown below, but the invention is not restricted thereto.

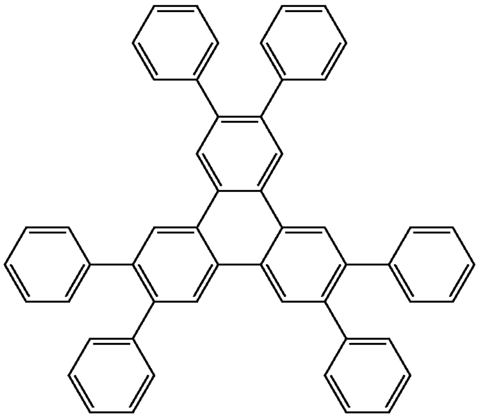

-continued

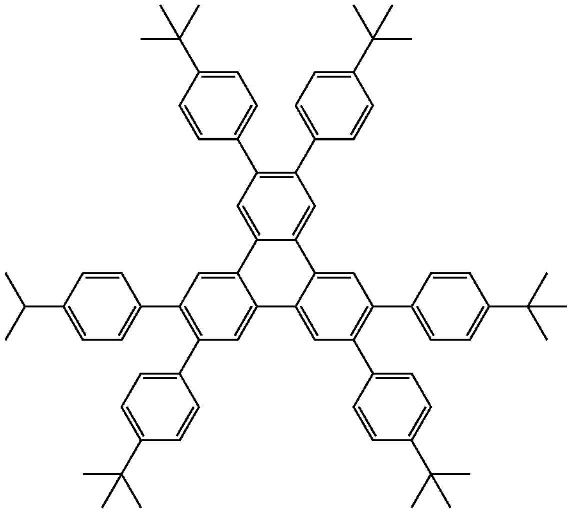

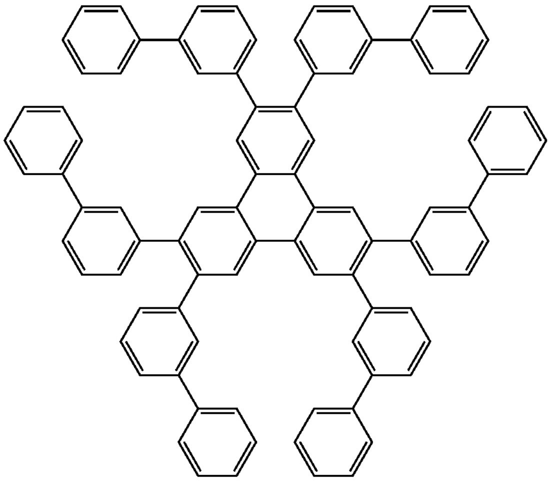

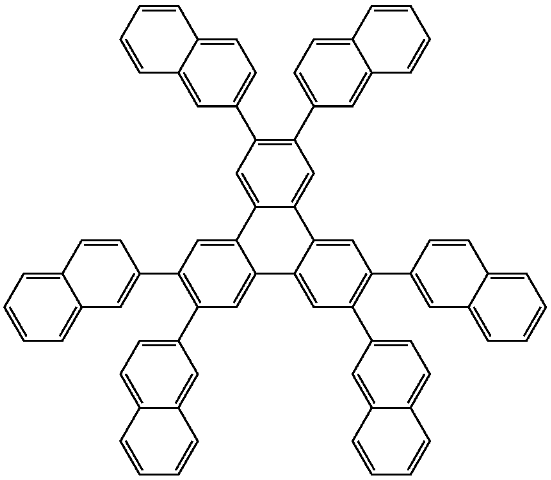

-continued
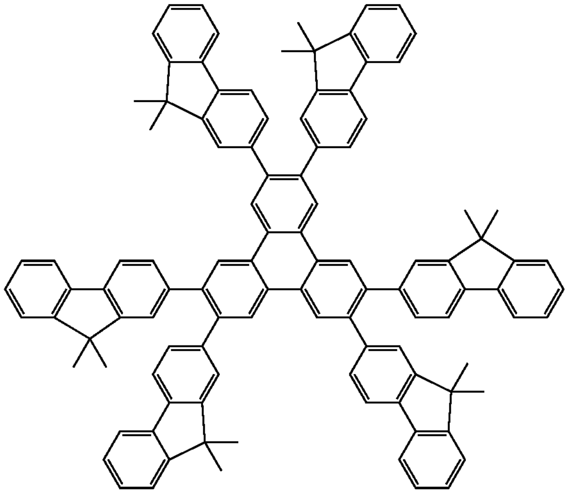
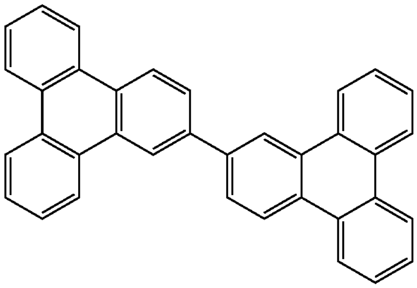
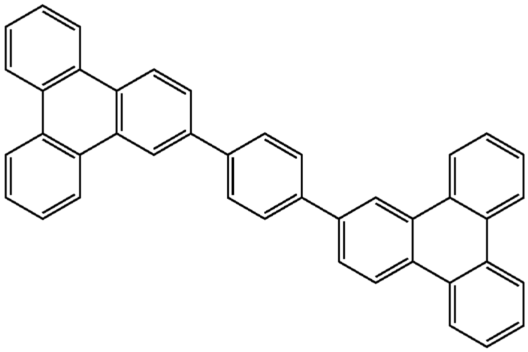
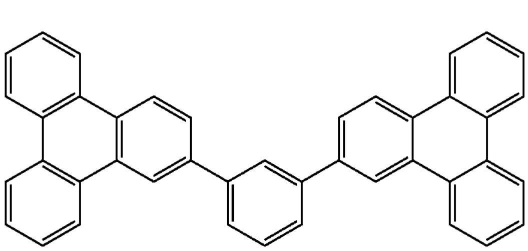
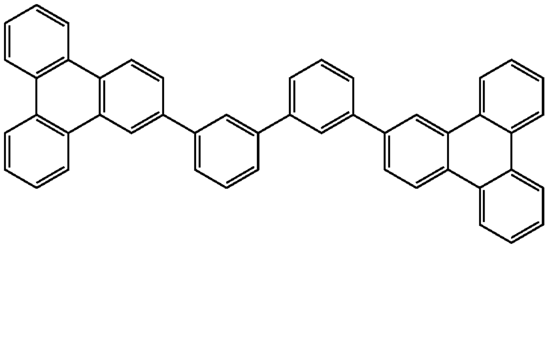
-continued
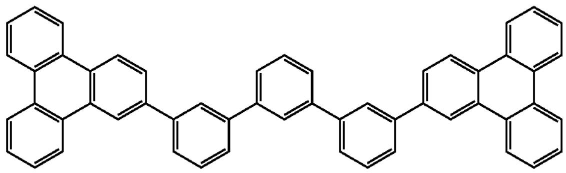
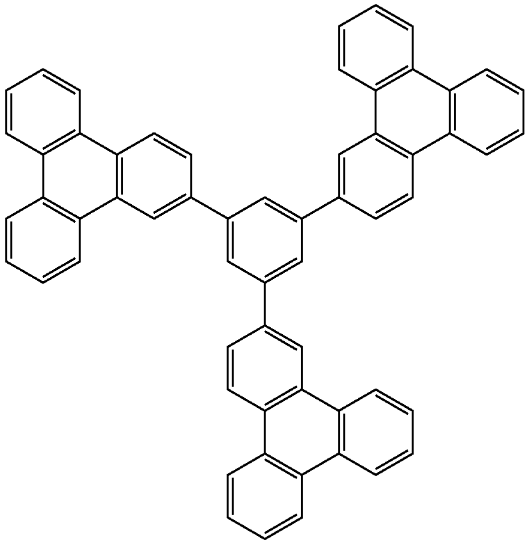
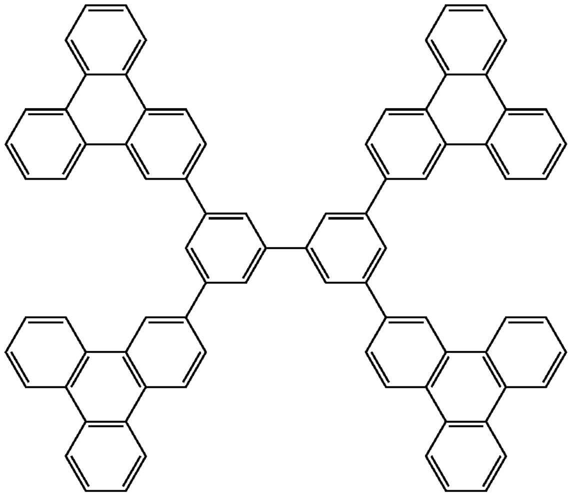
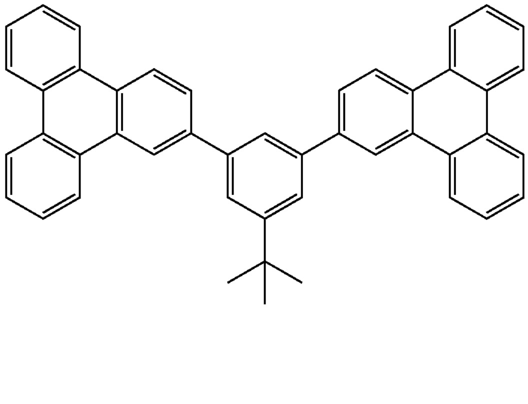

-continued
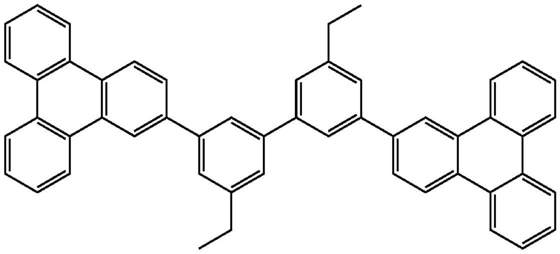
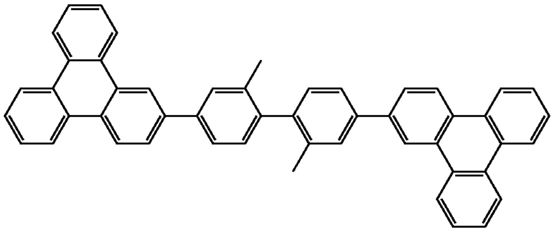
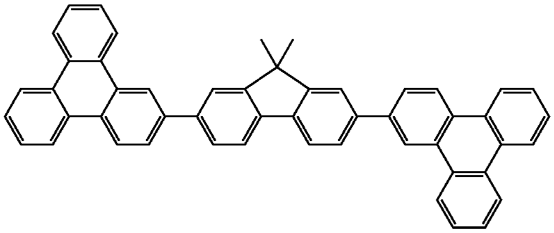
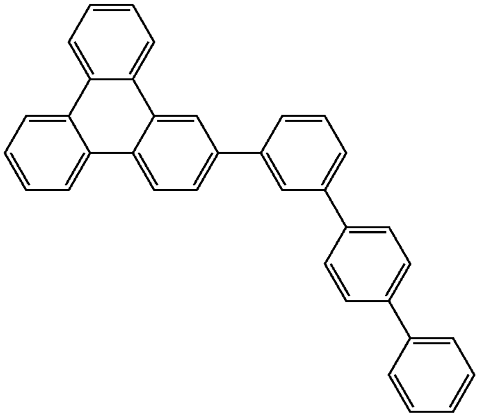
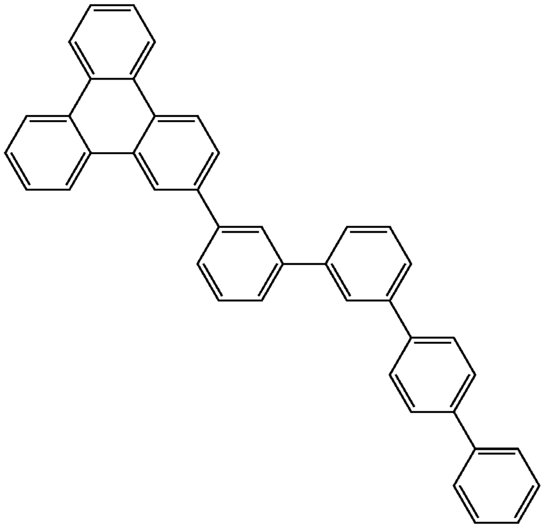
-continued
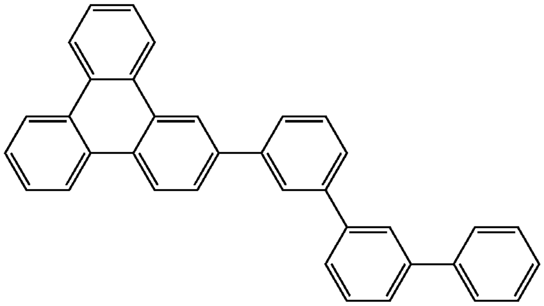
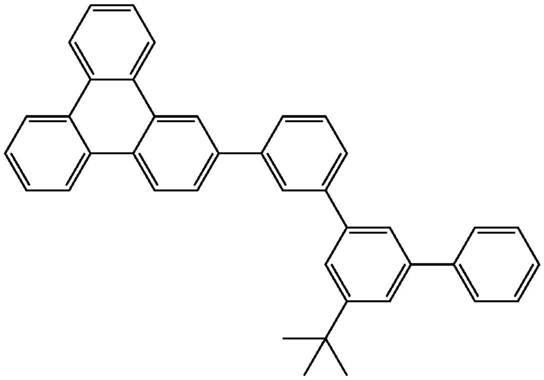
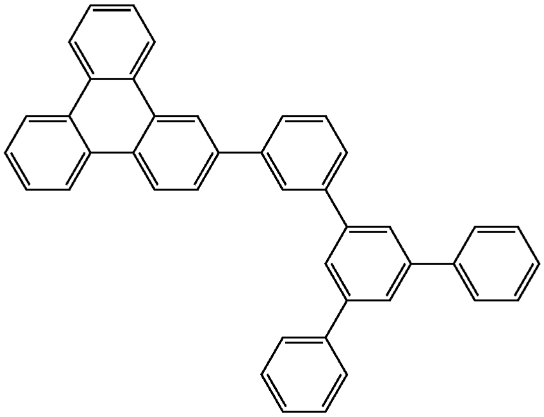
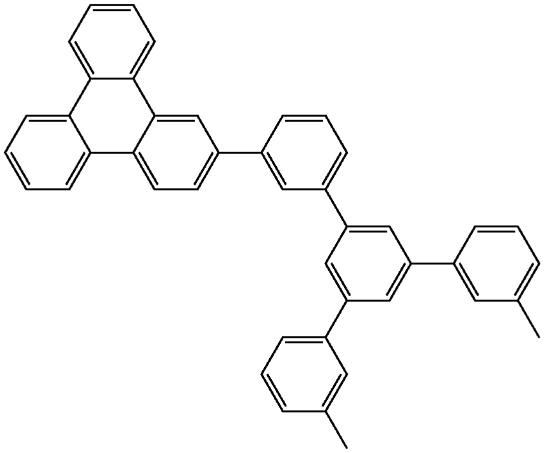

-continued

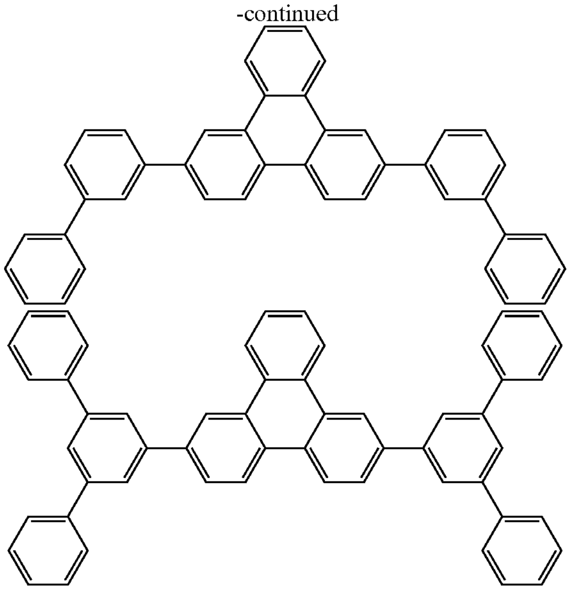

The above exemplified hydrocarbon compounds according to the invention can be synthesized by the methods described in WO 05/013388, WO 06/130598, WO 09/021, 107, U.S. Patent 2009/0,009,065, WO 09/008,311, and WO 04/018587.

The synthesized compound is preferably purified by sublimation purification after having been subjected to purification treatment by column chromatography, recrystallization and the like. Not only organic impurities can be separated but also inorganic salts and residual solvents can be effectually removed by sublimation purification.

[Compound Represented by Formula (O-1)]

It is preferred for the luminescence device in the invention to include at last one organic layer between the light-emitting layer and the cathode, and to contain at least one kind of a compound represented by the following formula (O-1) in the organic layer from the viewpoint of efficiency and driving voltage of the device. Formula (O-1) is described below.

(O-1)

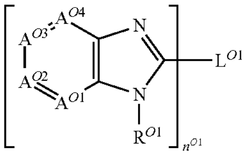

In formula (O-1), $R^{01}$ represents an alkyl group, an aryl group or a heteroaryl group. Each of $A^{01}$ to $A^{04}$ independently represents C—$R^A$ or a nitrogen atom. $R^A$ represents a hydrogen atom, an alkyl group, an aryl group or a heteroaryl group. A plurality of $R^A$ may be the same or different. $L^{01}$ represents a 2-valent to 6-valent linking group comprising an aryl ring or a heteroaryl ring. $n^{01}$ represents an integer of 2 to 6.

$R^{01}$ represents an alkyl group (preferably having 1 to 8 carbon atoms), an aryl group (preferably having 6 to 30 carbon atoms), or a heteroaryl group (preferably having 4 to 12 carbon atoms). These groups may have the above substituent Z'. $R^{01}$ preferably represents an aryl group, or a heteroaryl group, and more preferably an aryl group. As preferred substituents in the case where the aryl group of $R^{01}$ has a substituent, an alkyl group, an aryl group and a cyano group are exemplified, more preferably an alkyl group and an aryl group, and still more preferably an aryl group. When the aryl group of $R^{01}$ has a plurality of substituents, the plurality of substituents may be bonded to each other to form a 5- or 6-membered ring. The aryl group represented by $R^{01}$ is preferably a phenyl group which may have substituent Z', more preferably a phenyl group which may be substituted with an alkyl group or an aryl group, and still more preferably an unsubstituted phenyl group or a 2-phenylphenyl group.

Each of $A^{01}$ to $A^{04}$ independently represents C—$R^A$ or a nitrogen atom. It is preferred that zero to two of $A^{01}$ to $A^{04}$ represent a nitrogen atom, and more preferably zero or one represents a nitrogen atom. It is preferred that all of $A^{01}$ to $A^{04}$ represent C—$R^A$, or $A^{01}$ represents a nitrogen atom, and each of $A^{02}$ to $A^{04}$ represents C—$R^A$, more preferably $A^{01}$ represents a nitrogen atom, and each of $A^{02}$ to $A^{04}$ represents C—$R^A$, and still more preferably $A^{01}$ represents a nitrogen atom, each of $A^{02}$ to $A^{04}$ represents C—$R^A$, and $R^A$ all represent a hydrogen atom.

$R^A$ represents a hydrogen atom, an alkyl group (preferably having 1 to 8 carbon atoms), an aryl group (preferably having 6 to 30 carbon atoms), or a heteroaryl group (preferably having 4 to 12 carbon atoms), and these groups may have the above substituent Z'. Two or more $R^A$ may be the same or different.

$R^A$ preferably represents a hydrogen atom or an alkyl group, and more preferably a hydrogen atom.

L represents a 2-divalent to 6-valent linking group consisting of an aryl ring (preferably having 6 to 30 carbon atoms), or a heteroaryl ring (preferably having 4 to 12 carbon atoms). $L^{01}$ preferably represents an arylene group, a heteroarylene group, an aryltriyl group, or a heteroaryltriyl group, more preferably a phenylene group, a biphenylene group or a benzenetriyl group, and still preferably a biphenylene group or a benzenetriyl group. $L^{01}$ may have substituent Z'. As the substituent at the time of having a substituent, an alkyl group, an aryl group, or a cyano group is preferred. The specific examples of $L^{01}$ are shown below.

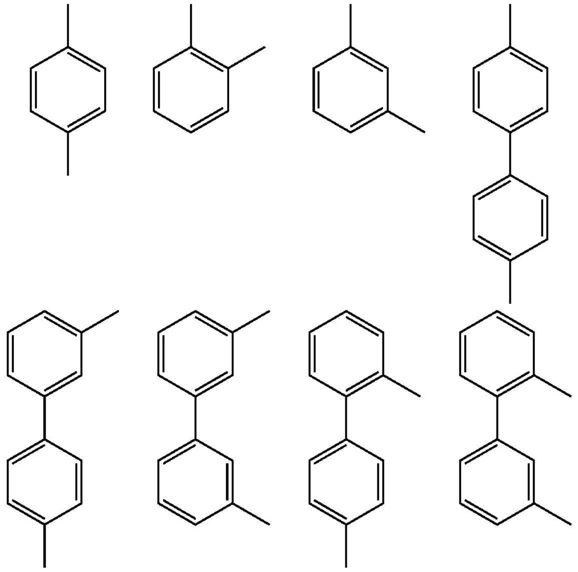

-continued

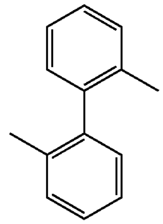
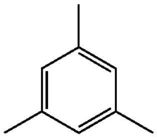
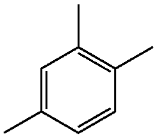
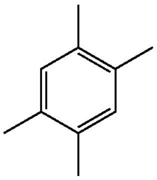
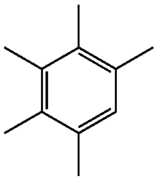
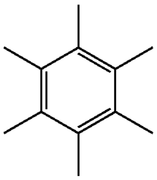
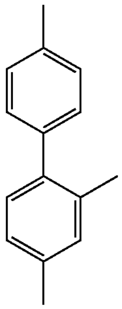
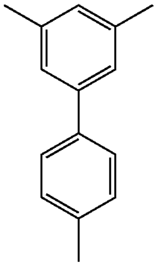
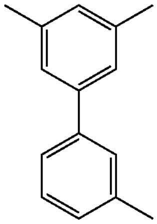
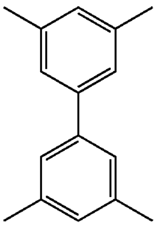
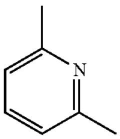
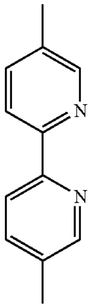
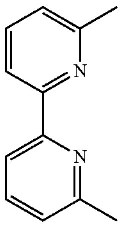
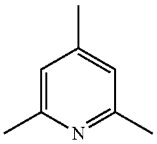
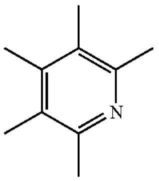
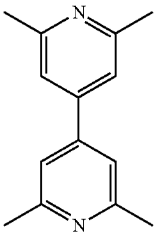
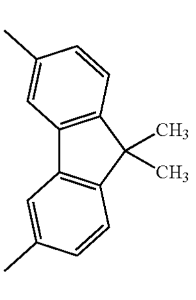
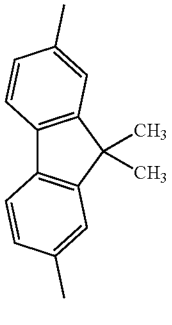
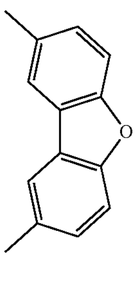

-continued

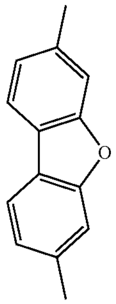
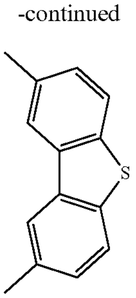
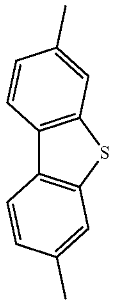
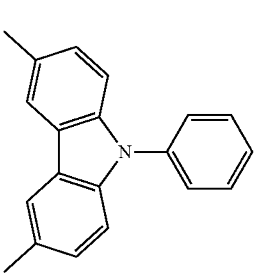
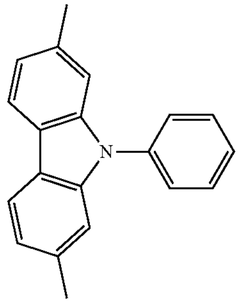

$n^{01}$ represents an integer of 2 to 6, preferably 2 to 4, and more preferably 2 or 3. $n^{01}$ most preferably 3 in the point of efficiency of the device, and most preferably 2 in the point of durability of the device.

The compound represented by formula (O-1) is more preferably a compound represented by the following formula (O-2).

(O-2)

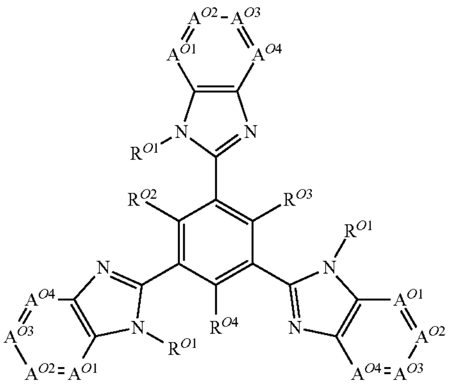

In formula (O-2), $R^{01}$ represents an alkyl group, an aryl group or a heteroaryl group. Each of $R^{02}$ to $R^{04}$ independently represents a hydrogen atom, an alkyl group, an aryl group, or a heteroaryl group. Each of $A^{01}$ to $A^{04}$ independently represents C—$R^{A}$ or a nitrogen atom. $R^{A}$ represents a hydrogen atom, an alkyl group, an aryl group or a heteroaryl group. A plurality of $R^{A}$ may be the same or different.

$R^{01}$ and $A^{01}$ to $A^{04}$ have the same meaning with $R^{01}$ and $A^{01}$ to $A^{04}$ in formula (O-1) and their preferred ranges are also the same.

Each of $R^{02}$ to $R^{04}$ independently represents a hydrogen atom, an alkyl group (preferably having 1 to 8 carbon atoms), an aryl group (preferably having 6 to 30 carbon atoms), or a heteroaryl group (preferably having 4 to 12 carbon atoms, and these groups may have substituent Z'. Each of $R^{02}$ to $R^{04}$ preferably represents a hydrogen atom, an alkyl group or an aryl group, more preferably a hydrogen atom or an aryl group, and most preferably a hydrogen atom.

From the aspect of preservation stability at high temperature, at the time of high temperature driving, and stable actuation of the device against calorification during driving, the glass transition temperature (Tg) of the compound represented by formula (O-1) is preferably 100° C. to 300° C., more preferably 120° C. to 300° C., still more preferably 120° C. to 300° C., and still yet preferably 140° C. to 300° C.

The specific examples of the compound represented by formula (O-1) are shown below, but the invention is not restricted thereto.

OM-1

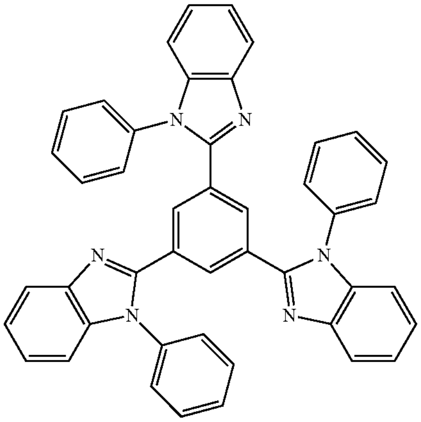

OM-2

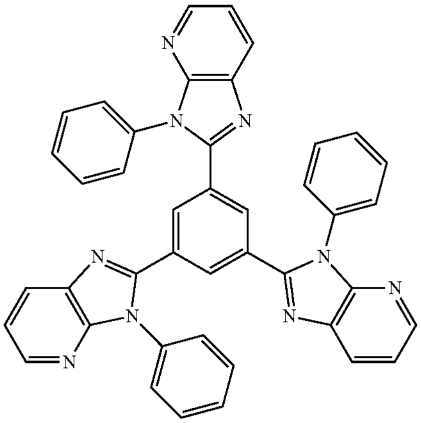

OM-3

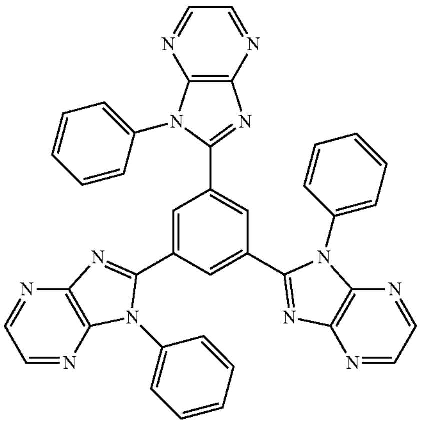

-continued

OM-4

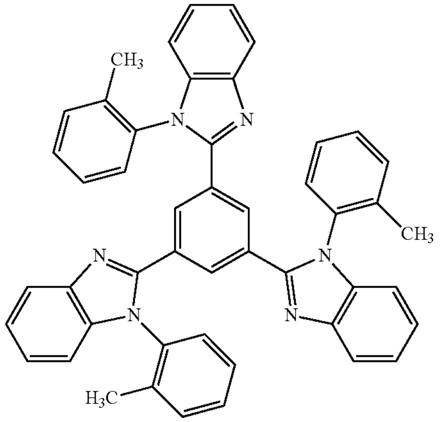

OM-5

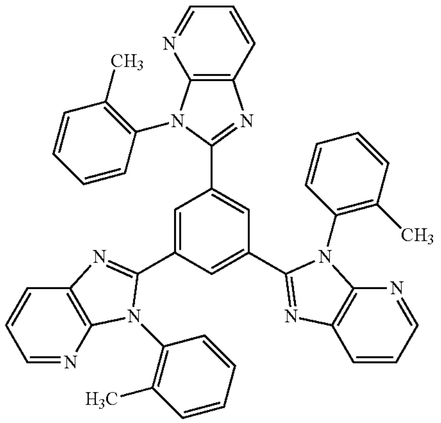

OM-6

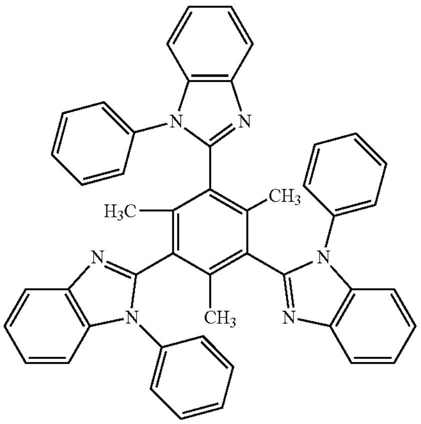

-continued
OM-7
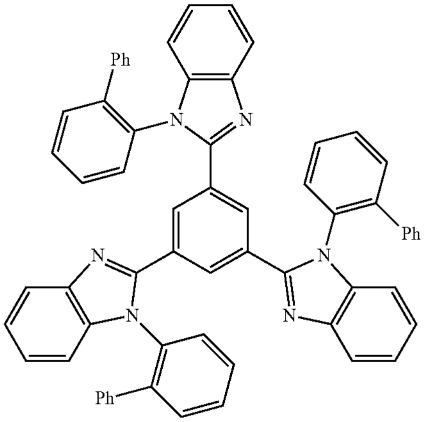
OM-8
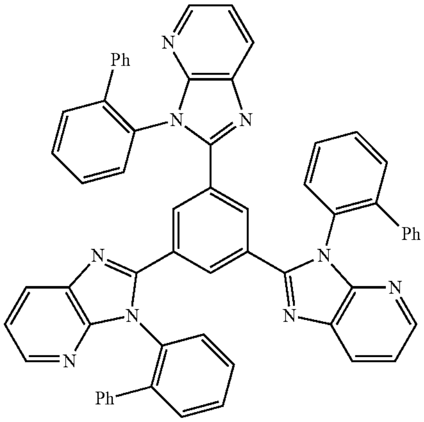
OM-9
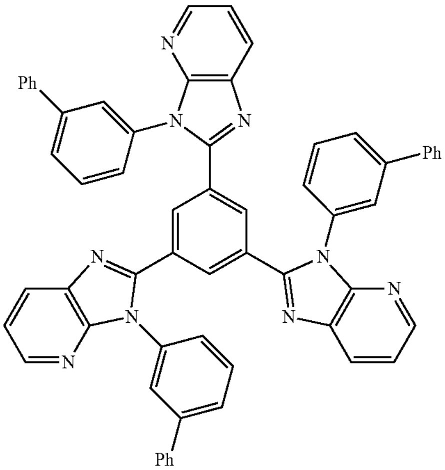
-continued
OM-10
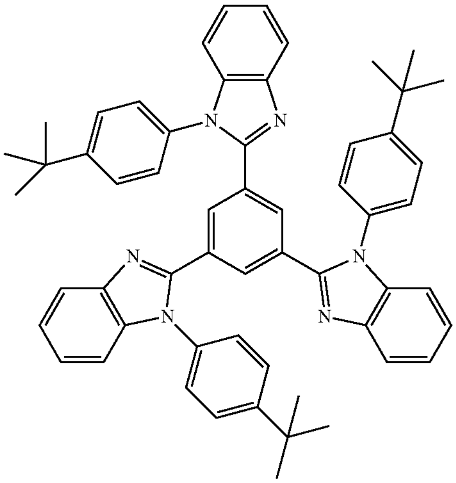
OM-11
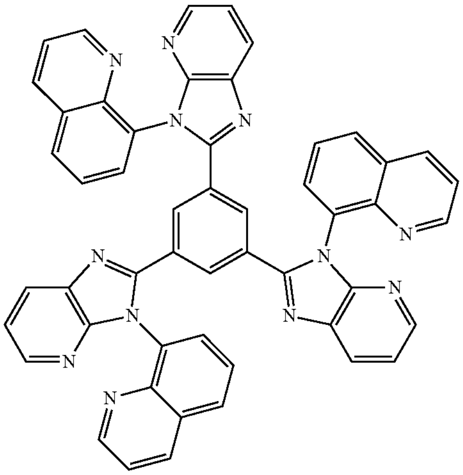
OM-12
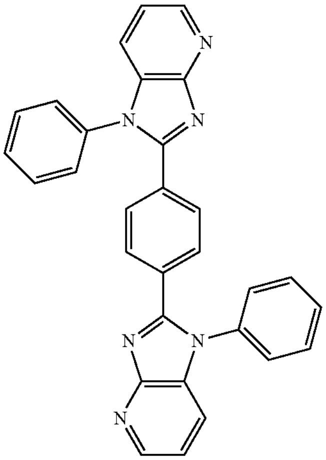

-continued

OM-13

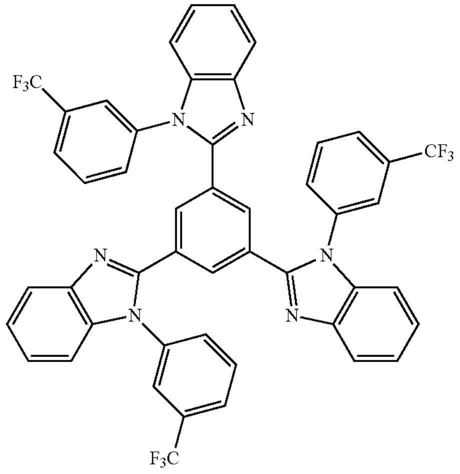

OM-14

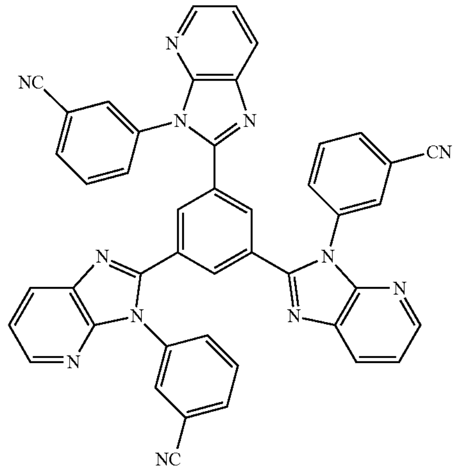

OM-15

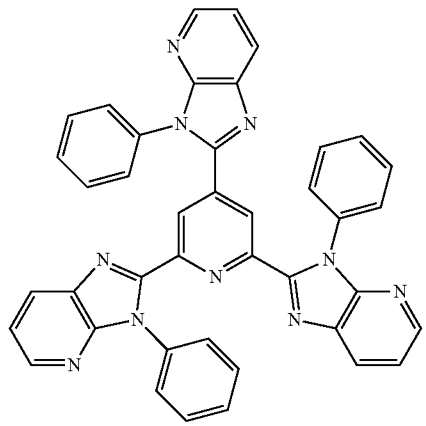

-continued

OM-16

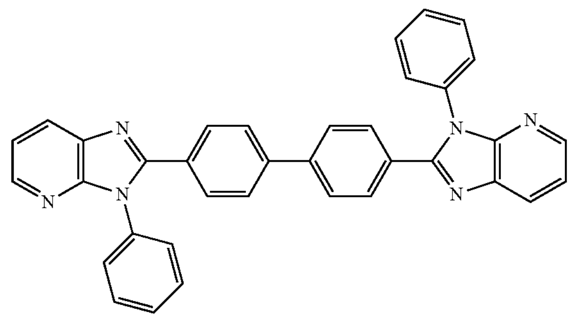

The compound represented by formula (O-1) can be synthesized by the method described in JP-A-2001-335776. The synthesized compound is preferably purified by sublimation purification after having been subjected to purification treatment by column chromatography, recrystallization and reprecipitation. Not only organic impurities can be separated but also inorganic salts and residual solvents can be effectually removed by sublimation purification.

In the luminescence device in the invention, the compound represented by formula (O-1) is contained in the organic layer between the light-emitting layer and the cathode. It is preferred for the compound to be contained in the layer contiguous to the light-emitting layer on the cathode side.

(Charge-Transporting Layer)

A charge-transporting layer means a layer in which charge movement occurs at the time of voltage application to the organic electroluminescence device. Specifically, a hole-injecting layer, a hole-transporting layer, an electron-blocking layer, a light-emitting layer, a hole-blocking layer, an electron-transporting layer and an electron-injecting layer are exemplified.

Preferred is a hole-injecting layer, a hole-transporting layer, an electron-blocking layer, or a light-emitting layer.

When a charge-transporting layer formed by a coating method is a hole-injecting layer, a hole-transporting layer, an electron-blocking layer, or a light-emitting layer, manufacture of an organic electroluminescence device by low cost and high efficiency becomes possible.

As a charge-transporting layer, more preferred is a hole-injecting layer, a hole-transporting layer, or an electron-blocking layer.

(Hole-Injecting Layer, Hole-Transporting Layer)

The hole-injecting layer and the hole-transporting layer are layers having functions of receiving holes from the anode or anode side and transporting the holes to the cathode side.

Concerning the hole-injecting layer and the hole-transporting layer, the items described in JP-A-2008-270736, paragraphs [0165] to [0167] can be applied to the invention.

It is preferred that the hole-injecting layer contains an electron-accepting dopant. By the introduction of an electron-accepting dopant to the hole-injecting layer, hole-injecting property is improved, driving voltage lowers, and efficiency is improved. Electron-accepting dopants may be organic materials or inorganic materials so long as they are materials capable of extracting electrons from the materials to be doped and generating radical cations. For example, tetracyanoquinodimethane (TCNQ), tetrafluorotetracyanoquinodimethane ($F_4$-TCNQ), and molybdenum oxide are exemplified.

Electron-accepting dopant is preferably contained in the hole-injecting layer in an amount of 0.01% by mass to 50% by mass based on the gross mass of the compounds for forming the hole-injecting layer, more preferably 0.1% by mass to 40% by mass, and still more preferably 0.2% by mass to 30% by mass.

(Electron-Injecting Layer, Electron-Transporting Layer)

The electron-injecting layer and the electron-transporting layer are layers having functions of receiving electrons from the cathode or cathode side and transporting the electrons to the anode side. The electron-injecting materials and the electron-transporting materials used in these layers may be low molecular weight compounds or high molecular weight compounds.

The compounds represented by any of formulae (1) to (3) of the invention can be used as the electron-transporting material. These layers are preferably layers containing, besides the compounds of the invention, pyridine derivatives, quinoline derivatives, pyrimidine derivatives, pyrazine derivatives, phthalazine derivatives, phenanthroline derivatives, triazine derivatives, triazole derivatives, oxazole derivatives, oxadiazole derivatives, imidazole derivatives, fluorenone derivatives, anthraquinodimethane derivatives, anthrone derivatives, diphenylquinone derivatives, thiopyran dioxide derivatives, carbodiimide derivatives, fluorenylidenemethane derivatives, distyrylpyrazine derivatives, aromatic cyclic tetracarboxylic anhydrides such as naphthalene and perylene, phthalocyanine derivatives, metal complexes of 8-quinolinol derivatives, various metal complexes represented by metal complexes having metalphthalocyanine, benzoxazole or benzothiazole as a ligand, and organic silane derivatives represented by silole.

The thickness of each of the electron-injecting layer and electron-transporting layer is preferably 500 nm or less from the viewpoint of lowering driving voltage.

The thickness of the electron-transporting layer is preferably 1 nm to 500 nm, more preferably 5 nm to 200 nm, and still more preferably 10 nm to 100 nm. The thickness of the electron-injecting layer is preferably 0.1 nm to 200 nm, more preferably 0.2 nm to 100 nm, and still more preferably 0.5 nm to 50 nm.

The electron-injecting layer and electron-transporting layer may have a monolayer structure containing one or two or more kinds of the above materials, or may have a multilayer structure comprising two or more layers of the same composition or different compositions.

It is preferred for the electron-injecting layer to contain an electron-donating dopant. By introducing an electron-injecting layer to the electron-injecting layer, electron-injecting property is improved and driving voltage lowers and efficiency is improved. Electron-donating dopants may be organic materials or inorganic materials so long as they are materials capable of giving electrons to the materials to be doped and generating radical anions. For example, tetrathiafulvalene (TTF), tetrathianaphthacene (TTT), dihydroimidazole compounds such as bis-[1,3-diethyl-2-methyl-1,2-dihydrobenzimidazolyl], lithium, and cesium are exemplified.

Electron-donating dopant is preferably contained in the electron-injecting layer in an amount of 0.01% by mass to 50% by mass based on the gross mass of the compounds for forming the electron-injecting layer, more preferably 0.1% by mass to 40% by mass, and still more preferably 0.5% by mass to 30% by mass.

(Hole-Blocking Layer)

The hole-blocking layer is a layer having a function of preventing the holes transported from the anode side to the light-emitting layer from passing through to the cathode side. In the invention, the hole-blocking layer can be provided as an organic layer contiguous to the light-emitting layer on the cathode side.

As the examples of organic compounds for constituting the hole-blocking layer, aluminum complexes such as aluminum(III)bis(2-methyl-8-quinolinato)-4-phenylphenolate (abbreviated to BAlq), triazole derivatives, phenanthroline derivatives such as 2,9-dimethyl-4,7-diphenyl-1,10-phenanthroline (abbreviated to BCP), and the compounds of the invention can be exemplified.

In the invention, the hole-blocking layer is not limited to have only the function of blocking the holes but the hole-blocking layer may have functions of not diffusing excitons in the light-emitting layer to the electron-transporting layer, or blocking quenching by energy movement. The compound according to the invention can also be preferably applied to the hole-blocking layer.

The thickness of the hole-blocking layer is preferably 1 nm to 500 nm, more preferably 5 nm to 200 nm, and still more preferably 10 nm to 100 nm.

The hole-blocking layer may have a monolayer structure containing one or two or more kinds of the above materials, or may be a multilayer structure comprising two or more layers of the same composition or different compositions.

(Electron-Blocking Layer)

The electron-blocking layer is a layer having a function of preventing the electrons transported from the cathode side to the light-emitting layer from passing through to the anode side. In the invention, the electron-blocking layer can be provided as an organic layer contiguous to the light-emitting layer on the anode side.

As the examples of organic compounds for constituting the electron-blocking layer, for example, the hole-transporting materials described above can be applied.

The thickness of the electron-blocking layer is preferably 1 nm to 500 nm, more preferably 5 nm to 200 nm, and still more preferably 10 nm to 100 nm.

The electron-blocking layer may have a monolayer structure containing one or two or more kinds of the above materials, or may be a multilayer structure comprising two or more layers of the same composition or different compositions.

(Protective layer)

In the invention, the organic EL device may be entirely protected with a protective layer.

Concerning the protective layer, the items described in JP-A-2008-270736, paragraphs [0169] to [0170] can be applied to the invention.

(Sealing Case)

The device in the invention may be entirely sealed with a sealing case.

Concerning the sealing case, the items described in JP-A-2008-270736, paragraph [0171] can be applied to the invention.

(Driving)

By the application of D.C. (if necessary, A.C. component may be contained) voltage (generally 2 to 15 volts) between the anode and the cathode, or by the application of D.C. electric current, light emission of the organic electroluminescence device of the invention can be obtained.

With respect to the driving method of the organic electroluminescence device of the invention, the driving methods disclosed in JP-A-2-148687, JP-A-6-301355, JP-A-5-29080, JP-A-7-134558, JP-A-8-234685, JP-A-8-241047, U.S. Pat. Nos. 2,784,615, 5,828,429 and 6,023,308 can be applied to the invention.

The external quantum efficiency of the organic electroluminescence device in the invention is preferably 7% or more, more preferably 10% or more, and still more preferably 12% or more. As the value of external quantum efficiency, the maximum value of external quantum efficiency at the time of driving the device at 20° C., alternatively the value of external quantum efficiency near 300 to 400 cd/$m^2$ at the time of driving the device at 20° C., can be used.

The internal quantum efficiency of the organic electroluminescence device in the invention is preferably 30% or more, more preferably 50% or more, and still more preferably 70% or more. The internal quantum efficiency of the device is computed by dividing the external quantum efficiency by the light collecting efficiency. The light collecting efficiency of ordinary organic EL devices is about 20%, but it is possible to make the light collecting efficiency 20% or more by variously designing the shape of substrate, the shape of electrode, the thickness of organic layer, the thickness of inorganic layer, the refractive index of organic layer, the refractive index of inorganic layer, etc.

(Use of the Device of the Invention)

The device in the invention can be preferably used in display devices, displays, backlights, electrophotography, light sources for illumination, light sources for recording, light sources for exposure, light sources for reading, indicators, signboards, interior designs, optical communications, and the like. The devices in the invention are particularly preferably used in devices driven in the region high in light emission luminance such as illumination apparatus and display apparatus.

(Light Emission Apparatus)

Figure 2:
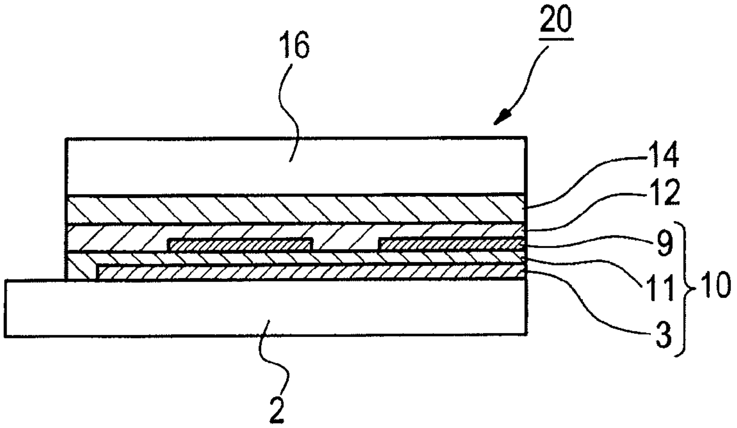
FIG. 2 is a schematic drawing showing an example of a light emission apparatus according to the invention.

In the next place, the light emission apparatus in the invention is described with referring to FIG. 2.

The light emission apparatus in the invention comprises the organic electroluminescence device.

FIG. 2 is a cross-sectional view schematically showing an example of the light emission apparatus according to the invention. Light emission apparatus 20 in FIG. 2 consists of substrate (a supporting substrate) 2, organic electroluminescence device 10, and sealing case 16.

Organic electroluminescence device 10 includes substrate 2 having thereon laminated anode (first electrode) 3, organic layer 11, and cathode (second electrode) 9 in this order. On cathode 9 is laminated protective layer 12, and sealing case 16 is provided on protective layer 12 sandwiching adhesive layer 14 in. Parts of electrodes 3 and 9, bulkhead and insulating layer are omitted.

As adhesive layer 14, photo-curable adhesives such as epoxy resin and the like and thermosetting adhesives can be used and, for example, a thermosetting adhesive sheet can also be used.

The uses of the light emission apparatus in the invention are not especially restricted and, besides illuminating apparatus, the light emission apparatus can be used, for example, as display apparatus such as television, personal computer, portable telephone, electronic paper, and the like.

(Illumination Apparatus)

Figure 3:
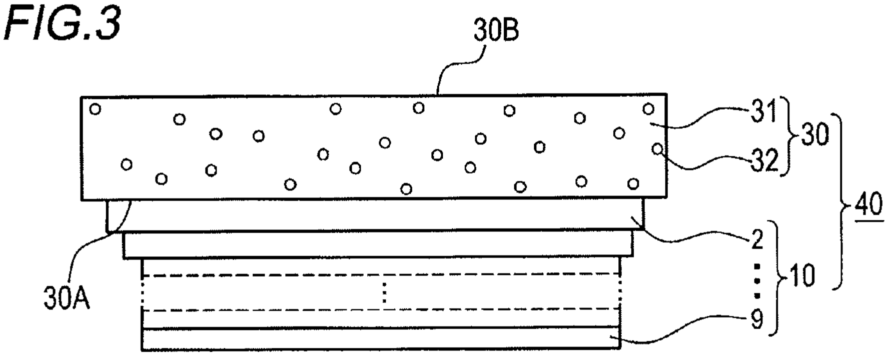
FIG. 3 is a schematic drawing showing an example of an illumination apparatus according to the invention.

In the next place, the illumination apparatus of the invention is described with referring to FIG. 3.

FIG. 3 is a cross-sectional view schematically showing an example of the illumination apparatus according to the invention. Illumination apparatus 40 in the invention is equipped with organic EL device 10 and light-scattering member 30, as shown in FIG. 3. More specifically, illumination apparatus 40 is constituted so that substrate 2 of organic EL device 10 is contiguous to light-scattering member 30.

Light-scattering member 30 is not especially restricted so long as it can scatter light, but in FIG. 3, light-scattering member 30 is a member comprising transparent substrate 31 containing particles 32 having been dispersed therein. As transparent substrate 31, e.g., a glass substrate is preferably exemplified. As particles 32, transparent resin particles are preferably exemplified. As the glass substrate and transparent resin particles, known materials can be used. In illumination apparatus 40, when light emission from organic electroluminescence device 10 is incident to plane of incidence of light 30A of light-scattering member 30, the incident light is scattered by light-scattering member 30, and the scattered light is outgoing from plane of outgoing of light 30B as illumination light.

EXAMPLE

The invention will be described in further detail with reference to examples, but the range of the invention is not restricted thereto.

1. Synthesis Example (Synthesis Example 1)

Synthesis of Compound (1-4)

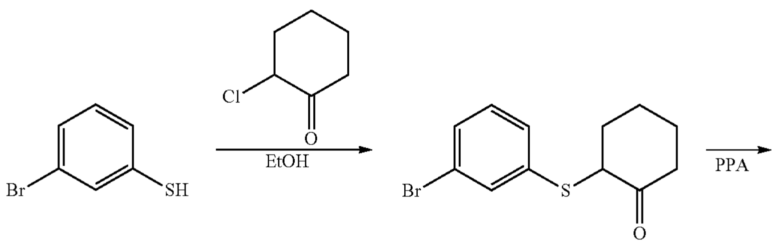

Intermediate (1-1)

-continued

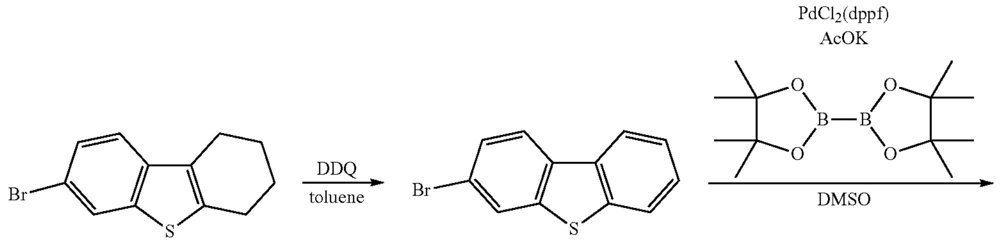

Intermediate (1-2)

Intermediate (1-3)

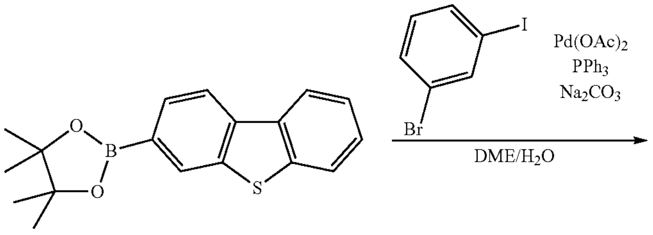

Intermediate (1-4)

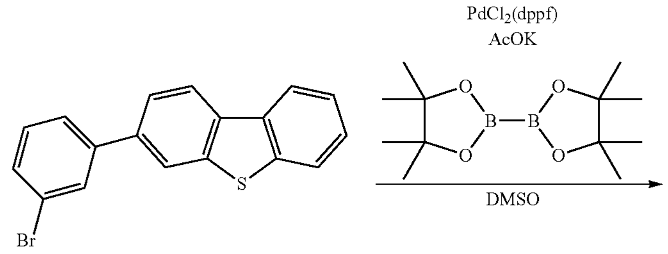

Intermediate (1-5)

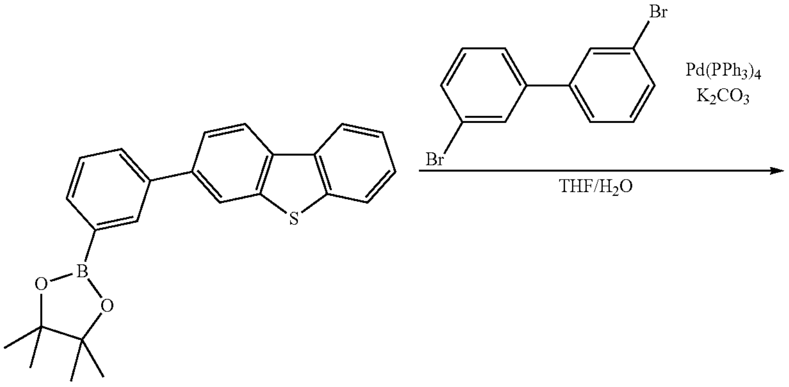

Intermediate (1-6)

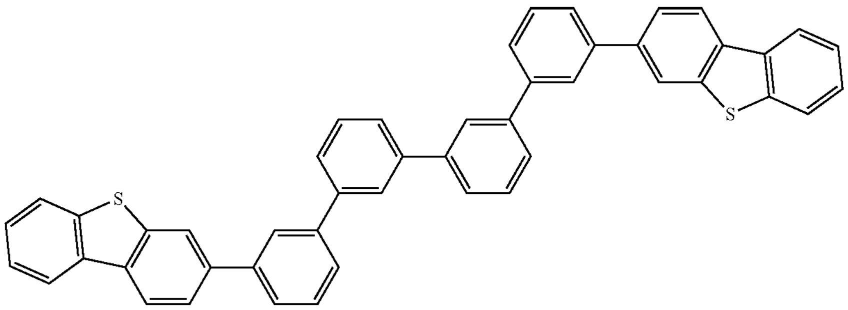

Compound (1-4)

Under a nitrogen atmosphere, 50 g of m-bromobenzenethiol and 300 mL of ethanol were put in a three-necked flask having a capacity of 2 liters, the flask was immersed in an ice bath, and the reaction system was stirred. A 28% methanol solution of sodium methoxide (51 g) was dropped to the flask, and then a solution obtained by diluting 32 mL of 2-chlorocyclohexanone with 50 mL of ethanol was dropped to the flask slowly. After stirring the reaction solution for 4 hours, 600 mL of distilled water was added and the reaction system was allowed to stand for three days. The obtained oily precipitate was collected with a pipette, and purified by silica gel column chromatography with ethyl acetate/hexane=1/4 as the eluate, thus 47 g of an oily substance containing intermediate (1-1) was obtained.

Under a nitrogen atmosphere, 34 g of the oily substance containing intermediate (1-1) and 75 g of polyphosphoric acid were put in a three-necked flask having a capacity of 500 mL, the flask was immersed in an oil bath at a temperature of 130° C., and the reaction system was stirred for 4 hours. The temperature was lowered to room temperature, and 300 mL of distilled water was added thereto. The formed precipitate was purified by silica gel column chromatography with hexane as the eluate to thereby obtain 6 g of an oily substance containing intermediate (1-2).

Under a nitrogen atmosphere, 6 g of the oily substance containing intermediate (1-2) and 30 mL of toluene were put in a three-necked flask having a capacity of 300 mL, and the reaction system was stirred. Thereto was added 10.2 g of 2,3-dichloro-5,6-dicyano-1,4-benzoquinone, and the flask was immersed in an oil bath at 110° C. and stirred for 5 hours. The temperature was lowered to room temperature, and 100 mL of an aqueous solution containing 5 g of sodium hydroxide and 68 mL of 1 mol/liter of sodium thiosulfate were added thereto and stirred for a while, and then the precipitate was filtered out by suction filtration. The obtained filtrate was purified by silica gel column chromatography with hexane as the eluate to thereby obtain 5 g of white solid containing intermediate (1-3).

Under a nitrogen atmosphere, 5 g of white solid containing intermediate (1-3), 4.29 g of potassium acetate, 5.79 g of bis-pinacolate diboron, and 50 mL of dimethyl sulfoxide were put in a three-necked flask having a capacity of 300 mL. The reaction system is then subjected to deaeration by using vacuum line, subsequently nitrogen replacement. To the system was added 0.47 g of [1,1'-bis(diphenylphosphino)-pherocene] palladium (II) dichloride dichloromethane complex (1:1), and the flask was immersed in an oil bath at 90° C. and the reaction solution was stirred for 4 hours. The temperature was lowered to room temperature, and 200 mL of distilled water was added thereto and the system was stirred. The obtained precipitate was filtered out by suction filtration. The obtained filtrate was purified by silica gel column chromatography with hexane as the eluate to thereby obtain 5 g of white solid containing intermediate (1-4).

Into a three-necked flask having a capacity of 300 mL were put 7.66 g of 1-bromo-3-iodobenzene, 5.74 g of sodium carbonate, 10 mL of dimethoxyethane, and 10 mL of distilled water, and the reaction system was subjected to deaeration by using vacuum line and then nitrogen replacement. Triphenylphosphine (0.71 g), 4.2 g of white solid containing intermediate (1-4), and 0.16 g of palladium acetate were added to the reaction mixture, and the flask was immersed in an oil bath at 100° C. and the system was refluxed for 5 hours with heating. The temperature was lowered to room temperature, and the precipitate was filtered out by suction filtration. The obtained filtrate was purified by silica gel column chromatography with toluene/hexane (1/9) as the eluate to thereby obtain 2 g of intermediate (1-5).

Under a nitrogen atmosphere, 2 g of intermediate (1-5), 1.33 g of potassium acetate, 1.8 g of bis-pinacolate diboron and 20 mL of dimethyl sulfoxide were put in a three-necked flask having a capacity of 100 mL, the reaction system was then subjected to deaeration by using vacuum line, and then nitrogen replacement. To the system was added 0.144 g of [1,1'-bis(diphenylphosphino)pherocene]palladium (II) dichloride dichloromethane complex (1:1), and the flask was immersed in an oil bath at 90° C. and the reaction mixture was stirred for 4 hours. The temperature was lowered to room temperature, and 80 mL of distilled water was added to the reaction mixture, followed by stirring. The obtained precipitate was filtered out by suction filtration. The obtained filtrate was purified by silica gel column chromatography with toluene/hexane=1/1 and toluene alone as the eluates to thereby obtain 1.5 g of intermediate (1-6).

Figure 4:
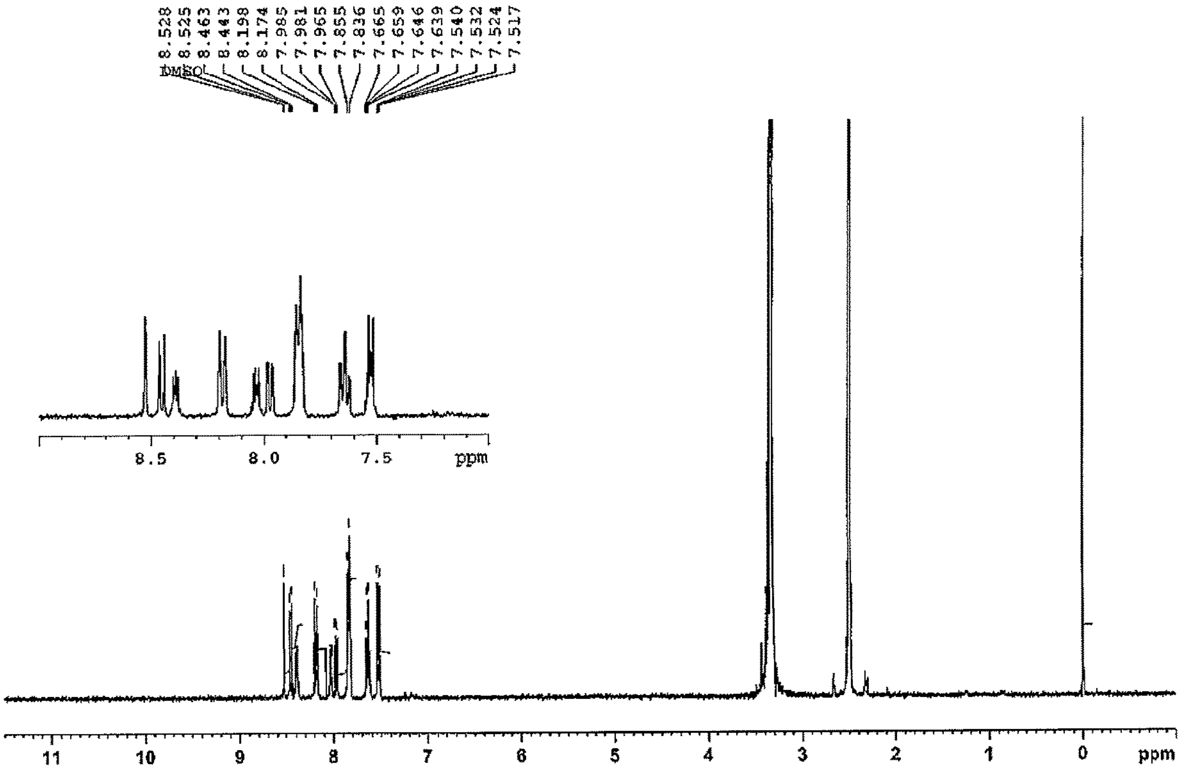
FIG. 4 is a drawing of the spectrum of $^1$H-NMR of Compound (1-4) synthesized according to Synthesis Example 1.

Into a three-necked flask having a capacity of 100 mL were put 1.5 g of intermediate (1-6), 15 mL of tetrahydrofuran and 15 mL of distilled water, and the reaction system was subjected to deaeration by using vacuum line and then nitrogen replacement. Subsequently, 1.34 g of potassium carbonate, 0.5 g of 3,3'-dibromobiphenyl were added to the reaction system, and 0.187 g of tetrakis(triphenylphosphine) palladium was added thereto with stirring, and the flask was immersed in an oil bath at 80° C. and refluxed for 5 hours while heating. The temperature was lowered to room temperature. The formed precipitate was filtered out by suction filtration and the reaction product was washed with a trace amount of tetrahydrofuran. The obtained filtrate was dissolved in 100 mL of tetrahydrofuran and 200 mL of toluene was further added. The precipitate obtained by distilling tetrahydrofuran under reduced pressure was filtered by suction filtration and washed with toluene. The obtained filtrate was dispersed in 100 mL of acetone, refluxed with heating for 1 hour, and the temperature was lowered to room temperature. The obtained precipitate was filtered out by suction filtration, washed with acetone, followed by drying to obtain 0.7 g of white solid. The solid was purified by sublimation, thus 0.53 g of compound (1-4) was obtained. The compound was identified by 400 MHz $^1$H-NMR. $^1$H-NMR data are shown in FIG. 4.

Other compounds represented by formula (1) were also synthesized in the same manner.

Compound (1-1) to compound (1-3), compound (1-44), compound (1-49), compound (1-66), compound (1-67) and compound (1-69) were synthesized in the similar manner as in the synthesis of compound (1-4). The schemes of some compounds are shown.

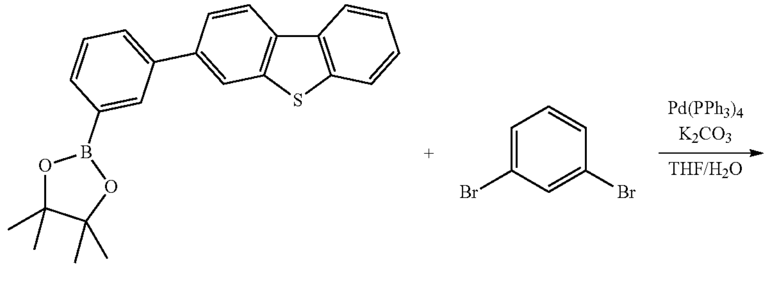

Intermediate (1-6)

-continued
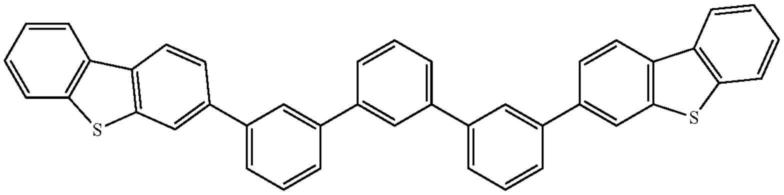
Compound (1-3)
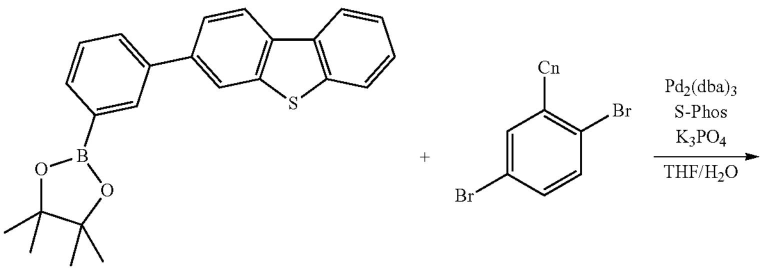
Intermediate (1-6)
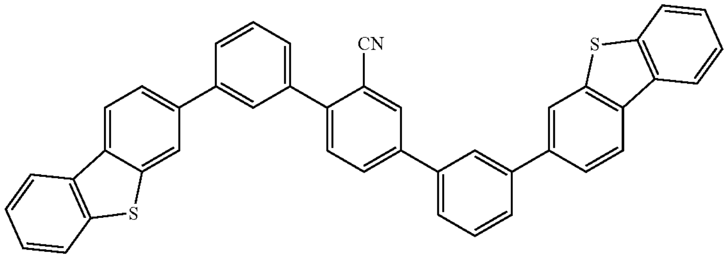
Compound (1-66)
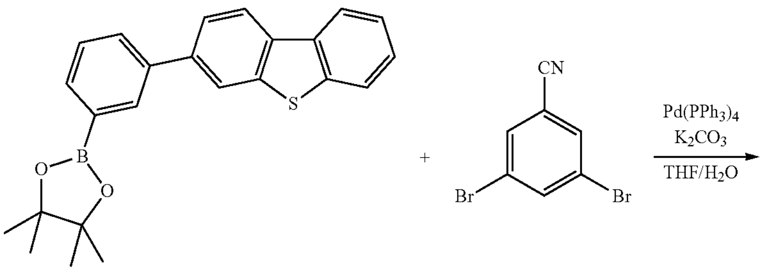
Intermediate (1-6)
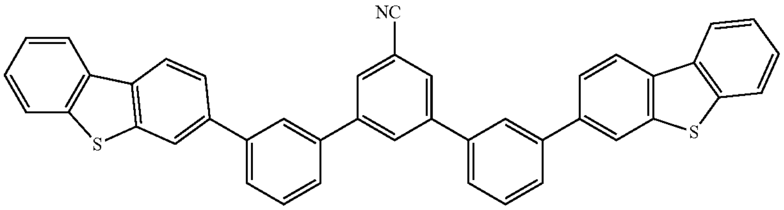
Compound (1-67)

The compounds thus synthesized and used in the examples are shown below with the comparative compounds also used in the examples.

Comparative Compound (1)

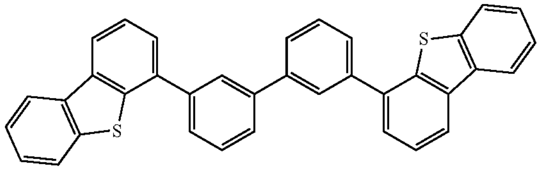

Compound described in WO 2008/085344

Comparative Compound (2)

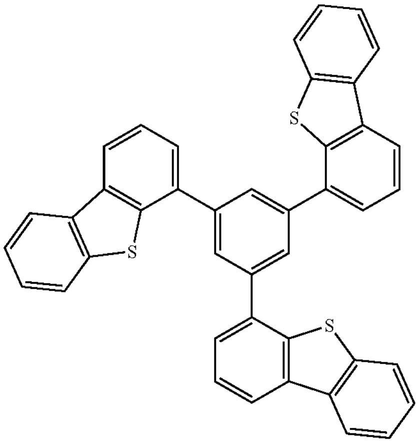

Compound descibed in U.S. 2006/0134538

Comparative Compound (3)

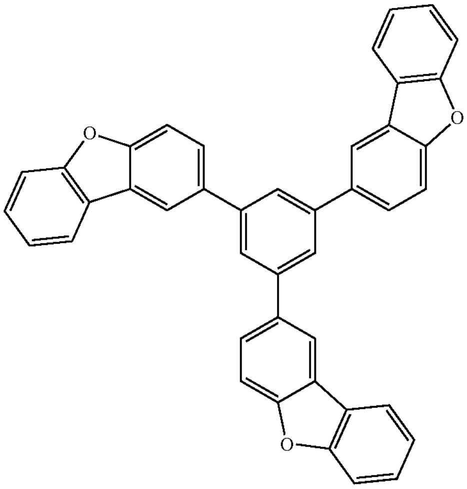

Compound descibed in WO 2009/008099

Comparative Compound (4)

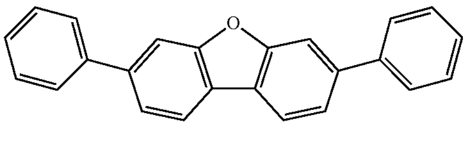

Compound described in Bull. Chem. Soc. Japan 9 (1934) 55

-continued

Comparative Compound (5)

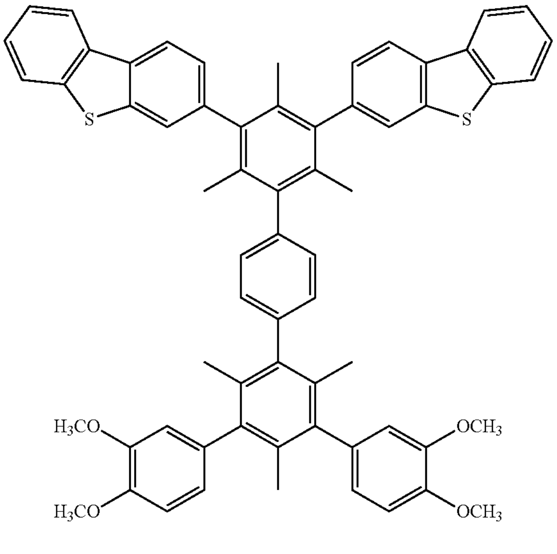

Compound described in JP-A-2004-214050

Comparative Compound (6)

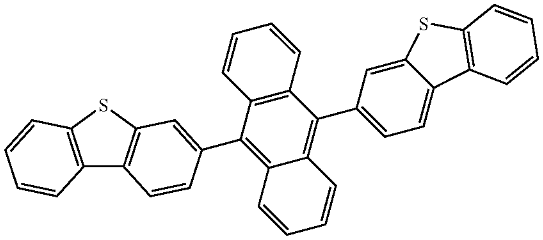

Compound described in JP-A-2005-314239

2. Manufacture and Evaluation of Device

All the materials used in the manufacture of devices were purified by sublimation and confirmed that the purity (area ratio of the absorption intensity at 254 nm) was 99.1% or more by high performance liquid chromatography (TSKgel ODS-100Z, manufactured by TOSO CORPORATION).

Example 1

A glass substrate having an ITO film (manufactured by Geomatec Co., Ltd., surface resistance: 10Ω/□ (sqr)) having a thickness of 0.5 mm and a size of 2.5 cm square was put in a washer and subjected to ultrasonic wave washing in 2-propanol, and then UV-ozone treatment for 30 minutes. The organic layers shown below were deposited on the transparent anode (ITO film) in sequence by a vacuum deposition method.

First layer: Compound (A), film thickness 10 nm

Second layer: Compound (B), film thickness 30 nm

Third layer: Compound (1-1) and Compound (C) (mass ratio: 90/10), film thickness 40 nm Fourth layer: Compound (D), film thickness 40 nm Lithium fluoride in a thickness of 0.1 nm and metal aluminum in a thickness of 100 nm were deposited thereon in this order to obtain the cathode.

The obtained laminate was put in a glove box replaced with nitrogen gas so as not to be in contact with air, and sealed with a glass sealing can and a UV-curing type adhesive (XNR5516HV, manufactured by Nagase Ciba Corp.) to obtain a device 1.

Examples 2 to 10 and Comparative Examples 1 to 5

Devices 2 to 10 and comparative devices 1 to 5 were obtained in the same manner as in the manufacture of device 1 except for replacing compound (1-1) of the third layer with the compound represented by formula (1) and comparative compounds (1) to (5) as shown in Table 1 below.

Efficiency, durability and driving voltage of these devices were evaluated according to the following methods. The results obtained are shown in Table 1.

(a) Efficiency

DC voltage was applied to each device for light emission with a source measure unit Model 2400 (manufactured by Toyo Corporation) and the luminance at that time was measured with a luminometer BM-8 (manufactured by Topcon Corporation). The light emission spectrum and emission wavelength were measured with a spectrum analyzer PMA-11 (manufactured by Hamamatsu Photonics K.K.). On the basis of these measurements, external quantum efficiency near the luminance of 1,000 cd/$m^2$ was computed by a luminance conversion method.

The case of external quantum efficiency of 15% or more was graded ◎.

The case of 12% or more and less than 15% was graded ○.

The case of less than 10% or more and less than 12% was graded Δ.

The case of less than 10% was graded X.

The results are shown in Table 1.

(b) Durability

DC voltage was applied to the sample to reach the luminance of 5,000 cd/$m^2$ at room temperature (20° C.) and light emission was continued, and the required time to reach luminance of 4,000 cd/$m^2$ was taken as the index of durability.

The case of requiring 700 hours or more was graded ◎.

The case of requiring 500 hour or more and less than 700 hours was graded ○.

The case of requiring 300 hour or more and less than 500 hours was graded Δ.

The case of requiring less than 300 hours was graded X.

The results are shown in Table 1.

(c) Driving Voltage

DC voltage was applied to the sample to reach the luminance of 1,000 cd/$m^2$. The applied voltage at this time was taken as the index of driving voltage evaluation.

The case of the driving voltage of less than 6V was graded ◎.

The case of 6V or more and less than 7V was graded ○.

The case of 7V or more and less than 8V was graded Δ.

The case of 8V or more was graded X.

The results are shown in Table 1.

TABLE 1

| | Compound (third layer) | Driving Voltage | External Quantum Efficiency | Durability |
|---|---|---|---|---|
| Example 1 | Compound (1-1) | ○ | ○ | ◎ |
| Example 2 | Compound (1-2) | ○ | ○ | ◎ |
| Example 3 | Compound (1-3) | ○ | ○ | ◎ |

TABLE 1-continued

| | Compound (third layer) | Driving Voltage | External Quantum Efficiency | Durability |
|---|---|---|---|---|
| Example 4 | Compound (1-4) | ○ | ◎ | ◎ |
| Example 5 | Compound (1-49) | ○ | ○ | ○ |
| Example 6 | Compound (2-6) | ○ | ◎ | ○ |
| Example 7 | Compound (1-44) | ○ | ○ | ○ |
| Example 8 | Compound (1-66) | ◎ | ○ | ○ |
| Example 9 | Compound (1-67) | ◎ | ○ | ◎ |
| Example 10 | Compound (1-69) | ◎ | ○ | ○ |
| Comparative Example 1 | Comparative Compound (1) | × | ○ | × |
| Comparative Example 2 | Comparative Compound (2) | × | ○ | × |
| Comparative Example 3 | Comparative Compound (3) | × | ○ | × |
| Comparative Example 4 | Comparative Compound (4) | × | × | × |
| Comparative Example 5 | Comparative Compound (5) | Δ | × | × |
| Comparative Example 6 | Comparative Compound (6) | × | × | × |

It was found that by using the compound of the invention, the device having high efficiency, low in driving voltage and excellent in durability can be obtained.

In the case of light emission apparatus, display apparatus and illumination apparatus, instantaneous high luminance light emission through high current density at each pixel area is necessary. The luminescence device according to the invention is designed such that light emission efficiency becomes high in such a case, therefore, the luminescence device of the invention can be advantageously used.

Also, the device of the invention is excellent in light emission efficiency and durability and preferably used in light emission apparatus, display apparatus and illumination apparatus.

The structures of the compounds other than the compounds of the invention and comparative examples used in Examples 1 to 25 and Comparative Examples 1 to 10 are shown below.

(A)

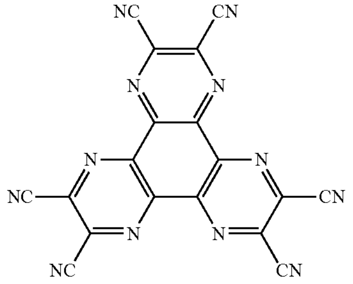

-continued (B)

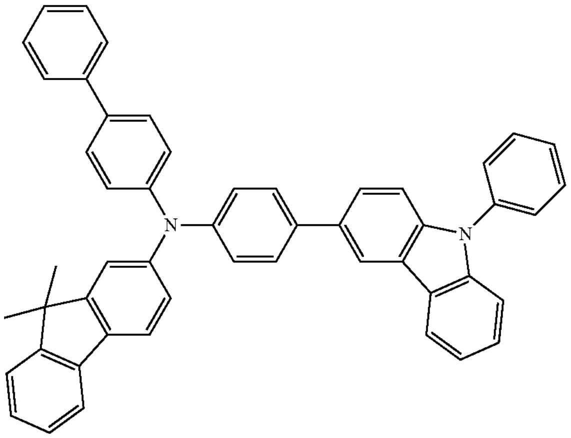

(C)

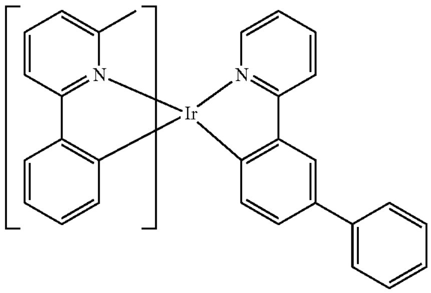

(D)

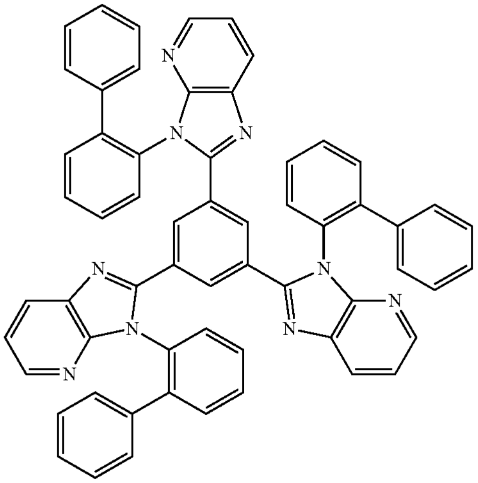

INDUSTRIAL APPLICABILITY

The invention can provide organic electroluminescence device excellent in efficiency and durability and capable of low voltage driving. The organic electroluminescence device can be used in display device, display, backlight, electrophotography, illumination light source, recording light source, exposure light source, reader light source, indicator, signboard, interior design, optical communication, and the like.

The invention has been described in detail with reference to specific embodiments thereof, it will be apparent to one skilled in the art that various changes and modifications can be made therein without departing from the spirit and scope thereof.

The present application is related to Japanese patent application filed on Sep. 8, 2010 (Japanese Patent Application No. 2010-201490) and Japanese patent application filed on Mar. 31, 2011 (Japanese Patent Application No. 2011-080874), and the disclosures of which are incorporated herein by reference.

DESCRIPTION OF SIGNS

2: Substrate
3: Anode
4: Hole-injecting layer
5: Hole-transporting layer
6: Light-emitting layer
7: Hole-blocking layer
8: Electron-transporting layer
9: Cathode
10: Organic electroluminescence device (organic EL device)
11: Organic layer
12: Protective layer
14: Adhesive layer
16: Sealing case
20: Light emission apparatus
30: Light-scattering member
30A: Light incident plane
30B: Light outgoing plane
31: Transparent substrate
32: Particle
40: Illumination apparatus

The invention claimed is:

1. A compound represented by formula (1):

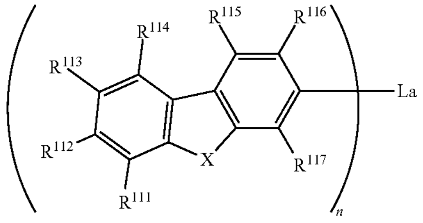

(1)

wherein each of X independently represents an oxygen atom or a sulfur atom; each of $R^{111}$ to $R^{114}$ independently represents a hydrogen atom, an alkyl group, a fluorine atom, or a cyano group; each of $R^{115}$ to $R^{117}$ independently represents a hydrogen atom or a substituent;

n represents an integer of 1, 3, or 4;

contiguous two of $R^{111}$ to $R^{116}$ are not bonded to each other to form an aromatic 6-membered ring; and La represents an n-valent aromatic group in which 3 to 10 aromatic groups each represented by formula (AR) are linked by a single bond:

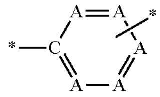

(AR)

wherein A represents =C(R)— or =N— for forming an aromatic ring, the number of nitrogen atoms represented by A is 0 to 3, and when the number of nitrogen atoms represented by A is 1 to 3, a plurality of R are not bonded to form a cyclic structure, * means a bonding hand, and each occurrence of R independently represents a hydrogen or a substituent selected from the group consisting of an alkyl group, a $C_6$-$C_{12}$ aryl group, a $C_1$-$C_6$ heteroaryl group, a fluorine atom, and a cyano group;

with the provisos that:

(a) when n represents 3 or 4 and the compound represented by formula (1) has a benzene ring as La or a part of La, and has a structure in which a plurality of dibenzofuran (when X represents an oxygen atom) or dibenzothiophene (when X represents a sulfur atom) in formula (1) are bonded to the benzene ring, the benzene ring has at least one hydrogen atom;

(b) when the number of nitrogen atoms represented by A is 3, R is not aryl;

(c) when n is 1, the R are each independently selected from the group consisting of hydrogen, an alkyl group, an $C_6$-$C_{12}$ aryl group, a fluorine atom, and a cyano group, wherein R is optionally substituted with a substituent and wherein when R is an aryl group the substituent is selected from the group consisting of alkyl group, an alkenyl group, an alkynyl group, an aryl group, an alkoxy group, an aryloxy group, a heterocyclic oxy group, an acyl group, an alkoxycarbonyl group, an aryloxycarbonyl group, an acyloxy group, an alkylthio group, an arylthio group, a heterocyclic thio group, a sulfonyl group, a sulfonyl group, a halogen atom, a cyano group, a sulfo group, a carboxyl group, a nitro group, a sulfino group, an imino group, a heterocyclic group, a silyl group, a silyloxy group, and a phosphoryl group, and wherein contiguous two of R are not bonded to each other to form an aromatic ring; and (d) when La is 3 aromatic groups each represented by formula (AR) linked by a single bond, n is 3 or 4.

2. An organic electroluminescence device comprising, a substrate having thereon: a pair of electrodes of an anode and a cathode; and at least one organic layer comprising a light-emitting layer between the pair of electrodes, wherein at least one layer of the at least one organic layer comprises at least one compound of claim 1.

3. The organic electroluminescence device of claim 2, wherein the light-emitting layer comprises an iridium complex.

4. The organic electroluminescence device of claim 3, wherein the iridium complex is represented by formula (T-1):

(T-1)

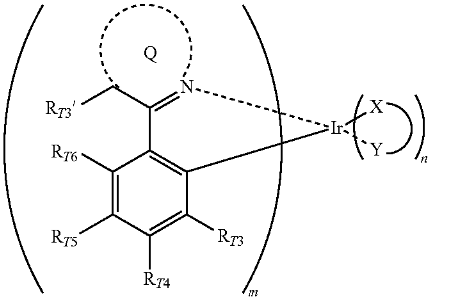

in formula (T-1), each of $R_{T3}'$, $R_{T3}$, $R_{T4}$, $R_{T5}$ and $R_{T6}$ independently represents a hydrogen atom or a substituent, contiguous arbitrary two of $R_{T3}$, $R_{T4}$, $R_{T5}$ and $R_{T6}$ may be bonded to each other to form a condensed 4- to 7-membered ring, and the condensed 4- to 7-membered ring is cycloalkyl, aryl or heteroaryl, and the condensed 4-to 7-membered ring may further have a substituent, $R_{T3'}$ and $R_{T6}$ may be linked to form a ring by a linking group selected from $—C(R_T)_2—C(R_T)_2$, $—CR_T{=}CR_T—$, $—C(R_T)_2—$, $—O—$, $—NR_T—$, $—O—C(R_T)_2—$, $—NR_T—C(R_T)_2—$ and $—N{=}CR_T—$, and each of $R_T$ independently represents a hydrogen atom, an alkyl group, an alkenyl group, an alkynyl group, an aryl group, or a heteroaryl group, and these groups may further have a substituent, ring Q represents a 5- or 6-membered aromatic heterocyclic ring comprising a nitrogen atom or a condensed aromatic heterocyclic ring comprising a nitrogen atom, and (X-Y) represents an auxiliary ligand, m represents an integer of 1 to 3, n represents an integer of 0 to 2, and m+n=3.

5. An apparatus comprising the organic electroluminescence device as claimed in claim 2, wherein the apparatus is a light emission apparatus, a display apparatus, or an illumination apparatus.

6. A compound represented by formula (1):

(1)

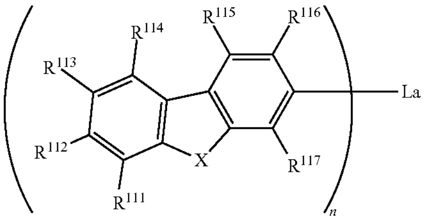

wherein each of X independently represents an oxygen atom or a sulfur atom; each of $R^{111}$ to $R^{114}$ independently represents a hydrogen atom, an alkyl group, a fluorine atom, or a cyano group; each of $R^{115}$ to $R^{117}$ independently represents a hydrogen atom or a substituent; n represents an integer of 1 or more; contiguous two of $R^{111}$ to $R^{116}$ are not bonded to each other to form an aromatic 6-membered ring; and La represents an n-valent aromatic group having a structure of L14 or L15

(L14)

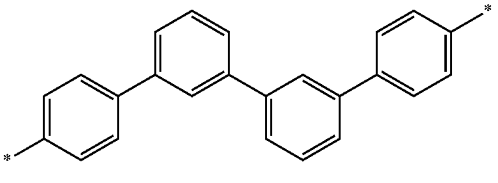

-continued (L15)

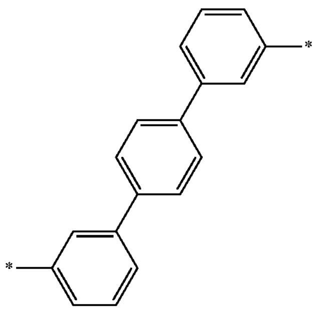

wherein * means a bonding hand.

7. An organic electroluminescence device comprising, a substrate having thereon: a pair of electrodes of an anode and a cathode; and at least one organic layer comprising a light-emitting layer between the pair of electrodes, wherein at least one layer of the at least one organic layer comprises at least one compound of claim 6.

8. The organic electroluminescence device of claim 7, wherein the light-emitting layer comprises an iridium complex.

9. The organic electroluminescence device of claim 8, wherein the iridium complex is represented by formula (T-1):

(T-1)

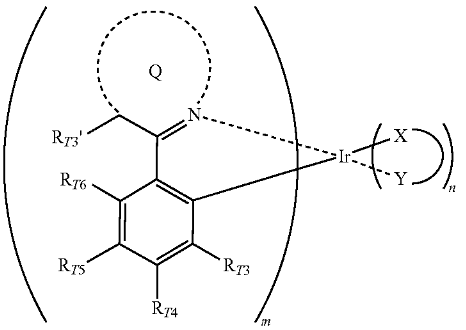

in formula (T-1), each of $R_{T3}'$, $R_{T3}$, $R_{T4}$, $R_{T5}$ and $R_{T6}$ independently represents a hydrogen atom or a substituent, contiguous arbitrary two of $R_{T3}$, $R_{T4}$, $R_{T5}$ and $R_{T6}$ may be bonded to each other to form a condensed 4- to 7-membered ring, and the condensed 4- to 7-membered ring is cycloalkyl, aryl or heteroaryl, and the condensed 4- to 7-membered ring may further have a substituent, $R_{T3}'$ and $R_{T6}$ may be linked to form a ring by a linking group selected from $—C(R_T)_2—C(R_T)_2—$, $—CR_T{=}CR_T—$, $—C(R_T)_2—$, $—O—$, $—NR_T—$, $—O—C(R_T)_2—$, $—NR_T—C(R_T)_2—$ and $—N{=}CR_T—$, and each of $R_T$ independently represents a hydrogen atom, an alkyl group, an alkenyl group, an alkynyl group, an aryl group, or a heteroaryl group, and these groups may further have a substituent, ring Q represents a 5- or 6-membered aromatic heterocyclic ring comprising a nitrogen atom or a condensed aromatic heterocyclic ring comprising a nitrogen atom, and (X—Y) represents an auxiliary ligand, m represents an integer of 1 to 3, n represents an integer of 0 to 2, and m+n=3.

10. An apparatus comprising the organic electroluminescence device as claimed in claim 7, wherein the apparatus is a light emission apparatus, a display apparatus, or an illumination apparatus.

11. A compound represented by formula (1):

(1)

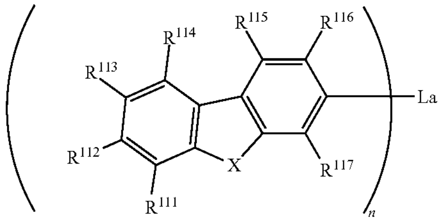

wherein each of X independently represents an oxygen atom or a sulfur atom;

each of $R^{111}$ to $R^{114}$ independently represents a hydrogen atom, an alkyl group, a fluorine atom, or a cyano group;

each of $R^{115}$ to $R^{117}$ independently represents a hydrogen atom or a substituent;

n represents an integer of 2;

contiguous two of $R^{111}$ to $R^{116}$ are not bonded to each other to form an aromatic 6-membered ring; and La represents an n-valent aromatic group represented by formula (A)

(A)

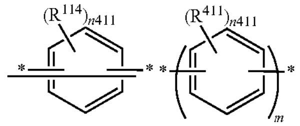

wherein each occurrence of $R^{411}$ independently represents a substituent selected from the group consisting of an alkyl group, a $C_6$-$C_{12}$ aryl group, a $C_1$-$C_6$ heteroaryl group, a fluorine atom, and a cyano group, wherein plurality of $R^{411}$ are not bonded to form a cyclic structure;

each occurrence of $n_{411}$ independently represents an integer of 0 to 4; and m represents an integer of 3 or more, with the provisos that:

(a) when the compound represented by formula (1) has a benzene ring as La or a part of La, and has a structure in which a plurality of dibenzofuran (when X represents an oxygen atom) or dibenzothiophene (when X represents a sulfur atom) in formula (1) are bonded to the benzene ring, the benzene ring has at least one hydrogen atom; and (b) when m is an integer from 3 to 10, $n_{411}$ represents an integer of 1 to 4 and each occurrence of $R^{411}$ independently represents an aryl group, a heteroaryl group, a fluorine atom, or a cyano group.

12. An organic electroluminescence device comprising, a substrate having thereon: a pair of electrodes of an anode and a cathode; and at least one organic layer comprising a light-emitting layer between the pair of electrodes, wherein at least one layer of the at least one organic layer comprises at least one compound of claim 11.

13. The organic electroluminescence device of claim 12, wherein the light-emitting layer comprises an iridium complex.

14. The organic electroluminescence device of claim 13, wherein the iridium complex is represented by formula (T-1):

(T-1)

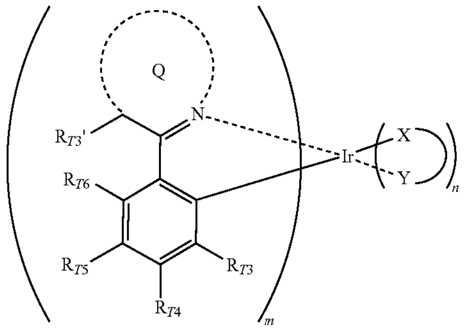

in formula (T-1), each of $R_{T3}'$, $R_{T3}$, $R_{T4}$, $R_{T5}$ and $R_{T6}$ independently represents a hydrogen atom or a substituent, contiguous arbitrary two of $R_{T3}$, $R_{T4}$, $R_{T5}$ and $R_{T6}$ may be bonded to each other to form a condensed 4- to 7-membered ring, and the condensed 4- to 7-membered ring is cycloalkyl, aryl or heteroaryl, and the condensed 4- to 7-membered ring may further have a substituent, $R_{T3}'$ and $R_{T6}$ may be linked to form a ring by a linking group selected from $—C(R_T)_2—C(R_T)_2—$, $—CR_T{=}CR_T—$, $—C(R_T)_2—$, —O—, $—NR_T—$, $—O—C(R_T)_2—$, $—NR_T—C(R_T)_2—$ and $—N{=}CR_T—$, and each of $R_T$ independently represents a hydrogen atom, an alkyl group, an alkenyl group, an alkynyl group, an aryl group, or a heteroaryl group, and these groups may further have a substituent, ring Q represents a 5- or 6-membered aromatic heterocyclic ring comprising a nitrogen atom or a condensed aromatic heterocyclic ring comprising a nitrogen atom, and (X—Y) represents an auxiliary ligand, m represents an integer of 1 to 3, n represents an integer of 0 to 2, and m+n=3.

15. An apparatus comprising the organic electroluminescence device as claimed in claim 12, wherein the apparatus is a light emission apparatus, a display apparatus, or an illumination apparatus.

16. A compound selected from the group consisting of:

(1-1)

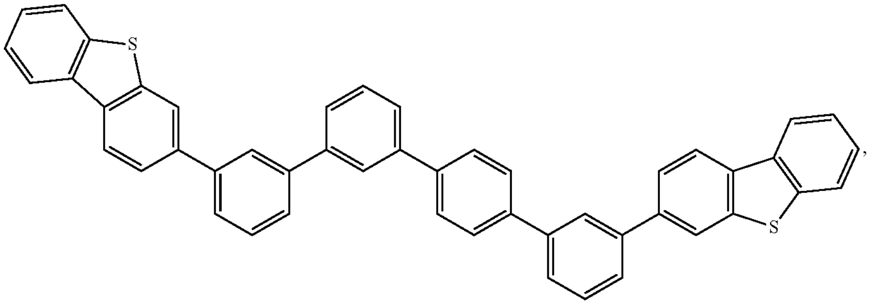

, (1-2)

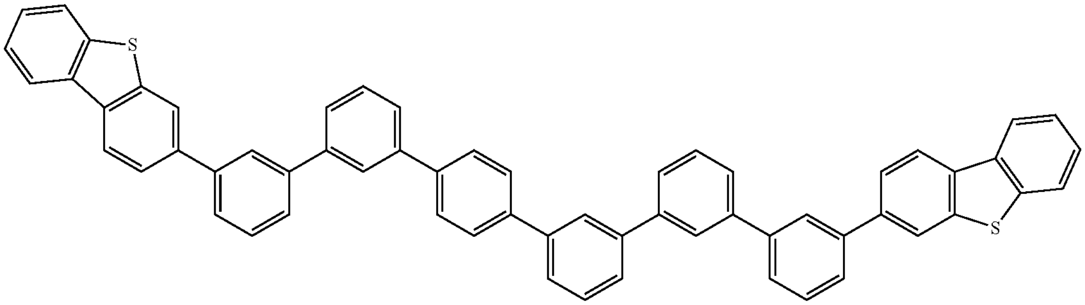

, (1-5)

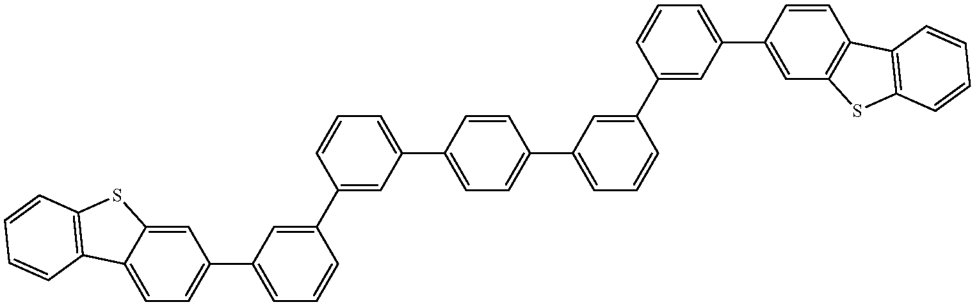

,

-continued
(1-6)
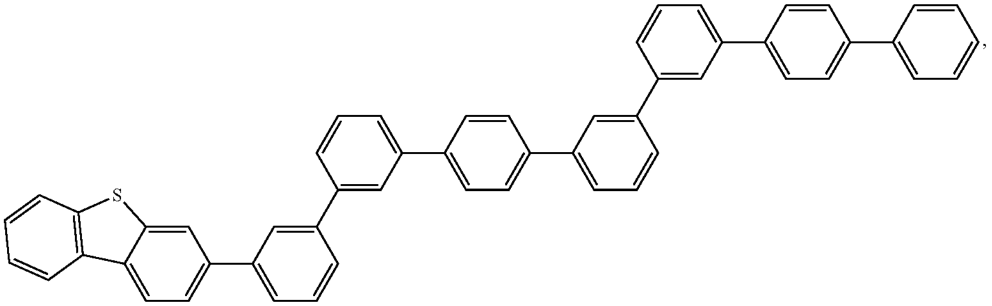
(1-7)
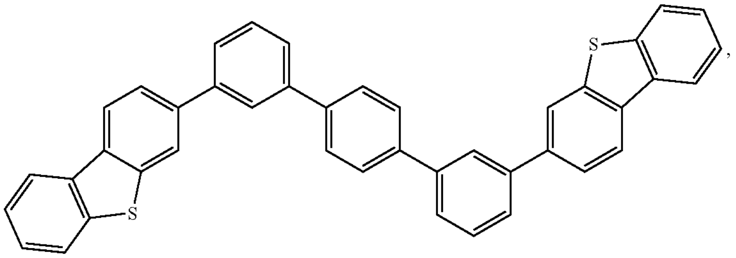
(1-8)
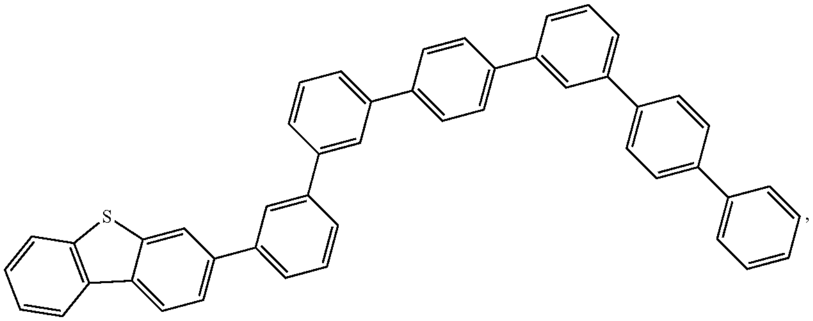
(1-17)
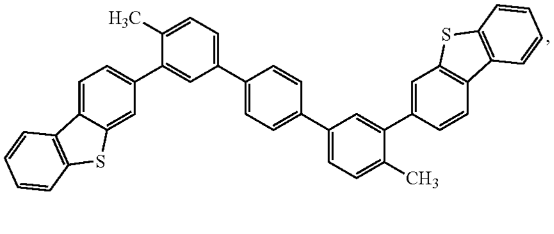
(1-18)
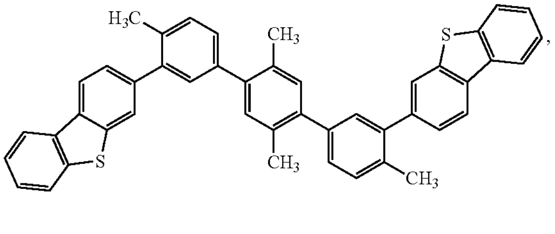
(1-19)
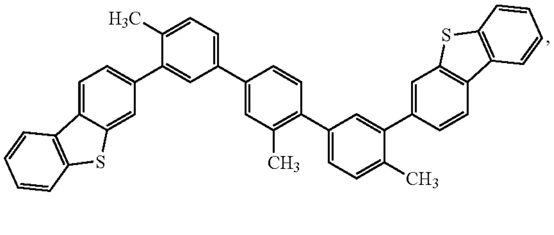
(1-20)
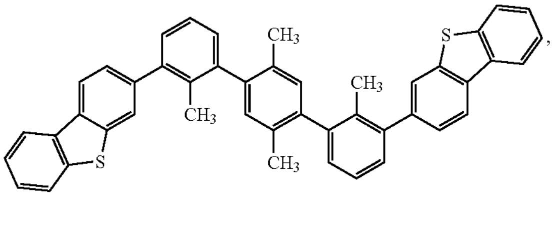

-continued
(1-31)
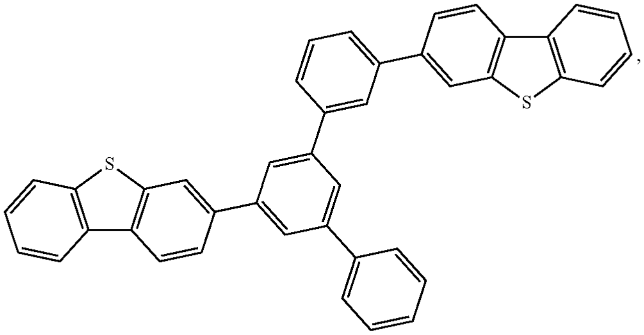
,
(1-33)
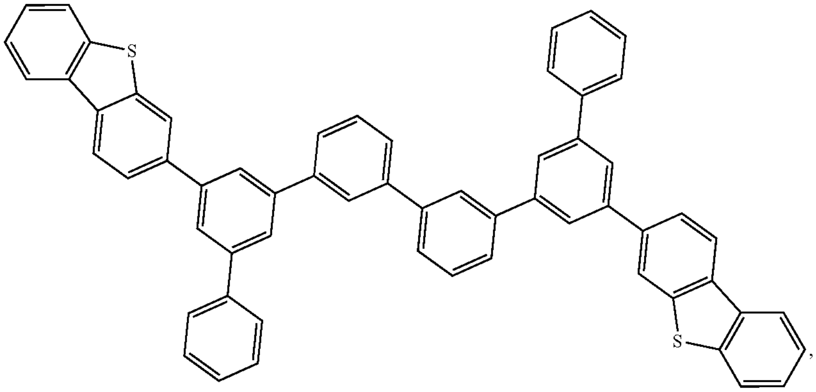
,
(1-34)
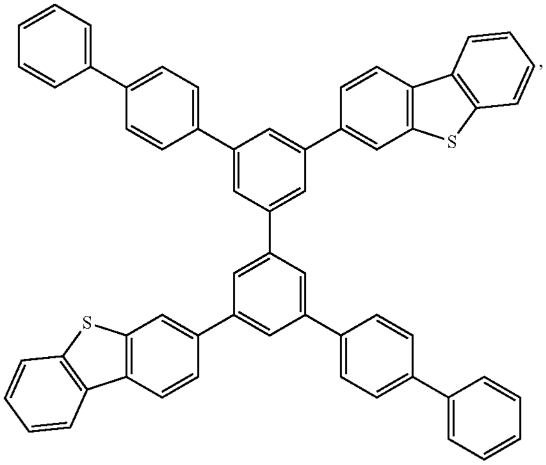
,
(1-35)
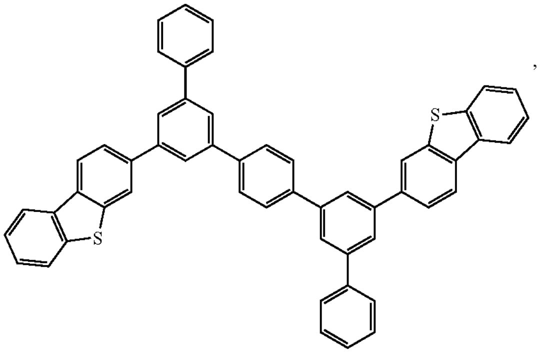
, -continued
(1-36)
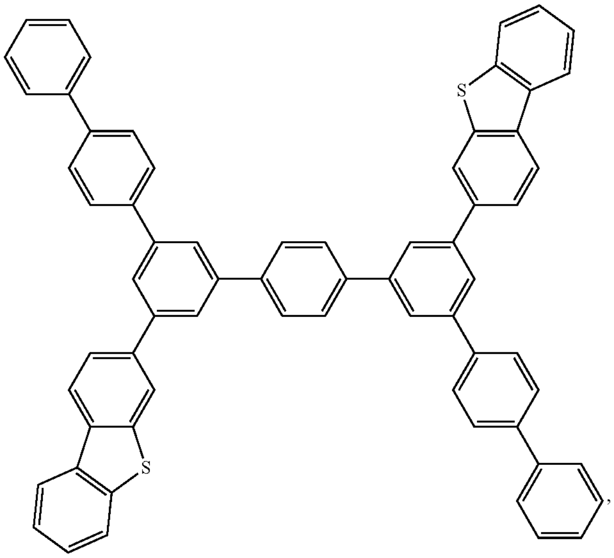
,
(1-37)
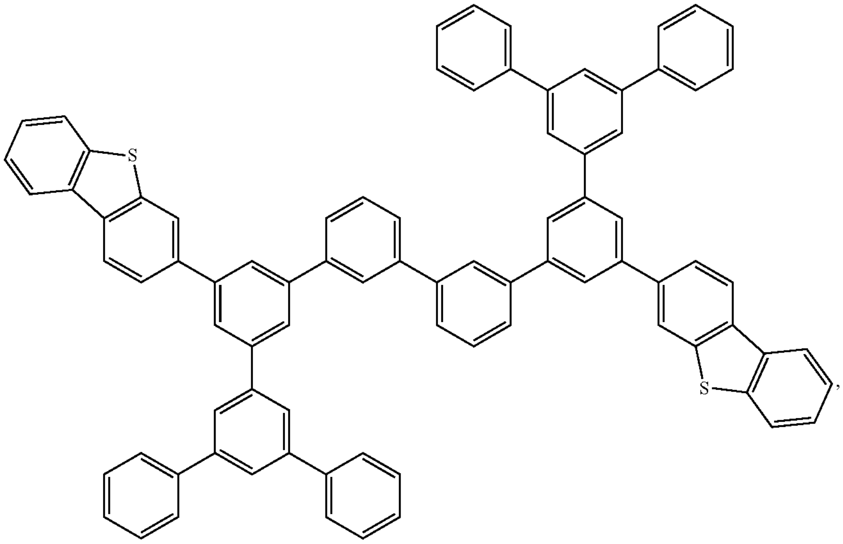
,
(1-38)
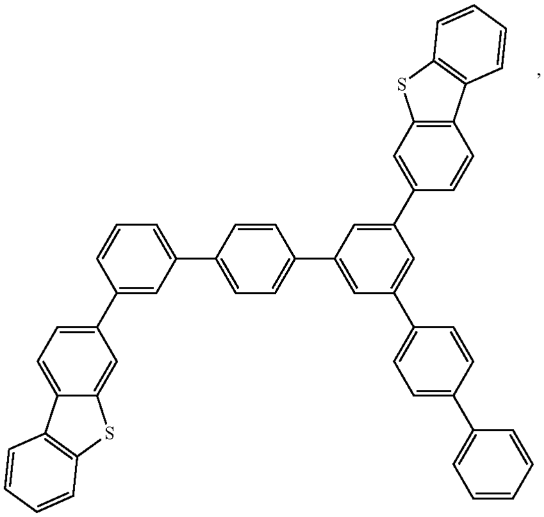
,
(1-39)
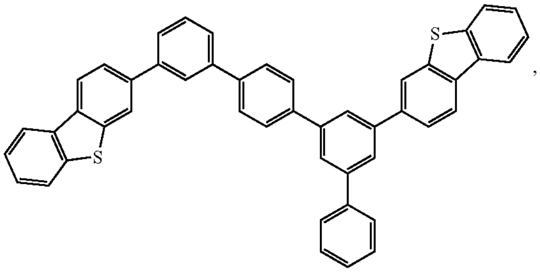
, -continued
(1-42)
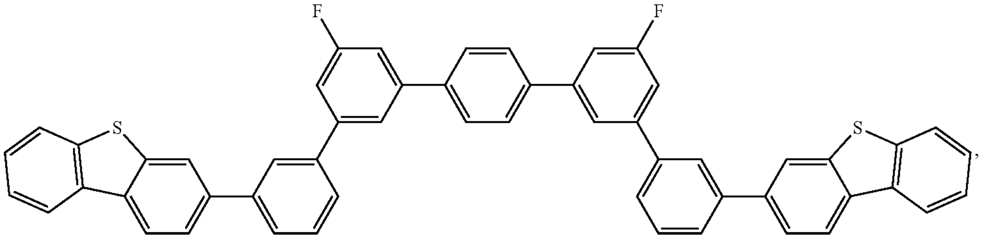
(1-44)
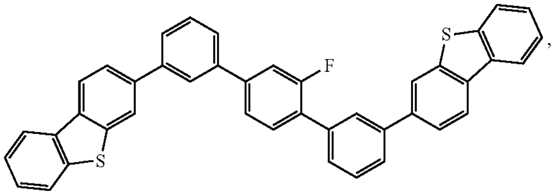
(1-45)
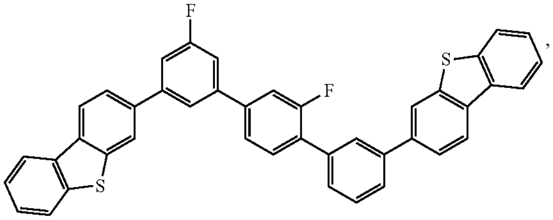
(1-46)
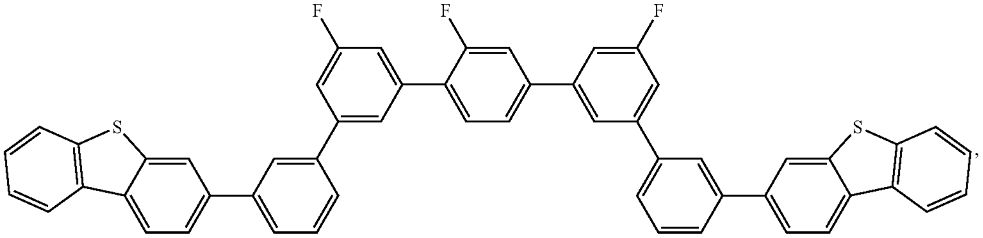
(1-47)
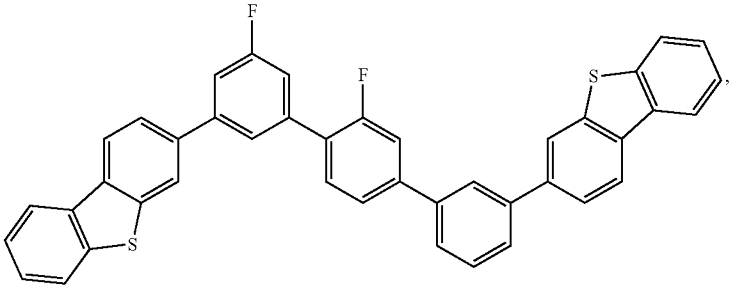
(1-48)
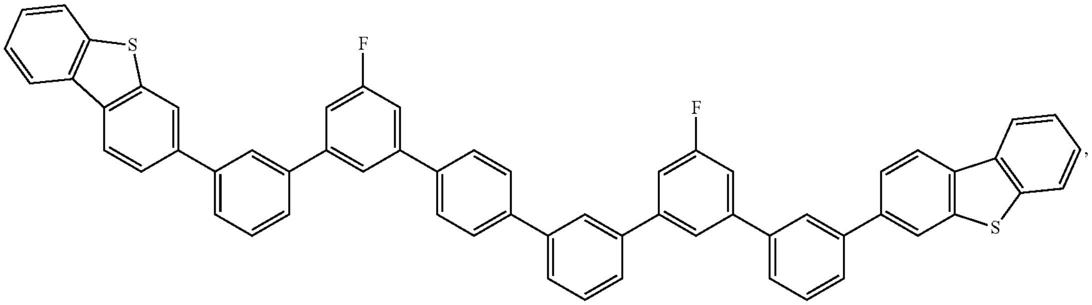

-continued
(1-49)
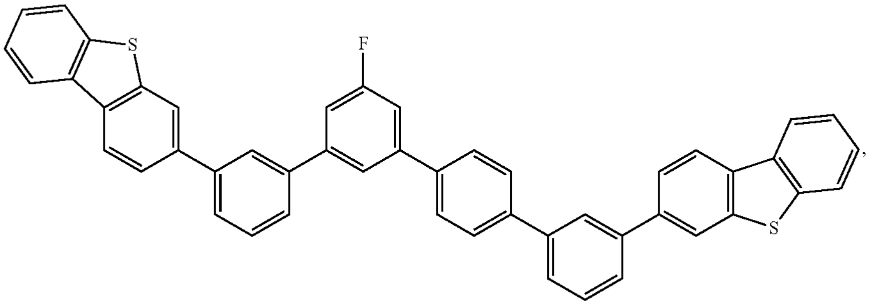
,
(1-50)
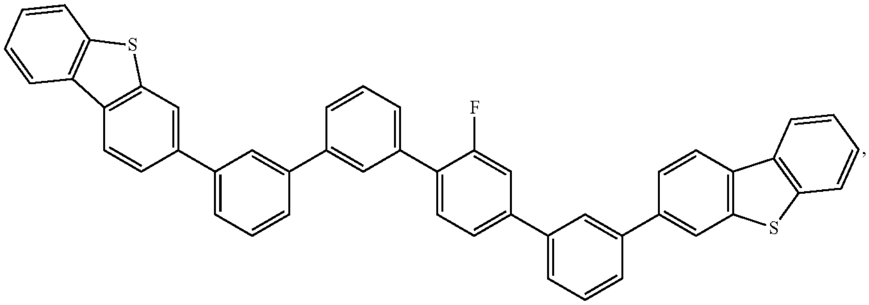
,
(1-54)
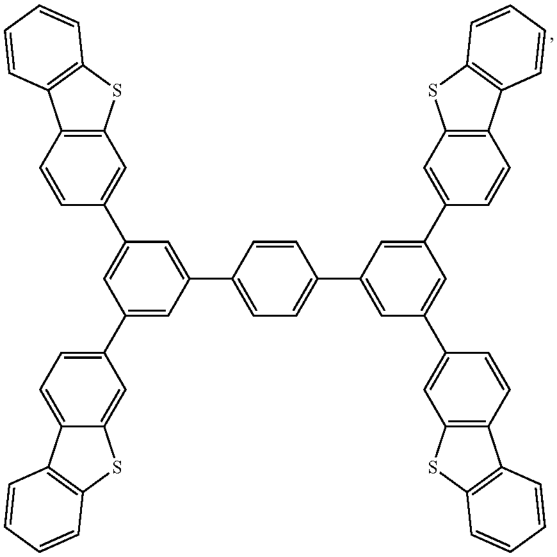
,
(1-55)
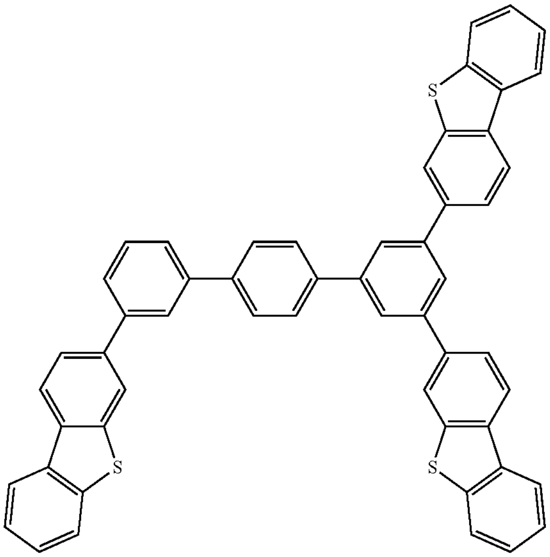
,
(1-56)
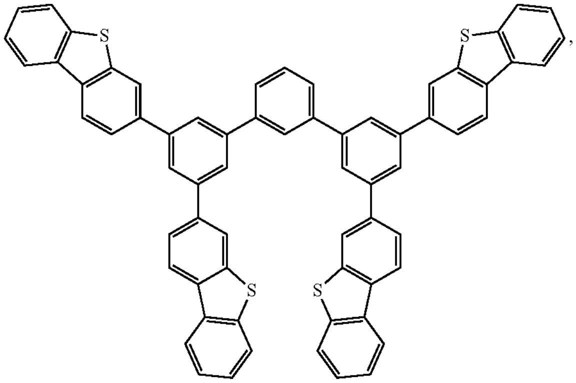
,
(1-57)
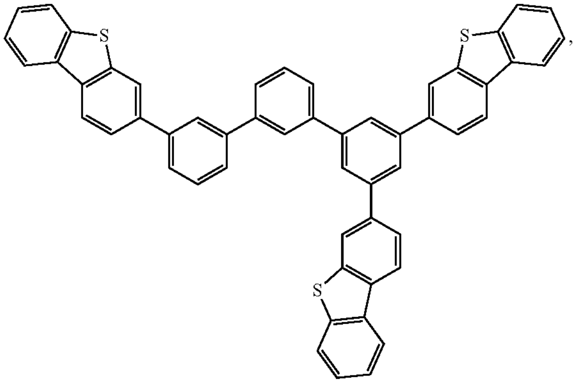
, -continued
(1-58)
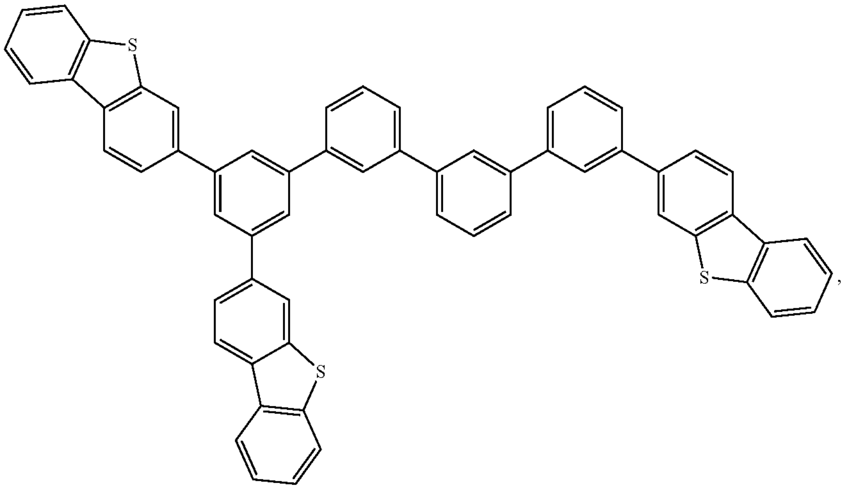
(1-62)
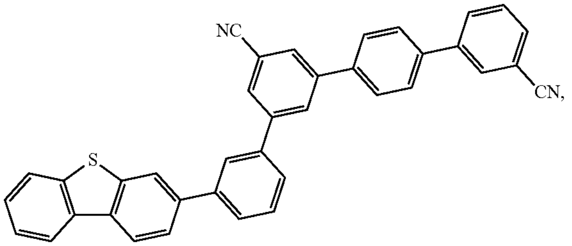
(1-66)
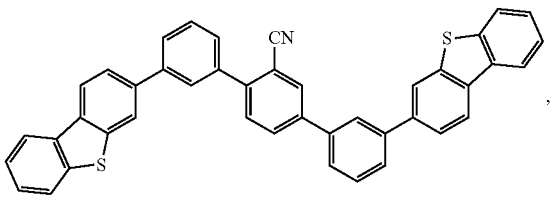
(1-69)
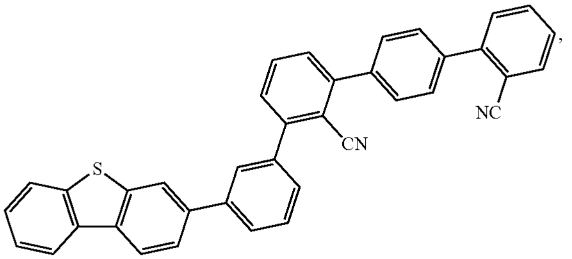
(1-70)
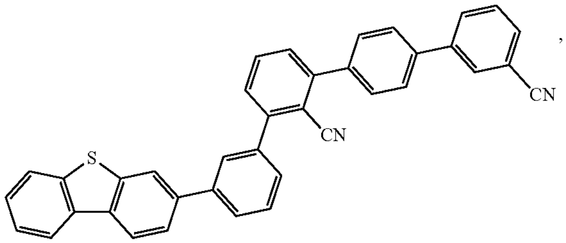
(1-71)
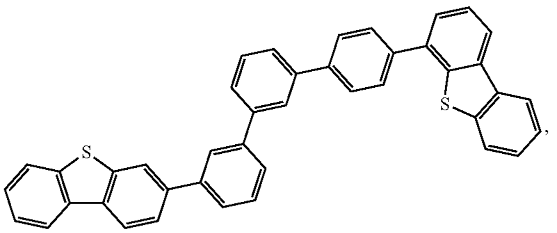
(1-73)
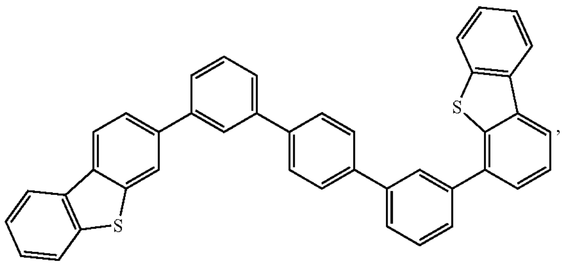
(2-7)
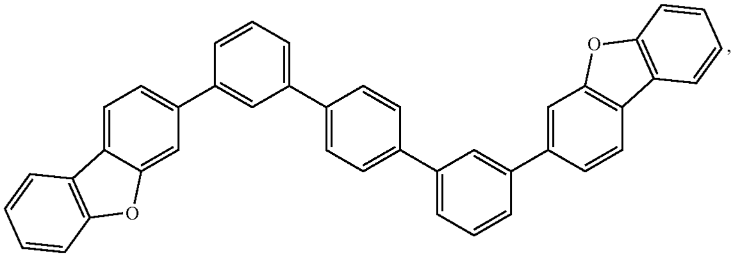

-continued
(2-8)
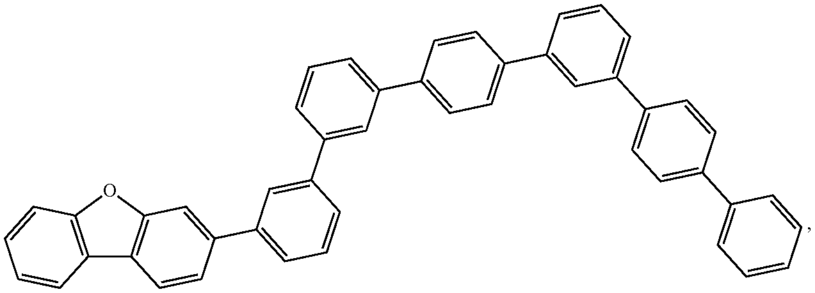
(3-5)
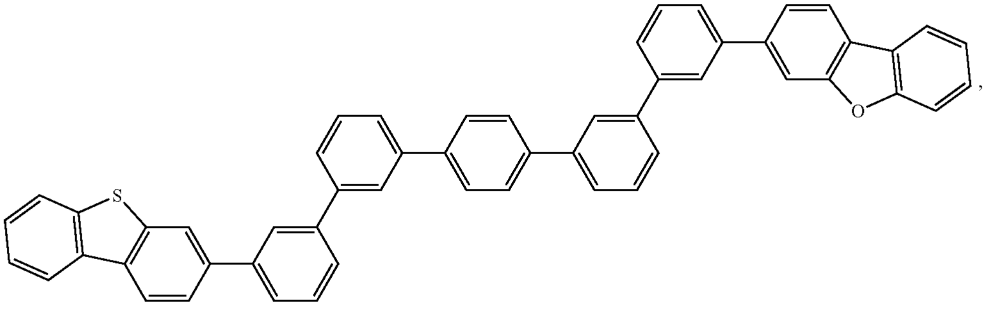
(3-6)
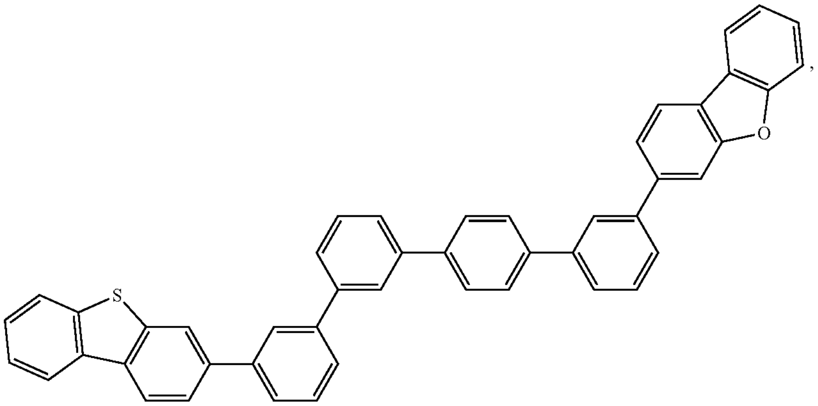
(3-7)
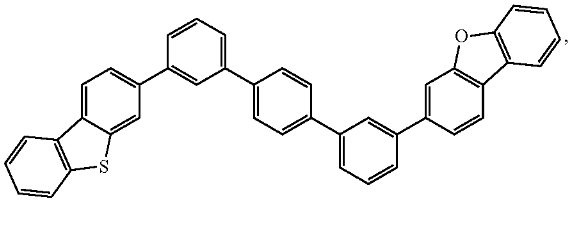
(4-2)
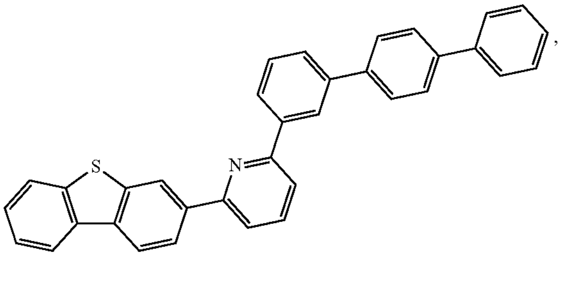

-continued
(4-7)
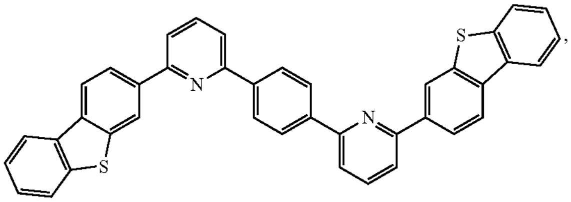
,
(4-8)
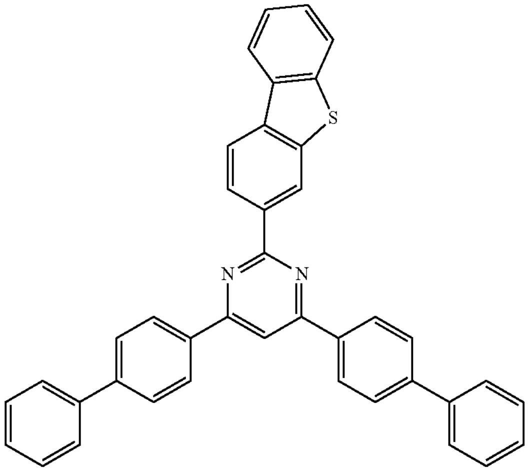
,
(4-9)
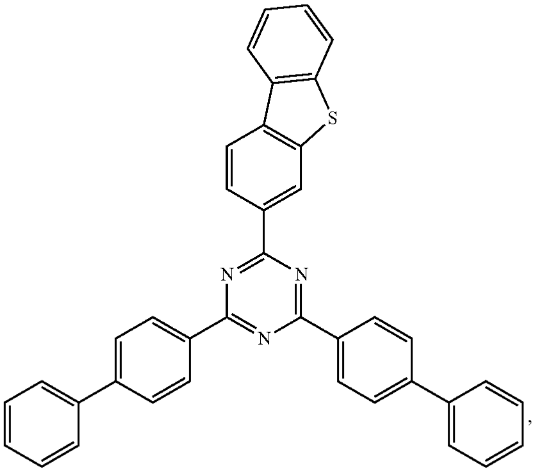
, and
(4-10)
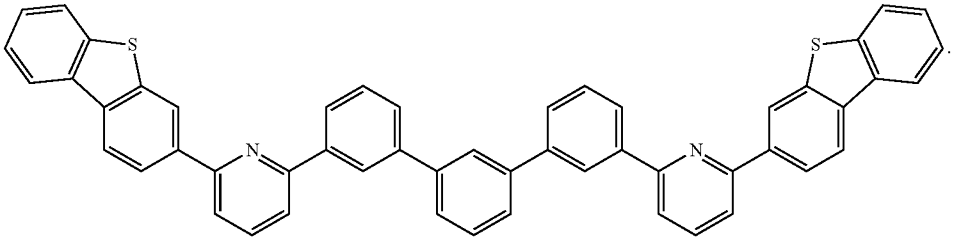
.

17. An organic electroluminescence device comprising, a substrate having thereon: a pair of electrodes of an anode and a cathode; and at least one organic layer comprising a light-emitting layer between the pair of electrodes, wherein at least one layer of the at least one organic layer comprises at least one compound of claim 16.

18. The organic electroluminescence device of claim 17, wherein the light-emitting layer comprises an iridium complex.

19. The organic electroluminescence device of claim 18, wherein the iridium complex is represented by formula (T-1):

(T-1)

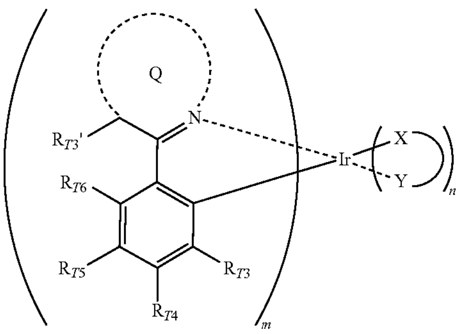

in formula (T-1), each of $R_{T3}'$, $R_{T3}$, $R_{T4}$, $R_{T5}$ and $R_{T6}$ independently represents a hydrogen atom or a substituent, contiguous arbitrary two of $R_{T3}$, $R_{T4}$, $R_{T5}$ and $R_{T6}$ may be bonded to each other to form a condensed 4- to 7-membered ring, and the condensed 4- to 7-membered ring is cycloalkyl, aryl or heteroaryl, and the condensed 4- to 7-membered ring may further have a substituent, $R_{T3}'$ and $R_{T6}$ may be linked to form a ring by a linking group selected from $—C(R_T)_2—C(R_T)_2—$, $—CR_T=CR_T—$, $—C(R_T)_2—$, —O—, $—NR_T—$, $—O—C(R_T)_2—$, $—NR_T—C(R_T)_2—$ and $—N=CR_T—$, and each of $R_T$ independently represents a hydrogen atom, an alkyl group, an alkenyl group, an alkynyl group, an aryl group, or a heteroaryl group, and these groups may further have a substituent, ring Q represents a 5- or 6-membered aromatic heterocyclic ring comprising a nitrogen atom or a condensed aromatic heterocyclic ring comprising a nitrogen atom, and (X—Y) represents an auxiliary ligand, m represents an integer of 1 to 3, n represents an integer of 0 to 2, and m+n=3.

20. An apparatus comprising the organic electroluminescence device as claimed in claim 17 wherein the apparatus is a light emission apparatus, a display apparatus, or an illumination apparatus.

* * * * *